United States Patent
Tessier-Lavigne et al.

(10) Patent No.: US 6,623,738 B1
(45) Date of Patent: Sep. 23, 2003

(54) SEMAPHORIN RECEPTORS

(75) Inventors: Marc Tessier-Lavigne, San Francisco, CA (US); Zhigang He, San Francisco, CA (US); Hang Chen, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/439,711

(22) Filed: Nov. 12, 1999

Related U.S. Application Data

(62) Division of application No. 08/936,135, filed on Sep. 24, 1997, now Pat. No. 6,054,293, which is a continuation of application No. 08/889,458, filed on Jul. 8, 1997, now abandoned.

(51) Int. Cl.[7] .................. A61K 39/395; G01N 33/53; C07K 16/00
(52) U.S. Cl. .................. 424/139.1; 424/141.1; 424/148.1; 424/154.1; 424/172.1; 424/145.1; 435/7.1; 435/332; 530/387.9
(58) Field of Search ............ 424/139.1, 141.1, 424/148.1, 154.1, 172.1; 435/7.1, 332; 530/387.9

(56) References Cited

PUBLICATIONS

Kawakami A. et al., Developmentally regulated Expression of a Cell Suface Protein, Neuropilin, in Mouse Nervous System, Jan. 1, 1996 Journal of Neurobiology, vol. 29, No. 1, p. 1–17.

He Z. et al., Neuropilin is a Receptor for the Axonal Chemorepellent Semaphorin II. 1997 Cell, vol. 90, p. 739–751.

Kolodkin A. et al., Neuropilin is a Semaphorin III Receptor, 1997 Cell, vol. 90 p. 753–762.

Takagi S. et al., Expression of a Cell Adhesion Molecule, Neuropilin, in the Developing Chick Nervous system, 1995 Developmental Biology, vol. 170, p. 207–222.

Takagi S. et al., The A5 Antigen, a candidate for the Neuronal Recognition Molecule, has Homologies to Complement Components and Coagulation Factors, 1991 Neuron, vol. 7, p. 295–307.

Chen, H. et al., Neuropilin–2, a Novel member of the Neuropilin family, is a high affinity receptor for the Semaphorins Sema E and Sema IV but not Sema III, Sep. 1997 Neuron, vol. 19, p. 547–559.

Pharmagenics Inc., 1993 ID Q31949 standard, DNA, 405 bp, Accession No. Q31949, N–geneseq 32 Database.

Harvard College, 1994 ID R51427 standard, Protein, 33 AA, Accession No. R51726, A–geneseq32 Database.

Hoeschst Japan Ltd., 1994 ID R49994 standard, 1128 AA, Accession No. R49994, A–geneseq32 Database.

Weissenbach, J. et al., 1994 HS24XB10, H. sapiens (D5S429) DNA Segment containing (CA) repeat; Clone AFM24xb10, Accession No. Z17097 emb156 Database.

Hillier, L. et al., 1995 H99253 497 bp mRNA, yx21h06.s1 Homo sapiens cDNA 262427 3', human clone 26247, Accession No. H99253, embl–est56 Database.

*Primary Examiner*—Yvonne Eyler
*Assistant Examiner*—Nirmal S. Basi
(74) *Attorney, Agent, or Firm*—Richard Aron Osman

(57) ABSTRACT

The invention provides methods and compositions relating to two classes of semaphorin receptors, SR1 and SR2. The polypeptides may be produced recombinantly from transformed host cells from the disclosed SR encoding nucleic acids or purified from human cells. The invention provides isolated SR hybridization probes and primers, capable of specifically hybridizing with the disclosed SR genes. SR-specific binding agents such as specific antibodies, and methods of making and using the subject compositions in diagnosis, therapy and in the biopharmaceutical industry.

6 Claims, 10 Drawing Sheets

FIG. 1A1

|  |  | | |
|---|---|---|---|
| Rat | 490 | DEKIVRGVIIQGGKHRENKVFMRKFKIAYSNNGSDWKMIMDDSKRKAKSFEGNNYDTPELRAFTPLSTR |
| Human | 491 | EEKIVRGIIIQGGKHRENKVFMRKFKICYSNNGSDWKMIMDDSKRKAKSFEGNNYDTPELRTFPALSTR |
| Mouse | 491 | DEKIVRGVIIHGGKHRENKVFMRKFKIAYSNNGSDWKTIMDDSKRKAKSFEGNNYDTPELRTFSPLSTR |
| | | |
| Rat | 560 | FIRIYPERATHSGLGLRMELLGCEVEVPTAGPTTPNGNPVDECDDDQANCHSGTGDDFQLTGGTTVLATE |
| Human | 561 | FIRIYPERATHGGLGLRMELLGCEVEAPTAGPTTPNGNLVDECDDDQANCHSGTGDDFQLTGGTTVLATE |
| Mouse | 561 | FIRIYPERATHSGLGLRMELLGCEVEAPTAGPTTPNGNPVHECDDDQANCHSGTGDDFQLTGGTTVLATE |
| | | ⊤c |
| Rat | 630 | KPTIIDSTIQSEFPTYGFNCEFGWGSHKTFCHWEHDSHAQLRWKLRVKLHYQKPEEYDQLVWMVVGHQGDHWKEGRVLL |
| Human | 631 | KPTVIDSTIQSEFPTYGFNCEFGWGSHKTFCHWEHDNHVQLKWSVLTSKTGPIQDHTGDGNFIYSQADEN |
| Mouse | 631 | KPTIIDSTIQSEFPTYGFNCEFGWGSHKTFCHWEHDSHAQLRWSVLTSKTGPIQDHTGDGNFIYSQADEN |
| | | |
| Rat | 700 | QKGKVARLVSPVVYSQSSAHCMTFWYHMSGSHVGTLRVKLHYQKPEEYDQLVWMVVGHQGDHWKEGRVLL |
| Human | 701 | QKGKVARLVSPVVYSQNSAHCMTFWYHMSGSHVGTLRVKLRYQKPEEYDQLVWMAIGHQGDHWKEGRVLL |
| Mouse | 701 | QKGKVARLVSPVVYSQSSAHCMTFWYHMSGSHVGTLRVKLRYQKPEEYDQLVWMVVGHQGDHWKEGRVLL |
| | | |
| Rat | 770 | HKSLKLYQVIFEGEIGKGNLGGIAVDDDISINNHIPQEDCAKPTDLDKKNTEIKIDETGSTPGYE-EGKGD |
| Human | 771 | HKSLKLYQVIFEGEIGKGNLGGIAVDDDISINNHISQEDCAKPADLDKKNPEIKIDETGSTPGYEGEGEGD |
| Mouse | 771 | HKSLKLYQVIFEGEIGKGNLGGIAVDDDISINNHISQEDCAKPTDLDKKNTEIKIDETGSTPGYEGEGEGD |
| | | ⊤TM |
| Rat | 839 | KNISRKPGNVLKTLDPILITIIAMSALGVLLGAVCGVVLYCACWHNGSERNLSALENYNFELVDGVKLK |
| Human | 841 | KNISRKPGNVLKTLEPILITIIAMSALGVLLGAVCGVVLYCACWHNGSERNLSALENYNFELVDGVKLK |
| Mouse | 841 | KNISRKPGNVLKTLDPILITIIAMSALGVLLGAVCGVVLYCACWHNGSERNLSALENYNFELVDGVKLK |
| | | ⊤Cytoplasmic Domain |
| Rat | 909 | KDKLNPHSNYSEA |
| Human | 911 | KDKLNTQSTYSEA |
| Mouse | 911 | KDKLNPQSNYSEA |

SEQUENCE LISTING

```
<160> NUMBER OF SEQ ID NOS: 26

<210> SEQ ID NO 1
<211> LENGTH: 2772
<212> TYPE: DNA
<213> ORGANISM: human
<220> FEATURE:
<221> NAME/KEY: CDS
<222> LOCATION: (1)..(2769)

<400> SEQUENCE: 1 atg gag agg ggg ctg ccg ctc ctc tgc gcc gtg ctc gcc ctc gtc ctc      48
Met Glu Arg Gly Leu Pro Leu Leu Cys Ala Val Leu Ala Leu Val Leu
 1               5                  10                  15 gcc ccg gcc ggc gct ttt cgc aac gat gaa tgt ggc gat act ata aaa      96
Ala Pro Ala Gly Ala Phe Arg Asn Asp Glu Cys Gly Asp Thr Ile Lys
             20                  25                  30 att gaa agc ccc ggg tac ctt aca tct cct ggt tat cct cat tct tat     144
Ile Glu Ser Pro Gly Tyr Leu Thr Ser Pro Gly Tyr Pro His Ser Tyr
         35                  40                  45 cac cca agt gaa aaa tgc gaa tgg ctg att cag gct ccg gac cca tac     192
His Pro Ser Glu Lys Cys Glu Trp Leu Ile Gln Ala Pro Asp Pro Tyr
     50                  55                  60 cag aga att atg atc aac ttc aac cct cac ttc gat ttg gag gac aga     240
Gln Arg Ile Met Ile Asn Phe Asn Pro His Phe Asp Leu Glu Asp Arg
 65                  70                  75                  80 gac tgc aag tat gac tac gtg gaa gtc ttc gat gga gaa aat gaa aat     288
Asp Cys Lys Tyr Asp Tyr Val Glu Val Phe Asp Gly Glu Asn Glu Asn
                 85                  90                  95 gga cat ttt agg gga aag ttc tgt gga aag ata gcc cct cct cct gtt     336
Gly His Phe Arg Gly Lys Phe Cys Gly Lys Ile Ala Pro Pro Pro Val
            100                 105                 110 gtg tct tca ggg cca ttt ctt ttt atc aaa ttt gtc tct gac tac gaa     384
```

-continued

```
Val Ser Ser Gly Pro Phe Leu Phe Ile Lys Phe Val Ser Asp Tyr Glu
        115                 120                 125 aca cat ggt gca gga ttt tcc ata cgt tat gaa att ttc aag aga ggt          432
Thr His Gly Ala Gly Phe Ser Ile Arg Tyr Glu Ile Phe Lys Arg Gly
    130                 135                 140 cct gaa tgt tcc cag aac tac aca aca cct agt gga gtg ata aag tcc          480
Pro Glu Cys Ser Gln Asn Tyr Thr Thr Pro Ser Gly Val Ile Lys Ser
145                 150                 155                 160 ccc gga ttc cct gaa aaa tat ccc aac agc ctt gaa tgc act tat att          528
Pro Gly Phe Pro Glu Lys Tyr Pro Asn Ser Leu Glu Cys Thr Tyr Ile
                165                 170                 175 gtc ttt gcg cca aag atg tca gag att atc ctg gaa ttt gaa agc ttt          576
Val Phe Ala Pro Lys Met Ser Glu Ile Ile Leu Glu Phe Glu Ser Phe
            180                 185                 190 gac ctg gag cct gac tca aat cct cca ggg ggg atg ttc tgt cgc tac          624
Asp Leu Glu Pro Asp Ser Asn Pro Pro Gly Gly Met Phe Cys Arg Tyr
        195                 200                 205 gac cgg cta gaa atc tgg gat gga ttc cct gat gtt ggc cct cac att          672
Asp Arg Leu Glu Ile Trp Asp Gly Phe Pro Asp Val Gly Pro His Ile
    210                 215                 220 ggg cgt tac tgt gga cag aaa aca cca ggt cga atc cga tcc tca tcg          720
Gly Arg Tyr Cys Gly Gln Lys Thr Pro Gly Arg Ile Arg Ser Ser Ser
225                 230                 235                 240 ggc att ctc tcc atg gtt ttt tac acc gac agc gcg ata gca aaa gaa          768
Gly Ile Leu Ser Met Val Phe Tyr Thr Asp Ser Ala Ile Ala Lys Glu
                245                 250                 255 ggt ttc tca gca aac tac agt gtc ttg cag agc agt gtc tca gaa gat          816
Gly Phe Ser Ala Asn Tyr Ser Val Leu Gln Ser Ser Val Ser Glu Asp
            260                 265                 270 ttc aaa tgt atg gaa gct ctg ggc atg gaa tca gga gaa att cat tct          864
Phe Lys Cys Met Glu Ala Leu Gly Met Glu Ser Gly Glu Ile His Ser
        275                 280                 285 gac cag atc aca gct tct tcc cag tat agc acc aac tgg tct gca gag          912
Asp Gln Ile Thr Ala Ser Ser Gln Tyr Ser Thr Asn Trp Ser Ala Glu
    290                 295                 300 cgc tcc cgc ctg aac tac cct gag aat ggg tgg act ccc gga gag gat          960
Arg Ser Arg Leu Asn Tyr Pro Glu Asn Gly Trp Thr Pro Gly Glu Asp
305                 310                 315                 320 tcc tac cga gag tgg ata cag gta gac ttg ggc ctt ctg cgc ttt gtc         1008
Ser Tyr Arg Glu Trp Ile Gln Val Asp Leu Gly Leu Leu Arg Phe Val
                325                 330                 335 acg gct gtc ggg aca cag ggc gcc att tca aaa gaa acc aag aag aaa         1056
Thr Ala Val Gly Thr Gln Gly Ala Ile Ser Lys Glu Thr Lys Lys Lys
            340                 345                 350 tat tat gtc aag act tac aag atc gac gtt agc tcc aac ggg gaa gac         1104
Tyr Tyr Val Lys Thr Tyr Lys Ile Asp Val Ser Ser Asn Gly Glu Asp
        355                 360                 365 tgg atc acc ata aaa gaa gga aac aaa cct gtt ctc ttt cag gga aac         1152
Trp Ile Thr Ile Lys Glu Gly Asn Lys Pro Val Leu Phe Gln Gly Asn
    370                 375                 380 acc aac ccc aca gat gtt gtg gtt gca gta ttc ccc aaa cca ctg ata         1200
Thr Asn Pro Thr Asp Val Val Val Ala Val Phe Pro Lys Pro Leu Ile
385                 390                 395                 400 act cga ttt gtc cga atc aag cct gca act tgg gaa act ggc ata tct         1248
Thr Arg Phe Val Arg Ile Lys Pro Ala Thr Trp Glu Thr Gly Ile Ser
                405                 410                 415 atg aga ttt gaa gta tac ggt tgc aag ata aca gat tat cct tgc tct         1296
Met Arg Phe Glu Val Tyr Gly Cys Lys Ile Thr Asp Tyr Pro Cys Ser
            420                 425                 430
```

```
gga atg ttg ggt atg gtg tct gga ctt att tct gac tcc cag atc aca    1344
Gly Met Leu Gly Met Val Ser Gly Leu Ile Ser Asp Ser Gln Ile Thr
        435                 440                 445 tca tcc aac caa gga gac aga aac tgg atg cct gaa aac atc cgc ctg    1392
Ser Ser Asn Gln Gly Asp Arg Asn Trp Met Pro Glu Asn Ile Arg Leu
    450                 455                 460 gta acc agt cgc tct ggc tgg gca ctt cca ccc gca cct cat tcc tac    1440
Val Thr Ser Arg Ser Gly Trp Ala Leu Pro Pro Ala Pro His Ser Tyr
465                 470                 475                 480 atc aat gag tgg ctc caa ata gac ctg ggg gag gag aag atc gtg agg    1488
Ile Asn Glu Trp Leu Gln Ile Asp Leu Gly Glu Glu Lys Ile Val Arg
            485                 490                 495 ggc atc atc att cag ggt ggg aag cac cga gag aac aag gtg ttc atg    1536
Gly Ile Ile Ile Gln Gly Gly Lys His Arg Glu Asn Lys Val Phe Met
        500                 505                 510 agg aag ttc aag atc ggg tac agc aac aac ggc tcg gac tgg aag atg    1584
Arg Lys Phe Lys Ile Gly Tyr Ser Asn Asn Gly Ser Asp Trp Lys Met
    515                 520                 525 atc atg gat gac agc aaa cgc aag gcg aag tct ttt gag ggc aac aac    1632
Ile Met Asp Asp Ser Lys Arg Lys Ala Lys Ser Phe Glu Gly Asn Asn
530                 535                 540 aac tat gat aca cct gag ctg cgg act ttt cca gct ctc tcc acg cga    1680
Asn Tyr Asp Thr Pro Glu Leu Arg Thr Phe Pro Ala Leu Ser Thr Arg
545                 550                 555                 560 ttc atc agg atc tac ccc gag aga gcc act cat ggc gga ctg ggg ctc    1728
Phe Ile Arg Ile Tyr Pro Glu Arg Ala Thr His Gly Gly Leu Gly Leu
                565                 570                 575 aga atg gag ctg ctg ggc tgt gaa gtg gaa gcc cct aca gct gga ccg    1776
Arg Met Glu Leu Leu Gly Cys Glu Val Glu Ala Pro Thr Ala Gly Pro
            580                 585                 590 acc act ccc aac ggg aac ttg gtg gat gaa tgt gat gac gac cag gcc    1824
Thr Thr Pro Asn Gly Asn Leu Val Asp Glu Cys Asp Asp Asp Gln Ala
        595                 600                 605 aac tgc cac agt gga aca ggt gat gac ttc cag ctc aca ggt ggc acc    1872
Asn Cys His Ser Gly Thr Gly Asp Asp Phe Gln Leu Thr Gly Gly Thr
    610                 615                 620 act gtg ctg gcc aca gaa aag ccc acg gtc ata gac agc acc ata caa    1920
Thr Val Leu Ala Thr Glu Lys Pro Thr Val Ile Asp Ser Thr Ile Gln
625                 630                 635                 640 tca gag ttt cca aca tat ggt ttt aac tgt gaa ttt ggc tgg ggc tct    1968
Ser Glu Phe Pro Thr Tyr Gly Phe Asn Cys Glu Phe Gly Trp Gly Ser
                645                 650                 655 cac aag acc ttc tgc cac tgg gaa cat gac aat cac gtg cag ctc aag    2016
His Lys Thr Phe Cys His Trp Glu His Asp Asn His Val Gln Leu Lys
            660                 665                 670 tgg agt gtg ttg acc agc aag acg gga ccc att cag gat cac aca gga    2064
Trp Ser Val Leu Thr Ser Lys Thr Gly Pro Ile Gln Asp His Thr Gly
        675                 680                 685 gat ggc aac ttc atc tat tcc caa gct gac gaa aat cag aag ggc aaa    2112
Asp Gly Asn Phe Ile Tyr Ser Gln Ala Asp Glu Asn Gln Lys Gly Lys
    690                 695                 700 gtg gct cgc ctg gtg agc cct gtg gtt tat tcc cag aac tct gcc cac    2160
Val Ala Arg Leu Val Ser Pro Val Val Tyr Ser Gln Asn Ser Ala His
705                 710                 715                 720 tgc atg acc ttc tgg tat cac atg tct ggg tcc cac gtc ggc aca ctc    2208
Cys Met Thr Phe Trp Tyr His Met Ser Gly Ser His Val Gly Thr Leu
                725                 730                 735 agg gtc aaa ctg cgc tac cag aag cca gag gag tac gat cag ctg gtc    2256
Arg Val Lys Leu Arg Tyr Gln Lys Pro Glu Glu Tyr Asp Gln Leu Val
            740                 745                 750
```

```
tgg atg gcc att gga cac caa ggt gac cac tgg aag gaa ggg cgt gtc      2304
Trp Met Ala Ile Gly His Gln Gly Asp His Trp Lys Glu Gly Arg Val
        755                 760                 765 ttg ctc cac aag tct ctg aaa ctt tat cag gtg att ttc gag ggc gaa      2352
Leu Leu His Lys Ser Leu Lys Leu Tyr Gln Val Ile Phe Glu Gly Glu
770                 775                 780 atc gga aaa gga aac ctt ggt ggg att gct gtg gat gac att agt att      2400
Ile Gly Lys Gly Asn Leu Gly Gly Ile Ala Val Asp Asp Ile Ser Ile
785                 790                 795                 800 aat aac cac att tca caa gaa gat tgt gca aaa cca gca gac ctg gat      2448
Asn Asn His Ile Ser Gln Glu Asp Cys Ala Lys Pro Ala Asp Leu Asp
                805                 810                 815 aaa aag aac cca gaa att aaa att gat gaa aca ggg agc acg cca gga      2496
Lys Lys Asn Pro Glu Ile Lys Ile Asp Glu Thr Gly Ser Thr Pro Gly
            820                 825                 830 tac gaa ggt gaa gga gaa ggt gac aag aac atc tcc agg aag cca ggc      2544
Tyr Glu Gly Glu Gly Glu Gly Asp Lys Asn Ile Ser Arg Lys Pro Gly
        835                 840                 845 aat gtg ttg aag acc tta gaa ccc atc ctc atc acc atc ata gcc atg      2592
Asn Val Leu Lys Thr Leu Glu Pro Ile Leu Ile Thr Ile Ile Ala Met
850                 855                 860 agc gcc ctg ggg gtc ctc ctg ggg gct gtc tgt ggg gtc gtg ctg tac      2640
Ser Ala Leu Gly Val Leu Leu Gly Ala Val Cys Gly Val Val Leu Tyr
865                 870                 875                 880 tgt gcc tgt tgg cat aat ggg atg tca gaa aga aac ttg tct gcc ctg      2688
Cys Ala Cys Trp His Asn Gly Met Ser Glu Arg Asn Leu Ser Ala Leu
                885                 890                 895 gag aac tat aac ttt gaa ctt gtg gat ggt gtg aag ttg aaa aaa gac      2736
Glu Asn Tyr Asn Phe Glu Leu Val Asp Gly Val Lys Leu Lys Lys Asp
            900                 905                 910 aaa ctg aat aca cag agt act tat tcg gag gca tga                      2772
Lys Leu Asn Thr Gln Ser Thr Tyr Ser Glu Ala
        915                 920
```

<210> SEQ ID NO 2
<211> LENGTH: 923
<212> TYPE: PRT
<213> ORGANISM: human

<400> SEQUENCE: 2

```
Met Glu Arg Gly Leu Pro Leu Leu Cys Ala Val Leu Ala Leu Val Leu
1               5                   10                  15

Ala Pro Ala Gly Ala Phe Arg Asn Asp Glu Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Ile Phe Lys Arg Gly
    130                 135                 140
```

-continued

```
Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Tyr Ser Thr Asn Trp Ser Ala Glu
    290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
            340                 345                 350

Tyr Tyr Val Lys Thr Tyr Lys Ile Asp Val Ser Ser Asn Gly Glu Asp
        355                 360                 365

Trp Ile Thr Ile Lys Glu Gly Asn Lys Pro Val Leu Phe Gln Gly Asn
    370                 375                 380

Thr Asn Pro Thr Asp Val Val Ala Val Phe Pro Lys Pro Leu Ile
385                 390                 395                 400

Thr Arg Phe Val Arg Ile Lys Pro Ala Thr Trp Glu Thr Gly Ile Ser
                405                 410                 415

Met Arg Phe Glu Val Tyr Gly Cys Lys Ile Thr Asp Tyr Pro Cys Ser
            420                 425                 430

Gly Met Leu Gly Met Val Ser Gly Leu Ile Ser Asp Ser Gln Ile Thr
        435                 440                 445

Ser Ser Asn Gln Gly Asp Arg Asn Trp Met Pro Glu Asn Ile Arg Leu
    450                 455                 460

Val Thr Ser Arg Ser Gly Trp Ala Leu Pro Pro Ala Pro His Ser Tyr
465                 470                 475                 480

Ile Asn Glu Trp Leu Gln Ile Asp Leu Gly Glu Lys Ile Val Arg
                485                 490                 495

Gly Ile Ile Ile Gln Gly Gly Lys His Arg Glu Asn Lys Val Phe Met
            500                 505                 510

Arg Lys Phe Lys Ile Gly Tyr Ser Asn Asn Gly Ser Asp Trp Lys Met
        515                 520                 525

Ile Met Asp Asp Ser Lys Arg Lys Ala Lys Ser Phe Glu Gly Asn Asn
    530                 535                 540

Asn Tyr Asp Thr Pro Glu Leu Arg Thr Phe Pro Ala Leu Ser Thr Arg
545                 550                 555                 560
```

```
Phe Ile Arg Ile Tyr Pro Glu Arg Ala Thr His Gly Gly Leu Gly Leu
                565                 570                 575

Arg Met Glu Leu Leu Gly Cys Glu Val Glu Ala Pro Thr Ala Gly Pro
            580                 585                 590

Thr Thr Pro Asn Gly Asn Leu Val Asp Glu Cys Asp Asp Gln Ala
        595                 600                 605

Asn Cys His Ser Gly Thr Gly Asp Asp Phe Gln Leu Thr Gly Gly Thr
    610                 615                 620

Thr Val Leu Ala Thr Glu Lys Pro Thr Val Ile Asp Ser Thr Ile Gln
625                 630                 635                 640

Ser Glu Phe Pro Thr Tyr Gly Phe Asn Cys Glu Phe Gly Trp Gly Ser
                645                 650                 655

His Lys Thr Phe Cys His Trp Glu His Asp Asn His Val Gln Leu Lys
            660                 665                 670

Trp Ser Val Leu Thr Ser Lys Thr Gly Pro Ile Gln Asp His Thr Gly
        675                 680                 685

Asp Gly Asn Phe Ile Tyr Ser Gln Ala Asp Glu Asn Gln Lys Gly Lys
    690                 695                 700

Val Ala Arg Leu Val Ser Pro Val Val Tyr Ser Gln Asn Ser Ala His
705                 710                 715                 720

Cys Met Thr Phe Trp Tyr His Met Ser Gly Ser His Val Gly Thr Leu
                725                 730                 735

Arg Val Lys Leu Arg Tyr Gln Lys Pro Glu Glu Tyr Asp Gln Leu Val
            740                 745                 750

Trp Met Ala Ile Gly His Gln Gly Asp His Trp Lys Glu Gly Arg Val
        755                 760                 765

Leu Leu His Lys Ser Leu Lys Leu Tyr Gln Val Ile Phe Glu Gly Glu
    770                 775                 780

Ile Gly Lys Gly Asn Leu Gly Gly Ile Ala Val Asp Asp Ile Ser Ile
785                 790                 795                 800

Asn Asn His Ile Ser Gln Glu Asp Cys Ala Lys Pro Ala Asp Leu Asp
                805                 810                 815

Lys Lys Asn Pro Glu Ile Lys Ile Asp Glu Thr Gly Ser Thr Pro Gly
            820                 825                 830

Tyr Glu Gly Glu Gly Glu Gly Asp Lys Asn Ile Ser Arg Lys Pro Gly
        835                 840                 845

Asn Val Leu Lys Thr Leu Glu Pro Ile Leu Ile Thr Ile Ala Met
    850                 855                 860

Ser Ala Leu Gly Val Leu Leu Gly Ala Val Cys Gly Val Val Leu Tyr
865                 870                 875                 880

Cys Ala Cys Trp His Asn Gly Met Ser Glu Arg Asn Leu Ser Ala Leu
                885                 890                 895

Glu Asn Tyr Asn Phe Glu Leu Val Asp Gly Val Lys Leu Lys Lys Asp
            900                 905                 910

Lys Leu Asn Thr Gln Ser Thr Tyr Ser Glu Ala
        915                 920

<210> SEQ ID NO 3
<211> LENGTH: 2766
<212> TYPE: DNA
<213> ORGANISM: rat
<220> FEATURE:
<221> NAME/KEY: CDS
<222> LOCATION: (1)..(2763)

<400> SEQUENCE: 3
```

```
atg gag agg ggg ctg ccg ttg ctg tgc gcc acg ctc gcc ctt gcc ctc     48
Met Glu Arg Gly Leu Pro Leu Leu Cys Ala Thr Leu Ala Leu Ala Leu
 1               5                  10                  15 gcc ctg ggg gct ttc cgc agc gat aaa tgt ggc ggg act ata aaa att     96
Ala Leu Gly Ala Phe Arg Ser Asp Lys Cys Gly Gly Thr Ile Lys Ile
            20                  25                  30 gaa aac ccg ggg tac ctt aca tct ccc ggc tac cct cat tct tac cat    144
Glu Asn Pro Gly Tyr Leu Thr Ser Pro Gly Tyr Pro His Ser Tyr His
        35                  40                  45 cca agt gag aaa tgt gaa tgg cta atc caa gct ccg gag ccc tac cag    192
Pro Ser Glu Lys Cys Glu Trp Leu Ile Gln Ala Pro Glu Pro Tyr Gln
 50                  55                  60 aga atc atg atc aac ttc aac cca cat ttc gat ttg gag gac aga gac    240
Arg Ile Met Ile Asn Phe Asn Pro His Phe Asp Leu Glu Asp Arg Asp
 65                  70                  75                  80 tgc aag tat gac tat gtg gaa gtg atc gat gga gag aat gaa ggt ggc    288
Cys Lys Tyr Asp Tyr Val Glu Val Ile Asp Gly Glu Asn Glu Gly Gly
                 85                  90                  95 cgc ctg tgg ggg aag ttc tgt ggg aag atc gca cct tca cct gtg gtg    336
Arg Leu Trp Gly Lys Phe Cys Gly Lys Ile Ala Pro Ser Pro Val Val
            100                 105                 110 tct tca ggg cca ttt ctc ttc atc aaa ttt gtc tct gac tat gag acc    384
Ser Ser Gly Pro Phe Leu Phe Ile Lys Phe Val Ser Asp Tyr Glu Thr
        115                 120                 125 cac ggg gca gga ttt tcc atc cgc tat gaa atc ttc aag aga ggg ccc    432
His Gly Ala Gly Phe Ser Ile Arg Tyr Glu Ile Phe Lys Arg Gly Pro
130                 135                 140 gaa tgt tct cag aac tat aca gca cct act gga gtg ata aag tcc cct    480
Glu Cys Ser Gln Asn Tyr Thr Ala Pro Thr Gly Val Ile Lys Ser Pro
145                 150                 155                 160 ggg ttc cct gaa aaa tac ccc aac agc ttg gag tgc acc tac atc atc    528
Gly Phe Pro Glu Lys Tyr Pro Asn Ser Leu Glu Cys Thr Tyr Ile Ile
                165                 170                 175 ttt gca cca aag atg tct gag ata atc cta gag ttt gaa agt ttt gac    576
Phe Ala Pro Lys Met Ser Glu Ile Ile Leu Glu Phe Glu Ser Phe Asp
            180                 185                 190 ctg gag caa gac tca aat cct ccc gga gga atg ttc tgt cgc tat gac    624
Leu Glu Gln Asp Ser Asn Pro Pro Gly Gly Met Phe Cys Arg Tyr Asp
        195                 200                 205 cgg ctg gag atc tgg gat gga ttc cct gaa gtt ggc cct cac att ggg    672
Arg Leu Glu Ile Trp Asp Gly Phe Pro Glu Val Gly Pro His Ile Gly
210                 215                 220 cgt tac tgt ggg cag aaa act cct ggc cgg atc cgc tcc tct tca ggc    720
Arg Tyr Cys Gly Gln Lys Thr Pro Gly Arg Ile Arg Ser Ser Ser Gly
225                 230                 235                 240 att cta tcc atg gtc ttc tac act gac agc gca ata gca aag gaa ggt    768
Ile Leu Ser Met Val Phe Tyr Thr Asp Ser Ala Ile Ala Lys Glu Gly
                245                 250                 255 ttc tca gcc aac tac agc gtg ctg cag agc agc atc tct gaa gat ttc    816
Phe Ser Ala Asn Tyr Ser Val Leu Gln Ser Ser Ile Ser Glu Asp Phe
            260                 265                 270 aag tgt atg gag gct ctg ggc atg gaa tct gga gag atc cat tct gac    864
Lys Cys Met Glu Ala Leu Gly Met Glu Ser Gly Glu Ile His Ser Asp
        275                 280                 285 cag atc act gca tct tcc cag tat ggt acc aac tgg tct gtt gag cgc    912
Gln Ile Thr Ala Ser Ser Gln Tyr Gly Thr Asn Trp Ser Val Glu Arg
290                 295                 300 tcc cgc ctg aac tac cct gaa aac ggg tgg aca cca gga gag gac tcc    960
Ser Arg Leu Asn Tyr Pro Glu Asn Gly Trp Thr Pro Gly Glu Asp Ser
```

```
                                                                -continued 305                     310                     315                     320
tac agg gag tgg atc cag gtg gac ttg ggc ctc ctg cga ttc gtt act          1008
Tyr Arg Glu Trp Ile Gln Val Asp Leu Gly Leu Leu Arg Phe Val Thr
                325                     330                     335 gct gtg ggg aca cag ggt gcc att tcc aag gaa acc aag aag aaa tat          1056
Ala Val Gly Thr Gln Gly Ala Ile Ser Lys Glu Thr Lys Lys Lys Tyr
                340                     345                     350 tat gtc aag act tac aga gta gac atc agc tcc aac gga gag gac tgg         1104
Tyr Val Lys Thr Tyr Arg Val Asp Ile Ser Ser Asn Gly Glu Asp Trp
                355                     360                     365 atc acc ctg aag gag gga aat aaa gcc att atc ttt cag gga aac acc         1152
Ile Thr Leu Lys Glu Gly Asn Lys Ala Ile Ile Phe Gln Gly Asn Thr
                370                     375                     380 aat ccc acg gat gtt gtc ttt gga gtt ttc ccc aaa cca ctg ata act         1200
Asn Pro Thr Asp Val Val Phe Gly Val Phe Pro Lys Pro Leu Ile Thr
385                     390                     395                     400 cga ttt gtc cga atc aaa cct gca tcc tgg gaa act gga ata tct atg         1248
Arg Phe Val Arg Ile Lys Pro Ala Ser Trp Glu Thr Gly Ile Ser Met
                        405                     410                     415 aga ttt gaa gtt tat ggc tgc aag ata aca gat tac cct tgc tct gga         1296
Arg Phe Glu Val Tyr Gly Cys Lys Ile Thr Asp Tyr Pro Cys Ser Gly
                        420                     425                     430 atg ttg ggc atg gtg tct gga ctt att tca gac tcc cag att aca gca         1344
Met Leu Gly Met Val Ser Gly Leu Ile Ser Asp Ser Gln Ile Thr Ala
                435                     440                     445 tcc aac caa gga gac agg aac tgg atg cca gaa aac atc cgc ctg gtg         1392
Ser Asn Gln Gly Asp Arg Asn Trp Met Pro Glu Asn Ile Arg Leu Val
                450                     455                     460 acc agt cga acc ggc tgg gcc ctg cca ccc tca ccc cac cca tac atc         1440
Thr Ser Arg Thr Gly Trp Ala Leu Pro Pro Ser Pro His Pro Tyr Ile
465                     470                     475                     480 aat gaa tgg ctc caa gtg gac ctg gga gat gag aag ata gta aga ggt         1488
Asn Glu Trp Leu Gln Val Asp Leu Gly Asp Glu Lys Ile Val Arg Gly
                        485                     490                     495 gtc atc att caa ggt ggg aag cac cga gaa aac aaa gtg ttc atg agg         1536
Val Ile Ile Gln Gly Gly Lys His Arg Glu Asn Lys Val Phe Met Arg
                500                     505                     510 aag ttc aag atc gcc tac agt aac aat ggt tct gac tgg aaa atg atc         1584
Lys Phe Lys Ile Ala Tyr Ser Asn Asn Gly Ser Asp Trp Lys Met Ile
                515                     520                     525 atg gat gac agc aag cgc aag gct aag tct ttt gaa ggc aac aac aac         1632
Met Asp Asp Ser Lys Arg Lys Ala Lys Ser Phe Glu Gly Asn Asn Asn
                530                     535                     540 tat gac aca cct gag ctc cgg gcc ttt aca cct ctc tcc aca aga ttc         1680
Tyr Asp Thr Pro Glu Leu Arg Ala Phe Thr Pro Leu Ser Thr Arg Phe
545                     550                     555                     560 atc agg atc tac ccc gag aga gcc aca cat agt ggg ctc gga ctg agg         1728
Ile Arg Ile Tyr Pro Glu Arg Ala Thr His Ser Gly Leu Gly Leu Arg
                        565                     570                     575 atg gag cta ctg ggc tgt gaa gta gaa gtg cct aca gct gga ccc acg         1776
Met Glu Leu Leu Gly Cys Glu Val Glu Val Pro Thr Ala Gly Pro Thr
                580                     585                     590 aca ccc aat ggg aac ccc gtg gac gag tgt gac gat gac cag gcc aac         1824
Thr Pro Asn Gly Asn Pro Val Asp Glu Cys Asp Asp Asp Gln Ala Asn
                595                     600                     605 tgc cac agt ggc aca ggt gat gac ttc cag ctc aca gga ggc acc act         1872
Cys His Ser Gly Thr Gly Asp Asp Phe Gln Leu Thr Gly Gly Thr Thr
                610                     615                     620 gtc ctg gcc aca gag aag ccc acc att ata gac agc acc atc caa tca         1920
```

```
Val Leu Ala Thr Glu Lys Pro Thr Ile Ile Asp Ser Thr Ile Gln Ser
625                 630                 635                 640 gag ttc ccg aca tac ggt ttt aac tgc gag ttt ggc tgg ggc tct cac    1968
Glu Phe Pro Thr Tyr Gly Phe Asn Cys Glu Phe Gly Trp Gly Ser His
                645                 650                 655 aag aca ttc tgc cac tgg gaa cat gac agc cac gcg cag ctc agg tgg    2016
Lys Thr Phe Cys His Trp Glu His Asp Ser His Ala Gln Leu Arg Trp
            660                 665                 670 agg gtg ctg acc agc aag acg ggg ccc att cag gac cac aca gga gat    2064
Arg Val Leu Thr Ser Lys Thr Gly Pro Ile Gln Asp His Thr Gly Asp
        675                 680                 685 ggc aac ttc atc tat tcc caa gct gat gaa aat cag aaa ggc aaa gta    2112
Gly Asn Phe Ile Tyr Ser Gln Ala Asp Glu Asn Gln Lys Gly Lys Val
690                 695                 700 gcc cgc ctg gtg agc cct gtc gtc tat tcc cag agt tct gcc cac tgc    2160
Ala Arg Leu Val Ser Pro Val Val Tyr Ser Gln Ser Ser Ala His Cys
705                 710                 715                 720 atg acc ttc tgg tat cac atg tcc ggc tct cat gtg ggt aca ctg agg    2208
Met Thr Phe Trp Tyr His Met Ser Gly Ser His Val Gly Thr Leu Arg
                725                 730                 735 gtc aaa ctg cac tac cag aag cca gag gaa tat gat caa ctg gtc tgg    2256
Val Lys Leu His Tyr Gln Lys Pro Glu Glu Tyr Asp Gln Leu Val Trp
            740                 745                 750 atg gtg gtc ggg cac caa gga gac cac tgg aag gaa ggg cgt gtc ttg    2304
Met Val Val Gly His Gln Gly Asp His Trp Lys Glu Gly Arg Val Leu
        755                 760                 765 ctg cac aaa tct ctg aaa ctg tat cag gtt att ttt gaa ggt gaa atc    2352
Leu His Lys Ser Leu Lys Leu Tyr Gln Val Ile Phe Glu Gly Glu Ile
770                 775                 780 gga aaa gga aac ctc ggt ggg att gct gtg gat gat atc agt att aac    2400
Gly Lys Gly Asn Leu Gly Gly Ile Ala Val Asp Asp Ile Ser Ile Asn
785                 790                 795                 800 aac cac att cct cag gag gac tgt gca aaa cca aca gac cta gat aaa    2448
Asn His Ile Pro Gln Glu Asp Cys Ala Lys Pro Thr Asp Leu Asp Lys
                805                 810                 815 aag aac aca gaa att aaa ata gat gaa aca ggg agc acc cca gga tat    2496
Lys Asn Thr Glu Ile Lys Ile Asp Glu Thr Gly Ser Thr Pro Gly Tyr
            820                 825                 830 gaa gaa ggg aaa ggc gac aag aac atc tcc agg aag cca ggc aat gtg    2544
Glu Glu Gly Lys Gly Asp Lys Asn Ile Ser Arg Lys Pro Gly Asn Val
        835                 840                 845 ctt aag acc ctg gac ccc atc ctg atc acc atc ata gcc atg agt gcc    2592
Leu Lys Thr Leu Asp Pro Ile Leu Ile Thr Ile Ile Ala Met Ser Ala
850                 855                 860 ctg ggg gtg ctc ctg ggt gca gtc tgt gga gtt gtg ctg tac tgt gcc    2640
Leu Gly Val Leu Leu Gly Ala Val Cys Gly Val Val Leu Tyr Cys Ala
865                 870                 875                 880 tgt tgg cac aat ggg atg tcg gaa agg aac cta tct gcc ctg gag aac    2688
Cys Trp His Asn Gly Met Ser Glu Arg Asn Leu Ser Ala Leu Glu Asn
                885                 890                 895 tat aac ttt gaa ctt gtg gat ggt gta aag ttg aaa aaa gat aaa ctg    2736
Tyr Asn Phe Glu Leu Val Asp Gly Val Lys Leu Lys Lys Asp Lys Leu
            900                 905                 910 aac cca cac agt aat tac tca gag gcg tga                            2766
Asn Pro His Ser Asn Tyr Ser Glu Ala
        915                 920

<210> SEQ ID NO 4
<211> LENGTH: 921
<212> TYPE: PRT
```

-continued

```
<213> ORGANISM: rat

<400> SEQUENCE: 4

Met Glu Arg Gly Leu Pro Leu Leu Cys Ala Thr Leu Ala Leu Ala Leu
  1               5                  10                  15

Ala Leu Gly Ala Phe Arg Ser Asp Lys Cys Gly Gly Thr Ile Lys Ile
             20                  25                  30

Glu Asn Pro Gly Tyr Leu Thr Ser Pro Gly Tyr Pro His Ser Tyr His
         35                  40                  45

Pro Ser Glu Lys Cys Glu Trp Leu Ile Gln Ala Pro Glu Pro Tyr Gln
     50                  55                  60

Arg Ile Met Ile Asn Phe Asn Pro His Phe Asp Leu Glu Asp Arg Asp
 65                  70                  75                  80

Cys Lys Tyr Asp Tyr Val Glu Val Ile Asp Gly Glu Asn Glu Gly Gly
                 85                  90                  95

Arg Leu Trp Gly Lys Phe Cys Gly Lys Ile Ala Pro Ser Pro Val Val
            100                 105                 110

Ser Ser Gly Pro Phe Leu Phe Ile Lys Phe Val Ser Asp Tyr Glu Thr
        115                 120                 125

His Gly Ala Gly Phe Ser Ile Arg Tyr Glu Ile Phe Lys Arg Gly Pro
    130                 135                 140

Glu Cys Ser Gln Asn Tyr Thr Ala Pro Thr Gly Val Ile Lys Ser Pro
145                 150                 155                 160

Gly Phe Pro Glu Lys Tyr Pro Asn Ser Leu Glu Cys Thr Tyr Ile Ile
                165                 170                 175

Phe Ala Pro Lys Met Ser Glu Ile Ile Leu Glu Phe Glu Ser Phe Asp
            180                 185                 190

Leu Glu Gln Asp Ser Asn Pro Pro Gly Gly Met Phe Cys Arg Tyr Asp
        195                 200                 205

Arg Leu Glu Ile Trp Asp Gly Phe Pro Glu Val Gly Pro His Ile Gly
    210                 215                 220

Arg Tyr Cys Gly Gln Lys Thr Pro Gly Arg Ile Arg Ser Ser Ser Gly
225                 230                 235                 240

Ile Leu Ser Met Val Phe Tyr Thr Asp Ser Ala Ile Ala Lys Glu Gly
                245                 250                 255

Phe Ser Ala Asn Tyr Ser Val Leu Gln Ser Ser Ile Ser Glu Asp Phe
            260                 265                 270

Lys Cys Met Glu Ala Leu Gly Met Glu Ser Gly Glu Ile His Ser Asp
        275                 280                 285

Gln Ile Thr Ala Ser Ser Gln Tyr Gly Thr Asn Trp Ser Val Glu Arg
    290                 295                 300

Ser Arg Leu Asn Tyr Pro Glu Asn Gly Trp Thr Pro Gly Glu Asp Ser
305                 310                 315                 320

Tyr Arg Glu Trp Ile Gln Val Asp Leu Gly Leu Leu Arg Phe Val Thr
                325                 330                 335

Ala Val Gly Thr Gln Gly Ala Ile Ser Lys Glu Thr Lys Lys Lys Tyr
            340                 345                 350

Tyr Val Lys Thr Tyr Arg Val Asp Ile Ser Ser Asn Gly Glu Asp Trp
        355                 360                 365

Ile Thr Leu Lys Glu Gly Asn Lys Ala Ile Ile Phe Gln Gly Asn Thr
    370                 375                 380

Asn Pro Thr Asp Val Val Phe Gly Val Phe Pro Lys Pro Leu Ile Thr
385                 390                 395                 400
```

```
Arg Phe Val Arg Ile Lys Pro Ala Ser Trp Glu Thr Gly Ile Ser Met
                405                 410                 415
Arg Phe Glu Val Tyr Gly Cys Lys Ile Thr Asp Tyr Pro Cys Ser Gly
            420                 425                 430
Met Leu Gly Met Val Ser Gly Leu Ile Ser Asp Ser Gln Ile Thr Ala
        435                 440                 445
Ser Asn Gln Gly Asp Arg Asn Trp Met Pro Glu Asn Ile Arg Leu Val
    450                 455                 460
Thr Ser Arg Thr Gly Trp Ala Leu Pro Pro Ser Pro His Pro Tyr Ile
465                 470                 475                 480
Asn Glu Trp Leu Gln Val Asp Leu Gly Asp Glu Lys Ile Val Arg Gly
                485                 490                 495
Val Ile Ile Gln Gly Gly Lys His Arg Glu Asn Lys Val Phe Met Arg
            500                 505                 510
Lys Phe Lys Ile Ala Tyr Ser Asn Asn Gly Ser Asp Trp Lys Met Ile
        515                 520                 525
Met Asp Asp Ser Lys Arg Lys Ala Lys Ser Phe Glu Gly Asn Asn Asn
    530                 535                 540
Tyr Asp Thr Pro Glu Leu Arg Ala Phe Thr Pro Leu Ser Thr Arg Phe
545                 550                 555                 560
Ile Arg Ile Tyr Pro Glu Arg Ala Thr His Ser Gly Leu Gly Leu Arg
                565                 570                 575
Met Glu Leu Leu Gly Cys Glu Val Glu Val Pro Thr Ala Gly Pro Thr
            580                 585                 590
Thr Pro Asn Gly Asn Pro Val Asp Glu Cys Asp Asp Gln Ala Asn
    595                 600                 605
Cys His Ser Gly Thr Gly Asp Asp Phe Gln Leu Thr Gly Gly Thr Thr
    610                 615                 620
Val Leu Ala Thr Glu Lys Pro Thr Ile Ile Asp Ser Thr Ile Gln Ser
625                 630                 635                 640
Glu Phe Pro Thr Tyr Gly Phe Asn Cys Glu Phe Gly Trp Gly Ser His
                645                 650                 655
Lys Thr Phe Cys His Trp Glu His Asp Ser His Ala Gln Leu Arg Trp
            660                 665                 670
Arg Val Leu Thr Ser Lys Thr Gly Pro Ile Gln Asp His Thr Gly Asp
        675                 680                 685
Gly Asn Phe Ile Tyr Ser Gln Ala Asp Glu Asn Gln Lys Gly Lys Val
    690                 695                 700
Ala Arg Leu Val Ser Pro Val Val Tyr Ser Gln Ser Ala His Cys
705                 710                 715                 720
Met Thr Phe Trp Tyr His Met Ser Gly Ser His Val Gly Thr Leu Arg
                725                 730                 735
Val Lys Leu His Tyr Gln Lys Pro Glu Glu Tyr Asp Gln Leu Val Trp
            740                 745                 750
Met Val Val Gly His Gln Gly Asp His Trp Lys Glu Gly Arg Val Leu
        755                 760                 765
Leu His Lys Ser Leu Lys Leu Tyr Gln Val Ile Phe Glu Gly Glu Ile
    770                 775                 780
Gly Lys Gly Asn Leu Gly Gly Ile Ala Val Asp Asp Ile Ser Ile Asn
785                 790                 795                 800
Asn His Ile Pro Gln Glu Asp Cys Ala Lys Pro Thr Asp Leu Asp Lys
                805                 810                 815
Lys Asn Thr Glu Ile Lys Ile Asp Glu Thr Gly Ser Thr Pro Gly Tyr
```

```
                    820                 825                 830
Glu Glu Gly Lys Gly Asp Lys Asn Ile Ser Arg Lys Pro Gly Asn Val
            835                 840                 845

Leu Lys Thr Leu Asp Pro Ile Leu Ile Thr Ile Ala Met Ser Ala
    850                 855                 860

Leu Gly Val Leu Gly Ala Val Cys Gly Val Val Leu Tyr Cys Ala
865                 870                 875                 880

Cys Trp His Asn Gly Met Ser Glu Arg Asn Leu Ser Ala Leu Glu Asn
                885                 890                 895

Tyr Asn Phe Glu Leu Val Asp Gly Val Lys Leu Lys Asp Lys Leu
            900                 905                 910

Asn Pro His Ser Asn Tyr Ser Glu Ala
            915                 920

<210> SEQ ID NO 5
<211> LENGTH: 3652
<212> TYPE: DNA
<213> ORGANISM: mouse
<220> FEATURE:
<221> NAME/KEY: CDS
<222> LOCATION: (348)..(3116)

<400> SEQUENCE: 5
tttttttttt tttttttttt tttttttttt ttttttcctcc ttcttcttct tcctgagaca      60
tggcccgggc agtggctcct ggaagaggaa caagtgtggg aaaagggaga ggaaatcgga     120
gctaaatgac aggatgcagg cgacttgaga cacaaaaaga gaagcgcttc tcgcgaattc     180
aggcattgcc tcgccgctag ccttccccgc caagacccgc tgaggatttt atggttctta     240
ggcggactta agagcgtttc ggattgttaa gattatcgtt tgctggtttt tcgtccgcgc     300
aatcgtgttc tcctgcggct gcctggggac tggcttggcg aaggagg atg gag agg     356
                                                    Met Glu Arg
                                                      1 ggg ctg ccg ttg ctg tgc gcc acg ctc gcc ctt gcc ctc gcc ctg gcg     404
Gly Leu Pro Leu Leu Cys Ala Thr Leu Ala Leu Ala Leu Ala Leu Ala
  5                  10                  15 ggc gct ttc cgc agc gac aaa tgt ggc ggg acc ata aaa atc gaa aac     452
Gly Ala Phe Arg Ser Asp Lys Cys Gly Gly Thr Ile Lys Ile Glu Asn
 20                  25                  30                  35 cca ggg tac ctc aca tct ccc ggt tac cct cat tct tac cat cca agt     500
Pro Gly Tyr Leu Thr Ser Pro Gly Tyr Pro His Ser Tyr His Pro Ser
                 40                  45                  50 gag aag tgt gaa tgg cta atc caa gct ccg gaa ccc tac cag aga atc     548
Glu Lys Cys Glu Trp Leu Ile Gln Ala Pro Glu Pro Tyr Gln Arg Ile
             55                  60                  65 ata atc aac ttc aac cca cat ttc gat ttg gag gac aga gac tgc aag     596
Ile Ile Asn Phe Asn Pro His Phe Asp Leu Glu Asp Arg Asp Cys Lys
         70                  75                  80 tat gac tac gtg gaa gta att gat ggg gag aat gaa ggc ggc cgc ctg     644
Tyr Asp Tyr Val Glu Val Ile Asp Gly Glu Asn Glu Gly Gly Arg Leu
     85                  90                  95 tgg ggg aag ttc tgt ggg aag att gca cct tct cct gtg gtg tct tca     692
Trp Gly Lys Phe Cys Gly Lys Ile Ala Pro Ser Pro Val Val Ser Ser
100                 105                 110                 115 ggg ccc ttt ctc ttc atc aaa ttt gtc tct gac tat gag aca cat ggg     740
Gly Pro Phe Leu Phe Ile Lys Phe Val Ser Asp Tyr Glu Thr His Gly
                120                 125                 130 gca ggg ttt tcc atc cgc tat gaa atc ttc aag aga ggg ccc gaa tgt     788
Ala Gly Phe Ser Ile Arg Tyr Glu Ile Phe Lys Arg Gly Pro Glu Cys
```

-continued

| | 135 | | | | 140 | | | | 145 | | | | |
|---|---|---|---|---|---|---|---|---|---|---|---|---|---|
| tct | cag | aac | tat | aca | gca | cct | act | gga | gtg | ata | aag | tcc | cct | ggg | ttc | 836 |
| Ser | Gln | Asn | Tyr | Thr | Ala | Pro | Thr | Gly | Val | Ile | Lys | Ser | Pro | Gly | Phe | |
| | | 150 | | | | | 155 | | | | | 160 | | | | | cct gaa aaa tac ccc aac tgc ttg gag tgc acc tac atc atc ttt gca    884
Pro Glu Lys Tyr Pro Asn Cys Leu Glu Cys Thr Tyr Ile Ile Phe Ala
    165             170             175 cca aag atg tct gag ata atc ctg gag ttt gaa agt ttt gac ctg gag    932
Pro Lys Met Ser Glu Ile Ile Leu Glu Phe Glu Ser Phe Asp Leu Glu
180             185             190             195 caa gac tcg aat cct ccc gga gga atg ttc tgt cgc tat gac cgg ctg    980
Gln Asp Ser Asn Pro Pro Gly Gly Met Phe Cys Arg Tyr Asp Arg Leu
            200             205             210 gag atc tgg gat gga ttc cct gaa gtt ggc cct cac att ggg cgt tat   1028
Glu Ile Trp Asp Gly Phe Pro Glu Val Gly Pro His Ile Gly Arg Tyr
            215             220             225 tgt ggg cag aaa act cct ggc cgg atc cgc tcc tca ggc gtt cta       1076
Cys Gly Gln Lys Thr Pro Gly Arg Ile Arg Ser Ser Gly Val Leu
        230             235             240 tcc atg gtc ttt tac act gac agc gca ata gca aaa gaa ggt ttc tca   1124
Ser Met Val Phe Tyr Thr Asp Ser Ala Ile Ala Lys Glu Gly Phe Ser
245             250             255 gcc aac tac agt gtg cta cag agc agc atc tct gaa gat ttt aag tgt   1172
Ala Asn Tyr Ser Val Leu Gln Ser Ser Ile Ser Glu Asp Phe Lys Cys
260             265             270             275 atg gag gct ctg ggc atg gaa tct gga gag atc cat tct gat cag atc   1220
Met Glu Ala Leu Gly Met Glu Ser Gly Glu Ile His Ser Asp Gln Ile
            280             285             290 act gca tct tca cag tat ggt acc aac tgg tct gta gag cgc tcc cgc   1268
Thr Ala Ser Ser Gln Tyr Gly Thr Asn Trp Ser Val Glu Arg Ser Arg
        295             300             305 ctg aac tac cct gaa aat ggg tgg act cca gga gaa gac tcc tac aag   1316
Leu Asn Tyr Pro Glu Asn Gly Trp Thr Pro Gly Glu Asp Ser Tyr Lys
        310             315             320 gag tgg atc cag gtg gac ttg ggc ctc ctg cga ttc gtt act gct gta   1364
Glu Trp Ile Gln Val Asp Leu Gly Leu Leu Arg Phe Val Thr Ala Val
325             330             335 ggg aca cag ggt gcc att tcc aag gaa acc aag aag aaa tat tat gtc   1412
Gly Thr Gln Gly Ala Ile Ser Lys Glu Thr Lys Lys Lys Tyr Tyr Val
340             345             350             355 aag act tac aga gta gac atc agc tcc aac gga gag gac tgg atc tcc   1460
Lys Thr Tyr Arg Val Asp Ile Ser Ser Asn Gly Glu Asp Trp Ile Ser
            360             365             370 ctg aaa gag gga aat aaa gcc att atc ttt cag gga aac acc aac ccc   1508
Leu Lys Glu Gly Asn Lys Ala Ile Ile Phe Gln Gly Asn Thr Asn Pro
        375             380             385 aca gat gtt gtc tta gga gtt ttc tcc aaa cca ctg ata act cga ttt   1556
Thr Asp Val Val Leu Gly Val Phe Ser Lys Pro Leu Ile Thr Arg Phe
    390             395             400 gtc cga atc aaa cct gta tcc tgg gaa act ggt ata tct atg aga ttt   1604
Val Arg Ile Lys Pro Val Ser Trp Glu Thr Gly Ile Ser Met Arg Phe
    405             410             415 gaa gtt tat ggc tgc aag ata aca gat tat cct tgc tct gga atg ttg   1652
Glu Val Tyr Gly Cys Lys Ile Thr Asp Tyr Pro Cys Ser Gly Met Leu
420             425             430             435 ggc atg gtg tct gga ctt att tca gac tcc cag att aca gca tcc aat   1700
Gly Met Val Ser Gly Leu Ile Ser Asp Ser Gln Ile Thr Ala Ser Asn
            440             445             450 caa gcc gac agg aat tgg atg cca gaa aac atc cgt ctg gtg acc agt   1748

```
                Gln Ala Asp Arg Asn Trp Met Pro Glu Asn Ile Arg Leu Val Thr Ser
                            455                 460                 465 cgt acc ggc tgg gca ctg cca ccc tca ccc cac cca tac acc aat gaa      1796
Arg Thr Gly Trp Ala Leu Pro Pro Ser Pro His Pro Tyr Thr Asn Glu
            470                 475                 480 tgg ctc caa gtg gac ctg gga gat gag aag ata gta aga ggt gtc atc      1844
Trp Leu Gln Val Asp Leu Gly Asp Glu Lys Ile Val Arg Gly Val Ile
    485                 490                 495 att cag ggt ggg aag cac cga gaa aac aag gtg ttc atg agg aag ttc      1892
Ile Gln Gly Gly Lys His Arg Glu Asn Lys Val Phe Met Arg Lys Phe
500                 505                 510                 515 aag atc gcc tat agt aac aat ggc tct gac tgg aaa act atc atg gat      1940
Lys Ile Ala Tyr Ser Asn Asn Gly Ser Asp Trp Lys Thr Ile Met Asp
                520                 525                 530 gac agc aag cgc aag gct aag tcg ttc gaa ggc aac aac aac tat gac      1988
Asp Ser Lys Arg Lys Ala Lys Ser Phe Glu Gly Asn Asn Asn Tyr Asp
            535                 540                 545 aca cct gag ctt cgg acg ttt tca cct ctc tcc aca agg ttc atc agg      2036
Thr Pro Glu Leu Arg Thr Phe Ser Pro Leu Ser Thr Arg Phe Ile Arg
    550                 555                 560 atc tac cct gag aga gcc aca cac agt ggg ctt ggg ctg agg atg gag      2084
Ile Tyr Pro Glu Arg Ala Thr His Ser Gly Leu Gly Leu Arg Met Glu
565                 570                 575 cta ctg ggc tgt gaa gtg gaa gca cct aca gct gga cca acc aca ccc      2132
Leu Leu Gly Cys Glu Val Glu Ala Pro Thr Ala Gly Pro Thr Thr Pro
580                 585                 590                 595 aat ggg aac cca gtg cat gag tgt gac gac gac cag gcc aac tgc cac      2180
Asn Gly Asn Pro Val His Glu Cys Asp Asp Asp Gln Ala Asn Cys His
                600                 605                 610 agt ggc aca ggt gat gac ttc cag ctc aca gga ggc acc act gtc ctg      2228
Ser Gly Thr Gly Asp Asp Phe Gln Leu Thr Gly Gly Thr Thr Val Leu
            615                 620                 625 gcc aca gag aag cca acc att ata gac agc acc atc caa tca gag ttc      2276
Ala Thr Glu Lys Pro Thr Ile Ile Asp Ser Thr Ile Gln Ser Glu Phe
    630                 635                 640 ccg aca tac ggt ttt aac tgc gag ttt ggc tgg ggc tct cac aag aca      2324
Pro Thr Tyr Gly Phe Asn Cys Glu Phe Gly Trp Gly Ser His Lys Thr
645                 650                 655 ttc tgc cac tgg gag cat gac agc cat gca cag ctc agg tgg agt gtg      2372
Phe Cys His Trp Glu His Asp Ser His Ala Gln Leu Arg Trp Ser Val
660                 665                 670                 675 ctg acc agc aag aca ggg ccg att cag gac cat aca gga gat ggc aac      2420
Leu Thr Ser Lys Thr Gly Pro Ile Gln Asp His Thr Gly Asp Gly Asn
                680                 685                 690 ttc atc tat tcc caa gct gat gaa aat cag aaa ggc aaa gta gcc cgc      2468
Phe Ile Tyr Ser Gln Ala Asp Glu Asn Gln Lys Gly Lys Val Ala Arg
            695                 700                 705 ctg gtg agc cct gtg gtc tat tcc cag agc tct gcc cac tgt atg acc      2516
Leu Val Ser Pro Val Val Tyr Ser Gln Ser Ser Ala His Cys Met Thr
    710                 715                 720 ttc tgg tat cac atg tcc ggc tct cat gtg ggt aca ctg agg gtc aaa      2564
Phe Trp Tyr His Met Ser Gly Ser His Val Gly Thr Leu Arg Val Lys
725                 730                 735 cta cgc tac cag aag cca gag gaa tat gat caa ctg gtc tgg atg gtg      2612
Leu Arg Tyr Gln Lys Pro Glu Glu Tyr Asp Gln Leu Val Trp Met Val
740                 745                 750                 755 gtt ggg cac caa gga gac cac tgg aaa gaa gga cgt gtc ttg ctg cac      2660
Val Gly His Gln Gly Asp His Trp Lys Glu Gly Arg Val Leu Leu His
                760                 765                 770
```

-continued

```
aaa tct ctg aaa cta tat cag gtt att ttt gaa ggt gaa atc gga aaa      2708
Lys Ser Leu Lys Leu Tyr Gln Val Ile Phe Glu Gly Glu Ile Gly Lys
        775                 780                 785 gga aac ctt ggt gga att gct gtg gat gat atc agt att aac aac cat      2756
Gly Asn Leu Gly Gly Ile Ala Val Asp Asp Ile Ser Ile Asn Asn His
    790                 795                 800 att tct cag gaa gac tgt gca aaa cca aca gac cta gat aaa aag aac      2804
Ile Ser Gln Glu Asp Cys Ala Lys Pro Thr Asp Leu Asp Lys Lys Asn
805                 810                 815 aca gaa att aaa att gat gaa aca ggg agc act cca gga tat gaa gga      2852
Thr Glu Ile Lys Ile Asp Glu Thr Gly Ser Thr Pro Gly Tyr Glu Gly
820                 825                 830                 835 gaa ggg gaa ggt gac aag aac atc tcc agg aag cca ggc aat gtg ctt      2900
Glu Gly Glu Gly Asp Lys Asn Ile Ser Arg Lys Pro Gly Asn Val Leu
                840                 845                 850 aag acc ctg gat ccc atc ctg atc acc atc ata gcc atg agt gcc ctg      2948
Lys Thr Leu Asp Pro Ile Leu Ile Thr Ile Ile Ala Met Ser Ala Leu
            855                 860                 865 gga gta ctc ctg ggt gca gtc tgt gga gtt gtg ctg tac tgt gcc tgt      2996
Gly Val Leu Leu Gly Ala Val Cys Gly Val Val Leu Tyr Cys Ala Cys
        870                 875                 880 tgg cac aat ggg atg tca gaa agg aac cta tct gcc ctg gag aac tat      3044
Trp His Asn Gly Met Ser Glu Arg Asn Leu Ser Ala Leu Glu Asn Tyr
885                 890                 895 aac ttt gaa ctt gtg gat ggt gta aag ttg aaa aaa gat aaa ctg aac      3092
Asn Phe Glu Leu Val Asp Gly Val Lys Leu Lys Lys Asp Lys Leu Asn
900                 905                 910                 915 cca cag agt aat tac tca gag gcg tgaaggcacg gagctggagg gaacaaggga    3146
Pro Gln Ser Asn Tyr Ser Glu Ala
                920 ggagcacggc aggagaacag gtggaggcat ggggactctg ttactctgct ttcactgtaa    3206 gctgggaagg gcggggactc tgttactccg ctttcactgt aagctcggaa gggcatccac    3266 gatgccatgc caggctttc tcaggagctt caatgagcgt cacctacaga cacaagcagg    3326 tgactgcggt aacaacagga atcatgtaca agcctgcttt cttctcttgg tttcatttgg    3386 gtaatcagaa gccatttgag accaagtgtg actgacttca tggttcatcc tactagcccc    3446 cttttttcct ctctttctcc ttaccctgtg gtggattctt ctcggaaact gcaaaatcca    3506 agatgctggc actaggcgtt attcagtggg ccctttgat ggacatgtga cctgtagccc    3566 agtgcccaga gcatattatc ataaccacat ttcaggggac gccaacgtcc atccaccttt    3626 gcatcgctac ctgcagcgag cacagg                                        3652
```

<210> SEQ ID NO 6
<211> LENGTH: 923
<212> TYPE: PRT
<213> ORGANISM: mouse

<400> SEQUENCE: 6

```
Met Glu Arg Gly Leu Pro Leu Leu Cys Ala Thr Leu Ala Leu Ala Leu
1               5                   10                  15

Ala Leu Ala Gly Ala Phe Arg Ser Asp Lys Cys Gly Gly Thr Ile Lys
            20                  25                  30

Ile Glu Asn Pro Gly Tyr Leu Thr Ser Pro Gly Tyr Pro His Ser Tyr
        35                  40                  45

His Pro Ser Glu Lys Cys Glu Trp Leu Ile Gln Ala Pro Glu Pro Tyr
    50                  55                  60

Gln Arg Ile Ile Ile Asn Phe Asn Pro His Phe Asp Leu Glu Asp Arg
```

```
              65                  70                  75                  80
Asp Cys Lys Tyr Asp Tyr Val Glu Val Ile Asp Gly Glu Asn Glu Gly
                     85                  90                  95
Gly Arg Leu Trp Gly Lys Phe Cys Gly Lys Ile Ala Pro Ser Pro Val
            100                 105                 110
Val Ser Ser Gly Pro Phe Leu Phe Ile Lys Phe Val Ser Asp Tyr Glu
            115                 120                 125
Thr His Gly Ala Gly Phe Ser Ile Arg Tyr Glu Ile Phe Lys Arg Gly
            130                 135                 140
Pro Glu Cys Ser Gln Asn Tyr Thr Ala Pro Thr Gly Val Ile Lys Ser
145                 150                 155                 160
Pro Gly Phe Pro Glu Lys Tyr Pro Asn Cys Leu Glu Cys Thr Tyr Ile
                165                 170                 175
Ile Phe Ala Pro Lys Met Ser Glu Ile Ile Leu Glu Phe Glu Ser Phe
            180                 185                 190
Asp Leu Glu Gln Asp Ser Asn Pro Pro Gly Gly Met Phe Cys Arg Tyr
            195                 200                 205
Asp Arg Leu Glu Ile Trp Asp Gly Phe Pro Glu Val Gly Pro His Ile
            210                 215                 220
Gly Arg Tyr Cys Gly Gln Lys Thr Pro Gly Arg Ile Arg Ser Ser Ser
225                 230                 235                 240
Gly Val Leu Ser Met Val Phe Tyr Thr Asp Ser Ala Ile Ala Lys Glu
                245                 250                 255
Gly Phe Ser Ala Asn Tyr Ser Val Leu Gln Ser Ser Ile Ser Glu Asp
                260                 265                 270
Phe Lys Cys Met Glu Ala Leu Gly Met Glu Ser Gly Glu Ile His Ser
            275                 280                 285
Asp Gln Ile Thr Ala Ser Ser Gln Tyr Gly Thr Asn Trp Ser Val Glu
290                 295                 300
Arg Ser Arg Leu Asn Tyr Pro Glu Asn Gly Trp Thr Pro Gly Glu Asp
305                 310                 315                 320
Ser Tyr Lys Glu Trp Ile Gln Val Asp Leu Gly Leu Leu Arg Phe Val
                325                 330                 335
Thr Ala Val Gly Thr Gln Gly Ala Ile Ser Lys Glu Thr Lys Lys Lys
            340                 345                 350
Tyr Tyr Val Lys Thr Tyr Arg Val Asp Ile Ser Ser Asn Gly Glu Asp
            355                 360                 365
Trp Ile Ser Leu Lys Glu Gly Asn Lys Ala Ile Ile Phe Gln Gly Asn
370                 375                 380
Thr Asn Pro Thr Asp Val Val Leu Gly Val Phe Ser Lys Pro Leu Ile
385                 390                 395                 400
Thr Arg Phe Val Arg Ile Lys Pro Val Ser Trp Glu Thr Gly Ile Ser
                405                 410                 415
Met Arg Phe Glu Val Tyr Gly Cys Lys Ile Thr Asp Tyr Pro Cys Ser
            420                 425                 430
Gly Met Leu Gly Met Val Ser Gly Leu Ile Ser Asp Ser Gln Ile Thr
            435                 440                 445
Ala Ser Asn Gln Ala Asp Arg Asn Trp Met Pro Glu Asn Ile Arg Leu
450                 455                 460
Val Thr Ser Arg Thr Gly Trp Ala Leu Pro Pro Ser Pro His Pro Tyr
465                 470                 475                 480
Thr Asn Glu Trp Leu Gln Val Asp Leu Gly Asp Glu Lys Ile Val Arg
                485                 490                 495
```

```
Gly Val Ile Ile Gln Gly Gly Lys His Arg Glu Asn Lys Val Phe Met
            500                 505                 510

Arg Lys Phe Lys Ile Ala Tyr Ser Asn Asn Gly Ser Asp Trp Lys Thr
        515                 520                 525

Ile Met Asp Asp Ser Lys Arg Lys Ala Lys Ser Phe Glu Gly Asn Asn
    530                 535                 540

Asn Tyr Asp Thr Pro Glu Leu Arg Thr Phe Ser Pro Leu Ser Thr Arg
545                 550                 555                 560

Phe Ile Arg Ile Tyr Pro Glu Arg Ala Thr His Ser Gly Leu Gly Leu
                565                 570                 575

Arg Met Glu Leu Leu Gly Cys Glu Val Glu Ala Pro Thr Ala Gly Pro
            580                 585                 590

Thr Thr Pro Asn Gly Asn Pro Val His Glu Cys Asp Asp Gln Ala
            595                 600                 605

Asn Cys His Ser Gly Thr Gly Asp Asp Phe Gln Leu Thr Gly Gly Thr
            610                 615                 620

Thr Val Leu Ala Thr Glu Lys Pro Thr Ile Ile Asp Ser Thr Ile Gln
625                 630                 635                 640

Ser Glu Phe Pro Thr Tyr Gly Phe Asn Cys Glu Phe Gly Trp Gly Ser
                645                 650                 655

His Lys Thr Phe Cys His Trp Glu His Asp Ser His Ala Gln Leu Arg
                660                 665                 670

Trp Ser Val Leu Thr Ser Lys Thr Gly Pro Ile Gln Asp His Thr Gly
            675                 680                 685

Asp Gly Asn Phe Ile Tyr Ser Gln Ala Asp Glu Asn Gln Lys Gly Lys
        690                 695                 700

Val Ala Arg Leu Val Ser Pro Val Val Tyr Ser Gln Ser Ser Ala His
705                 710                 715                 720

Cys Met Thr Phe Trp Tyr His Met Ser Gly Ser His Val Gly Thr Leu
                725                 730                 735

Arg Val Lys Leu Arg Tyr Gln Lys Pro Glu Glu Tyr Asp Gln Leu Val
            740                 745                 750

Trp Met Val Val Gly His Gln Gly Asp His Trp Lys Glu Gly Arg Val
            755                 760                 765

Leu Leu His Lys Ser Leu Lys Leu Tyr Gln Val Ile Phe Glu Gly Glu
    770                 775                 780

Ile Gly Lys Gly Asn Leu Gly Gly Ile Ala Val Asp Asp Ile Ser Ile
785                 790                 795                 800

Asn Asn His Ile Ser Gln Glu Asp Cys Ala Lys Pro Thr Asp Leu Asp
                805                 810                 815

Lys Lys Asn Thr Glu Ile Lys Ile Asp Glu Thr Gly Ser Thr Pro Gly
            820                 825                 830

Tyr Glu Gly Glu Gly Glu Gly Asp Lys Asn Ile Ser Arg Lys Pro Gly
        835                 840                 845

Asn Val Leu Lys Thr Leu Asp Pro Ile Leu Ile Thr Ile Ala Met
            850                 855                 860

Ser Ala Leu Gly Val Leu Leu Gly Ala Val Cys Gly Val Val Leu Tyr
865                 870                 875                 880

Cys Ala Cys Trp His Asn Gly Met Ser Glu Arg Asn Leu Ser Ala Leu
                885                 890                 895

Glu Asn Tyr Asn Phe Glu Leu Val Asp Gly Val Lys Leu Lys Lys Asp
            900                 905                 910
```

Lys Leu Asn Pro Gln Ser Asn Tyr Ser Glu Ala
        915                 920

<210> SEQ ID NO 7
<211> LENGTH: 3539
<212> TYPE: DNA
<213> ORGANISM: rat
<220> FEATURE:
<221> NAME/KEY: CDS
<222> LOCATION: (568)..(3294)

<400> SEQUENCE: 7

| | | |
|---|---|---|
| aaactggagc tccaccgcgg tgcggccgc ccgggcaggt ctagaattca gcggccgctg | 60 |
| aattctatcc agcggtcggt gcctctgccc gcgtgtgtgt cccgggtgcc ggggacctg | 120 |
| tgtcagttag cgcttctgag atcacacagc tgcctagggg ccgtgtgatg cccagggcaa | 180 |
| ttcttggctt tgattttat tattattact attattttgc gttcagcttt cgggaaaccc | 240 |
| tcgtgatgtt gtaggataaa ggaaatgaca ctttgaggaa ctggagagaa catacacgcg | 300 |
| tttgggtttg aagaggaaac cggtctccgc ttccttagct tgctccctct ttgctgattt | 360 |
| caagagctat ctcctatgag gtggagatat tccagcaaga ataaaggtga agacagactg | 420 |
| actgccagga cccaggagga aaacgttgat cgttagagac ctttgcagaa gacaccacca | 480 |
| ggaggaaaat tagagaggaa aaacacaaag acataattat atggagatcc cacaaactta | 540 |
| gcccgggaga gagcttctct gtcaaaa atg gat atg ttt cct ctt acc tgg gtt | 594 |
|                                Met Asp Met Phe Pro Leu Thr Trp Val | |
|                                 1               5                   | |

| | | |
|---|---|---|
| ttc tta gct ctg tac ttt tca gga cac gaa gtg aga agc cag caa gat | 642 |
| Phe Leu Ala Leu Tyr Phe Ser Gly His Glu Val Arg Ser Gln Gln Asp | |
|  10              15                  20                  25     | |

| | | |
|---|---|---|
| cca cct tgc gga ggt cgg ccg aat tcc aag gat gct ggc tac atc act | 690 |
| Pro Pro Cys Gly Gly Arg Pro Asn Ser Lys Asp Ala Gly Tyr Ile Thr | |
|             30                  35                  40          | |

| | | |
|---|---|---|
| tcc cca ggc tac ccc cag gac tat ccc tcc cac cag aac tgt gag tgg | 738 |
| Ser Pro Gly Tyr Pro Gln Asp Tyr Pro Ser His Gln Asn Cys Glu Trp | |
|                 45                  50                  55      | |

| | | |
|---|---|---|
| att gtc tac gcc ccc gaa ccc aac cag aag att gtt ctc aac ttc aac | 786 |
| Ile Val Tyr Ala Pro Glu Pro Asn Gln Lys Ile Val Leu Asn Phe Asn | |
|             60                  65                  70          | |

| | | |
|---|---|---|
| cct cac ttt gaa atc gag aaa cac gac tgc aag tat gac ttc att gag | 834 |
| Pro His Phe Glu Ile Glu Lys His Asp Cys Lys Tyr Asp Phe Ile Glu | |
|         75                  80                  85              | |

| | | |
|---|---|---|
| att cgg gat ggg gac agt gag tca gct gac ctc ctg ggc aag cac tgt | 882 |
| Ile Arg Asp Gly Asp Ser Glu Ser Ala Asp Leu Leu Gly Lys His Cys | |
|  90                  95                 100                 105 | |

| | | |
|---|---|---|
| ggg aac atc gcc ccg ccc acc atc atc tcc tca ggc tcc gtg tta tac | 930 |
| Gly Asn Ile Ala Pro Pro Thr Ile Ile Ser Ser Gly Ser Val Leu Tyr | |
|                 110                 115                 120     | |

| | | |
|---|---|---|
| atc aag ttc acc tca gac tac gcc cgg cag ggg gca ggt ttc tct cta | 978 |
| Ile Lys Phe Thr Ser Asp Tyr Ala Arg Gln Gly Ala Gly Phe Ser Leu | |
|             125                 130                 135         | |

| | | |
|---|---|---|
| cgc tat gag atc ttc aaa aca ggc tct gaa gat tgt tcc aag aac ttt | 1026 |
| Arg Tyr Glu Ile Phe Lys Thr Gly Ser Glu Asp Cys Ser Lys Asn Phe | |
|         140                 145                 150             | |

| | | |
|---|---|---|
| aca agc ccc aat ggg acc att gaa tct cca ggg ttt cca gag aag tat | 1074 |
| Thr Ser Pro Asn Gly Thr Ile Glu Ser Pro Gly Phe Pro Glu Lys Tyr | |
|     155                 160                 165                 | |

| | | |
|---|---|---|
| cca cac aat ctg gac tgt acc ttc acc atc ctg gcc aaa ccc agg atg | 1122 |
| Pro His Asn Leu Asp Cys Thr Phe Thr Ile Leu Ala Lys Pro Arg Met | |
| 170                 175                 180                 185 | |

```
gag atc atc cta cag ttc ctg acc ttt gac ctg gag cat gac cct cta        1170
Glu Ile Ile Leu Gln Phe Leu Thr Phe Asp Leu Glu His Asp Pro Leu
                190                 195                 200 caa gtg ggg gaa gga gac tgt aaa tat gac tgg ctg gac atc tgg gat        1218
Gln Val Gly Glu Gly Asp Cys Lys Tyr Asp Trp Leu Asp Ile Trp Asp
            205                 210                 215 ggc att cca cat gtt gga cct ctg att ggc aag tac tgt ggg acg aaa        1266
Gly Ile Pro His Val Gly Pro Leu Ile Gly Lys Tyr Cys Gly Thr Lys
        220                 225                 230 aca ccc tcc aaa ctc cgc tcg tcc acg ggg atc ctc tcc ttg acc ttt        1314
Thr Pro Ser Lys Leu Arg Ser Ser Thr Gly Ile Leu Ser Leu Thr Phe
    235                 240                 245 cac acg gac atg gca gtg gcc aag gat ggc ttc tcc gca cgt tac tat        1362
His Thr Asp Met Ala Val Ala Lys Asp Gly Phe Ser Ala Arg Tyr Tyr
250                 255                 260                 265 ttg atc cac cag gag cca cct gag aat ttt cag tgc aat gtc cct ttg        1410
Leu Ile His Gln Glu Pro Pro Glu Asn Phe Gln Cys Asn Val Pro Leu
                270                 275                 280 gga atg gag tct ggc cgg att gct aat gaa cag atc agt gcc tcc tcc        1458
Gly Met Glu Ser Gly Arg Ile Ala Asn Glu Gln Ile Ser Ala Ser Ser
            285                 290                 295 acc ttc tct gat ggg agg tgg act cct caa cag agc cgg ctc cat ggt        1506
Thr Phe Ser Asp Gly Arg Trp Thr Pro Gln Gln Ser Arg Leu His Gly
        300                 305                 310 gat gac aat ggc tgg aca ccc aat ttg gat tcc aac aag gag tat ctc        1554
Asp Asp Asn Gly Trp Thr Pro Asn Leu Asp Ser Asn Lys Glu Tyr Leu
    315                 320                 325 cag gtg gac ctg cgc ttc cta acc atg ctc aca gcc att gca aca cag        1602
Gln Val Asp Leu Arg Phe Leu Thr Met Leu Thr Ala Ile Ala Thr Gln
330                 335                 340                 345 gga gcc att tcc agg gaa acc cag aaa ggc tac tac gtc aaa tcg tac        1650
Gly Ala Ile Ser Arg Glu Thr Gln Lys Gly Tyr Tyr Val Lys Ser Tyr
                350                 355                 360 aag ctg gaa gtc agc aca aat ggt gaa gat tgg atg gtc tac cgg cat        1698
Lys Leu Glu Val Ser Thr Asn Gly Glu Asp Trp Met Val Tyr Arg His
            365                 370                 375 ggc aaa aac cac aag ata ttc caa gcg aac aat gat gcg acc gag gtg        1746
Gly Lys Asn His Lys Ile Phe Gln Ala Asn Asn Asp Ala Thr Glu Val
        380                 385                 390 gtg cta aac aag ctc cac atg cca ctg ctg act cgg ttc atc agg atc        1794
Val Leu Asn Lys Leu His Met Pro Leu Leu Thr Arg Phe Ile Arg Ile
    395                 400                 405 cgc ccg cag acg tgg cat ttg ggc att gcc ctt cgc ctg gag ctc ttt        1842
Arg Pro Gln Thr Trp His Leu Gly Ile Ala Leu Arg Leu Glu Leu Phe
410                 415                 420                 425 ggc tgc cgg gtc aca gat gca ccc tgc tcc aac atg ctg ggg atg ctc        1890
Gly Cys Arg Val Thr Asp Ala Pro Cys Ser Asn Met Leu Gly Met Leu
                430                 435                 440 tcg ggc ctc att gct gat acc cag atc tct gcc tcc tcc acc cga gag        1938
Ser Gly Leu Ile Ala Asp Thr Gln Ile Ser Ala Ser Ser Thr Arg Glu
            445                 450                 455 tac ctc tgg agc ccc agt gct gcc cgc ctg gtt agt agc cgc tct ggc        1986
Tyr Leu Trp Ser Pro Ser Ala Ala Arg Leu Val Ser Ser Arg Ser Gly
        460                 465                 470 tgg ttt cct cgg aac cct caa gcc cag cca ggt gaa gaa tgg ctt cag        2034
Trp Phe Pro Arg Asn Pro Gln Ala Gln Pro Gly Glu Glu Trp Leu Gln
    475                 480                 485 gtt gac ctg ggg aca ccc aag aca gtg aaa ggg gtc atc atc cag gga        2082
Val Asp Leu Gly Thr Pro Lys Thr Val Lys Gly Val Ile Ile Gln Gly
```

```
                                                          -continued 490                    495                    500                    505 gcc cga gga gga gac agc atc act gcc gtg gaa gcc agg gcg ttt gta    2130
Ala Arg Gly Gly Asp Ser Ile Thr Ala Val Glu Ala Arg Ala Phe Val
                510                    515                    520 cgc aag ttc aaa gtc tcc tac agc cta aat ggc aag gac tgg gaa tat    2178
Arg Lys Phe Lys Val Ser Tyr Ser Leu Asn Gly Lys Asp Trp Glu Tyr
            525                    530                    535 atc cag gac ccc agg act cag cag aca aag ctg ttt gaa ggg aac atg    2226
Ile Gln Asp Pro Arg Thr Gln Gln Thr Lys Leu Phe Glu Gly Asn Met
        540                    545                    550 cac tat gac acc cct gac atc cga agg ttc gat cct gtt cca gcg cag    2274
His Tyr Asp Thr Pro Asp Ile Arg Arg Phe Asp Pro Val Pro Ala Gln
    555                    560                    565 tat gtg cgg gtg tac cca gag agg tgg tcg cca gca ggc atc ggg atg    2322
Tyr Val Arg Val Tyr Pro Glu Arg Trp Ser Pro Ala Gly Ile Gly Met
570                    575                    580                    585 agg ctg gag gtg ctg ggc tgt gac tgg aca gac tca aag ccc aca gtg    2370
Arg Leu Glu Val Leu Gly Cys Asp Trp Thr Asp Ser Lys Pro Thr Val
                590                    595                    600 gag acg ctg gga ccc acc gtg aag agt gaa gag act acc acc cca tat    2418
Glu Thr Leu Gly Pro Thr Val Lys Ser Glu Glu Thr Thr Thr Pro Tyr
            605                    610                    615 ccc atg gat gag gat gcc acc gag tgt ggg gaa aac tgc agc ttt gag    2466
Pro Met Asp Glu Asp Ala Thr Glu Cys Gly Glu Asn Cys Ser Phe Glu
        620                    625                    630 gat gac aaa gat ttg caa ctt cct tca gga ttc aac tgc aac ttt gat    2514
Asp Asp Lys Asp Leu Gln Leu Pro Ser Gly Phe Asn Cys Asn Phe Asp
    635                    640                    645 ttt ccg gaa gag acc tgt ggt tgg gtg tac gac cat gcc aag tgg ctc    2562
Phe Pro Glu Glu Thr Cys Gly Trp Val Tyr Asp His Ala Lys Trp Leu
650                    655                    660                    665 cgg agc acg tgg atc agc agc gct aac ccc aat gac aga aca ttt cca    2610
Arg Ser Thr Trp Ile Ser Ser Ala Asn Pro Asn Asp Arg Thr Phe Pro
                670                    675                    680 gat gac aag aac ttc ttg aaa ctg cag agt gat ggc cga cga gag ggc    2658
Asp Asp Lys Asn Phe Leu Lys Leu Gln Ser Asp Gly Arg Arg Glu Gly
            685                    690                    695 cag tac ggg cgg ctc atc agc cca ccg gtg cac ctg ccc cga agc cct    2706
Gln Tyr Gly Arg Leu Ile Ser Pro Pro Val His Leu Pro Arg Ser Pro
        700                    705                    710 gtg tgc atg gag ttc cag tac caa gcc atg ggc ggc cac ggg gtg gca    2754
Val Cys Met Glu Phe Gln Tyr Gln Ala Met Gly Gly His Gly Val Ala
    715                    720                    725 ctg cag gtg gtt cgg gaa gcc agc cag gaa agc aaa ctc ctt tgg gtc    2802
Leu Gln Val Val Arg Glu Ala Ser Gln Glu Ser Lys Leu Leu Trp Val
730                    735                    740                    745 atc cgt gag gac cag ggc agc gag tgg aag cac ggg cgc att atc ctg    2850
Ile Arg Glu Asp Gln Gly Ser Glu Trp Lys His Gly Arg Ile Ile Leu
                750                    755                    760 ccc agc tat gac atg gag tat cag atc gtg ttc gag gga gtg ata ggg    2898
Pro Ser Tyr Asp Met Glu Tyr Gln Ile Val Phe Glu Gly Val Ile Gly
            765                    770                    775 aag gga cga tcg gga gag att tcc atc gat gac att cgg ata agc act    2946
Lys Gly Arg Ser Gly Glu Ile Ser Ile Asp Asp Ile Arg Ile Ser Thr
        780                    785                    790 gat gtc cca ctg gag aac tgc atg gaa ccc ata tca gct ttt gca gat    2994
Asp Val Pro Leu Glu Asn Cys Met Glu Pro Ile Ser Ala Phe Ala Asp
    795                    800                    805 gaa tat gaa gga gat tgg agc aac tct tct tcc tct acc tca ggg gct    3042
```

-continued

```
Glu Tyr Glu Gly Asp Trp Ser Asn Ser Ser Ser Thr Ser Gly Ala
810                 815                 820                 825 ggt gac ccc tca tct ggc aaa gaa aag agc tgg ctg tac acc cta gat      3090
Gly Asp Pro Ser Ser Gly Lys Glu Lys Ser Trp Leu Tyr Thr Leu Asp
                830                 835                 840 ccc att ctg atc acc atc atc gcc atg agc tcg ctg ggg gtc ctg ctg      3138
Pro Ile Leu Ile Thr Ile Ile Ala Met Ser Ser Leu Gly Val Leu Leu
            845                 850                 855 ggg gcc acc tgt gcg ggc ctc ctc ctt tac tgc acc tgc tcc tat tcg      3186
Gly Ala Thr Cys Ala Gly Leu Leu Leu Tyr Cys Thr Cys Ser Tyr Ser
        860                 865                 870 ggt ctg agt tcg agg agc tgc acc aca ctg gag aac tac aac ttt gag      3234
Gly Leu Ser Ser Arg Ser Cys Thr Thr Leu Glu Asn Tyr Asn Phe Glu
    875                 880                 885 ctc tac gat ggc ctc aag cac aag gtc aag atc aat cat cag aag tgc      3282
Leu Tyr Asp Gly Leu Lys His Lys Val Lys Ile Asn His Gln Lys Cys
890                 895                 900                 905 tgc tcg gag gca tgaccgattg tgtctggatc gcttctggcg tttcattcca          3334
Cys Ser Glu Ala gtgagagggg ctagcgaaga ttacagtttt gttttgtttt gttttgtttt ccctttggaa    3394
actgaatgcc ataatctgga tcaaagtgtt ccagaatact gaaggtatgg acaggacaga    3454
caggccagtc tagggagaaa gggagatgca gctgtgaagg ggatcgttgc ccaccaggac    3514
tgtggtggcc aagtgaatgc aggaa                                          3539

<210> SEQ ID NO 8
<211> LENGTH: 909
<212> TYPE: PRT
<213> ORGANISM: rat

<400> SEQUENCE: 8

Met Asp Met Phe Pro Leu Thr Trp Val Phe Leu Ala Leu Tyr Phe Ser
1               5                   10                  15

Gly His Glu Val Arg Ser Gln Gln Asp Pro Pro Cys Gly Gly Arg Pro
            20                  25                  30

Asn Ser Lys Asp Ala Gly Tyr Ile Thr Ser Pro Gly Tyr Pro Gln Asp
        35                  40                  45

Tyr Pro Ser His Gln Asn Cys Glu Trp Ile Val Tyr Ala Pro Glu Pro
    50                  55                  60

Asn Gln Lys Ile Val Leu Asn Phe Asn Pro His Phe Glu Ile Glu Lys
65                  70                  75                  80

His Asp Cys Lys Tyr Asp Phe Ile Glu Ile Arg Asp Gly Asp Ser Glu
                85                  90                  95

Ser Ala Asp Leu Leu Gly Lys His Cys Gly Asn Ile Ala Pro Pro Thr
            100                 105                 110

Ile Ile Ser Ser Gly Ser Val Leu Tyr Ile Lys Phe Thr Ser Asp Tyr
        115                 120                 125

Ala Arg Gln Gly Ala Gly Phe Ser Leu Arg Tyr Glu Ile Phe Lys Thr
    130                 135                 140

Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                165                 170                 175

Phe Thr Ile Leu Ala Lys Pro Arg Met Glu Ile Ile Leu Gln Phe Leu
            180                 185                 190

Thr Phe Asp Leu Glu His Asp Pro Leu Gln Val Gly Glu Gly Asp Cys
```

-continued

```
            195                 200                 205
Lys Tyr Asp Trp Leu Asp Ile Trp Asp Gly Ile Pro His Val Gly Pro
            210                 215                 220
Leu Ile Gly Lys Tyr Cys Gly Thr Lys Thr Pro Ser Lys Leu Arg Ser
225                 230                 235                 240
Ser Thr Gly Ile Leu Ser Leu Thr Phe His Thr Asp Met Ala Val Ala
                    245                 250                 255
Lys Asp Gly Phe Ser Ala Arg Tyr Tyr Leu Ile His Gln Glu Pro Pro
                260                 265                 270
Glu Asn Phe Gln Cys Asn Val Pro Leu Gly Met Glu Ser Gly Arg Ile
            275                 280                 285
Ala Asn Glu Gln Ile Ser Ala Ser Ser Thr Phe Ser Asp Gly Arg Trp
            290                 295                 300
Thr Pro Gln Gln Ser Arg Leu His Gly Asp Asp Asn Gly Trp Thr Pro
305                 310                 315                 320
Asn Leu Asp Ser Asn Lys Glu Tyr Leu Gln Val Asp Leu Arg Phe Leu
                    325                 330                 335
Thr Met Leu Thr Ala Ile Ala Thr Gln Gly Ala Ile Ser Arg Glu Thr
                340                 345                 350
Gln Lys Gly Tyr Tyr Val Lys Ser Tyr Lys Leu Glu Val Ser Thr Asn
            355                 360                 365
Gly Glu Asp Trp Met Val Tyr Arg His Gly Lys Asn His Lys Ile Phe
            370                 375                 380
Gln Ala Asn Asn Asp Ala Thr Glu Val Val Leu Asn Lys Leu His Met
385                 390                 395                 400
Pro Leu Leu Thr Arg Phe Ile Arg Ile Arg Pro Gln Thr Trp His Leu
                    405                 410                 415
Gly Ile Ala Leu Arg Leu Glu Leu Phe Gly Cys Arg Val Thr Asp Ala
                420                 425                 430
Pro Cys Ser Asn Met Leu Gly Met Leu Ser Gly Leu Ile Ala Asp Thr
            435                 440                 445
Gln Ile Ser Ala Ser Ser Thr Arg Glu Tyr Leu Trp Ser Pro Ser Ala
            450                 455                 460
Ala Arg Leu Val Ser Ser Arg Ser Gly Trp Phe Pro Arg Asn Pro Gln
465                 470                 475                 480
Ala Gln Pro Gly Glu Glu Trp Leu Gln Val Asp Leu Gly Thr Pro Lys
                485                 490                 495
Thr Val Lys Gly Val Ile Ile Gln Gly Ala Arg Gly Gly Asp Ser Ile
                500                 505                 510
Thr Ala Val Glu Ala Arg Ala Phe Val Arg Lys Phe Lys Val Ser Tyr
            515                 520                 525
Ser Leu Asn Gly Lys Asp Trp Glu Tyr Ile Gln Asp Pro Arg Thr Gln
530                 535                 540
Gln Thr Lys Leu Phe Glu Gly Asn Met His Tyr Asp Thr Pro Asp Ile
545                 550                 555                 560
Arg Arg Phe Asp Pro Val Pro Ala Gln Tyr Val Arg Val Tyr Pro Glu
                565                 570                 575
Arg Trp Ser Pro Ala Gly Ile Gly Met Arg Leu Glu Val Leu Gly Cys
            580                 585                 590
Asp Trp Thr Asp Ser Lys Pro Thr Val Glu Thr Leu Gly Pro Thr Val
            595                 600                 605
Lys Ser Glu Glu Thr Thr Thr Pro Tyr Pro Met Asp Glu Asp Ala Thr
610                 615                 620
```

-continued

Glu Cys Gly Glu Asn Cys Ser Phe Glu Asp Lys Asp Leu Gln Leu
625                 630                 635                 640

Pro Ser Gly Phe Asn Cys Asn Phe Asp Phe Pro Glu Glu Thr Cys Gly
            645                 650                 655

Trp Val Tyr Asp His Ala Lys Trp Leu Arg Ser Thr Trp Ile Ser Ser
            660                 665                 670

Ala Asn Pro Asn Asp Arg Thr Phe Pro Asp Asp Lys Asn Phe Leu Lys
            675                 680                 685

Leu Gln Ser Asp Gly Arg Arg Glu Gly Gln Tyr Gly Arg Leu Ile Ser
    690                 695                 700

Pro Pro Val His Leu Pro Arg Ser Pro Val Cys Met Glu Phe Gln Tyr
705                 710                 715                 720

Gln Ala Met Gly Gly His Gly Val Ala Leu Gln Val Val Arg Glu Ala
                725                 730                 735

Ser Gln Glu Ser Lys Leu Leu Trp Val Ile Arg Glu Asp Gln Gly Ser
            740                 745                 750

Glu Trp Lys His Gly Arg Ile Ile Leu Pro Ser Tyr Asp Met Glu Tyr
    755                 760                 765

Gln Ile Val Phe Glu Gly Val Ile Gly Lys Gly Arg Ser Gly Glu Ile
770                 775                 780

Ser Ile Asp Asp Ile Arg Ile Ser Thr Asp Val Pro Leu Glu Asn Cys
785                 790                 795                 800

Met Glu Pro Ile Ser Ala Phe Ala Asp Glu Tyr Glu Gly Asp Trp Ser
                805                 810                 815

Asn Ser Ser Ser Ser Thr Ser Gly Ala Gly Asp Pro Ser Ser Gly Lys
            820                 825                 830

Glu Lys Ser Trp Leu Tyr Thr Leu Asp Pro Ile Leu Ile Thr Ile Ile
    835                 840                 845

Ala Met Ser Ser Leu Gly Val Leu Leu Gly Ala Thr Cys Ala Gly Leu
850                 855                 860

Leu Leu Tyr Cys Thr Cys Ser Tyr Ser Gly Leu Ser Ser Arg Ser Cys
865                 870                 875                 880

Thr Thr Leu Glu Asn Tyr Asn Phe Glu Leu Tyr Asp Gly Leu Lys His
                885                 890                 895

Lys Val Lys Ile Asn His Gln Lys Cys Cys Ser Glu Ala
                900                 905

<210> SEQ ID NO 9
<211> LENGTH: 4718
<212> TYPE: DNA
<213> ORGANISM: mouse
<220> FEATURE:
<221> NAME/KEY: CDS
<222> LOCATION: (567)..(3293)

<400> SEQUENCE: 9
aaactggagc tccaccgcgg tggcggccgc ccgggcaggt ctagaattca gcggccgctg      60
aattctatcc agcggtcggt gcctctgccc gcgtgtgtgt cccgggtgcc ggggggacctg    120 tgtcagttag cgcttctgag atcacacagc tgcctagggg ccgtgtgatg cccagggcaa    180
ttcttggctt tgatttttat tattattact attattttgc gttcagcttt cgggaaaccc    240
tcgtgatgtt gtaggataaa ggaaatgaca ctttgaggaa ctggagagaa catacacgcg    300
tttgggtttg aagaggaaac cggtctccgc ttccttagct tgctccctct ttgctgattt    360
caagagctat ctcctatgag gtggagatat tccagcaaga ataaggtga agacagactg     420

```
actgccagga cccaggagga aaacgttgat cgttagagac ctttgcagaa gacaccacca    480
ggaggaaaat tagagaggaa aaacacaaag acataattat aggagatccc acaaacctag    540
cccgggagag agcctctctg tcaaaa atg gat atg ttt cct ctt acc tgg gtt    593
                             Met Asp Met Phe Pro Leu Thr Trp Val
                              1               5 ttc tta gct ctg tac ttt tca gga cac gaa gtg aga agc cag caa gat    641
Phe Leu Ala Leu Tyr Phe Ser Gly His Glu Val Arg Ser Gln Gln Asp
 10              15                  20                  25 cca ccc tgc gga ggt cgg ccg aat tcc aaa gat gct ggc tac atc act    689
Pro Pro Cys Gly Gly Arg Pro Asn Ser Lys Asp Ala Gly Tyr Ile Thr
                 30                  35                  40 tcc cca ggc tac ccc cag gac tat ccc tcc cac cag aac tgt gag tgg    737
Ser Pro Gly Tyr Pro Gln Asp Tyr Pro Ser His Gln Asn Cys Glu Trp
             45                  50                  55 att gtc tac gcc ccc gaa ccc aac cag aag att gtt ctc aac ttc aac    785
Ile Val Tyr Ala Pro Glu Pro Asn Gln Lys Ile Val Leu Asn Phe Asn
         60                  65                  70 cct cac ttt gaa atc gag aaa cac gac tgc aag tat gac ttc att gag    833
Pro His Phe Glu Ile Glu Lys His Asp Cys Lys Tyr Asp Phe Ile Glu
     75                  80                  85 att cgg gat ggg gac agt gag tca gct gac ctc ctg ggc aag cac tgt    881
Ile Arg Asp Gly Asp Ser Glu Ser Ala Asp Leu Leu Gly Lys His Cys
 90                  95                 100                 105 ggg aac atc gcc ccg ccc acc atc atc tcc tca ggc tcc gtg tta tac    929
Gly Asn Ile Ala Pro Pro Thr Ile Ile Ser Ser Gly Ser Val Leu Tyr
                110                 115                 120 atc aag ttc acc tca gac tac gcc cgg cag ggg gca ggt ttc tct cta    977
Ile Lys Phe Thr Ser Asp Tyr Ala Arg Gln Gly Ala Gly Phe Ser Leu
            125                 130                 135 cgc tat gag atc ttc aaa aca ggc tct gaa gat tgt tcc aag aac ttt   1025
Arg Tyr Glu Ile Phe Lys Thr Gly Ser Glu Asp Cys Ser Lys Asn Phe
        140                 145                 150 aca agc ccc aat ggg acc att gaa tct cca ggg ttt cca gag aag tat   1073
Thr Ser Pro Asn Gly Thr Ile Glu Ser Pro Gly Phe Pro Glu Lys Tyr
    155                 160                 165 cca cac aat ctg gac tgt acc ttc acc atc ctg gcc aaa ccc agg atg   1121
Pro His Asn Leu Asp Cys Thr Phe Thr Ile Leu Ala Lys Pro Arg Met
170                 175                 180                 185 gag atc atc cta cag ttc ctg acc ttt gac ctg gag cat gac cct cta   1169
Glu Ile Ile Leu Gln Phe Leu Thr Phe Asp Leu Glu His Asp Pro Leu
                190                 195                 200 caa gtg ggg gaa gga gac tgt aaa tat gac tgg ctg gac atc tgg gat   1217
Gln Val Gly Glu Gly Asp Cys Lys Tyr Asp Trp Leu Asp Ile Trp Asp
            205                 210                 215 ggc att cca cat gtt gga cct ctg att ggc aag tac tgt ggg acg aaa   1265
Gly Ile Pro His Val Gly Pro Leu Ile Gly Lys Tyr Cys Gly Thr Lys
        220                 225                 230 aca ccc tcc aaa ctc cgc tcg tcc acg ggg atc ctc tcc ttg acc ttt   1313
Thr Pro Ser Lys Leu Arg Ser Ser Thr Gly Ile Leu Ser Leu Thr Phe
    235                 240                 245 cac acg gac atg gca gtg gcc aag gat ggc ttc tcc gca cgt tac tat   1361
His Thr Asp Met Ala Val Ala Lys Asp Gly Phe Ser Ala Arg Tyr Tyr
250                 255                 260                 265 ttg atc cac cag gag cca cct gag aat ttt cag tgc aat gtc cct ttg   1409
Leu Ile His Gln Glu Pro Pro Glu Asn Phe Gln Cys Asn Val Pro Leu
                270                 275                 280 gga atg gag tct ggc cgg att gct aat gaa cag atc agt gcc tcc tcc   1457
Gly Met Glu Ser Gly Arg Ile Ala Asn Glu Gln Ile Ser Ala Ser Ser
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 285 |     |     |     |     | 290 |     |     |     |     | 295 |     |     |      |
| acc | ttc | tct | gat | ggg | agg | tgg | act | cct | caa | cag | agc | cgg | ctc | cat | ggt | 1505 |
| Thr | Phe | Ser | Asp | Gly | Arg | Trp | Thr | Pro | Gln | Gln | Ser | Arg | Leu | His | Gly |      |
|     |     |     | 300 |     |     |     |     | 305 |     |     |     |     | 310 |     |     |      |
| gat | gac | aat | ggc | tgg | aca | ccc | aat | ttg | gat | tcc | aac | aag | gag | tat | ctc | 1553 |
| Asp | Asp | Asn | Gly | Trp | Thr | Pro | Asn | Leu | Asp | Ser | Asn | Lys | Glu | Tyr | Leu |      |
|     |     |     | 315 |     |     |     |     | 320 |     |     |     |     | 325 |     |     |      |
| cag | gtg | gac | ctg | cgc | ttc | cta | acc | atg | ctc | aca | gcc | att | gca | aca | cag | 1601 |
| Gln | Val | Asp | Leu | Arg | Phe | Leu | Thr | Met | Leu | Thr | Ala | Ile | Ala | Thr | Gln |      |
| 330 |     |     |     |     | 335 |     |     |     |     | 340 |     |     |     |     | 345 |      |
| gga | gcc | att | tcc | agg | gaa | acc | cag | aaa | ggc | tac | tac | gtc | aaa | tcg | tac | 1649 |
| Gly | Ala | Ile | Ser | Arg | Glu | Thr | Gln | Lys | Gly | Tyr | Tyr | Val | Lys | Ser | Tyr |      |
|     |     |     |     | 350 |     |     |     |     | 355 |     |     |     |     | 360 |     |      |
| aag | ctg | gaa | gtc | agc | aca | aat | ggt | gaa | gat | tgg | atg | gtc | tac | cgg | cat | 1697 |
| Lys | Leu | Glu | Val | Ser | Thr | Asn | Gly | Glu | Asp | Trp | Met | Val | Tyr | Arg | His |      |
|     |     |     |     | 365 |     |     |     |     | 370 |     |     |     |     | 375 |     |      |
| ggc | aaa | aac | cac | aag | ata | ttc | caa | gcg | aac | aat | gat | gcg | acc | gag | gtg | 1745 |
| Gly | Lys | Asn | His | Lys | Ile | Phe | Gln | Ala | Asn | Asn | Asp | Ala | Thr | Glu | Val |      |
|     |     |     | 380 |     |     |     |     | 385 |     |     |     |     | 390 |     |     |      |
| gtg | cta | aac | aag | ctc | cac | atg | cca | ctg | ctg | act | cgg | ttc | atc | agg | atc | 1793 |
| Val | Leu | Asn | Lys | Leu | His | Met | Pro | Leu | Leu | Thr | Arg | Phe | Ile | Arg | Ile |      |
|     | 395 |     |     |     |     | 400 |     |     |     |     | 405 |     |     |     |     |      |
| cgc | ccg | cag | acg | tgg | cat | ttg | ggc | att | gcc | ctt | cgc | ctg | gag | ctc | ttt | 1841 |
| Arg | Pro | Gln | Thr | Trp | His | Leu | Gly | Ile | Ala | Leu | Arg | Leu | Glu | Leu | Phe |      |
| 410 |     |     |     |     | 415 |     |     |     |     | 420 |     |     |     |     | 425 |      |
| ggc | tgc | cgg | gtc | aca | gat | gca | ccc | tgc | tcc | aac | atg | ctg | ggg | atg | ctc | 1889 |
| Gly | Cys | Arg | Val | Thr | Asp | Ala | Pro | Cys | Ser | Asn | Met | Leu | Gly | Met | Leu |      |
|     |     |     |     | 430 |     |     |     |     | 435 |     |     |     |     | 440 |     |      |
| tcg | ggc | ctc | att | gct | gat | acc | cag | atc | tct | gcc | tcc | tcc | acc | cga | gag | 1937 |
| Ser | Gly | Leu | Ile | Ala | Asp | Thr | Gln | Ile | Ser | Ala | Ser | Ser | Thr | Arg | Glu |      |
|     |     |     | 445 |     |     |     |     | 450 |     |     |     |     | 455 |     |     |      |
| tac | ctc | tgg | agc | ccc | agt | gct | gcc | cgc | ctg | gtt | agt | agc | cgc | tct | ggc | 1985 |
| Tyr | Leu | Trp | Ser | Pro | Ser | Ala | Ala | Arg | Leu | Val | Ser | Ser | Arg | Ser | Gly |      |
|     |     |     | 460 |     |     |     |     | 465 |     |     |     |     | 470 |     |     |      |
| tgg | ttt | cct | cgg | aac | cct | caa | gcc | cag | cca | ggt | gaa | gaa | tgg | ctt | cag | 2033 |
| Trp | Phe | Pro | Arg | Asn | Pro | Gln | Ala | Gln | Pro | Gly | Glu | Glu | Trp | Leu | Gln |      |
|     | 475 |     |     |     |     | 480 |     |     |     |     | 485 |     |     |     |     |      |
| gta | gac | ctg | ggg | aca | ccc | aag | aca | gtg | aaa | ggg | gtc | atc | atc | cag | gga | 2081 |
| Val | Asp | Leu | Gly | Thr | Pro | Lys | Thr | Val | Lys | Gly | Val | Ile | Ile | Gln | Gly |      |
| 490 |     |     |     |     | 495 |     |     |     |     | 500 |     |     |     |     | 505 |      |
| gcc | cga | gga | gga | gac | agc | atc | act | gcc | gtg | gaa | gcc | agg | gcg | ttt | gta | 2129 |
| Ala | Arg | Gly | Gly | Asp | Ser | Ile | Thr | Ala | Val | Glu | Ala | Arg | Ala | Phe | Val |      |
|     |     |     |     | 510 |     |     |     |     | 515 |     |     |     |     | 520 |     |      |
| cgc | aag | ttc | aaa | gtc | tcc | tac | agc | cta | aat | ggc | aag | gac | tgg | gaa | tat | 2177 |
| Arg | Lys | Phe | Lys | Val | Ser | Tyr | Ser | Leu | Asn | Gly | Lys | Asp | Trp | Glu | Tyr |      |
|     |     |     | 525 |     |     |     |     | 530 |     |     |     |     | 535 |     |     |      |
| atc | cag | gac | ccc | agg | act | cag | cag | aca | aag | ctg | ttt | gaa | ggg | aac | atg | 2225 |
| Ile | Gln | Asp | Pro | Arg | Thr | Gln | Gln | Thr | Lys | Leu | Phe | Glu | Gly | Asn | Met |      |
|     |     |     | 540 |     |     |     |     | 545 |     |     |     |     | 550 |     |     |      |
| cac | tat | gac | acc | cct | gac | atc | cga | agg | ttc | gat | cct | gtt | cca | gcg | cag | 2273 |
| His | Tyr | Asp | Thr | Pro | Asp | Ile | Arg | Arg | Phe | Asp | Pro | Val | Pro | Ala | Gln |      |
|     | 555 |     |     |     |     | 560 |     |     |     |     | 565 |     |     |     |     |      |
| tat | gtg | cgg | gtg | tac | cca | gag | agg | tgg | tcg | cca | gca | ggc | atc | ggg | atg | 2321 |
| Tyr | Val | Arg | Val | Tyr | Pro | Glu | Arg | Trp | Ser | Pro | Ala | Gly | Ile | Gly | Met |      |
| 570 |     |     |     |     | 575 |     |     |     |     | 580 |     |     |     |     | 585 |      |
| agg | ctg | gag | gtg | ctg | ggc | tgt | gac | tgg | aca | gac | tca | aag | ccc | aca | gtg | 2369 |
| Arg | Leu | Glu | Val | Leu | Gly | Cys | Asp | Trp | Thr | Asp | Ser | Lys | Pro | Thr | Val |      |
|     |     |     |     | 590 |     |     |     |     | 595 |     |     |     |     | 600 |     |      |
| gag | acg | ctg | gga | ccc | acc | gtg | aag | agt | gaa | gag | act | acc | acc | cca | tat | 2417 |

```
                                                                                -continued Glu Thr Leu Gly Pro Thr Val Lys Ser Glu Thr Thr Thr Pro Tyr
                605                 610                 615 ccc atg gat gag gat gcc acc gag tgt ggg gaa aac tgc agc ttt gag          2465
Pro Met Asp Glu Asp Ala Thr Glu Cys Gly Glu Asn Cys Ser Phe Glu
            620                 625                 630 gat gac aaa gat ttg caa ctt cct tca gga ttc aac tgc aac ttt gat          2513
Asp Asp Lys Asp Leu Gln Leu Pro Ser Gly Phe Asn Cys Asn Phe Asp
        635                 640                 645 ttt ccg gaa gag acc tgt ggt tgg gtg tac gac cat gcc aag tgg ctc          2561
Phe Pro Glu Glu Thr Cys Gly Trp Val Tyr Asp His Ala Lys Trp Leu
650                 655                 660                 665 cgg agc acg tgg atc agc agc gct aac ccc aat gac aga aca ttt cca          2609
Arg Ser Thr Trp Ile Ser Ser Ala Asn Pro Asn Asp Arg Thr Phe Pro
                670                 675                 680 gat gac aag aac ttc ttg aaa ctg cag agt gat ggc cga cga gag ggc          2657
Asp Asp Lys Asn Phe Leu Lys Leu Gln Ser Asp Gly Arg Arg Glu Gly
            685                 690                 695 cag tac ggg cgg ctc atc agc cca ccg gtg cac ctg ccc cga agc cct          2705
Gln Tyr Gly Arg Leu Ile Ser Pro Pro Val His Leu Pro Arg Ser Pro
        700                 705                 710 gtg tgc atg gag ttc cag tac caa gcc atg ggc ggc cac ggg gtg gca          2753
Val Cys Met Glu Phe Gln Tyr Gln Ala Met Gly Gly His Gly Val Ala
715                 720                 725 ctg cag gtg gtt cgg gaa gcc agc cag gaa agc aaa ctc ctt tgg gtc          2801
Leu Gln Val Val Arg Glu Ala Ser Gln Glu Ser Lys Leu Leu Trp Val
730                 735                 740                 745 atc cgt gag gac cag ggc agc gag tgg aag cac ggg cgc att atc ctg          2849
Ile Arg Glu Asp Gln Gly Ser Glu Trp Lys His Gly Arg Ile Ile Leu
                750                 755                 760 ccc agc tat gac atg gag tat cag atc gtg ttc gag gga gtg ata ggg          2897
Pro Ser Tyr Asp Met Glu Tyr Gln Ile Val Phe Glu Gly Val Ile Gly
            765                 770                 775 aag gga cga tcg gga gag att tcc ggc gat gac att cgg ata agc act          2945
Lys Gly Arg Ser Gly Glu Ile Ser Gly Asp Asp Ile Arg Ile Ser Thr
        780                 785                 790 gat gtc cca ctg gag aac tgc atg gaa ccc ata tca gct ttt gca gat          2993
Asp Val Pro Leu Glu Asn Cys Met Glu Pro Ile Ser Ala Phe Ala Asp
795                 800                 805 gaa tat gaa gga gat tgg agc aac tct tct tcc tct acc tca ggg gct          3041
Glu Tyr Glu Gly Asp Trp Ser Asn Ser Ser Ser Ser Thr Ser Gly Ala
810                 815                 820                 825 ggt gac ccc tca tct ggc aaa gaa aag agc tgg ctg tac acc cta gat          3089
Gly Asp Pro Ser Ser Gly Lys Glu Lys Ser Trp Leu Tyr Thr Leu Asp
                830                 835                 840 ccc att ctg atc acc atc atc gcc atg agc tcg ctg ggg gtc ctg ctg          3137
Pro Ile Leu Ile Thr Ile Ile Ala Met Ser Ser Leu Gly Val Leu Leu
            845                 850                 855 ggg gcc acc tgt gcg ggc ctc ctc ctt tac tgc acc tgc tcc tat tcg          3185
Gly Ala Thr Cys Ala Gly Leu Leu Leu Tyr Cys Thr Cys Ser Tyr Ser
        860                 865                 870 ggt ctg agt tcg agg agc tgc acc aca ctg gag aac tac aac ttt gag          3233
Gly Leu Ser Ser Arg Ser Cys Thr Thr Leu Glu Asn Tyr Asn Phe Glu
875                 880                 885 ctc tac gat ggc ctc aag cac aag gtc aag atc aat cat cag aag tgc          3281
Leu Tyr Asp Gly Leu Lys His Lys Val Lys Ile Asn His Gln Lys Cys
890                 895                 900                 905 tgc tcg gag gca tgaccgattg tgtctggatc gcttctggcg tttcattcca             3333
Cys Ser Glu Ala gtgagagggg ctagcgaaga ttacagtttt gttttgtttt gttttgtttt ccctttggaa       3393
```

```
actgaatgcc ataatctgga tcaaagtgtt ccagaatact gaaggtatgg acaggacaga    3453
caggccagtc tagggagaaa gggagatgca gctgtgaagg ggatcgttgc ccaccaggac    3513
tgtggtggcc aagtgaatgc aggaaccggg cccggaattc cggctctcgg ctaaaatctc    3573
agctgcctct ggaaaggctc aaccatactc agtgccaact cagactctgt tgctgtggtg    3633
tcaacatgga tggatcatct gtaccttgta tttttagcag aattcatgct cagatttctt    3693
tgttctgaat ccttgctttg tgctagacac aaagcataca tgtccttcta aaattaatat    3753
gatcactata atctcctgtg tgcagaattc agaaatagac ctttgaaacc atttgcattg    3813
tgagtgcaga tccatgactg gggctagtgc agcaatgaaa cagaattcca gaaacagtgt    3873 gttctttta ttatgggaaa atacagataa aaatggccac tgatgaacat gaaagttagc    3933
actttcccaa cacagtgtac acttgcaacc ttgttttgga tttctcatac accaagactg    3993
tgaaacacaa atttcaagaa tgtgttcaaa tgtgtgtgtg tgtgtgtgtg tgtgtgtgtg    4053
tgtgtgtgta tgtgtgtgtg tgtgtgtgtg cttgtgtgtt tctgtcagtg gtatgagtga    4113
tatgtatgca tgtgtgtatg tatatgtatg tatgtatgta tgtatgtacg tacatatgta    4173
tgtatgtatg tatgtatgta tgtatgtata tgtgtgtgtg tgtttgtgtg tgtgtgtgtt    4233
tgtgtgtgtg tgtgtggtaa gtgtggtatg tgtgtatgca tttgtctata tgtgtatctg    4293
tgtgtctatg tgtttctgtc agtggaatga gtggcatgtg tgcatgtgta tgtatgtgga    4353
tatgtgtgtt gtgtttatgt gcttgtgtat aagaggtaag tgtggtgtgt gtgcatgtgt    4413
ctctgtgtgt gtttgtctgt gtacctcttt gtataagtac ctgtgtttgt atgtgggaat    4473
atgtatattg aggcattgct gtgttagtat gtttatagaa aagaagacag tctgagatgt    4533
cttcctcaat acctctccac ttatatcttg gatagacaaa agtaatgaca aaaaattgct    4593
ggtgtgtata tggaaaaggg ggacacatat ccatggatgg tagaagtgta aactgtgcag    4653
tcactgtgga catcaatatg caggttcttc acaaatgtag atataaagct actatagtta    4713
taccc                                                                 4718
```

<210> SEQ ID NO 10
<211> LENGTH: 909
<212> TYPE: PRT
<213> ORGANISM: mouse

<400> SEQUENCE: 10

```
Met Asp Met Phe Pro Leu Thr Trp Val Phe Leu Ala Leu Tyr Phe Ser
 1               5                  10                  15

Gly His Glu Val Arg Ser Gln Gln Asp Pro Pro Cys Gly Gly Arg Pro
            20                  25                  30

Asn Ser Lys Asp Ala Gly Tyr Ile Thr Ser Pro Gly Tyr Pro Gln Asp
        35                  40                  45

Tyr Pro Ser His Gln Asn Cys Glu Trp Ile Val Tyr Ala Pro Glu Pro
    50                  55                  60

Asn Gln Lys Ile Val Leu Asn Phe Asn Pro His Phe Glu Ile Glu Lys
65                  70                  75                  80

His Asp Cys Lys Tyr Asp Phe Ile Glu Ile Arg Asp Gly Asp Ser Glu
                85                  90                  95

Ser Ala Asp Leu Leu Gly Lys His Cys Gly Asn Ile Ala Pro Pro Thr
            100                 105                 110

Ile Ile Ser Ser Gly Ser Val Leu Tyr Ile Lys Phe Thr Ser Asp Tyr
        115                 120                 125
```

```
Ala Arg Gln Gly Ala Gly Phe Ser Leu Arg Tyr Glu Ile Phe Lys Thr
    130                 135                 140
Gly Ser Glu Asp Cys Ser Lys Asn Phe Thr Ser Pro Asn Gly Thr Ile
145                 150                 155                 160
Glu Ser Pro Gly Phe Pro Glu Lys Tyr Pro His Asn Leu Asp Cys Thr
                165                 170                 175
Phe Thr Ile Leu Ala Lys Pro Arg Met Glu Ile Ile Leu Gln Phe Leu
            180                 185                 190
Thr Phe Asp Leu Glu His Asp Pro Leu Gln Val Gly Glu Gly Asp Cys
        195                 200                 205
Lys Tyr Asp Trp Leu Asp Ile Trp Asp Gly Ile Pro His Val Gly Pro
    210                 215                 220
Leu Ile Gly Lys Tyr Cys Gly Thr Lys Thr Pro Ser Lys Leu Arg Ser
225                 230                 235                 240
Ser Thr Gly Ile Leu Ser Leu Thr Phe His Thr Asp Met Ala Val Ala
                245                 250                 255
Lys Asp Gly Phe Ser Ala Arg Tyr Tyr Leu Ile His Gln Glu Pro Pro
            260                 265                 270
Glu Asn Phe Gln Cys Asn Val Pro Leu Gly Met Glu Ser Gly Arg Ile
        275                 280                 285
Ala Asn Glu Gln Ile Ser Ala Ser Ser Thr Phe Ser Asp Gly Arg Trp
    290                 295                 300
Thr Pro Gln Gln Ser Arg Leu His Gly Asp Asp Asn Gly Trp Thr Pro
305                 310                 315                 320
Asn Leu Asp Ser Asn Lys Glu Tyr Leu Gln Val Asp Leu Arg Phe Leu
                325                 330                 335
Thr Met Leu Thr Ala Ile Ala Thr Gln Gly Ala Ile Ser Arg Glu Thr
            340                 345                 350
Gln Lys Gly Tyr Tyr Val Lys Ser Tyr Lys Leu Glu Val Ser Thr Asn
        355                 360                 365
Gly Glu Asp Trp Met Val Tyr Arg His Gly Lys Asn His Lys Ile Phe
    370                 375                 380
Gln Ala Asn Asn Asp Ala Thr Glu Val Val Leu Asn Lys Leu His Met
385                 390                 395                 400
Pro Leu Leu Thr Arg Phe Ile Arg Ile Arg Pro Gln Thr Trp His Leu
                405                 410                 415
Gly Ile Ala Leu Arg Leu Glu Leu Phe Gly Cys Arg Val Thr Asp Ala
            420                 425                 430
Pro Cys Ser Asn Met Leu Gly Met Leu Ser Gly Leu Ile Ala Asp Thr
        435                 440                 445
Gln Ile Ser Ala Ser Ser Thr Arg Glu Tyr Leu Trp Ser Pro Ser Ala
    450                 455                 460
Ala Arg Leu Val Ser Ser Arg Ser Gly Trp Phe Pro Arg Asn Pro Gln
465                 470                 475                 480
Ala Gln Pro Gly Glu Glu Trp Leu Gln Val Asp Leu Gly Thr Pro Lys
                485                 490                 495
Thr Val Lys Gly Val Ile Ile Gln Gly Ala Arg Gly Gly Asp Ser Ile
            500                 505                 510
Thr Ala Val Glu Ala Arg Ala Phe Val Arg Lys Phe Lys Val Ser Tyr
        515                 520                 525
Ser Leu Asn Gly Lys Asp Trp Glu Tyr Ile Gln Asp Pro Arg Thr Gln
    530                 535                 540
Gln Thr Lys Leu Phe Glu Gly Asn Met His Tyr Asp Thr Pro Asp Ile
```

-continued

```
545                 550                 555                 560

Arg Arg Phe Asp Pro Val Pro Ala Gln Tyr Val Arg Val Tyr Pro Glu
                565                 570                 575

Arg Trp Ser Pro Ala Gly Ile Gly Met Arg Leu Glu Val Leu Gly Cys
            580                 585                 590

Asp Trp Thr Asp Ser Lys Pro Thr Val Glu Thr Leu Gly Pro Thr Val
            595                 600                 605

Lys Ser Glu Glu Thr Thr Thr Pro Tyr Pro Met Asp Glu Asp Ala Thr
            610                 615                 620

Glu Cys Gly Glu Asn Cys Ser Phe Glu Asp Lys Asp Leu Gln Leu
625                 630                 635                 640

Pro Ser Gly Phe Asn Cys Asn Phe Asp Phe Pro Glu Glu Thr Cys Gly
                645                 650                 655

Trp Val Tyr Asp His Ala Lys Trp Leu Arg Ser Thr Trp Ile Ser Ser
                660                 665                 670

Ala Asn Pro Asn Asp Arg Thr Phe Pro Asp Asp Lys Asn Phe Leu Lys
                675                 680                 685

Leu Gln Ser Asp Gly Arg Arg Glu Gly Gln Tyr Gly Arg Leu Ile Ser
            690                 695                 700

Pro Pro Val His Leu Pro Arg Ser Pro Val Cys Met Glu Phe Gln Tyr
705                 710                 715                 720

Gln Ala Met Gly Gly His Gly Val Ala Leu Gln Val Val Arg Glu Ala
                725                 730                 735

Ser Gln Glu Ser Lys Leu Leu Trp Val Ile Arg Glu Asp Gln Gly Ser
                740                 745                 750

Glu Trp Lys His Gly Arg Ile Ile Leu Pro Ser Tyr Asp Met Glu Tyr
                755                 760                 765

Gln Ile Val Phe Glu Gly Val Ile Gly Lys Gly Arg Ser Gly Glu Ile
770                 775                 780

Ser Gly Asp Asp Ile Arg Ile Ser Thr Asp Val Pro Leu Glu Asn Cys
785                 790                 795                 800

Met Glu Pro Ile Ser Ala Phe Ala Asp Glu Tyr Glu Gly Asp Trp Ser
                805                 810                 815

Asn Ser Ser Ser Ser Thr Ser Gly Ala Gly Asp Pro Ser Ser Gly Lys
                820                 825                 830

Glu Lys Ser Trp Leu Tyr Thr Leu Asp Pro Ile Leu Ile Thr Ile Ile
            835                 840                 845

Ala Met Ser Ser Leu Gly Val Leu Leu Gly Ala Thr Cys Ala Gly Leu
850                 855                 860

Leu Leu Tyr Cys Thr Cys Ser Tyr Ser Gly Leu Ser Ser Arg Ser Cys
865                 870                 875                 880

Thr Thr Leu Glu Asn Tyr Asn Phe Glu Leu Tyr Asp Gly Leu Lys His
                885                 890                 895

Lys Val Lys Ile Asn His Gln Lys Cys Cys Ser Glu Ala
            900                 905
```

```
<210> SEQ ID NO 11
<211> LENGTH: 4733
<212> TYPE: DNA
<213> ORGANISM: mouse
<220> FEATURE:
<221> NAME/KEY: CDS
<222> LOCATION: (567)..(3308)

<400> SEQUENCE: 11
```

-continued

```
aaactggagc tccaccgcgg tggcggccgc ccgggcaggt ctagaattca gcggccgctg    60
aattctatcc agcggtcggt gcctctgccc gcgtgtgtgt cccgggtgcc gggggacctg   120
tgtcagttag cgcttctgag atcacacagc tgcctagggg ccgtgtgatg cccagggcaa   180
ttcttggctt tgatttttat tattattact attattttgc gttcagcttt cgggaaaccc   240
tcgtgatgtt gtaggataaa ggaaatgaca ctttgaggaa ctggagagaa catacacgcg   300
tttgggtttg aagaggaaac cggtctccgc ttccttagct tgctccctct ttgctgattt   360
caagagctat ctcctatgag gtggagatat tccagcaaga ataaaggtga agacagactg   420
actgccagga cccaggagga aaacgttgat cgttagagac ctttgcagaa gacaccacca   480
ggaggaaaat tagagaggaa aaacacaaag acataattat aggagatccc acaaacctag   540
cccgggagag agcctctctg tcaaaa atg gat atg ttt cct ctt acc tgg gtt   593
                                Met Asp Met Phe Pro Leu Thr Trp Val
                                  1               5
```

| | |
|---|---|
| ttc tta gct ctg tac ttt tca gga cac gaa gtg aga agc cag caa gat<br>Phe Leu Ala Leu Tyr Phe Ser Gly His Glu Val Arg Ser Gln Gln Asp<br>   10               15              20              25 | 641 |
| cca ccc tgc gga ggt cgg ccg aat tcc aaa gat gct ggc tac atc act<br>Pro Pro Cys Gly Gly Arg Pro Asn Ser Lys Asp Ala Gly Tyr Ile Thr<br>          30                  35              40 | 689 |
| tcc cca ggc tac ccc cag gac tat ccc tcc cac cag aac tgt gag tgg<br>Ser Pro Gly Tyr Pro Gln Asp Tyr Pro Ser His Gln Asn Cys Glu Trp<br>              45                  50              55 | 737 |
| att gtc tac gcc ccc gaa ccc aac cag aag att gtt ctc aac ttc aac<br>Ile Val Tyr Ala Pro Glu Pro Asn Gln Lys Ile Val Leu Asn Phe Asn<br>              60                  65              70 | 785 |
| cct cac ttt gaa atc gag aaa cac gac tgc aag tat gac ttc att gag<br>Pro His Phe Glu Ile Glu Lys His Asp Cys Lys Tyr Asp Phe Ile Glu<br>  75                  80                  85 | 833 |
| att cgg gat ggg gac agt gag tca gct gac ctc ctg ggc aag cac tgt<br>Ile Arg Asp Gly Asp Ser Glu Ser Ala Asp Leu Leu Gly Lys His Cys<br>  90                  95              100          105 | 881 |
| ggg aac atc gcc ccg ccc acc atc atc tcc tca ggc tcc gtg tta tac<br>Gly Asn Ile Ala Pro Pro Thr Ile Ile Ser Ser Gly Ser Val Leu Tyr<br>              110                115              120 | 929 |
| atc aag ttc acc tca gac tac gcc cgg cag ggg gca ggt ttc tct cta<br>Ile Lys Phe Thr Ser Asp Tyr Ala Arg Gln Gly Ala Gly Phe Ser Leu<br>              125                130              135 | 977 |
| cgc tat gag atc ttc aaa aca ggc tct gaa gat tgt tcc aag aac ttt<br>Arg Tyr Glu Ile Phe Lys Thr Gly Ser Glu Asp Cys Ser Lys Asn Phe<br>          140                145              150 | 1025 |
| aca agc ccc aat ggg acc att gaa tct cca ggg ttt cca gag aag tat<br>Thr Ser Pro Asn Gly Thr Ile Glu Ser Pro Gly Phe Pro Glu Lys Tyr<br>   155                 160              165 | 1073 |
| cca cac aat ctg gac tgt acc ttc acc atc ctg gcc aaa ccc agg atg<br>Pro His Asn Leu Asp Cys Thr Phe Thr Ile Leu Ala Lys Pro Arg Met<br>170                  175              180              185 | 1121 |
| gag atc atc cta cag ttc ctg acc ttt gac ctg gag cat gac cct cta<br>Glu Ile Ile Leu Gln Phe Leu Thr Phe Asp Leu Glu His Asp Pro Leu<br>              190                195              200 | 1169 |
| caa gtg ggg gaa gga gac tgt aaa tat gac tgg ctg gac atc tgg gat<br>Gln Val Gly Glu Gly Asp Cys Lys Tyr Asp Trp Leu Asp Ile Trp Asp<br>          205                210              215 | 1217 |
| ggc att cca cat gtt gga cct ctg att ggc aag tac tgt ggg acg aaa<br>Gly Ile Pro His Val Gly Pro Leu Ile Gly Lys Tyr Cys Gly Thr Lys<br>          220                225              230 | 1265 |
| aca ccc tcc aaa ctc cgc tcg tcc acg ggg atc ctc tcc ttg acc ttt | 1313 |

```
Thr Pro Ser Lys Leu Arg Ser Ser Thr Gly Ile Leu Ser Leu Thr Phe
    235                 240                 245 cac acg gac atg gca gtg gcc aag gat ggc ttc tcc gca cgt tac tat    1361
His Thr Asp Met Ala Val Ala Lys Asp Gly Phe Ser Ala Arg Tyr Tyr
250                 255                 260                 265 ttg atc cac cag gag cca cct gag aat ttt cag tgc aat gtc cct ttg    1409
Leu Ile His Gln Glu Pro Pro Glu Asn Phe Gln Cys Asn Val Pro Leu
                270                 275                 280 gga atg gag tct ggc cgg att gct aat gaa cag atc agt gcc tcc tcc    1457
Gly Met Glu Ser Gly Arg Ile Ala Asn Glu Gln Ile Ser Ala Ser Ser
            285                 290                 295 acc ttc tct gat ggg agg tgg act cct caa cag agc cgg ctc cat ggt    1505
Thr Phe Ser Asp Gly Arg Trp Thr Pro Gln Gln Ser Arg Leu His Gly
        300                 305                 310 gat gac aat ggc tgg aca ccc aat ttg gat tcc aac aag gag tat ctc    1553
Asp Asp Asn Gly Trp Thr Pro Asn Leu Asp Ser Asn Lys Glu Tyr Leu
    315                 320                 325 cag gtg gac ctg cgc ttc cta acc atg ctc aca gcc att gca aca cag    1601
Gln Val Asp Leu Arg Phe Leu Thr Met Leu Thr Ala Ile Ala Thr Gln
330                 335                 340                 345 gga gcc att tcc agg gaa acc cag aaa ggc tac tac gtc aaa tcg tac    1649
Gly Ala Ile Ser Arg Glu Thr Gln Lys Gly Tyr Tyr Val Lys Ser Tyr
                350                 355                 360 aag ctg gaa gtc agc aca aat ggt gaa gat tgg atg gtc tac cgg cat    1697
Lys Leu Glu Val Ser Thr Asn Gly Glu Asp Trp Met Val Tyr Arg His
            365                 370                 375 ggc aaa aac cac aag ata ttc caa gcg aac aat gat gcg acc gag gtg    1745
Gly Lys Asn His Lys Ile Phe Gln Ala Asn Asn Asp Ala Thr Glu Val
        380                 385                 390 gtg cta aac aag ctc cac atg cca ctg ctg act cgg ttc atc agg atc    1793
Val Leu Asn Lys Leu His Met Pro Leu Leu Thr Arg Phe Ile Arg Ile
    395                 400                 405 cgc ccg cag acg tgg cat ttg ggc att gcc ctt cgc ctg gag ctc ttt    1841
Arg Pro Gln Thr Trp His Leu Gly Ile Ala Leu Arg Leu Glu Leu Phe
410                 415                 420                 425 ggc tgc cgg gtc aca gat gca ccc tgc tcc aac atg ctg ggg atg ctc    1889
Gly Cys Arg Val Thr Asp Ala Pro Cys Ser Asn Met Leu Gly Met Leu
                430                 435                 440 tcg ggc ctc att gct gat acc cag atc tct gcc tcc tcc acc cga gag    1937
Ser Gly Leu Ile Ala Asp Thr Gln Ile Ser Ala Ser Ser Thr Arg Glu
            445                 450                 455 tac ctc tgg agc ccc agt gct gcc cgc ctg gtt agt agc cgc tct ggc    1985
Tyr Leu Trp Ser Pro Ser Ala Ala Arg Leu Val Ser Ser Arg Ser Gly
        460                 465                 470 tgg ttt cct cgg aac cct caa gcc cag cca ggt gaa gaa tgg ctt cag    2033
Trp Phe Pro Arg Asn Pro Gln Ala Gln Pro Gly Glu Glu Trp Leu Gln
    475                 480                 485 gta gac ctg ggg aca ccc aag aca gtg aaa ggg gtc atc atc cag gga    2081
Val Asp Leu Gly Thr Pro Lys Thr Val Lys Gly Val Ile Ile Gln Gly
490                 495                 500                 505 gcc cga gga gga gac agc atc act gcc gtg gaa gcc agg gcg ttt gta    2129
Ala Arg Gly Gly Asp Ser Ile Thr Ala Val Glu Ala Arg Ala Phe Val
                510                 515                 520 cgc aag ttc aaa gtc tcc tac agc cta aat ggc aag gac tgg gaa tat    2177
Arg Lys Phe Lys Val Ser Tyr Ser Leu Asn Gly Lys Asp Trp Glu Tyr
            525                 530                 535 atc cag gac ccc agg act cag cag aca aag ctg ttt gaa ggg aac atg    2225
Ile Gln Asp Pro Arg Thr Gln Gln Thr Lys Leu Phe Glu Gly Asn Met
        540                 545                 550
```

```
cac tat gac acc cct gac atc cga agg ttc gat cct gtt cca gcg cag    2273
His Tyr Asp Thr Pro Asp Ile Arg Arg Phe Asp Pro Val Pro Ala Gln
555                 560                 565 tat gtg cgg gtg tac cca gag agg tgg tcg cca gca ggc atc ggg atg    2321
Tyr Val Arg Val Tyr Pro Glu Arg Trp Ser Pro Ala Gly Ile Gly Met
570                 575                 580                 585 agg ctg gag gtg ctg ggc tgt gac tgg aca gac tca aag ccc aca gtg    2369
Arg Leu Glu Val Leu Gly Cys Asp Trp Thr Asp Ser Lys Pro Thr Val
            590                 595                 600 gag acg ctg gga ccc acc gtg aag agt gaa gag act acc acc cca tat    2417
Glu Thr Leu Gly Pro Thr Val Lys Ser Glu Glu Thr Thr Thr Pro Tyr
            605                 610                 615 ccc atg gat gag gat gcc acc gag tgt ggg gaa aac tgc agc ttt gag    2465
Pro Met Asp Glu Asp Ala Thr Glu Cys Gly Glu Asn Cys Ser Phe Glu
            620                 625                 630 gat gac aaa gat ttg caa ctt cct tca gga ttc aac tgc aac ttt gat    2513
Asp Asp Lys Asp Leu Gln Leu Pro Ser Gly Phe Asn Cys Asn Phe Asp
635                 640                 645 ttt ccg gaa gag acc tgt ggt tgg gtg tac gac cat gcc aag tgg ctc    2561
Phe Pro Glu Glu Thr Cys Gly Trp Val Tyr Asp His Ala Lys Trp Leu
650                 655                 660                 665 cgg agc acg tgg atc agc agc gct aac ccc aat gac aga aca ttt cca    2609
Arg Ser Thr Trp Ile Ser Ser Ala Asn Pro Asn Asp Arg Thr Phe Pro
                670                 675                 680 gat gac aag aac ttc ttg aaa ctg cag agt gat ggc cga cga gag ggc    2657
Asp Asp Lys Asn Phe Leu Lys Leu Gln Ser Asp Gly Arg Arg Glu Gly
                685                 690                 695 cag tac ggg cgg ctc atc agc cca ccg gtg cac ctg ccc cga agc cct    2705
Gln Tyr Gly Arg Leu Ile Ser Pro Pro Val His Leu Pro Arg Ser Pro
                700                 705                 710 gtg tgc atg gag ttc cag tac caa gcc atg ggc ggc cac ggg gtg gca    2753
Val Cys Met Glu Phe Gln Tyr Gln Ala Met Gly Gly His Gly Val Ala
715                 720                 725 ctg cag gtg gtt cgg gaa gcc agc cag gaa agc aaa ctc ctt tgg gtc    2801
Leu Gln Val Val Arg Glu Ala Ser Gln Glu Ser Lys Leu Leu Trp Val
730                 735                 740                 745 atc cgt gag gac cag ggc agc gag tgg aag cac ggg cgc att atc ctg    2849
Ile Arg Glu Asp Gln Gly Ser Glu Trp Lys His Gly Arg Ile Ile Leu
                750                 755                 760 ccc agc tat gac atg gag tat cag atc gtg ttc gag gga gtg ata ggg    2897
Pro Ser Tyr Asp Met Glu Tyr Gln Ile Val Phe Glu Gly Val Ile Gly
                765                 770                 775 aag gga cga tcg gga gag att tcc ggc gat gac att cgg ata agc act    2945
Lys Gly Arg Ser Gly Glu Ile Ser Gly Asp Asp Ile Arg Ile Ser Thr
                780                 785                 790 gat gtc cca ctg gag aac tgc atg gaa ccc ata tca gct ttt gca ggt    2993
Asp Val Pro Leu Glu Asn Cys Met Glu Pro Ile Ser Ala Phe Ala Gly
795                 800                 805 gag gat ttt aaa gat gaa tat gaa gga gat tgg agc aac tct tct tcc    3041
Glu Asp Phe Lys Asp Glu Tyr Glu Gly Asp Trp Ser Asn Ser Ser Ser
810                 815                 820                 825 tct acc tca ggg gct ggt gac ccc tca tct ggc aaa gaa aag agc tgg    3089
Ser Thr Ser Gly Ala Gly Asp Pro Ser Ser Gly Lys Glu Lys Ser Trp
                830                 835                 840 ctg tac acc cta gat ccc att ctg atc acc atc atc gcc atg agc tcg    3137
Leu Tyr Thr Leu Asp Pro Ile Leu Ile Thr Ile Ile Ala Met Ser Ser
                845                 850                 855 ctg ggg gtc ctg ctg ggg gcc acc tgt gcg ggc ctc ctc ctt tac tgc    3185
Leu Gly Val Leu Leu Gly Ala Thr Cys Ala Gly Leu Leu Leu Tyr Cys
860                 865                 870
```

-continued

```
acc tgc tcc tat tcg ggt ctg agt tcg agg agc tgc acc aca ctg gag    3233
Thr Cys Ser Tyr Ser Gly Leu Ser Ser Arg Ser Cys Thr Thr Leu Glu
    875                 880                 885 aac tac aac ttt gag ctc tac gat ggc ctc aag cac aag gtc aag atc    3281
Asn Tyr Asn Phe Glu Leu Tyr Asp Gly Leu Lys His Lys Val Lys Ile
890                 895                 900                 905 aat cat cag aag tgc tgc tcg gag gca tgaccgattg tgtctggatc          3328
Asn His Gln Lys Cys Cys Ser Glu Ala
                910 gcttctggcg tttcattcca gtgagagggg ctagcgaaga ttacagtttt gttttgtttt   3388 gttttgtttt ccctttggaa actgaatgcc ataatctgga tcaaagtgtt ccagaatact   3448 gaaggtatgg acaggacaga caggccagtc tagggagaaa gggagatgca gctgtgaagg   3508 ggatcgttgc ccaccaggac tgtggtggcc aagtgaatgc aggaaccggg cccggaattc   3568 cggctctcgg ctaaaatctc agctgcctct ggaaaggctc aaccatactc agtgccaact   3628 cagactctgt tgctgtggtg tcaacatgga tggatcatct gtaccttgta tttttagcag   3688 aattcatgct cagatttctt tgttctgaat ccttgctttg tgctagacac aaagcataca   3748 tgtccttcta aaattaatat gatcactata atctcctgtg tgcagaattc agaaatagac   3808 ctttgaaacc atttgcattg tgagtgcaga tccatgactg gggctagtgc agcaatgaaa   3868 cagaattcca gaaacagtgt gttcttttta ttatgggaaa atacagataa aaatggccac   3928 tgatgaacat gaaagttagc actttcccaa cacagtgtac acttgcaacc ttgttttgga   3988 tttctcatac accaagactg tgaaacacaa atttcaagaa tgtgttcaaa tgtgtgtgtg   4048 tgtgtgtgtg tgtgtgtgta tgtgtgtgtg tgtgtgtgtg cttgtgtgtt              4108 tctgtcagtg gtatgagtga tatgtatgca tgtgtgtatg tatatgtatg tatgtatgta   4168 tgtatgtacg tacatatgta tgtatgtatg tatgtatgta tgtatgtata tgtgtgtgtg   4228 tgtttgtgtg tgtgtgtgtt tgtgtgtgtg tgtgtggtaa gtgtggtatg tgtgtatgca   4288 tttgtctata tgtgtatctg tgtgtctatg tgtttctgtc agtggaatga gtggcatgtg   4348 tgcatgtgta tgtatgtgga tatgtgtgtt gtgtttatgt gcttgtgtat aagaggtaag   4408 tgtggtgtgt gtgcatgtgt ctctgtgtgt gtttgtctgt gtacctcttt gtataagtac   4468 ctgtgtttgt atgtgggaat atgtatattg aggcattgct gtgttagtat gtttatagaa   4528 aagaagacag tctgagatgt cttcctcaat acctctccac ttatatcttg gatagacaaa   4588 agtaatgaca aaaaattgct ggtgtgtata tggaaaaggg ggacacatat ccatggatgg   4648 tagaagtgta aactgtgcag tcactgtgga catcaatatg caggttcttc acaaatgtag   4708 atataaagct actatagtta taccc                                         4733
```

<210> SEQ ID NO 12
<211> LENGTH: 914
<212> TYPE: PRT
<213> ORGANISM: mouse

<400> SEQUENCE: 12

```
Met Asp Met Phe Pro Leu Thr Trp Val Phe Leu Ala Leu Tyr Phe Ser
 1               5                  10                  15

Gly His Glu Val Arg Ser Gln Gln Asp Pro Pro Cys Gly Gly Arg Pro
            20                  25                  30

Asn Ser Lys Asp Ala Gly Tyr Ile Thr Ser Pro Gly Tyr Pro Gln Asp
        35                  40                  45

Tyr Pro Ser His Gln Asn Cys Glu Trp Ile Val Tyr Ala Pro Glu Pro
```

-continued

```
            50                     55                      60
Asn Gln Lys Ile Val Leu Asn Phe Asn Pro His Phe Glu Ile Glu Lys
 65                      70                      75                      80

His Asp Cys Lys Tyr Asp Phe Ile Glu Ile Arg Asp Gly Asp Ser Glu
                     85                      90                      95

Ser Ala Asp Leu Leu Gly Lys His Cys Gly Asn Ile Ala Pro Pro Thr
                    100                     105                     110

Ile Ile Ser Ser Gly Ser Val Leu Tyr Ile Lys Phe Thr Ser Asp Tyr
                    115                     120                     125

Ala Arg Gln Gly Ala Gly Phe Ser Leu Arg Tyr Glu Ile Phe Lys Thr
                    130                     135                     140

Gly Ser Glu Asp Cys Ser Lys Asn Phe Thr Ser Pro Asn Gly Thr Ile
145                     150                     155                     160

Glu Ser Pro Gly Phe Pro Glu Lys Tyr Pro His Asn Leu Asp Cys Thr
                    165                     170                     175

Phe Thr Ile Leu Ala Lys Pro Arg Met Glu Ile Ile Leu Gln Phe Leu
                    180                     185                     190

Thr Phe Asp Leu Glu His Asp Pro Leu Gln Val Gly Glu Gly Asp Cys
                    195                     200                     205

Lys Tyr Asp Trp Leu Asp Ile Trp Asp Gly Ile Pro His Val Gly Pro
                    210                     215                     220

Leu Ile Gly Lys Tyr Cys Gly Thr Lys Thr Pro Ser Lys Leu Arg Ser
225                     230                     235                     240

Ser Thr Gly Ile Leu Ser Leu Thr Phe His Thr Asp Met Ala Val Ala
                    245                     250                     255

Lys Asp Gly Phe Ser Ala Arg Tyr Tyr Leu Ile His Gln Glu Pro Pro
                    260                     265                     270

Glu Asn Phe Gln Cys Asn Val Pro Leu Gly Met Glu Ser Gly Arg Ile
                    275                     280                     285

Ala Asn Glu Gln Ile Ser Ala Ser Ser Thr Phe Ser Asp Gly Arg Trp
                    290                     295                     300

Thr Pro Gln Gln Ser Arg Leu His Gly Asp Asp Asn Gly Trp Thr Pro
305                     310                     315                     320

Asn Leu Asp Ser Asn Lys Glu Tyr Leu Gln Val Asp Leu Arg Phe Leu
                    325                     330                     335

Thr Met Leu Thr Ala Ile Ala Thr Gln Gly Ala Ile Ser Arg Glu Thr
                    340                     345                     350

Gln Lys Gly Tyr Tyr Val Lys Ser Tyr Lys Leu Glu Val Ser Thr Asn
                    355                     360                     365

Gly Glu Asp Trp Met Val Tyr Arg His Gly Lys Asn His Lys Ile Phe
                    370                     375                     380

Gln Ala Asn Asn Asp Ala Thr Glu Val Val Leu Asn Lys Leu His Met
385                     390                     395                     400

Pro Leu Leu Thr Arg Phe Ile Arg Ile Arg Pro Gln Thr Trp His Leu
                    405                     410                     415

Gly Ile Ala Leu Arg Leu Glu Leu Phe Gly Cys Arg Val Thr Asp Ala
                    420                     425                     430

Pro Cys Ser Asn Met Leu Gly Met Leu Ser Gly Leu Ile Ala Asp Thr
                    435                     440                     445

Gln Ile Ser Ala Ser Ser Thr Arg Glu Tyr Leu Trp Ser Pro Ser Ala
                    450                     455                     460

Ala Arg Leu Val Ser Ser Arg Ser Gly Trp Phe Pro Arg Asn Pro Gln
465                     470                     475                     480
```

```
Ala Gln Pro Gly Glu Glu Trp Leu Gln Val Asp Leu Gly Thr Pro Lys
                485                 490                 495

Thr Val Lys Gly Val Ile Ile Gln Gly Ala Arg Gly Gly Asp Ser Ile
            500                 505                 510

Thr Ala Val Glu Ala Arg Ala Phe Val Arg Lys Phe Lys Val Ser Tyr
        515                 520                 525

Ser Leu Asn Gly Lys Asp Trp Glu Tyr Ile Gln Asp Pro Arg Thr Gln
    530                 535                 540

Gln Thr Lys Leu Phe Glu Gly Asn Met His Tyr Asp Thr Pro Asp Ile
545                 550                 555                 560

Arg Arg Phe Asp Pro Val Pro Ala Gln Tyr Val Arg Val Tyr Pro Glu
            565                 570                 575

Arg Trp Ser Pro Ala Gly Ile Gly Met Arg Leu Glu Val Leu Gly Cys
            580                 585                 590

Asp Trp Thr Asp Ser Lys Pro Thr Val Glu Thr Leu Gly Pro Thr Val
            595                 600                 605

Lys Ser Glu Glu Thr Thr Thr Pro Tyr Pro Met Asp Glu Asp Ala Thr
            610                 615                 620

Glu Cys Gly Glu Asn Cys Ser Phe Glu Asp Asp Lys Asp Leu Gln Leu
625                 630                 635                 640

Pro Ser Gly Phe Asn Cys Asn Phe Asp Phe Pro Glu Glu Thr Cys Gly
                645                 650                 655

Trp Val Tyr Asp His Ala Lys Trp Leu Arg Ser Thr Trp Ile Ser Ser
                660                 665                 670

Ala Asn Pro Asn Asp Arg Thr Phe Pro Asp Asp Lys Asn Phe Leu Lys
            675                 680                 685

Leu Gln Ser Asp Gly Arg Arg Glu Gly Gln Tyr Gly Arg Leu Ile Ser
    690                 695                 700

Pro Pro Val His Leu Pro Arg Ser Pro Val Cys Met Glu Phe Gln Tyr
705                 710                 715                 720

Gln Ala Met Gly Gly His Gly Val Ala Leu Gln Val Val Arg Glu Ala
                725                 730                 735

Ser Gln Glu Ser Lys Leu Leu Trp Val Ile Arg Glu Asp Gln Gly Ser
            740                 745                 750

Glu Trp Lys His Gly Arg Ile Ile Leu Pro Ser Tyr Asp Met Glu Tyr
    755                 760                 765

Gln Ile Val Phe Glu Gly Val Ile Gly Lys Gly Arg Ser Gly Glu Ile
    770                 775                 780

Ser Gly Asp Asp Ile Arg Ile Ser Thr Asp Val Pro Leu Glu Asn Cys
785                 790                 795                 800

Met Glu Pro Ile Ser Ala Phe Ala Gly Glu Asp Phe Lys Asp Glu Tyr
                805                 810                 815

Glu Gly Asp Trp Ser Asn Ser Ser Ser Thr Ser Gly Ala Gly Asp
            820                 825                 830

Pro Ser Ser Gly Lys Glu Lys Ser Trp Leu Tyr Thr Leu Asp Pro Ile
            835                 840                 845

Leu Ile Thr Ile Ile Ala Met Ser Ser Leu Gly Val Leu Leu Gly Ala
    850                 855                 860

Thr Cys Ala Gly Leu Leu Leu Tyr Cys Thr Cys Ser Tyr Ser Gly Leu
865                 870                 875                 880

Ser Ser Arg Ser Cys Thr Thr Leu Glu Asn Tyr Asn Phe Glu Leu Tyr
                885                 890                 895
```

Asp Gly Leu Lys His Lys Val Lys Ile Asn His Gln Lys Cys Cys Ser
            900                 905                 910

Glu Ala

<210> SEQ ID NO 13
<211> LENGTH: 4769
<212> TYPE: DNA
<213> ORGANISM: mouse
<220> FEATURE:
<221> NAME/KEY: CDS
<222> LOCATION: (567)..(3344)

<400> SEQUENCE: 13

| | |
|---|---:|
| aaactggagc tccaccgcgg tggcggccgc ccgggcaggt ctagaattca gcggccgctg | 60 |
| aattctatcc agcggtcggt gcctctgccc gcgtgtgtgt cccgggtgcc ggggacctg | 120 |
| tgtcagttag cgcttctgag atcacacagc tgcctagggg ccgtgtgatg cccagggcaa | 180 |
| ttcttggctt tgattttat tattattact attattttgc gttcagcttt cgggaaaccc | 240 |
| tcgtgatgtt gtaggataaa ggaaatgaca ctttgaggaa ctggagagaa catacacgcg | 300 |
| tttgggtttg aagaggaaac cggtctccgc ttccttagct tgctccctct ttgctgattt | 360 |
| caagagctat ctcctatgag gtggagatat tccagcaaga ataaaggtga agacagactg | 420 |
| actgccagga cccaggagga aaacgttgat cgttagagac ctttgcagaa gacaccacca | 480 |
| ggaggaaaat tagagaggaa aaacacaaag acataattat aggagatccc acaaacctag | 540 |

```
cccgggagag agcctctctg tcaaaa atg gat atg ttt cct ctt acc tgg gtt      593
                             Met Asp Met Phe Pro Leu Thr Trp Val
                              1               5 ttc tta gct ctg tac ttt tca gga cac gaa gtg aga agc cag caa gat      641
Phe Leu Ala Leu Tyr Phe Ser Gly His Glu Val Arg Ser Gln Gln Asp
 10              15                  20                  25 cca ccc tgc gga ggt cgg ccg aat tcc aaa gat gct ggc tac atc act      689
Pro Pro Cys Gly Gly Arg Pro Asn Ser Lys Asp Ala Gly Tyr Ile Thr
             30                  35                  40 tcc cca ggc tac ccc cag gac tat ccc tcc cac cag aac tgt gag tgg      737
Ser Pro Gly Tyr Pro Gln Asp Tyr Pro Ser His Gln Asn Cys Glu Trp
         45                  50                  55 att gtc tac gcc ccc gaa ccc aac cag aag att gtt ctc aac ttc aac      785
Ile Val Tyr Ala Pro Glu Pro Asn Gln Lys Ile Val Leu Asn Phe Asn
     60                  65                  70 cct cac ttt gaa atc gag aaa cac gac tgc aag tat gac ttc att gag      833
Pro His Phe Glu Ile Glu Lys His Asp Cys Lys Tyr Asp Phe Ile Glu
 75                  80                  85 att cgg gat ggg gac agt gag tca gct gac ctc ctg ggc aag cac tgt      881
Ile Arg Asp Gly Asp Ser Glu Ser Ala Asp Leu Leu Gly Lys His Cys
 90                  95                 100                 105 ggg aac atc gcc ccg ccc acc atc atc tcc tca ggc tcc gtg tta tac      929
Gly Asn Ile Ala Pro Pro Thr Ile Ile Ser Ser Gly Ser Val Leu Tyr
             110                 115                 120 atc aag ttc acc tca gac tac gcc cgg cag ggg gca ggt ttc tct cta      977
Ile Lys Phe Thr Ser Asp Tyr Ala Arg Gln Gly Ala Gly Phe Ser Leu
         125                 130                 135 cgc tat gag atc ttc aaa aca ggc tct gaa gat tgt tcc aag aac ttt      1025
Arg Tyr Glu Ile Phe Lys Thr Gly Ser Glu Asp Cys Ser Lys Asn Phe
     140                 145                 150 aca agc ccc aat ggg acc att gaa tct cca ggg ttt cca gag aag tat      1073
Thr Ser Pro Asn Gly Thr Ile Glu Ser Pro Gly Phe Pro Glu Lys Tyr
 155                 160                 165 cca cac aat ctg gac tgt acc ttc acc atc ctg gcc aaa ccc agg atg      1121
```

```
                                                                          -continued Pro His Asn Leu Asp Cys Thr Phe Thr Ile Leu Ala Lys Pro Arg Met
170                 175                 180                 185 gag atc atc cta cag ttc ctg acc ttt gac ctg gag cat gac cct cta      1169
Glu Ile Ile Leu Gln Phe Leu Thr Phe Asp Leu Glu His Asp Pro Leu
            190                 195                 200 caa gtg ggg gaa gga gac tgt aaa tat gac tgg ctg gac atc tgg gat      1217
Gln Val Gly Glu Gly Asp Cys Lys Tyr Asp Trp Leu Asp Ile Trp Asp
                205                 210                 215 ggc att cca cat gtt gga cct ctg att ggc aag tac tgt ggg acg aaa      1265
Gly Ile Pro His Val Gly Pro Leu Ile Gly Lys Tyr Cys Gly Thr Lys
        220                 225                 230 aca ccc tcc aaa ctc cgc tcg tcc acg ggg atc ctc tcc ttg acc ttt      1313
Thr Pro Ser Lys Leu Arg Ser Ser Thr Gly Ile Leu Ser Leu Thr Phe
    235                 240                 245 cac acg gac atg gca gtg gcc aag gat ggc ttc tcc gca cgt tac tat      1361
His Thr Asp Met Ala Val Ala Lys Asp Gly Phe Ser Ala Arg Tyr Tyr
250                 255                 260                 265 ttg atc cac cag gag cca cct gag aat ttt cag tgc aat gtc cct ttg      1409
Leu Ile His Gln Glu Pro Pro Glu Asn Phe Gln Cys Asn Val Pro Leu
                270                 275                 280 gga atg gag tct ggc cgg att gct aat gaa cag atc agt gcc tcc tcc      1457
Gly Met Glu Ser Gly Arg Ile Ala Asn Glu Gln Ile Ser Ala Ser Ser
            285                 290                 295 acc ttc tct gat ggg agg tgg act cct caa cag agc cgg ctc cat ggt      1505
Thr Phe Ser Asp Gly Arg Trp Thr Pro Gln Gln Ser Arg Leu His Gly
                300                 305                 310 gat gac aat ggc tgg aca ccc aat ttg gat tcc aac aag gag tat ctc      1553
Asp Asp Asn Gly Trp Thr Pro Asn Leu Asp Ser Asn Lys Glu Tyr Leu
        315                 320                 325 cag gtg gac ctg cgc ttc cta acc atg ctc aca gcc att gca aca cag      1601
Gln Val Asp Leu Arg Phe Leu Thr Met Leu Thr Ala Ile Ala Thr Gln
330                 335                 340                 345 gga gcc att tcc agg gaa acc cag aaa ggc tac tac gtc aaa tcg tac      1649
Gly Ala Ile Ser Arg Glu Thr Gln Lys Gly Tyr Tyr Val Lys Ser Tyr
                350                 355                 360 aag ctg gaa gtc agc aca aat ggt gaa gat tgg atg gtc tac cgg cat      1697
Lys Leu Glu Val Ser Thr Asn Gly Glu Asp Trp Met Val Tyr Arg His
            365                 370                 375 ggc aaa aac cac aag ata ttc caa gcg aac aat gat gcg acc gag gtg      1745
Gly Lys Asn His Lys Ile Phe Gln Ala Asn Asn Asp Ala Thr Glu Val
        380                 385                 390 gtg cta aac aag ctc cac atg cca ctg ctg act cgg ttc atc agg atc      1793
Val Leu Asn Lys Leu His Met Pro Leu Leu Thr Arg Phe Ile Arg Ile
    395                 400                 405 cgc ccg cag acg tgg cat ttg ggc att gcc ctt cgc ctg gag ctc ttt      1841
Arg Pro Gln Thr Trp His Leu Gly Ile Ala Leu Arg Leu Glu Leu Phe
410                 415                 420                 425 ggc tgc cgg gtc aca gat gca ccc tgc tcc aac atg ctg ggg atg ctc      1889
Gly Cys Arg Val Thr Asp Ala Pro Cys Ser Asn Met Leu Gly Met Leu
                430                 435                 440 tcg ggc ctc att gct gat acc cag atc tct gcc tcc tcc acc cga gag      1937
Ser Gly Leu Ile Ala Asp Thr Gln Ile Ser Ala Ser Ser Thr Arg Glu
            445                 450                 455 tac ctc tgg agc ccc agt gct gcc cgc ctg gtt agt agc cgc tct ggc      1985
Tyr Leu Trp Ser Pro Ser Ala Ala Arg Leu Val Ser Ser Arg Ser Gly
        460                 465                 470 tgg ttt cct cgg aac cct caa gcc cag cca ggt gaa gaa tgg ctt cag      2033
Trp Phe Pro Arg Asn Pro Gln Ala Gln Pro Gly Glu Glu Trp Leu Gln
    475                 480                 485
```

```
gta gac ctg ggg aca ccc aag aca gtg aaa ggg gtc atc atc cag gga    2081
Val Asp Leu Gly Thr Pro Lys Thr Val Lys Gly Val Ile Ile Gln Gly
490             495                 500                 505 gcc cga gga gga gac agc atc act gcc gtg gaa gcc agg gcg ttt gta    2129
Ala Arg Gly Gly Asp Ser Ile Thr Ala Val Glu Ala Arg Ala Phe Val
                510                 515                 520 cgc aag ttc aaa gtc tcc tac agc cta aat ggc aag gac tgg gaa tat    2177
Arg Lys Phe Lys Val Ser Tyr Ser Leu Asn Gly Lys Asp Trp Glu Tyr
            525                 530                 535 atc cag gac ccc agg act cag cag aca aag ctg ttt gaa ggg aac atg    2225
Ile Gln Asp Pro Arg Thr Gln Gln Thr Lys Leu Phe Glu Gly Asn Met
        540                 545                 550 cac tat gac acc cct gac atc cga agg ttc gat cct gtt cca gcg cag    2273
His Tyr Asp Thr Pro Asp Ile Arg Arg Phe Asp Pro Val Pro Ala Gln
    555                 560                 565 tat gtg cgg gtg tac cca gag agg tgg tcg cca gca ggc atc ggg atg    2321
Tyr Val Arg Val Tyr Pro Glu Arg Trp Ser Pro Ala Gly Ile Gly Met
570                 575                 580                 585 agg ctg gag gtg ctg ggc tgt gac tgg aca gac tca aag ccc aca gtg    2369
Arg Leu Glu Val Leu Gly Cys Asp Trp Thr Asp Ser Lys Pro Thr Val
                590                 595                 600 gag acg ctg gga ccc acc gtg aag agt gaa gag act acc acc cca tat    2417
Glu Thr Leu Gly Pro Thr Val Lys Ser Glu Glu Thr Thr Thr Pro Tyr
            605                 610                 615 ccc atg gat gag gat gcc acc gag tgt ggg gaa aac tgc agc ttt gag    2465
Pro Met Asp Glu Asp Ala Thr Glu Cys Gly Glu Asn Cys Ser Phe Glu
        620                 625                 630 gat gac aaa gat ttg caa ctt cct tca gga ttc aac tgc aac ttt gat    2513
Asp Asp Lys Asp Leu Gln Leu Pro Ser Gly Phe Asn Cys Asn Phe Asp
    635                 640                 645 ttt ccg gaa gag acc tgt ggt tgg gtg tac gac cat gcc aag tgg ctc    2561
Phe Pro Glu Glu Thr Cys Gly Trp Val Tyr Asp His Ala Lys Trp Leu
650                 655                 660                 665 cgg agc acg tgg atc agc agc gct aac ccc aat gac aga aca ttt cca    2609
Arg Ser Thr Trp Ile Ser Ser Ala Asn Pro Asn Asp Arg Thr Phe Pro
                670                 675                 680 gat gac aag aac ttc ttg aaa ctg cag agt gat ggc cga cga gag ggc    2657
Asp Asp Lys Asn Phe Leu Lys Leu Gln Ser Asp Gly Arg Arg Glu Gly
            685                 690                 695 cag tac ggg cgg ctc atc agc cca ccg gtg cac ctg ccc cga agc cct    2705
Gln Tyr Gly Arg Leu Ile Ser Pro Pro Val His Leu Pro Arg Ser Pro
        700                 705                 710 gtg tgc atg gag ttc cag tac caa gcc atg ggc ggc cac ggg gtg gca    2753
Val Cys Met Glu Phe Gln Tyr Gln Ala Met Gly Gly His Gly Val Ala
    715                 720                 725 ctg cag gtg gtt cgg gaa gcc agc cag gaa agc aaa ctc ctt tgg gtc    2801
Leu Gln Val Val Arg Glu Ala Ser Gln Glu Ser Lys Leu Leu Trp Val
730                 735                 740                 745 atc cgt gag gac cag ggc agc gag tgg aag cac ggg cgc att atc ctg    2849
Ile Arg Glu Asp Gln Gly Ser Glu Trp Lys His Gly Arg Ile Ile Leu
                750                 755                 760 ccc agc tat gac atg gag tat cag atc gtg ttc gag gga gtg ata ggg    2897
Pro Ser Tyr Asp Met Glu Tyr Gln Ile Val Phe Glu Gly Val Ile Gly
            765                 770                 775 aag gga cga tcg gga gag att tcc ggc gat gac att cgg ata agc act    2945
Lys Gly Arg Ser Gly Glu Ile Ser Gly Asp Asp Ile Arg Ile Ser Thr
        780                 785                 790 gat gtc cca ctg gag aac tgc atg gaa ccc ata tca gct ttt gca gtg    2993
Asp Val Pro Leu Glu Asn Cys Met Glu Pro Ile Ser Ala Phe Ala Val
    795                 800                 805
```

```
gac atc cca gaa acc cat ggg gga gag ggc tat gaa gat gag att gat    3041
Asp Ile Pro Glu Thr His Gly Gly Glu Gly Tyr Glu Asp Glu Ile Asp
810                 815                 820                 825 gat gaa tat gaa gga gat tgg agc aac tct tct tcc tct acc tca ggg    3089
Asp Glu Tyr Glu Gly Asp Trp Ser Asn Ser Ser Ser Ser Thr Ser Gly
            830                 835                 840 gct ggt gac ccc tca tct ggc aaa gaa aag agc tgg ctg tac acc cta    3137
Ala Gly Asp Pro Ser Ser Gly Lys Glu Lys Ser Trp Leu Tyr Thr Leu
                845                 850                 855 gat ccc att ctg atc acc atc atc gcc atg agc tcg ctg ggg gtc ctg    3185
Asp Pro Ile Leu Ile Thr Ile Ile Ala Met Ser Ser Leu Gly Val Leu
            860                 865                 870 ctg ggg gcc acc tgt gcg ggc ctc ctc ctt tac tgc acc tgc tcc tat    3233
Leu Gly Ala Thr Cys Ala Gly Leu Leu Leu Tyr Cys Thr Cys Ser Tyr
    875                 880                 885 tcg ggt ctg agt tcg agg agc tgc acc aca ctg gag aac tac aac ttt    3281
Ser Gly Leu Ser Ser Arg Ser Cys Thr Thr Leu Glu Asn Tyr Asn Phe
890                 895                 900                 905 gag ctc tac gat ggc ctc aag cac aag gtc aag atc aat cat cag aag    3329
Glu Leu Tyr Asp Gly Leu Lys His Lys Val Lys Ile Asn His Gln Lys
                910                 915                 920 tgc tgc tcg gag gca tgaccgattg tgtctggatc gcttctggcg tttcattcca    3384
Cys Cys Ser Glu Ala
                925 gtgagagggg ctagcgaaga ttacagtttt gttttgtttt gttttgtttt ccctttggaa    3444 actgaatgcc ataatctgga tcaaagtgtt ccagaatact gaaggtatgg acaggacaga    3504 caggccagtc tagggagaaa gggagatgca gctgtgaagg gatcgttgc ccaccaggac     3564 tgtggtggcc aagtgaatgc aggaaccggg cccggaattc cggctctcgg ctaaaatctc    3624 agctgcctct ggaaaggctc aaccatactc agtgccaact cagactctgt tgctgtggtg    3684 tcaacatgga tggatcatct gtaccttgta tttttagcag aattcatgct cagatttctt    3744 tgttctgaat ccttgctttg tgctagacac aaagcataca tgtccttcta aaattaatat    3804 gatcactata atctcctgtg tgcagaattc agaaatagac ctttgaaacc atttgcattg    3864 tgagtgcaga tccatgactg gggctagtgc agcaatgaaa cagaattcca gaaacagtgt    3924 gttctttta ttatgggaaa atacagataa aaatggccac tgatgaacat gaaagttagc     3984 actttcccaa cacagtgtac acttgcaacc ttgttttgga tttctcatac accaagactg    4044 tgaaacacaa atttcaagaa tgtgttcaaa tgtgtgtgtg tgtgtgtgtg tgtgtgtgtg    4104 tgtgtgtgta tgtgtgtgtg tgtgtgtgtg cttgtgtgtt tctgtcagtg gtatgagtga    4164 tatgtatgca tgtgtgtatg tatatgtatg tatgtatgta tgtatgtacg tacatatgta    4224 tgtatgtatg tatgtgtata tgtgtgtgtg tgtttgtgtg tgtgtgtgtt               4284 tgtgtgtgtg tgtgtggtaa gtgtggtatg tgtgtatgca tttgtctata tgtgtatctg    4344 tgtgtctatg tgtttctgtc agtggaatga gtggcatgtg tgcatgtgta tgtatgtgga    4404 tatgtgtgtt gtgtttatgt gcttgtgtat aagaggtaag tgtggtgtgt gtgcatgtgt    4464 ctctgtgtgt gtttgtctgt gtacctcttt gtataagtac ctgtgtttgt atgtgggaat    4524 atgtatattg aggcattgct gtgttagtat gtttatagaa aagaagacag tctgagatgt    4584 cttcctcaat acctctccac ttatatcttg gatagacaaa agtaatgaca aaaaattgct    4644 ggtgtgtata tggaaaaggg ggacacatat ccatggatgg tagaagtgta aactgtgcag    4704 tcactgtgga catcaatatg caggttcttc acaaatgtag atataaagct actatagtta    4764
```

```
taccc                                                                    4769
```

<210> SEQ ID NO 14
<211> LENGTH: 926
<212> TYPE: PRT
<213> ORGANISM: mouse

<400> SEQUENCE: 14

```
Met Asp Met Phe Pro Leu Thr Trp Val Phe Leu Ala Leu Tyr Phe Ser
 1               5                  10                  15

Gly His Glu Val Arg Ser Gln Gln Asp Pro Pro Cys Gly Gly Arg Pro
             20                  25                  30

Asn Ser Lys Asp Ala Gly Tyr Ile Thr Ser Pro Gly Tyr Pro Gln Asp
         35                  40                  45

Tyr Pro Ser His Gln Asn Cys Glu Trp Ile Val Tyr Ala Pro Glu Pro
     50                  55                  60

Asn Gln Lys Ile Val Leu Asn Phe Asn Pro His Phe Glu Ile Glu Lys
 65                  70                  75                  80

His Asp Cys Lys Tyr Asp Phe Ile Glu Ile Arg Asp Gly Asp Ser Glu
                 85                  90                  95

Ser Ala Asp Leu Leu Gly Lys His Cys Gly Asn Ile Ala Pro Pro Thr
            100                 105                 110

Ile Ile Ser Ser Gly Ser Val Leu Tyr Ile Lys Phe Thr Ser Asp Tyr
        115                 120                 125

Ala Arg Gln Gly Ala Gly Phe Ser Leu Arg Tyr Glu Ile Phe Lys Thr
    130                 135                 140

Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                165                 170                 175

Phe Thr Ile Leu Ala Lys Pro Arg Met Glu Ile Ile Leu Gln Phe Leu
            180                 185                 190

Thr Phe Asp Leu Glu His Asp Pro Leu Gln Val Gly Glu Gly Asp Cys
        195                 200                 205

Lys Tyr Asp Trp Leu Asp Ile Trp Asp Gly Ile Pro His Val Gly Pro
    210                 215                 220

Leu Ile Gly Lys Tyr Cys Gly Thr Lys Thr Pro Ser Lys Leu Arg Ser
225                 230                 235                 240

Ser Thr Gly Ile Leu Ser Leu Thr Phe His Thr Asp Met Ala Val Ala
                245                 250                 255

Lys Asp Gly Phe Ser Ala Arg Tyr Tyr Leu Ile His Gln Glu Pro Pro
            260                 265                 270

Glu Asn Phe Gln Cys Asn Val Pro Leu Gly Met Glu Ser Gly Arg Ile
        275                 280                 285

Ala Asn Glu Gln Ile Ser Ala Ser Ser Thr Phe Ser Asp Gly Arg Trp
    290                 295                 300

Thr Pro Gln Gln Ser Arg Leu His Gly Asp Asp Asn Gly Trp Thr Pro
305                 310                 315                 320

Asn Leu Asp Ser Asn Lys Glu Tyr Leu Gln Val Asp Leu Arg Phe Leu
                325                 330                 335

Thr Met Leu Thr Ala Ile Ala Thr Gln Gly Ala Ile Ser Arg Glu Thr
            340                 345                 350

Gln Lys Gly Tyr Tyr Val Lys Ser Tyr Lys Leu Glu Val Ser Thr Asn
        355                 360                 365
```

-continued

```
Gly Glu Asp Trp Met Val Tyr Arg His Gly Lys Asn His Lys Ile Phe
        370                 375                 380

Gln Ala Asn Asn Asp Ala Thr Glu Val Val Leu Asn Lys Leu His Met
385                 390                 395                 400

Pro Leu Leu Thr Arg Phe Ile Arg Ile Arg Pro Gln Thr Trp His Leu
                405                 410                 415

Gly Ile Ala Leu Arg Leu Glu Leu Phe Gly Cys Arg Val Thr Asp Ala
                420                 425                 430

Pro Cys Ser Asn Met Leu Gly Met Leu Ser Gly Leu Ile Ala Asp Thr
                435                 440                 445

Gln Ile Ser Ala Ser Ser Thr Arg Glu Tyr Leu Trp Ser Pro Ser Ala
        450                 455                 460

Ala Arg Leu Val Ser Ser Arg Ser Gly Trp Phe Pro Arg Asn Pro Gln
465                 470                 475                 480

Ala Gln Pro Gly Glu Glu Trp Leu Gln Val Asp Leu Gly Thr Pro Lys
                485                 490                 495

Thr Val Lys Gly Val Ile Ile Gln Gly Ala Arg Gly Gly Asp Ser Ile
                500                 505                 510

Thr Ala Val Glu Ala Arg Ala Phe Val Arg Lys Phe Lys Val Ser Tyr
        515                 520                 525

Ser Leu Asn Gly Lys Asp Trp Glu Tyr Ile Gln Asp Pro Arg Thr Gln
        530                 535                 540

Gln Thr Lys Leu Phe Glu Gly Asn Met His Tyr Asp Thr Pro Asp Ile
545                 550                 555                 560

Arg Arg Phe Asp Pro Val Pro Ala Gln Tyr Val Arg Val Tyr Pro Glu
                565                 570                 575

Arg Trp Ser Pro Ala Gly Ile Gly Met Arg Leu Glu Val Leu Gly Cys
                580                 585                 590

Asp Trp Thr Asp Ser Lys Pro Thr Val Glu Thr Leu Gly Pro Thr Val
                595                 600                 605

Lys Ser Glu Glu Thr Thr Thr Pro Tyr Pro Met Asp Glu Asp Ala Thr
        610                 615                 620

Glu Cys Gly Glu Asn Cys Ser Phe Glu Asp Asp Lys Asp Leu Gln Leu
625                 630                 635                 640

Pro Ser Gly Phe Asn Cys Asn Phe Asp Phe Pro Glu Glu Thr Cys Gly
                645                 650                 655

Trp Val Tyr Asp His Ala Lys Trp Leu Arg Ser Thr Trp Ile Ser Ser
                660                 665                 670

Ala Asn Pro Asn Asp Arg Thr Phe Pro Asp Lys Asn Phe Leu Lys
        675                 680                 685

Leu Gln Ser Asp Gly Arg Arg Glu Gly Gln Tyr Gly Arg Leu Ile Ser
        690                 695                 700

Pro Pro Val His Leu Pro Arg Ser Pro Val Cys Met Glu Phe Gln Tyr
705                 710                 715                 720

Gln Ala Met Gly Gly His Gly Val Ala Leu Gln Val Val Arg Glu Ala
                725                 730                 735

Ser Gln Glu Ser Lys Leu Leu Trp Val Ile Arg Glu Asp Gln Gly Ser
                740                 745                 750

Glu Trp Lys His Gly Arg Ile Ile Leu Pro Ser Tyr Asp Met Glu Tyr
                755                 760                 765

Gln Ile Val Phe Glu Gly Val Ile Gly Lys Gly Arg Ser Gly Glu Ile
        770                 775                 780

Ser Gly Asp Asp Ile Arg Ile Ser Thr Asp Val Pro Leu Glu Asn Cys
```

```
                  785                 790                 795                 800
Met Glu Pro Ile Ser Ala Phe Ala Val Asp Ile Pro Glu Thr His Gly
                    805                 810                 815

Gly Glu Gly Tyr Glu Asp Glu Ile Asp Asp Tyr Glu Gly Asp Trp
                820                 825                 830

Ser Asn Ser Ser Ser Thr Ser Gly Ala Gly Asp Pro Ser Ser Gly
                835                 840                 845

Lys Glu Lys Ser Trp Leu Tyr Thr Leu Asp Pro Ile Leu Ile Thr Ile
            850                 855                 860

Ile Ala Met Ser Ser Leu Gly Val Leu Leu Gly Ala Thr Cys Ala Gly
865                 870                 875                 880

Leu Leu Leu Tyr Cys Thr Cys Ser Tyr Ser Gly Leu Ser Ser Arg Ser
                    885                 890                 895

Cys Thr Thr Leu Glu Asn Tyr Asn Phe Glu Leu Tyr Asp Gly Leu Lys
                900                 905                 910

His Lys Val Lys Ile Asn His Gln Lys Cys Cys Ser Glu Ala
            915                 920                 925

<210> SEQ ID NO 15
<211> LENGTH: 4784
<212> TYPE: DNA
<213> ORGANISM: mouse
<220> FEATURE:
<221> NAME/KEY: CDS
<222> LOCATION: (567)..(3359)

<400> SEQUENCE: 15
aaactggagc tccaccgcgg tggcggccgc ccgggcaggt ctagaattca gcggccgctg       60
aattctatcc agcggtcggt gcctctgccc gcgtgtgtgt cccgggtgcc ggggggaccctg    120 tgtcagttag cgcttctgag atcacacagc tgcctagggg ccgtgtgatg cccagggcaa     180
ttcttggctt tgattttttat tattattact attattttgc gttcagcttt cgggaaaccc    240
tcgtgatgtt gtaggataaa ggaaatgaca ctttgaggaa ctggagagaa catacacgcg     300
tttgggtttg aagaggaaac cggtctccgc ttccttagct tgctccctct ttgctgattt     360
caagagctat ctcctatgag gtggagatat tccagcaaga ataaaggtga agacagactg     420
actgccagga cccaggagga aaacgttgat cgttagagac cttttgcagaa gacaccacca    480 ggaggaaaat tagagaggaa aaacacaaag acataattat aggagatccc acaaacctag     540
cccgggagag agcctctctg tcaaaa atg gat atg ttt cct ctt acc tgg gtt      593
                              Met Asp Met Phe Pro Leu Thr Trp Val
                                1               5 ttc tta gct ctg tac ttt tca gga cac gaa gtg aga agc cag caa gat       641
Phe Leu Ala Leu Tyr Phe Ser Gly His Glu Val Arg Ser Gln Gln Asp
 10                  15                  20                  25 cca ccc tgc gga ggt cgg ccg aat tcc aaa gat gct ggc tac atc act       689
Pro Pro Cys Gly Gly Arg Pro Asn Ser Lys Asp Ala Gly Tyr Ile Thr
                 30                  35                  40 tcc cca ggc tac ccc cag gac tat ccc tcc cac cag aac tgt gag tgg       737
Ser Pro Gly Tyr Pro Gln Asp Tyr Pro Ser His Gln Asn Cys Glu Trp
             45                  50                  55 att gtc tac gcc ccc gaa ccc aac cag aag att gtt ctc aac ttc aac       785
Ile Val Tyr Ala Pro Glu Pro Asn Gln Lys Ile Val Leu Asn Phe Asn
         60                  65                  70 cct cac ttt gaa atc gag aaa cac gac tgc aag tat gac ttc att gag       833
Pro His Phe Glu Ile Glu Lys His Asp Cys Lys Tyr Asp Phe Ile Glu
     75                  80                  85
```

-continued

```
att cgg gat ggg gac agt gag tca gct gac ctc ctg ggc aag cac tgt      881
Ile Arg Asp Gly Asp Ser Glu Ser Ala Asp Leu Leu Gly Lys His Cys
 90              95                 100                 105 ggg aac atc gcc ccg ccc acc atc atc tcc tca ggc tcc gtg tta tac      929
Gly Asn Ile Ala Pro Pro Thr Ile Ile Ser Ser Gly Ser Val Leu Tyr
             110                 115                 120 atc aag ttc acc tca gac tac gcc cgg cag ggg gca ggt ttc tct cta      977
Ile Lys Phe Thr Ser Asp Tyr Ala Arg Gln Gly Ala Gly Phe Ser Leu
         125                 130                 135 cgc tat gag atc ttc aaa aca ggc tct gaa gat tgt tcc aag aac ttt     1025
Arg Tyr Glu Ile Phe Lys Thr Gly Ser Glu Asp Cys Ser Lys Asn Phe
     140                 145                 150 aca agc ccc aat ggg acc att gaa tct cca ggg ttt cca gag aag tat     1073
Thr Ser Pro Asn Gly Thr Ile Glu Ser Pro Gly Phe Pro Glu Lys Tyr
 155                 160                 165 cca cac aat ctg gac tgt acc ttc acc atc ctg gcc aaa ccc agg atg     1121
Pro His Asn Leu Asp Cys Thr Phe Thr Ile Leu Ala Lys Pro Arg Met
170                 175                 180                 185 gag atc atc cta cag ttc ctg acc ttt gac ctg gag cat gac cct cta     1169
Glu Ile Ile Leu Gln Phe Leu Thr Phe Asp Leu Glu His Asp Pro Leu
             190                 195                 200 caa gtg ggg gaa gga gac tgt aaa tat gac tgg ctg gac atc tgg gat     1217
Gln Val Gly Glu Gly Asp Cys Lys Tyr Asp Trp Leu Asp Ile Trp Asp
         205                 210                 215 ggc att cca cat gtt gga cct ctg att ggc aag tac tgt ggg acg aaa     1265
Gly Ile Pro His Val Gly Pro Leu Ile Gly Lys Tyr Cys Gly Thr Lys
     220                 225                 230 aca ccc tcc aaa ctc cgc tcg tcc acg ggg atc ctc tcc ttg acc ttt     1313
Thr Pro Ser Lys Leu Arg Ser Ser Thr Gly Ile Leu Ser Leu Thr Phe
 235                 240                 245 cac acg gac atg gca gtg gcc aag gat ggc ttc tcc gca cgt tac tat     1361
His Thr Asp Met Ala Val Ala Lys Asp Gly Phe Ser Ala Arg Tyr Tyr
250                 255                 260                 265 ttg atc cac cag gag cca cct gag aat ttt cag tgc aat gtc cct ttg     1409
Leu Ile His Gln Glu Pro Pro Glu Asn Phe Gln Cys Asn Val Pro Leu
             270                 275                 280 gga atg gag tct ggc cgg att gct aat gaa cag atc agt gcc tcc tcc     1457
Gly Met Glu Ser Gly Arg Ile Ala Asn Glu Gln Ile Ser Ala Ser Ser
         285                 290                 295 acc ttc tct gat ggg agg tgg act cct caa cag agc cgg ctc cat ggt     1505
Thr Phe Ser Asp Gly Arg Trp Thr Pro Gln Gln Ser Arg Leu His Gly
     300                 305                 310 gat gac aat ggc tgg aca ccc aat ttg gat tcc aac aag gag tat ctc     1553
Asp Asp Asn Gly Trp Thr Pro Asn Leu Asp Ser Asn Lys Glu Tyr Leu
 315                 320                 325 cag gtg gac ctg cgc ttc cta acc atg ctc aca gcc att gca aca cag     1601
Gln Val Asp Leu Arg Phe Leu Thr Met Leu Thr Ala Ile Ala Thr Gln
330                 335                 340                 345 gga gcc att tcc agg gaa acc cag aaa ggc tac tac gtc aaa tcg tac     1649
Gly Ala Ile Ser Arg Glu Thr Gln Lys Gly Tyr Tyr Val Lys Ser Tyr
             350                 355                 360 aag ctg gaa gtc agc aca aat ggt gaa gat tgg atg gtc tac cgg cat     1697
Lys Leu Glu Val Ser Thr Asn Gly Glu Asp Trp Met Val Tyr Arg His
         365                 370                 375 ggc aaa aac cac aag ata ttc caa gcg aac aat gat gcg acc gag gtg     1745
Gly Lys Asn His Lys Ile Phe Gln Ala Asn Asn Asp Ala Thr Glu Val
     380                 385                 390 gtg cta aac aag ctc cac atg cca ctg ctg act cgg ttc atc agg atc     1793
Val Leu Asn Lys Leu His Met Pro Leu Leu Thr Arg Phe Ile Arg Ile
 395                 400                 405
```

-continued

| | | |
|---|---|---|
| cgc ccg cag acg tgg cat ttg ggc att gcc ctt cgc ctg gag ctc ttt<br>Arg Pro Gln Thr Trp His Leu Gly Ile Ala Leu Arg Leu Glu Leu Phe<br>410                        415                    420                      425 | 1841 |
| ggc tgc cgg gtc aca gat gca ccc tgc tcc aac atg ctg ggg atg ctc<br>Gly Cys Arg Val Thr Asp Ala Pro Cys Ser Asn Met Leu Gly Met Leu<br>                                430                    435                      440 | 1889 |
| tcg ggc ctc att gct gat acc cag atc tct gcc tcc tcc acc cga gag<br>Ser Gly Leu Ile Ala Asp Thr Gln Ile Ser Ala Ser Ser Thr Arg Glu<br>                        445                    450                      455 | 1937 |
| tac ctc tgg agc ccc agt gct gcc cgc ctg gtt agt agc cgc tct ggc<br>Tyr Leu Trp Ser Pro Ser Ala Ala Arg Leu Val Ser Ser Arg Ser Gly<br>                460                    465                    470 | 1985 |
| tgg ttt cct cgg aac cct caa gcc cag cca ggt gaa gaa tgg ctt cag<br>Trp Phe Pro Arg Asn Pro Gln Ala Gln Pro Gly Glu Glu Trp Leu Gln<br>475                        480                    485 | 2033 |
| gta gac ctg gga aca ccc aag aca gtg aaa ggg gtc atc atc cag gga<br>Val Asp Leu Gly Thr Pro Lys Thr Val Lys Gly Val Ile Ile Gln Gly<br>490                        495                    500                    505 | 2081 |
| gcc cga gga gga gac agc atc act gcc gtg gaa gcc agg gcg ttt gta<br>Ala Arg Gly Gly Asp Ser Ile Thr Ala Val Glu Ala Arg Ala Phe Val<br>                        510                    515                    520 | 2129 |
| cgc aag ttc aaa gtc tcc tac agc cta aat ggc aag gac tgg gaa tat<br>Arg Lys Phe Lys Val Ser Tyr Ser Leu Asn Gly Lys Asp Trp Glu Tyr<br>                525                    530                    535 | 2177 |
| atc cag gac ccc agg act cag cag aca aag ctg ttt gaa ggg aac atg<br>Ile Gln Asp Pro Arg Thr Gln Gln Thr Lys Leu Phe Glu Gly Asn Met<br>                        540                    545                    550 | 2225 |
| cac tat gac acc cct gac atc cga agg ttc gat cct gtt cca gcg cag<br>His Tyr Asp Thr Pro Asp Ile Arg Arg Phe Asp Pro Val Pro Ala Gln<br>555                        560                    565 | 2273 |
| tat gtg cgg gtg tac cca gag agg tgg tcg cca gca ggc atc ggg atg<br>Tyr Val Arg Val Tyr Pro Glu Arg Trp Ser Pro Ala Gly Ile Gly Met<br>570                        575                    580                    585 | 2321 |
| agg ctg gag gtg ctg ggc tgt gac tgg aca gac tca aag ccc aca gtg<br>Arg Leu Glu Val Leu Gly Cys Asp Trp Thr Asp Ser Lys Pro Thr Val<br>                        590                    595                    600 | 2369 |
| gag acg ctg gga ccc acc gtg aag agt gaa gag act acc acc cca tat<br>Glu Thr Leu Gly Pro Thr Val Lys Ser Glu Glu Thr Thr Thr Pro Tyr<br>                605                    610                    615 | 2417 |
| ccc atg gat gag gat gcc acc gag tgt ggg gaa aac tgc agc ttt gag<br>Pro Met Asp Glu Asp Ala Thr Glu Cys Gly Glu Asn Cys Ser Phe Glu<br>                        620                    625                    630 | 2465 |
| gat gac aaa gat ttg caa ctt cct tca gga ttc aac tgc aac ttt gat<br>Asp Asp Lys Asp Leu Gln Leu Pro Ser Gly Phe Asn Cys Asn Phe Asp<br>635                        640                    645 | 2513 |
| ttt ccg gaa gag acc tgt ggt tgg gtg tac gac cat gcc aag tgg ctc<br>Phe Pro Glu Glu Thr Cys Gly Trp Val Tyr Asp His Ala Lys Trp Leu<br>650                        655                    660                    665 | 2561 |
| cgg agc acg tgg atc agc agc gct aac ccc aat gac aga aca ttt cca<br>Arg Ser Thr Trp Ile Ser Ser Ala Asn Pro Asn Asp Arg Thr Phe Pro<br>                        670                    675                    680 | 2609 |
| gat gac aag aac ttc ttg aaa ctg cag agt gat ggc cga cga gag ggc<br>Asp Asp Lys Asn Phe Leu Lys Leu Gln Ser Asp Gly Arg Arg Glu Gly<br>                685                    690                    695 | 2657 |
| cag tac ggg cgg ctc atc agc cca ccg gtg cac ctg ccc cga agc cct<br>Gln Tyr Gly Arg Leu Ile Ser Pro Pro Val His Leu Pro Arg Ser Pro<br>                        700                    705                    710 | 2705 |
| gtg tgc atg gag ttc cag tac caa gcc atg ggc ggc cac ggg gtg gca<br>Val Cys Met Glu Phe Gln Tyr Gln Ala Met Gly Gly His Gly Val Ala | 2753 |

```
                715                 720                 725
ctg cag gtg gtt cgg gaa gcc agc cag gaa agc aaa ctc ctt tgg gtc           2801
Leu Gln Val Val Arg Glu Ala Ser Gln Glu Ser Lys Leu Leu Trp Val
730                 735                 740                 745 atc cgt gag gac cag ggc agc gag tgg aag cac ggg cgc att atc ctg           2849
Ile Arg Glu Asp Gln Gly Ser Glu Trp Lys His Gly Arg Ile Ile Leu
                750                 755                 760 ccc agc tat gac atg gag tat cag atc gtg ttc gag gga gtg ata ggg           2897
Pro Ser Tyr Asp Met Glu Tyr Gln Ile Val Phe Glu Gly Val Ile Gly
            765                 770                 775 aag gga cga tcg gga gag att tcc ggc gat gac att cgg ata agc act           2945
Lys Gly Arg Ser Gly Glu Ile Ser Gly Asp Asp Ile Arg Ile Ser Thr
        780                 785                 790 gat gtc cca ctg gag aac tgc atg gaa ccc ata tca gct ttt gca ggt           2993
Asp Val Pro Leu Glu Asn Cys Met Glu Pro Ile Ser Ala Phe Ala Gly
    795                 800                 805 gag gat ttt aaa gtg gac atc cca gaa acc cat ggg gga gag ggc tat           3041
Glu Asp Phe Lys Val Asp Ile Pro Glu Thr His Gly Gly Glu Gly Tyr
810                 815                 820                 825 gaa gat gag att gat gat gaa tat gaa gga gat tgg agc aac tct tct           3089
Glu Asp Glu Ile Asp Asp Glu Tyr Glu Gly Asp Trp Ser Asn Ser Ser
                830                 835                 840 tcc tct acc tca ggg gct ggt gac ccc tca tct ggc aaa gaa aag agc           3137
Ser Ser Thr Ser Gly Ala Gly Asp Pro Ser Ser Gly Lys Glu Lys Ser
            845                 850                 855 tgg ctg tac acc cta gat ccc att ctg atc acc atc atc gcc atg agc           3185
Trp Leu Tyr Thr Leu Asp Pro Ile Leu Ile Thr Ile Ile Ala Met Ser
        860                 865                 870 tcg ctg ggg gtc ctg ctg ggg gcc acc tgt gcg ggc ctc ctc ctt tac           3233
Ser Leu Gly Val Leu Leu Gly Ala Thr Cys Ala Gly Leu Leu Leu Tyr
    875                 880                 885 tgc acc tgc tcc tat tcg ggt ctg agt tcg agg agc tgc acc aca ctg           3281
Cys Thr Cys Ser Tyr Ser Gly Leu Ser Ser Arg Ser Cys Thr Thr Leu
890                 895                 900                 905 gag aac tac aac ttt gag ctc tac gat ggc ctc aag cac aag gtc aag           3329
Glu Asn Tyr Asn Phe Glu Leu Tyr Asp Gly Leu Lys His Lys Val Lys
                910                 915                 920 atc aat cat cag aag tgc tgc tcg gag gca tgaccgattg tgtctggatc            3379
Ile Asn His Gln Lys Cys Cys Ser Glu Ala
                925                 930 gcttctggcg tttcattcca gtgagagggg ctagcgaaga ttacagtttt gttttgtttt        3439
gttttgtttt cccttttggaa actgaatgcc ataatctgga tcaaagtgtt ccagaatact       3499
gaaggtatgg acaggacaga caggccagtc tagggagaaa gggagatgca gctgtgaagg       3559
ggatcgttgc ccaccaggac tgtggtggcc aagtgaatgc aggaaccggg cccggaattc       3619
cggctctcgg ctaaaatctc agctgcctct ggaaaggctc aaccatactc agtgccaact       3679
cagactctgt tgctgtggtg tcaacatgga tggatcatct gtaccttgta tttttagcag       3739
aattcatgct cagatttctt tgttctgaat ccttgctttg tctagacac aaagcataca        3799 tgtccttcta aaattaatat gatcactata atctcctgtg tgcagaattc agaaatagac       3859
ctttgaaacc atttgcattg tgagtgcaga tccatgactg gggctagtgc agcaatgaaa       3919
cagaattcca gaaacagtgt gttctttta ttatgggaaa atacagataa aaatggccac        3979
tgatgaacat gaaagttagc actttcccaa cacagtgtac acttgcaacc ttgtttttgga      4039 tttctcatac accaagactg tgaaacacaa atttcaagaa tgtgttcaaa tgtgtgtgtg       4099
tgtgtgtgtg tgtgtgtgtg tgtgtgtgta tgtgtgtgtg tgtgtgtgtg cttgtgtgtt       4159
```

-continued

```
tctgtcagtg gtatgagtga tatgtatgca tgtgtgtatg tatatgtatg tatgtatgta      4219
tgtatgtacg tacatatgta tgtatgtatg tatgtatgta tgtatgtata tgtgtgtgtg      4279
tgtttgtgtg tgtgtgtgtt tgtgtgtgtg tgtgtggtaa gtgtggtatg tgtgtatgca      4339
tttgtctata tgtgtatctg tgtgtctatg tgtttctgtc agtggaatga gtggcatgtg      4399
tgcatgtgta tgtatgtgga tatgtgtgtt gtgtttatgt gcttgtgtat aagaggtaag      4459
tgtggtgtgt gtgcatgtgt ctctgtgtgt gtttgtctgt gtacctcttt gtataagtac      4519
ctgtgtttgt atgtgggaat atgtatattg aggcattgct gtgttagtat gtttatagaa      4579
aagaagacag tctgagatgt cttcctcaat acctctccac ttatatcttg gatagacaaa      4639
agtaatgaca aaaaattgct ggtgtgtata tggaaaaggg ggacacatat ccatggatgg      4699
tagaagtgta aactgtgcag tcactgtgga catcaatatg caggttcttc acaaatgtag      4759
atataaagct actatagtta taccc                                            4784
```

<210> SEQ ID NO 16
<211> LENGTH: 931
<212> TYPE: PRT
<213> ORGANISM: mouse

<400> SEQUENCE: 16

```
Met Asp Met Phe Pro Leu Thr Trp Val Phe Leu Ala Leu Tyr Phe Ser
  1               5                  10                  15

Gly His Glu Val Arg Ser Gln Gln Asp Pro Pro Cys Gly Gly Arg Pro
             20                  25                  30

Asn Ser Lys Asp Ala Gly Tyr Ile Thr Ser Pro Gly Tyr Pro Gln Asp
         35                  40                  45

Tyr Pro Ser His Gln Asn Cys Glu Trp Ile Val Tyr Ala Pro Glu Pro
     50                  55                  60

Asn Gln Lys Ile Val Leu Asn Phe Asn Pro His Phe Glu Ile Glu Lys
 65                  70                  75                  80

His Asp Cys Lys Tyr Asp Phe Ile Glu Ile Arg Asp Gly Asp Ser Glu
                 85                  90                  95

Ser Ala Asp Leu Leu Gly Lys His Cys Gly Asn Ile Ala Pro Pro Thr
            100                 105                 110

Ile Ile Ser Ser Gly Ser Val Leu Tyr Ile Lys Phe Thr Ser Asp Tyr
        115                 120                 125

Ala Arg Gln Gly Ala Gly Phe Ser Leu Arg Tyr Glu Ile Phe Lys Thr
    130                 135                 140

Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                165                 170                 175

Phe Thr Ile Leu Ala Lys Pro Arg Met Glu Ile Ile Leu Gln Phe Leu
            180                 185                 190

Thr Phe Asp Leu Glu His Asp Pro Leu Gln Val Gly Glu Gly Asp Cys
        195                 200                 205

Lys Tyr Asp Trp Leu Asp Ile Trp Asp Gly Ile Pro His Val Gly Pro
    210                 215                 220

Leu Ile Gly Lys Tyr Cys Gly Thr Lys Thr Pro Ser Lys Leu Arg Ser
225                 230                 235                 240

Ser Thr Gly Ile Leu Ser Leu Thr Phe His Thr Asp Met Ala Val Ala
                245                 250                 255
```

```
Lys Asp Gly Phe Ser Ala Arg Tyr Tyr Leu Ile His Gln Glu Pro Pro
            260                 265                 270

Glu Asn Phe Gln Cys Asn Val Pro Leu Gly Met Glu Ser Gly Arg Ile
            275                 280                 285

Ala Asn Glu Gln Ile Ser Ala Ser Ser Thr Phe Ser Asp Gly Arg Trp
            290                 295                 300

Thr Pro Gln Gln Ser Arg Leu His Gly Asp Asp Asn Gly Trp Thr Pro
305                 310                 315                 320

Asn Leu Asp Ser Asn Lys Glu Tyr Leu Gln Val Asp Leu Arg Phe Leu
            325                 330                 335

Thr Met Leu Thr Ala Ile Ala Thr Gln Gly Ala Ile Ser Arg Glu Thr
            340                 345                 350

Gln Lys Gly Tyr Tyr Val Lys Ser Tyr Lys Leu Glu Val Ser Thr Asn
            355                 360                 365

Gly Glu Asp Trp Met Val Tyr Arg His Gly Lys Asn His Lys Ile Phe
            370                 375                 380

Gln Ala Asn Asn Asp Ala Thr Glu Val Val Leu Asn Lys Leu His Met
385                 390                 395                 400

Pro Leu Leu Thr Arg Phe Ile Arg Ile Arg Pro Gln Thr Trp His Leu
            405                 410                 415

Gly Ile Ala Leu Arg Leu Glu Leu Phe Gly Cys Arg Val Thr Asp Ala
            420                 425                 430

Pro Cys Ser Asn Met Leu Gly Met Leu Ser Gly Leu Ile Ala Asp Thr
            435                 440                 445

Gln Ile Ser Ala Ser Ser Thr Arg Glu Tyr Leu Trp Ser Pro Ser Ala
            450                 455                 460

Ala Arg Leu Val Ser Ser Arg Ser Gly Trp Phe Pro Arg Asn Pro Gln
465                 470                 475                 480

Ala Gln Pro Gly Glu Glu Trp Leu Gln Val Asp Leu Gly Thr Pro Lys
            485                 490                 495

Thr Val Lys Gly Val Ile Ile Gln Gly Ala Arg Gly Gly Asp Ser Ile
            500                 505                 510

Thr Ala Val Glu Ala Arg Ala Phe Val Arg Lys Phe Lys Val Ser Tyr
            515                 520                 525

Ser Leu Asn Gly Lys Asp Trp Glu Tyr Ile Gln Asp Pro Arg Thr Gln
            530                 535                 540

Gln Thr Lys Leu Phe Glu Gly Asn Met His Tyr Asp Thr Pro Asp Ile
545                 550                 555                 560

Arg Arg Phe Asp Pro Val Pro Ala Gln Tyr Val Arg Val Tyr Pro Glu
            565                 570                 575

Arg Trp Ser Pro Ala Gly Ile Gly Met Arg Leu Glu Val Leu Gly Cys
            580                 585                 590

Asp Trp Thr Asp Ser Lys Pro Thr Val Glu Thr Leu Gly Pro Thr Val
            595                 600                 605

Lys Ser Glu Glu Thr Thr Thr Pro Tyr Pro Met Asp Glu Asp Ala Thr
            610                 615                 620

Glu Cys Gly Glu Asn Cys Ser Phe Glu Asp Asp Lys Asp Leu Gln Leu
625                 630                 635                 640

Pro Ser Gly Phe Asn Cys Asn Phe Asp Phe Pro Glu Glu Thr Cys Gly
            645                 650                 655

Trp Val Tyr Asp His Ala Lys Trp Leu Arg Ser Thr Trp Ile Ser Ser
            660                 665                 670

Ala Asn Pro Asn Asp Arg Thr Phe Pro Asp Asp Lys Asn Phe Leu Lys
```

```
                675                 680                 685
Leu Gln Ser Asp Gly Arg Arg Glu Gly Gln Tyr Gly Arg Leu Ile Ser
            690                 695                 700

Pro Pro Val His Leu Pro Arg Ser Pro Val Cys Met Glu Phe Gln Tyr
705                 710                 715                 720

Gln Ala Met Gly Gly His Gly Val Ala Leu Gln Val Val Arg Glu Ala
                725                 730                 735

Ser Gln Glu Ser Lys Leu Leu Trp Val Ile Arg Glu Asp Gln Gly Ser
            740                 745                 750

Glu Trp Lys His Gly Arg Ile Ile Leu Pro Ser Tyr Asp Met Glu Tyr
        755                 760                 765

Gln Ile Val Phe Glu Gly Val Ile Gly Lys Gly Arg Ser Gly Glu Ile
    770                 775                 780

Ser Gly Asp Asp Ile Arg Ile Ser Thr Asp Val Pro Leu Glu Asn Cys
785                 790                 795                 800

Met Glu Pro Ile Ser Ala Phe Ala Gly Glu Asp Phe Lys Val Asp Ile
                805                 810                 815

Pro Glu Thr His Gly Gly Glu Gly Tyr Glu Asp Glu Ile Asp Asp Glu
            820                 825                 830

Tyr Glu Gly Asp Trp Ser Asn Ser Ser Ser Thr Ser Gly Ala Gly
        835                 840                 845

Asp Pro Ser Ser Gly Lys Glu Lys Ser Trp Leu Tyr Thr Leu Asp Pro
    850                 855                 860

Ile Leu Ile Thr Ile Ile Ala Met Ser Ser Leu Gly Val Leu Leu Gly
865                 870                 875                 880

Ala Thr Cys Ala Gly Leu Leu Leu Tyr Cys Thr Cys Ser Tyr Ser Gly
                885                 890                 895

Leu Ser Ser Arg Ser Cys Thr Thr Leu Glu Asn Tyr Asn Phe Glu Leu
            900                 905                 910

Tyr Asp Gly Leu Lys His Lys Val Lys Ile Asn His Gln Lys Cys Cys
        915                 920                 925

Ser Glu Ala
    930

<210> SEQ ID NO 17
<211> LENGTH: 2730
<212> TYPE: DNA
<213> ORGANISM: human
<220> FEATURE:
<221> NAME/KEY: CDS
<222> LOCATION: (1)..(2727)

<400> SEQUENCE: 17 atg gat atg ttt cct ctc acc tgg gtt ttc tta gcc ctc tac ttt tca      48
Met Asp Met Phe Pro Leu Thr Trp Val Phe Leu Ala Leu Tyr Phe Ser
  1               5                  10                  15 aga cac caa gtg aga ggc caa cca gac cca ccg tgc gga ggt cgt ttg      96
Arg His Gln Val Arg Gly Gln Pro Asp Pro Pro Cys Gly Gly Arg Leu
             20                  25                  30 aat tcc aaa gat gct ggc tat atc acc tct ccc ggt tac ccc cag gac     144
Asn Ser Lys Asp Ala Gly Tyr Ile Thr Ser Pro Gly Tyr Pro Gln Asp
         35                  40                  45 tac ccc tcc cac cag aac tgc gag tgg att gtt tac gcc ccc gaa ccc     192
Tyr Pro Ser His Gln Asn Cys Glu Trp Ile Val Tyr Ala Pro Glu Pro
     50                  55                  60 aac cag aag att gtc ctc aac ttc aac cct cac ttt gaa atc gag aag     240
Asn Gln Lys Ile Val Leu Asn Phe Asn Pro His Phe Glu Ile Glu Lys
```

```
                65                  70                  75                  80
cac gac tgc aag tat gac ttt atc gag att cgg gat ggg gac agt gaa         288
His Asp Cys Lys Tyr Asp Phe Ile Glu Ile Arg Asp Gly Asp Ser Glu
                    85                  90                  95 tcc gca gac ctc ctg ggc aaa cac tgt ggg aac atc gcc ccg ccc acc         336
Ser Ala Asp Leu Leu Gly Lys His Cys Gly Asn Ile Ala Pro Pro Thr
                100                 105                 110 atc atc tcc tcg ggc tcc atg ctc tac atc aag ttc acc tcc gac tac         384
Ile Ile Ser Ser Gly Ser Met Leu Tyr Ile Lys Phe Thr Ser Asp Tyr
            115                 120                 125 gcc cgg cag ggg gca ggc ttc tct ctg cgc tac gag atc ttc aag aca         432
Ala Arg Gln Gly Ala Gly Phe Ser Leu Arg Tyr Glu Ile Phe Lys Thr
        130                 135                 140 ggc tct gaa gat tgc tca aaa aac ttc aca agc ccc aac ggg acc atc         480
Gly Ser Glu Asp Cys Ser Lys Asn Phe Thr Ser Pro Asn Gly Thr Ile
145                 150                 155                 160 gaa tct cct ggg ttt cct gag aag tat cca cac aac ttg gac tgc acc         528
Glu Ser Pro Gly Phe Pro Glu Lys Tyr Pro His Asn Leu Asp Cys Thr
                165                 170                 175 ttt acc atc ctg gcc aaa ccc aag atg gag atc atc ctg cag ttc ctg         576
Phe Thr Ile Leu Ala Lys Pro Lys Met Glu Ile Ile Leu Gln Phe Leu
                180                 185                 190 atc ttt gac ctg gag cat gac cct ttg cag gtg gga gag ggg gac tgc         624
Ile Phe Asp Leu Glu His Asp Pro Leu Gln Val Gly Glu Gly Asp Cys
            195                 200                 205 aag tac gat tgg ctg gac atc tgg gat ggc att cca cat gtt ggc ccc         672
Lys Tyr Asp Trp Leu Asp Ile Trp Asp Gly Ile Pro His Val Gly Pro
        210                 215                 220 ctg att ggc aag tac tgt ggg acc aaa aca ccc tct gaa ctt cgt tca         720
Leu Ile Gly Lys Tyr Cys Gly Thr Lys Thr Pro Ser Glu Leu Arg Ser
225                 230                 235                 240 tcg acg ggg atc ctc tcc ctg acc ttt cac acg gac atg gcg gtg gcc         768
Ser Thr Gly Ile Leu Ser Leu Thr Phe His Thr Asp Met Ala Val Ala
                245                 250                 255 aag gat ggc ttc tct gcg cgt tac tac ctg gtc cac caa gag cca cta         816
Lys Asp Gly Phe Ser Ala Arg Tyr Tyr Leu Val His Gln Glu Pro Leu
                260                 265                 270 gag aac ttt cag tgc aat gtt cct ctg ggc atg gag tct ggc cgg att         864
Glu Asn Phe Gln Cys Asn Val Pro Leu Gly Met Glu Ser Gly Arg Ile
            275                 280                 285 gct aat gaa cag atc agt gcc tca tct acc tac tct gat ggg agg tgg         912
Ala Asn Glu Gln Ile Ser Ala Ser Ser Thr Tyr Ser Asp Gly Arg Trp
        290                 295                 300 acc cct caa caa agc cgg ctc cat ggt gat gac aat ggc tgg acc ccc         960
Thr Pro Gln Gln Ser Arg Leu His Gly Asp Asp Asn Gly Trp Thr Pro
305                 310                 315                 320 aac ttg gat tcc aac aag gag tat ctc cag gtg gac ctg cgc ttt tta         1008
Asn Leu Asp Ser Asn Lys Glu Tyr Leu Gln Val Asp Leu Arg Phe Leu
                325                 330                 335 acc atg ctc acg gcc atc gca aca cag gga gcg att tcc agg gaa aca         1056
Thr Met Leu Thr Ala Ile Ala Thr Gln Gly Ala Ile Ser Arg Glu Thr
                340                 345                 350 cag aat ggc tac tac gtc aaa tcc tac aag ctg gaa gtc agc act aat         1104
Gln Asn Gly Tyr Tyr Val Lys Ser Tyr Lys Leu Glu Val Ser Thr Asn
            355                 360                 365 gga gag gac tgg atg gtg tac cgg cat ggc aaa aac cac aag gta ttt         1152
Gly Glu Asp Trp Met Val Tyr Arg His Gly Lys Asn His Lys Val Phe
        370                 375                 380 caa gcc aac aac gat gca act gag gtg gtt ctg aac aag ctc cac gct         1200
```

-continued

```
    Gln Ala Asn Asn Asp Ala Thr Glu Val Val Leu Asn Lys Leu His Ala
    385                 390                 395                 400 cca ctg ctg aca agg ttt gtt aga atc cgc cct cag acc tgg cac tca      1248
Pro Leu Leu Thr Arg Phe Val Arg Ile Arg Pro Gln Thr Trp His Ser
                    405                 410                 415 ggt atc gcc ctc cgg ctg gag ctc ttc ggc tgc cgg gtc aca gat gct      1296
Gly Ile Ala Leu Arg Leu Glu Leu Phe Gly Cys Arg Val Thr Asp Ala
                420                 425                 430 ccc tgc tcc aac atg ctg ggg atg ctc tca ggc ctc att gca gac tcc      1344
Pro Cys Ser Asn Met Leu Gly Met Leu Ser Gly Leu Ile Ala Asp Ser
            435                 440                 445 cag atc tcc gcc tct tcc acc cag gaa tac ctc tgg agc ccc agt gca      1392
Gln Ile Ser Ala Ser Ser Thr Gln Glu Tyr Leu Trp Ser Pro Ser Ala
        450                 455                 460 gcc cgc ctg gtc agc agc cgc tcg ggc tgg ttc cct cga atc cct cag      1440
Ala Arg Leu Val Ser Ser Arg Ser Gly Trp Phe Pro Arg Ile Pro Gln
465                 470                 475                 480 gcc cag ccc ggt gag gag tgg ctt cag gta gat ctg gga aca ccc aag      1488
Ala Gln Pro Gly Glu Glu Trp Leu Gln Val Asp Leu Gly Thr Pro Lys
                    485                 490                 495 aca gtg aaa ggt gtc atc atc cag gga gcc cgc gga gga gac agt atc      1536
Thr Val Lys Gly Val Ile Ile Gln Gly Ala Arg Gly Gly Asp Ser Ile
                500                 505                 510 act gct gtg gaa gcc aga gca ttt gtg cgc aag ttc aaa gtc tcc tac      1584
Thr Ala Val Glu Ala Arg Ala Phe Val Arg Lys Phe Lys Val Ser Tyr
            515                 520                 525 agc cta aac ggc aag gac tgg gaa tac att cag gac ccc agg acc cag      1632
Ser Leu Asn Gly Lys Asp Trp Glu Tyr Ile Gln Asp Pro Arg Thr Gln
        530                 535                 540 cag cca aag ctg ttc gaa ggg aac atg cac tat gac acc cct gac atc      1680
Gln Pro Lys Leu Phe Glu Gly Asn Met His Tyr Asp Thr Pro Asp Ile
545                 550                 555                 560 cga agg ttt gac ccc att ccg gca cag tat gtg cgg gta tac ccg gag      1728
Arg Arg Phe Asp Pro Ile Pro Ala Gln Tyr Val Arg Val Tyr Pro Glu
                    565                 570                 575 agg tgg tcg ccg gcg ggg att ggg atg cgg ctg gag gtg ctg ggc tgt      1776
Arg Trp Ser Pro Ala Gly Ile Gly Met Arg Leu Glu Val Leu Gly Cys
                580                 585                 590 gac tgg aca gac tcc aag ccc acg gta aaa acg ctg gga ccc act gtg      1824
Asp Trp Thr Asp Ser Lys Pro Thr Val Lys Thr Leu Gly Pro Thr Val
            595                 600                 605 aag agc gaa gag aca acc acc ccc tac ccc acc gaa gag gag gcc aca      1872
Lys Ser Glu Glu Thr Thr Thr Pro Tyr Pro Thr Glu Glu Glu Ala Thr
        610                 615                 620 gag tgt ggg gag aac tgc agc ttt gag gat gac aaa gat ttg cag ctc      1920
Glu Cys Gly Glu Asn Cys Ser Phe Glu Asp Asp Lys Asp Leu Gln Leu
625                 630                 635                 640 cct tcg gga ttc aat tgc aac ttc gat ttc ctc gag gag ccc tgt ggt      1968
Pro Ser Gly Phe Asn Cys Asn Phe Asp Phe Leu Glu Glu Pro Cys Gly
                    645                 650                 655 tgg atg tat gac cat gcc aag tgg ctc cgg acc acc tgg gcc agc agc      2016
Trp Met Tyr Asp His Ala Lys Trp Leu Arg Thr Thr Trp Ala Ser Ser
                660                 665                 670 tcc agc cca aac gac cgg acg ttt cca gat gac agg aat ttc ttg cgg      2064
Ser Ser Pro Asn Asp Arg Thr Phe Pro Asp Asp Arg Asn Phe Leu Arg
            675                 680                 685 ctg cag agt gac agc cag aga gag ggc cag tat gcc cgg ctc atc agc      2112
Leu Gln Ser Asp Ser Gln Arg Glu Gly Gln Tyr Ala Arg Leu Ile Ser
        690                 695                 700
```

```
ccc cct gtc cac ctg ccc cga agc ccg gtg tgc atg gag ttc cag tac    2160
Pro Pro Val His Leu Pro Arg Ser Pro Val Cys Met Glu Phe Gln Tyr
705             710                 715                 720 cag gcc acg ggc ggc cgc ggg gtg gcg ctg cag gtg gtg cgg gaa gcc    2208
Gln Ala Thr Gly Gly Arg Gly Val Ala Leu Gln Val Val Arg Glu Ala
            725                 730                 735 agc cag gag agc aag ttg ctg tgg gtc atc cgt gag gac cag ggc ggc    2256
Ser Gln Glu Ser Lys Leu Leu Trp Val Ile Arg Glu Asp Gln Gly Gly
        740                 745                 750 gag tgg aag cac ggg cgg atc atc ctg ccc agc tac gac atg gag tac    2304
Glu Trp Lys His Gly Arg Ile Ile Leu Pro Ser Tyr Asp Met Glu Tyr
    755                 760                 765 cag att gtg ttc gag gga gtg ata ggg aaa gga cgt tcc gga gag att    2352
Gln Ile Val Phe Glu Gly Val Ile Gly Lys Gly Arg Ser Gly Glu Ile
770                 775                 780 gcc att gat gac att cgg ata agc act gat gtc cca ctg gag aac tgc    2400
Ala Ile Asp Asp Ile Arg Ile Ser Thr Asp Val Pro Leu Glu Asn Cys
785                 790                 795                 800 atg gaa ccc atc tcg gct ttt gca gat gaa tac gag gtg gac tgg agc    2448
Met Glu Pro Ile Ser Ala Phe Ala Asp Glu Tyr Glu Val Asp Trp Ser
            805                 810                 815 aat tct tct tct gca acc tca ggg tct ggc gcc ccc tcg acc gac aaa    2496
Asn Ser Ser Ser Ala Thr Ser Gly Ser Gly Ala Pro Ser Thr Asp Lys
        820                 825                 830 gaa aag agc tgg ctg tac acc ctg gat ccc atc ctc atc acc atc atc    2544
Glu Lys Ser Trp Leu Tyr Thr Leu Asp Pro Ile Leu Ile Thr Ile Ile
    835                 840                 845 gcc atg agc tca ctg ggc gtc ctc ctg ggg gcc acc tgt gca ggc ctc    2592
Ala Met Ser Ser Leu Gly Val Leu Leu Gly Ala Thr Cys Ala Gly Leu
850                 855                 860 ctg ctc tac tgc acc tgt tcc tac tcg ggc ctg agc tcc cga agc tgc    2640
Leu Leu Tyr Cys Thr Cys Ser Tyr Ser Gly Leu Ser Ser Arg Ser Cys
865                 870                 875                 880 acc aca ctg gag aac tac aac ttc gag ctc tac gat ggc ctt aag cac    2688
Thr Thr Leu Glu Asn Tyr Asn Phe Glu Leu Tyr Asp Gly Leu Lys His
            885                 890                 895 aag gtc aag atg aac cac caa aag tgc tgc tcc gag gca tga            2730
Lys Val Lys Met Asn His Gln Lys Cys Cys Ser Glu Ala
        900                 905
```

<210> SEQ ID NO 18
<211> LENGTH: 909
<212> TYPE: PRT
<213> ORGANISM: human

<400> SEQUENCE: 18

```
Met Asp Met Phe Pro Leu Thr Trp Val Phe Leu Ala Leu Tyr Phe Ser
1               5                   10                  15

Arg His Gln Val Arg Gly Gln Pro Asp Pro Cys Gly Gly Arg Leu
                20                  25                  30

Asn Ser Lys Asp Ala Gly Tyr Ile Thr Ser Pro Gly Tyr Pro Gln Asp
            35                  40                  45

Tyr Pro Ser His Gln Asn Cys Glu Trp Ile Val Tyr Ala Pro Glu Pro
        50                  55                  60

Asn Gln Lys Ile Val Leu Asn Phe Asn Pro His Phe Glu Ile Glu Lys
65                  70                  75                  80

His Asp Cys Lys Tyr Asp Phe Ile Glu Ile Arg Asp Gly Asp Ser Glu
                85                  90                  95

Ser Ala Asp Leu Leu Gly Lys His Cys Gly Asn Ile Ala Pro Pro Thr
```

```
              100                 105                 110
Ile Ile Ser Ser Gly Ser Met Leu Tyr Ile Lys Phe Thr Ser Asp Tyr
            115                 120                 125

Ala Arg Gln Gly Ala Gly Phe Ser Leu Arg Tyr Glu Ile Phe Lys Thr
130                 135                 140

Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                165                 170                 175

Phe Thr Ile Leu Ala Lys Pro Lys Met Glu Ile Ile Leu Gln Phe Leu
            180                 185                 190

Ile Phe Asp Leu Glu His Asp Pro Leu Gln Val Gly Glu Gly Asp Cys
        195                 200                 205

Lys Tyr Asp Trp Leu Asp Ile Trp Asp Gly Ile Pro His Val Gly Pro
    210                 215                 220

Leu Ile Gly Lys Tyr Cys Gly Thr Lys Thr Pro Ser Glu Leu Arg Ser
225                 230                 235                 240

Ser Thr Gly Ile Leu Ser Leu Thr Phe His Thr Asp Met Ala Val Ala
                245                 250                 255

Lys Asp Gly Phe Ser Ala Arg Tyr Tyr Leu Val His Gln Glu Pro Leu
                260                 265                 270

Glu Asn Phe Gln Cys Asn Val Pro Leu Gly Met Glu Ser Gly Arg Ile
            275                 280                 285

Ala Asn Glu Gln Ile Ser Ala Ser Ser Thr Tyr Ser Asp Gly Arg Trp
        290                 295                 300

Thr Pro Gln Gln Ser Arg Leu His Gly Asp Asp Asn Gly Trp Thr Pro
305                 310                 315                 320

Asn Leu Asp Ser Asn Lys Glu Tyr Leu Gln Val Asp Leu Arg Phe Leu
                325                 330                 335

Thr Met Leu Thr Ala Ile Ala Thr Gln Gly Ala Ile Ser Arg Glu Thr
                340                 345                 350

Gln Asn Gly Tyr Tyr Val Lys Ser Tyr Lys Leu Glu Val Ser Thr Asn
            355                 360                 365

Gly Glu Asp Trp Met Val Tyr Arg His Gly Lys Asn His Lys Val Phe
        370                 375                 380

Gln Ala Asn Asn Asp Ala Thr Glu Val Val Leu Asn Lys Leu His Ala
385                 390                 395                 400

Pro Leu Leu Thr Arg Phe Val Arg Ile Arg Pro Gln Thr Trp His Ser
                405                 410                 415

Gly Ile Ala Leu Arg Leu Glu Leu Phe Gly Cys Arg Val Thr Asp Ala
            420                 425                 430

Pro Cys Ser Asn Met Leu Gly Met Leu Ser Gly Leu Ile Ala Asp Ser
        435                 440                 445

Gln Ile Ser Ala Ser Ser Thr Gln Glu Tyr Leu Trp Ser Pro Ser Ala
    450                 455                 460

Ala Arg Leu Val Ser Ser Arg Ser Gly Trp Phe Pro Arg Ile Pro Gln
465                 470                 475                 480

Ala Gln Pro Gly Glu Glu Trp Leu Gln Val Asp Leu Gly Thr Pro Lys
                485                 490                 495

Thr Val Lys Gly Val Ile Ile Gln Gly Ala Arg Gly Gly Asp Ser Ile
            500                 505                 510

Thr Ala Val Glu Ala Arg Ala Phe Val Arg Lys Phe Lys Val Ser Tyr
        515                 520                 525
```

```
Ser Leu Asn Gly Lys Asp Trp Glu Tyr Ile Gln Asp Pro Arg Thr Gln
    530                 535                 540
Gln Pro Lys Leu Phe Glu Gly Asn Met His Tyr Asp Thr Pro Asp Ile
545                 550                 555                 560
Arg Arg Phe Asp Pro Ile Pro Ala Gln Tyr Val Arg Val Tyr Pro Glu
                565                 570                 575
Arg Trp Ser Pro Ala Gly Ile Gly Met Arg Leu Glu Val Leu Gly Cys
                580                 585                 590
Asp Trp Thr Asp Ser Lys Pro Thr Val Lys Thr Leu Gly Pro Thr Val
                595                 600                 605
Lys Ser Glu Glu Thr Thr Thr Pro Tyr Pro Thr Glu Glu Ala Thr
    610                 615                 620
Glu Cys Gly Glu Asn Cys Ser Phe Glu Asp Asp Lys Asp Leu Gln Leu
625                 630                 635                 640
Pro Ser Gly Phe Asn Cys Asn Phe Asp Phe Leu Glu Glu Pro Cys Gly
                645                 650                 655
Trp Met Tyr Asp His Ala Lys Trp Leu Arg Thr Thr Trp Ala Ser Ser
                660                 665                 670
Ser Ser Pro Asn Asp Arg Thr Phe Pro Asp Asp Arg Asn Phe Leu Arg
                675                 680                 685
Leu Gln Ser Asp Ser Gln Arg Glu Gly Gln Tyr Ala Arg Leu Ile Ser
    690                 695                 700
Pro Pro Val His Leu Pro Arg Ser Pro Val Cys Met Glu Phe Gln Tyr
705                 710                 715                 720
Gln Ala Thr Gly Gly Arg Gly Val Ala Leu Gln Val Val Arg Glu Ala
                725                 730                 735
Ser Gln Glu Ser Lys Leu Leu Trp Val Ile Arg Glu Asp Gln Gly Gly
                740                 745                 750
Glu Trp Lys His Gly Arg Ile Ile Leu Pro Ser Tyr Asp Met Glu Tyr
                755                 760                 765
Gln Ile Val Phe Glu Gly Val Ile Gly Lys Gly Arg Ser Gly Glu Ile
    770                 775                 780
Ala Ile Asp Asp Ile Arg Ile Ser Thr Asp Val Pro Leu Glu Asn Cys
785                 790                 795                 800
Met Glu Pro Ile Ser Ala Phe Ala Asp Glu Tyr Glu Val Asp Trp Ser
                805                 810                 815
Asn Ser Ser Ser Ala Thr Ser Gly Ser Gly Ala Pro Ser Thr Asp Lys
                820                 825                 830
Glu Lys Ser Trp Leu Tyr Thr Leu Asp Pro Ile Leu Ile Thr Ile Ile
                835                 840                 845
Ala Met Ser Ser Leu Gly Val Leu Leu Gly Ala Thr Cys Ala Gly Leu
    850                 855                 860
Leu Leu Tyr Cys Thr Cys Ser Tyr Ser Gly Leu Ser Ser Arg Ser Cys
865                 870                 875                 880
Thr Thr Leu Glu Asn Tyr Asn Phe Glu Leu Tyr Asp Gly Leu Lys His
                885                 890                 895
Lys Val Lys Met Asn His Gln Lys Cys Cys Ser Glu Ala
                900                 905

<210> SEQ ID NO 19
<211> LENGTH: 2781
<212> TYPE: DNA
<213> ORGANISM: human
<220> FEATURE:
```

```
<221> NAME/KEY: CDS
<222> LOCATION: (1)..(2778)

<400> SEQUENCE: 19 atg gat atg ttt cct ctc acc tgg gtt ttc tta gcc ctc tac ttt tca        48
Met Asp Met Phe Pro Leu Thr Trp Val Phe Leu Ala Leu Tyr Phe Ser
1               5                   10                  15 aga cac caa gtg aga ggc caa cca gac cca ccg tgc gga ggt cgt ttg        96
Arg His Gln Val Arg Gly Gln Pro Asp Pro Pro Cys Gly Gly Arg Leu
            20                  25                  30 aat tcc aaa gat gct ggc tat atc acc tct ccc ggt tac ccc cag gac       144
Asn Ser Lys Asp Ala Gly Tyr Ile Thr Ser Pro Gly Tyr Pro Gln Asp
        35                  40                  45 tac ccc tcc cac cag aac tgc gag tgg att gtt tac gcc ccc gaa ccc       192
Tyr Pro Ser His Gln Asn Cys Glu Trp Ile Val Tyr Ala Pro Glu Pro
50                  55                  60 aac cag aag att gtc ctc aac ttc aac cct cac ttt gaa atc gag aag       240
Asn Gln Lys Ile Val Leu Asn Phe Asn Pro His Phe Glu Ile Glu Lys
 65                  70                  75                  80 cac gac tgc aag tat gac ttt atc gag att cgg gat ggg gac agt gaa       288
His Asp Cys Lys Tyr Asp Phe Ile Glu Ile Arg Asp Gly Asp Ser Glu
                85                  90                  95 tcc gca gac ctc ctg ggc aaa cac tgt ggg aac atc gcc ccg ccc acc       336
Ser Ala Asp Leu Leu Gly Lys His Cys Gly Asn Ile Ala Pro Pro Thr
            100                 105                 110 atc atc tcc tcg ggc tcc atg ctc tac atc aag ttc acc tcc gac tac       384
Ile Ile Ser Ser Gly Ser Met Leu Tyr Ile Lys Phe Thr Ser Asp Tyr
        115                 120                 125 gcc cgg cag ggg gca ggc ttc tct ctg cgc tac gag atc ttc aag aca       432
Ala Arg Gln Gly Ala Gly Phe Ser Leu Arg Tyr Glu Ile Phe Lys Thr
130                 135                 140 ggc tct gaa gat tgc tca aaa aac ttc aca agc ccc aac ggg acc atc       480
Gly Ser Glu Asp Cys Ser Lys Asn Phe Thr Ser Pro Asn Gly Thr Ile
145                 150                 155                 160 gaa tct cct ggg ttt cct gag aag tat cca cac aac ttg gac tgc acc       528
Glu Ser Pro Gly Phe Pro Glu Lys Tyr Pro His Asn Leu Asp Cys Thr
                165                 170                 175 ttt acc atc ctg gcc aaa ccc aag atg gag atc atc ctg cag ttc ctg       576
Phe Thr Ile Leu Ala Lys Pro Lys Met Glu Ile Ile Leu Gln Phe Leu
            180                 185                 190 atc ttt gac ctg gag cat gac cct ttg cag gtg gga gag ggg gac tgc       624
Ile Phe Asp Leu Glu His Asp Pro Leu Gln Val Gly Glu Gly Asp Cys
        195                 200                 205 aag tac gat tgg ctg gac atc tgg gat ggc att cca cat gtt ggc ccc       672
Lys Tyr Asp Trp Leu Asp Ile Trp Asp Gly Ile Pro His Val Gly Pro
210                 215                 220 ctg att ggc aag tac tgt ggg acc aaa aca ccc tct gaa ctt cgt tca       720
Leu Ile Gly Lys Tyr Cys Gly Thr Lys Thr Pro Ser Glu Leu Arg Ser
225                 230                 235                 240 tcg acg ggg atc ctc tcc ctg acc ttt cac acg gac atg gcg gtg gcc       768
Ser Thr Gly Ile Leu Ser Leu Thr Phe His Thr Asp Met Ala Val Ala
                245                 250                 255 aag gat ggc ttc tct gcg cgt tac tac ctg gtc cac caa gag cca cta       816
Lys Asp Gly Phe Ser Ala Arg Tyr Tyr Leu Val His Gln Glu Pro Leu
            260                 265                 270 gag aac ttt cag tgc aat gtt cct ctg ggc atg gag tct ggc cgg att       864
Glu Asn Phe Gln Cys Asn Val Pro Leu Gly Met Glu Ser Gly Arg Ile
        275                 280                 285 gct aat gaa cag atc agt gcc tca tct acc tac tct gat ggg agg tgg       912
Ala Asn Glu Gln Ile Ser Ala Ser Ser Thr Tyr Ser Asp Gly Arg Trp
290                 295                 300
```

```
              290                 295                 300
acc cct caa caa agc cgg ctc cat ggt gat gac aat ggc tgg acc ccc       960
Thr Pro Gln Gln Ser Arg Leu His Gly Asp Asp Asn Gly Trp Thr Pro
305                 310                 315                 320 aac ttg gat tcc aac aag gag tat ctc cag gtg gac ctg cgc ttt tta      1008
Asn Leu Asp Ser Asn Lys Glu Tyr Leu Gln Val Asp Leu Arg Phe Leu
                325                 330                 335 acc atg ctc acg gcc atc gca aca cag gga gcg att tcc agg gaa aca      1056
Thr Met Leu Thr Ala Ile Ala Thr Gln Gly Ala Ile Ser Arg Glu Thr
            340                 345                 350 cag aat ggc tac tac gtc aaa tcc tac aag ctg gaa gtc agc act aat      1104
Gln Asn Gly Tyr Tyr Val Lys Ser Tyr Lys Leu Glu Val Ser Thr Asn
        355                 360                 365 gga gag gac tgg atg gtg tac cgg cat ggc aaa aac cac aag gta ttt      1152
Gly Glu Asp Trp Met Val Tyr Arg His Gly Lys Asn His Lys Val Phe
370                 375                 380 caa gcc aac aac gat gca act gag gtg gtt ctg aac aag ctc cac gct      1200
Gln Ala Asn Asn Asp Ala Thr Glu Val Val Leu Asn Lys Leu His Ala
385                 390                 395                 400 cca ctg ctg aca agg ttt gtt aga atc cgc cct cag acc tgg cac tca      1248
Pro Leu Leu Thr Arg Phe Val Arg Ile Arg Pro Gln Thr Trp His Ser
                405                 410                 415 ggt atc gcc ctc cgg ctg gag ctc ttc ggc tgc cgg gtc aca gat gct      1296
Gly Ile Ala Leu Arg Leu Glu Leu Phe Gly Cys Arg Val Thr Asp Ala
            420                 425                 430 ccc tgc tcc aac atg ctg ggg atg ctc tca ggc ctc att gca gac tcc      1344
Pro Cys Ser Asn Met Leu Gly Met Leu Ser Gly Leu Ile Ala Asp Ser
        435                 440                 445 cag atc tcc gcc tct tcc acc cag gaa tac ctc tgg agc ccc agt gca      1392
Gln Ile Ser Ala Ser Ser Thr Gln Glu Tyr Leu Trp Ser Pro Ser Ala
450                 455                 460 gcc cgc ctg gtc agc agc cgc tcg ggc tgg ttc cct cga atc cct cag      1440
Ala Arg Leu Val Ser Ser Arg Ser Gly Trp Phe Pro Arg Ile Pro Gln
465                 470                 475                 480 gcc cag ccc ggt gag gag tgg ctt cag gta gat ctg gga aca ccc aag      1488
Ala Gln Pro Gly Glu Glu Trp Leu Gln Val Asp Leu Gly Thr Pro Lys
                485                 490                 495 aca gtg aaa ggt gtc atc atc cag gga gcc cgc gga gga gac agt atc      1536
Thr Val Lys Gly Val Ile Ile Gln Gly Ala Arg Gly Gly Asp Ser Ile
            500                 505                 510 act gct gtg gaa gcc aga gca ttt gtg cgc aag ttc aaa gtc tcc tac      1584
Thr Ala Val Glu Ala Arg Ala Phe Val Arg Lys Phe Lys Val Ser Tyr
        515                 520                 525 agc cta aac ggc aag gac tgg gaa tac att cag gac ccc agg acc cag      1632
Ser Leu Asn Gly Lys Asp Trp Glu Tyr Ile Gln Asp Pro Arg Thr Gln
530                 535                 540 cag cca aag ctg ttc gaa ggg aac atg cac tat gac acc cct gac atc      1680
Gln Pro Lys Leu Phe Glu Gly Asn Met His Tyr Asp Thr Pro Asp Ile
545                 550                 555                 560 cga agg ttt gac ccc att ccg gca cag tat gtg cgg gta tac ccg gag      1728
Arg Arg Phe Asp Pro Ile Pro Ala Gln Tyr Val Arg Val Tyr Pro Glu
                565                 570                 575 agg tgg tcg ccg gcg ggg att ggg atg cgg ctg gag gtg ctg ggc tgt      1776
Arg Trp Ser Pro Ala Gly Ile Gly Met Arg Leu Glu Val Leu Gly Cys
            580                 585                 590 gac tgg aca gac tcc aag ccc acg gta aaa acg ctg gga ccc act gtg      1824
Asp Trp Thr Asp Ser Lys Pro Thr Val Lys Thr Leu Gly Pro Thr Val
        595                 600                 605 aag agc gaa gag aca acc acc ccc tac ccc acc gaa gag gag gcc aca      1872
```

-continued

| | | | | | | | | | | | | |
|---|---|---|---|---|---|---|---|---|---|---|---|---|
| Lys | Ser | Glu | Glu | Thr | Thr | Thr | Pro | Tyr | Pro | Thr | Glu | Glu | Ala | Thr |
| | 610 | | | | | 615 | | | | | 620 | | | |

```
gag tgt ggg gag aac tgc agc ttt gag gat gac aaa gat ttg cag ctc     1920
Glu Cys Gly Glu Asn Cys Ser Phe Glu Asp Asp Lys Asp Leu Gln Leu
625                 630                 635                 640 cct tcg gga ttc aat tgc aac ttc gat ttc ctc gag gag ccc tgt ggt     1968
Pro Ser Gly Phe Asn Cys Asn Phe Asp Phe Leu Glu Glu Pro Cys Gly
                645                 650                 655 tgg atg tat gac cat gcc aag tgg ctc cgg acc acc tgg gcc agc agc     2016
Trp Met Tyr Asp His Ala Lys Trp Leu Arg Thr Thr Trp Ala Ser Ser
            660                 665                 670 tcc agc cca aac gac cgg acg ttt cca gat gac agg aat ttc ttg cgg     2064
Ser Ser Pro Asn Asp Arg Thr Phe Pro Asp Asp Arg Asn Phe Leu Arg
        675                 680                 685 ctg cag agt gac agc cag aga gag ggc cag tat gcc cgg ctc atc agc     2112
Leu Gln Ser Asp Ser Gln Arg Glu Gly Gln Tyr Ala Arg Leu Ile Ser
    690                 695                 700 ccc cct gtc cac ctg ccc cga agc ccg gtg tgc atg gag ttc cag tac     2160
Pro Pro Val His Leu Pro Arg Ser Pro Val Cys Met Glu Phe Gln Tyr
705                 710                 715                 720 cag gcc acg ggc ggc cgc ggg gtg gcg ctg cag gtg gtg cgg gaa gcc     2208
Gln Ala Thr Gly Gly Arg Gly Val Ala Leu Gln Val Val Arg Glu Ala
                725                 730                 735 agc cag gag agc aag ttg ctg tgg gtc atc cgt gag gac cag ggc ggc     2256
Ser Gln Glu Ser Lys Leu Leu Trp Val Ile Arg Glu Asp Gln Gly Gly
                740                 745                 750 gag tgg aag cac ggg cgg atc atc ctg ccc agc tac gac atg gag tac     2304
Glu Trp Lys His Gly Arg Ile Ile Leu Pro Ser Tyr Asp Met Glu Tyr
            755                 760                 765 cag att gtg ttc gag gga gtg ata ggg aaa gga cgt tcc gga gag att     2352
Gln Ile Val Phe Glu Gly Val Ile Gly Lys Gly Arg Ser Gly Glu Ile
        770                 775                 780 gcc att gat gac att cgg ata agc act gat gtc cca ctg gag aac tgc     2400
Ala Ile Asp Asp Ile Arg Ile Ser Thr Asp Val Pro Leu Glu Asn Cys
785                 790                 795                 800 atg gaa ccc atc tcg gct ttt gca gtg gac atc cca gaa ata cat gag     2448
Met Glu Pro Ile Ser Ala Phe Ala Val Asp Ile Pro Glu Ile His Glu
                805                 810                 815 aga gaa gga tat gaa gat gaa att gat gat gaa tac gag gtg gac tgg     2496
Arg Glu Gly Tyr Glu Asp Glu Ile Asp Asp Glu Tyr Glu Val Asp Trp
                820                 825                 830 agc aat tct tct tct gca acc tca ggg tct ggc gcc ccc tcg acc gac     2544
Ser Asn Ser Ser Ser Ala Thr Ser Gly Ser Gly Ala Pro Ser Thr Asp
            835                 840                 845 aaa gaa aag agc tgg ctg tac acc ctg gat ccc atc ctc atc acc atc     2592
Lys Glu Lys Ser Trp Leu Tyr Thr Leu Asp Pro Ile Leu Ile Thr Ile
850                 855                 860 atc gcc atg agc tca ctg ggc gtc ctc ctg ggg gcc acc tgt gca ggc     2640
Ile Ala Met Ser Ser Leu Gly Val Leu Leu Gly Ala Thr Cys Ala Gly
865                 870                 875                 880 ctc ctg ctc tac tgc acc tgt tcc tac tcg ggc ctg agc tcc cga agc     2688
Leu Leu Leu Tyr Cys Thr Cys Ser Tyr Ser Gly Leu Ser Ser Arg Ser
                885                 890                 895 tgc acc aca ctg gag aac tac aac ttc gag ctc tac gat ggc ctt aag     2736
Cys Thr Thr Leu Glu Asn Tyr Asn Phe Glu Leu Tyr Asp Gly Leu Lys
                900                 905                 910 cac aag gtc aag atg aac cac caa aag tgc tgc tcc gag gca tga         2781
His Lys Val Lys Met Asn His Gln Lys Cys Cys Ser Glu Ala
            915                 920                 925
```

```
<210> SEQ ID NO 20
<211> LENGTH: 926
<212> TYPE: PRT
<213> ORGANISM: human

<400> SEQUENCE: 20

Met Asp Met Phe Pro Leu Thr Trp Val Phe Leu Ala Leu Tyr Phe Ser
  1               5                  10                  15

Arg His Gln Val Arg Gly Gln Pro Asp Pro Cys Gly Gly Arg Leu
             20                  25                  30

Asn Ser Lys Asp Ala Gly Tyr Ile Thr Ser Pro Gly Tyr Pro Gln Asp
         35                  40                  45

Tyr Pro Ser His Gln Asn Cys Glu Trp Ile Val Tyr Ala Pro Glu Pro
     50                  55                  60

Asn Gln Lys Ile Val Leu Asn Phe Asn Pro His Phe Glu Ile Glu Lys
 65                  70                  75                  80

His Asp Cys Lys Tyr Asp Phe Ile Glu Ile Arg Asp Gly Asp Ser Glu
                 85                  90                  95

Ser Ala Asp Leu Leu Gly Lys His Cys Gly Asn Ile Ala Pro Pro Thr
            100                 105                 110

Ile Ile Ser Ser Gly Ser Met Leu Tyr Ile Lys Phe Thr Ser Asp Tyr
        115                 120                 125

Ala Arg Gln Gly Ala Gly Phe Ser Leu Arg Tyr Glu Ile Phe Lys Thr
    130                 135                 140

Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                165                 170                 175

Phe Thr Ile Leu Ala Lys Pro Lys Met Glu Ile Ile Leu Gln Phe Leu
            180                 185                 190

Ile Phe Asp Leu Glu His Asp Pro Leu Gln Val Gly Glu Gly Asp Cys
        195                 200                 205

Lys Tyr Asp Trp Leu Asp Ile Trp Asp Gly Ile Pro His Val Gly Pro
    210                 215                 220

Leu Ile Gly Lys Tyr Cys Gly Thr Lys Thr Pro Ser Glu Leu Arg Ser
225                 230                 235                 240

Ser Thr Gly Ile Leu Ser Leu Thr Phe His Thr Asp Met Ala Val Ala
                245                 250                 255

Lys Asp Gly Phe Ser Ala Arg Tyr Tyr Leu Val His Gln Glu Pro Leu
            260                 265                 270

Glu Asn Phe Gln Cys Asn Val Pro Leu Gly Met Glu Ser Gly Arg Ile
        275                 280                 285

Ala Asn Glu Gln Ile Ser Ala Ser Ser Thr Tyr Ser Asp Gly Arg Trp
    290                 295                 300

Thr Pro Gln Gln Ser Arg Leu His Gly Asp Asp Asn Gly Trp Thr Pro
305                 310                 315                 320

Asn Leu Asp Ser Asn Lys Glu Tyr Leu Gln Val Asp Leu Arg Phe Leu
                325                 330                 335

Thr Met Leu Thr Ala Ile Ala Thr Gln Gly Ala Ile Ser Arg Glu Thr
            340                 345                 350

Gln Asn Gly Tyr Tyr Val Lys Ser Tyr Lys Leu Glu Val Ser Thr Asn
        355                 360                 365

Gly Glu Asp Trp Met Val Tyr Arg His Gly Lys Asn His Lys Val Phe
    370                 375                 380
```

-continued

```
Gln Ala Asn Asn Asp Ala Thr Glu Val Val Leu Asn Lys Leu His Ala
385                 390                 395                 400
Pro Leu Leu Thr Arg Phe Val Arg Ile Arg Pro Gln Thr Trp His Ser
            405                 410                 415
Gly Ile Ala Leu Arg Leu Glu Leu Phe Gly Cys Arg Val Thr Asp Ala
            420                 425                 430
Pro Cys Ser Asn Met Leu Gly Met Leu Ser Gly Leu Ile Ala Asp Ser
            435                 440                 445
Gln Ile Ser Ala Ser Ser Thr Gln Glu Tyr Leu Trp Ser Pro Ser Ala
            450                 455                 460
Ala Arg Leu Val Ser Ser Arg Ser Gly Trp Phe Pro Arg Ile Pro Gln
465                 470                 475                 480
Ala Gln Pro Gly Glu Glu Trp Leu Gln Val Asp Leu Gly Thr Pro Lys
            485                 490                 495
Thr Val Lys Gly Val Ile Ile Gln Gly Ala Arg Gly Gly Asp Ser Ile
            500                 505                 510
Thr Ala Val Glu Ala Arg Ala Phe Val Arg Lys Phe Lys Val Ser Tyr
            515                 520                 525
Ser Leu Asn Gly Lys Asp Trp Glu Tyr Ile Gln Asp Pro Arg Thr Gln
530                 535                 540
Gln Pro Lys Leu Phe Glu Gly Asn Met His Tyr Asp Thr Pro Asp Ile
545                 550                 555                 560
Arg Arg Phe Asp Pro Ile Pro Ala Gln Tyr Val Arg Val Tyr Pro Glu
            565                 570                 575
Arg Trp Ser Pro Ala Gly Ile Gly Met Arg Leu Glu Val Leu Gly Cys
            580                 585                 590
Asp Trp Thr Asp Ser Lys Pro Thr Val Lys Thr Leu Gly Pro Thr Val
            595                 600                 605
Lys Ser Glu Glu Thr Thr Thr Pro Tyr Pro Thr Glu Glu Ala Thr
            610                 615                 620
Glu Cys Gly Glu Asn Cys Ser Phe Glu Asp Asp Lys Asp Leu Gln Leu
625                 630                 635                 640
Pro Ser Gly Phe Asn Cys Asn Phe Asp Phe Leu Glu Glu Pro Cys Gly
            645                 650                 655
Trp Met Tyr Asp His Ala Lys Trp Leu Arg Thr Thr Trp Ala Ser Ser
            660                 665                 670
Ser Ser Pro Asn Asp Arg Thr Phe Pro Asp Asp Arg Asn Phe Leu Arg
            675                 680                 685
Leu Gln Ser Asp Ser Gln Arg Glu Gly Gln Tyr Ala Arg Leu Ile Ser
            690                 695                 700
Pro Pro Val His Leu Pro Arg Ser Pro Val Cys Met Glu Phe Gln Tyr
705                 710                 715                 720
Gln Ala Thr Gly Gly Arg Gly Val Ala Leu Gln Val Val Arg Glu Ala
            725                 730                 735
Ser Gln Glu Ser Lys Leu Leu Trp Val Ile Arg Glu Asp Gln Gly Gly
            740                 745                 750
Glu Trp Lys His Gly Arg Ile Ile Leu Pro Ser Tyr Asp Met Glu Tyr
            755                 760                 765
Gln Ile Val Phe Glu Gly Val Ile Gly Lys Gly Arg Ser Gly Glu Ile
            770                 775                 780
Ala Ile Asp Asp Ile Arg Ile Ser Thr Asp Val Pro Leu Glu Asn Cys
785                 790                 795                 800
```

```
Met Glu Pro Ile Ser Ala Phe Ala Val Asp Ile Pro Glu Ile His Glu
                805                 810                 815
Arg Glu Gly Tyr Glu Asp Glu Ile Asp Asp Glu Tyr Glu Val Asp Trp
            820                 825                 830
Ser Asn Ser Ser Ser Ala Thr Ser Gly Ser Gly Ala Pro Ser Thr Asp
        835                 840                 845
Lys Glu Lys Ser Trp Leu Tyr Thr Leu Asp Pro Ile Leu Ile Thr Ile
    850                 855                 860
Ile Ala Met Ser Ser Leu Gly Val Leu Gly Ala Thr Cys Ala Gly
865                 870                 875                 880
Leu Leu Leu Tyr Cys Thr Cys Ser Tyr Ser Gly Leu Ser Ser Arg Ser
                885                 890                 895
Cys Thr Thr Leu Glu Asn Tyr Asn Phe Glu Leu Tyr Asp Gly Leu Lys
            900                 905                 910
His Lys Val Lys Met Asn His Gln Lys Cys Cys Ser Glu Ala
        915                 920                 925
```

<210> SEQ ID NO 21
<211> LENGTH: 4765
<212> TYPE: DNA
<213> ORGANISM: mouse
<220> FEATURE:
<221> NAME/KEY: CDS
<222> LOCATION: (567)..(3269)

<400> SEQUENCE: 21

```
aaactggagc tccaccgcgg tgcggccgc ccgggcaggt ctagaattca gcggccgctg      60
aattctatcc agcggtcggt gcctctgccc gcgtgtgtgt cccgggtgcc ggggacctg    120 tgtcagttag cgcttctgag atcacacagc tgcctagggg ccgtgtgatg cccagggcaa   180
ttcttggctt tgattttat tattattact attattttgc gttcagcttt cgggaaaccc    240
tcgtgatgtt gtaggataaa ggaaatgaca cttggaggaa ctggagagaa catacacgcg   300
tttgggtttg aagaggaaac cggtctccgc ttccttagct tgctccctct ttgctgattt   360
caagagctat ctcctatgag gtggagatat ccagcaaga ataaaggtga agacagactg    420
actgccagga cccaggagga aaacgttgat cgttagagac cttttgcagaa gacaccacca   480 ggaggaaaat tagagaggaa aaacacaaag acataattat aggagatccc acaaacctag   540
cccgggagag agcctctctg tcaaaa atg gat atg ttt cct ctt acc tgg gtt   593
                              Met Asp Met Phe Pro Leu Thr Trp Val
                                1               5 ttc tta gct ctg tac ttt tca gga cac gaa gtg aga agc cag caa gat   641
Phe Leu Ala Leu Tyr Phe Ser Gly His Glu Val Arg Ser Gln Gln Asp
 10              15                  20                  25 cca ccc tgc gga ggt cgg ccg aat tcc aaa gat gct ggc tac atc act   689
Pro Pro Cys Gly Gly Arg Pro Asn Ser Lys Asp Ala Gly Tyr Ile Thr
             30                  35                  40 tcc cca ggc tac ccc cag gac tat ccc tcc cac cag aac tgt gag tgg   737
Ser Pro Gly Tyr Pro Gln Asp Tyr Pro Ser His Gln Asn Cys Glu Trp
         45                  50                  55 att gtc tac gcc ccc gaa ccc aac cag aag att gtt ctc aac ttc aac   785
Ile Val Tyr Ala Pro Glu Pro Asn Gln Lys Ile Val Leu Asn Phe Asn
     60                  65                  70 cct cac ttt gaa atc gag aaa cac gac tgc aag tat gac ttc att gag   833
Pro His Phe Glu Ile Glu Lys His Asp Cys Lys Tyr Asp Phe Ile Glu
 75                  80                  85 att cgg gat ggg gac agt gag tca gct gac ctc ctg ggc aag cac tgt   881
Ile Arg Asp Gly Asp Ser Glu Ser Ala Asp Leu Leu Gly Lys His Cys
             90                  95                 100
```

```
                90                   95                  100                 105
        ggg aac atc gcc ccg ccc acc atc atc tcc tca ggc tcc gtg tta tac        929
        Gly Asn Ile Ala Pro Pro Thr Ile Ile Ser Ser Gly Ser Val Leu Tyr
                        110                 115                 120 atc aag ttc acc tca gac tac gcc cgg cag ggg gca ggt ttc tct cta        977
        Ile Lys Phe Thr Ser Asp Tyr Ala Arg Gln Gly Ala Gly Phe Ser Leu
                    125                 130                 135 cgc tat gag atc ttc aaa aca ggc tct gaa gat tgt tcc aag aac ttt       1025
        Arg Tyr Glu Ile Phe Lys Thr Gly Ser Glu Asp Cys Ser Lys Asn Phe
                140                 145                 150 aca agc ccc aat ggg acc att gaa tct cca ggg ttt cca gag aag tat       1073
        Thr Ser Pro Asn Gly Thr Ile Glu Ser Pro Gly Phe Pro Glu Lys Tyr
            155                 160                 165 cca cac aat ctg gac tgt acc ttc acc atc ctg gcc aaa ccc agg atg       1121
        Pro His Asn Leu Asp Cys Thr Phe Thr Ile Leu Ala Lys Pro Arg Met
        170                 175                 180                 185 gag atc atc cta cag ttc ctg acc ttt gac ctg gag cat gac cct cta       1169
        Glu Ile Ile Leu Gln Phe Leu Thr Phe Asp Leu Glu His Asp Pro Leu
                        190                 195                 200 caa gtg ggg gaa gga gac tgt aaa tat gac tgg ctg gac atc tgg gat       1217
        Gln Val Gly Glu Gly Asp Cys Lys Tyr Asp Trp Leu Asp Ile Trp Asp
                    205                 210                 215 ggc att cca cat gtt gga cct ctg att ggc aag tac tgt ggg acg aaa       1265
        Gly Ile Pro His Val Gly Pro Leu Ile Gly Lys Tyr Cys Gly Thr Lys
                220                 225                 230 aca ccc tcc aaa ctc cgc tcg tcc acg ggg atc ctc tcc ttg acc ttt       1313
        Thr Pro Ser Lys Leu Arg Ser Ser Thr Gly Ile Leu Ser Leu Thr Phe
            235                 240                 245 cac acg gac atg gca gtg gcc aag gat ggc ttc tcc gca cgt tac tat       1361
        His Thr Asp Met Ala Val Ala Lys Asp Gly Phe Ser Ala Arg Tyr Tyr
        250                 255                 260                 265 ttg atc cac cag gag cca cct gag aat ttt cag tgc aat gtc cct ttg       1409
        Leu Ile His Gln Glu Pro Pro Glu Asn Phe Gln Cys Asn Val Pro Leu
                        270                 275                 280 gga atg gag tct ggc cgg att gct aat gaa cag atc agt gcc tcc tcc       1457
        Gly Met Glu Ser Gly Arg Ile Ala Asn Glu Gln Ile Ser Ala Ser Ser
                    285                 290                 295 acc ttc tct gat ggg agg tgg act cct caa cag agc cgg ctc cat ggt       1505
        Thr Phe Ser Asp Gly Arg Trp Thr Pro Gln Gln Ser Arg Leu His Gly
                300                 305                 310 gat gac aat ggc tgg aca ccc aat ttg gat tcc aac aag gag tat ctc       1553
        Asp Asp Asn Gly Trp Thr Pro Asn Leu Asp Ser Asn Lys Glu Tyr Leu
            315                 320                 325 cag gtg gac ctg cgc ttc cta acc atg ctc aca gcc att gca aca cag       1601
        Gln Val Asp Leu Arg Phe Leu Thr Met Leu Thr Ala Ile Ala Thr Gln
        330                 335                 340                 345 gga gcc att tcc agg gaa acc cag aaa ggc tac tac gtc aaa tcg tac       1649
        Gly Ala Ile Ser Arg Glu Thr Gln Lys Gly Tyr Tyr Val Lys Ser Tyr
                        350                 355                 360 aag ctg gaa gtc agc aca aat ggt gaa gat tgg atg gtc tac cgg cat       1697
        Lys Leu Glu Val Ser Thr Asn Gly Glu Asp Trp Met Val Tyr Arg His
                    365                 370                 375 ggc aaa aac cac aag ata ttc caa gcg aac aat gat gcg acc gag gtg       1745
        Gly Lys Asn His Lys Ile Phe Gln Ala Asn Asn Asp Ala Thr Glu Val
                380                 385                 390 gtg cta aac aag ctc cac atg cca ctg ctg act cgg ttc atc agg atc       1793
        Val Leu Asn Lys Leu His Met Pro Leu Leu Thr Arg Phe Ile Arg Ile
            395                 400                 405 cgc ccg cag acg tgg cat ttg ggc att gcc ctt cgc ctg gag ctc ttt       1841
```

-continued

```
Arg Pro Gln Thr Trp His Leu Gly Ile Ala Leu Arg Leu Glu Leu Phe
410                 415                 420                 425 ggc tgc cgg gtc aca gat gca ccc tgc tcc aac atg ctg ggg atg ctc   1889
Gly Cys Arg Val Thr Asp Ala Pro Cys Ser Asn Met Leu Gly Met Leu
                430                 435                 440 tcg ggc ctc att gct gat acc cag atc tct gcc tcc tcc acc cga gag   1937
Ser Gly Leu Ile Ala Asp Thr Gln Ile Ser Ala Ser Ser Thr Arg Glu
            445                 450                 455 tac ctc tgg agc ccc agt gct gcc cgc ctg gtt agt agc cgc tct ggc   1985
Tyr Leu Trp Ser Pro Ser Ala Ala Arg Leu Val Ser Ser Arg Ser Gly
        460                 465                 470 tgg ttt cct cgg aac cct caa gcc cag cca ggt gaa gaa tgg ctt cag   2033
Trp Phe Pro Arg Asn Pro Gln Ala Gln Pro Gly Glo7/ o7/ p Leu Gln
    475                 480                 485 gta gac ctg ggg aca ccc aag aca gtg aaa ggg gtc atc atc cag gga   2081
Val Asp Leu Gly Thr Pro Lys Thr Val Lys Gly Val Ile Ile Gln Gly
490                 495                 500                 505 gcc cga gga gga gac agc atc act gcc gtg gaa gcc agg gcg ttt gta   2129
Ala Arg Gly Gly Asp Ser Ile Thr Ala Val Glu Ala Arg Ala Phe Val
                510                 515                 520 cgc aag ttc aaa gtc tcc tac agc cta aat ggc aag gac tgg gaa tat   2177
Arg Lys Phe Lys Val Ser Tyr Ser Leu Asn Gly Lys Asp Trp Glu Tyr
            525                 530                 535 atc cag gac ccc agg act cag cag aca aag ctg ttt gaa ggg aac atg   2225
Ile Gln Asp Pro Arg Thr Gln Gln Thr Lys Leu Phe Glu Gly Asn Met
        540                 545                 550 cac tat gac acc cct gac atc cga agg ttc gat cct gtt cca gcg cag   2273
His Tyr Asp Thr Pro Asp Ile Arg Arg Phe Asp Pro Val Pro Ala Gln
    555                 560                 565 tat gtg cgg gtg tac cca gag agg tgg tcg cca gca ggc atc ggg atg   2321
Tyr Val Arg Val Tyr Pro Glu Arg Trp Ser Pro Ala Gly Ile Gly Met
570                 575                 580                 585 agg ctg gag gtg ctg ggc tgt gac tgg aca gac tca aag ccc aca gtg   2369
Arg Leu Glu Val Leu Gly Cys Asp Trp Thr Asp Ser Lys Pro Thr Val
                590                 595                 600 gag acg ctg gga ccc acc gtg aag agt gaa gag act acc acc cca tat   2417
Glu Thr Leu Gly Pro Thr Val Lys Ser Glu Glu Thr Thr Thr Pro Tyr
            605                 610                 615 ccc atg gat gag gat gcc acc gag tgt ggg gaa aac tgc agc ttt gag   2465
Pro Met Asp Glu Asp Ala Thr Glu Cys Gly Glu Asn Cys Ser Phe Glu
        620                 625                 630 gat gac aaa gat ttg caa ctt cct tca gga ttc aac tgc aac ttt gat   2513
Asp Asp Lys Asp Leu Gln Leu Pro Ser Gly Phe Asn Cys Asn Phe Asp
    635                 640                 645 ttt ccg gaa gag acc tgt ggt tgg gtg tac gac cat gcc aag tgg ctc   2561
Phe Pro Glu Glu Thr Cys Gly Trp Val Tyr Asp His Ala Lys Trp Leu
650                 655                 660                 665 cgg agc acg tgg atc agc agc gct aac ccc aat gac aga aca ttt cca   2609
Arg Ser Thr Trp Ile Ser Ser Ala Asn Pro Asn Asp Arg Thr Phe Pro
                670                 675                 680 gat gac aag aac ttc ttg aaa ctg cag agt gat ggc cga cga gag ggc   2657
Asp Asp Lys Asn Phe Leu Lys Leu Gln Ser Asp Gly Arg Arg Glu Gly
            685                 690                 695 cag tac ggg cgg ctc atc agc cca ccg gtg cac ctg ccc cga agc cct   2705
Gln Tyr Gly Arg Leu Ile Ser Pro Pro Val His Leu Pro Arg Ser Pro
        700                 705                 710 gtg tgc atg gag ttc cag tac caa gcc atg ggc ggc cac ggg gtg gca   2753
Val Cys Met Glu Phe Gln Tyr Gln Ala Met Gly Gly His Gly Val Ala
    715                 720                 725
```

| | |
|---|---|
| ctg cag gtg gtt cgg gaa gcc agc cag gaa agc aaa ctc ctt tgg gtc<br>Leu Gln Val Val Arg Glu Ala Ser Gln Glu Ser Lys Leu Leu Trp Val<br>730                         735                    740                      745 | 2801 |
| atc cgt gag gac cag ggc agc gag tgg aag cac ggg cgc att atc ctg<br>Ile Arg Glu Asp Gln Gly Ser Glu Trp Lys His Gly Arg Ile Ile Leu<br>                        750                    755                      760 | 2849 |
| ccc agc tat gac atg gag tat cag atc gtg ttc gag gga gtg ata ggg<br>Pro Ser Tyr Asp Met Glu Tyr Gln Ile Val Phe Glu Gly Val Ile Gly<br>        765                    770                    775 | 2897 |
| aag gga cga tcg gga gag att tcc atc gat gac att cgg ata agc act<br>Lys Gly Arg Ser Gly Glu Ile Ser Ile Asp Asp Ile Arg Ile Ser Thr<br>780                         785                    790 | 2945 |
| gat gtc cca ctg gag aac tgc atg gaa ccc ata tca gct ttt gca ggg<br>Asp Val Pro Leu Glu Asn Cys Met Glu Pro Ile Ser Ala Phe Ala Gly<br>     795                    800                    805 | 2993 |
| ggc acc ctc ccg cca ggg acc gag ccc aca gtg gac acg gtg ccc gtg<br>Gly Thr Leu Pro Pro Gly Thr Glu Pro Thr Val Asp Thr Val Pro Val<br>810                         815                    820                    825 | 3041 |
| cag ccc atc cca gcc tac tgg tat tac gtt atg gcg gcc ggg ggc gcc<br>Gln Pro Ile Pro Ala Tyr Trp Tyr Tyr Val Met Ala Ala Gly Gly Ala<br>                        830                    835                      840 | 3089 |
| gtg ctg gtg ctg gcc tcc gtc gtc ctg gcc ctg gtg ctc cac tac cac<br>Val Leu Val Leu Ala Ser Val Val Leu Ala Leu Val Leu His Tyr His<br>        845                    850                    855 | 3137 |
| cgg ttc cgc tat gcg gcc aag aag acc gat cac tcc atc acc tac aaa<br>Arg Phe Arg Tyr Ala Ala Lys Lys Thr Asp His Ser Ile Thr Tyr Lys<br>860                         865                    870 | 3185 |
| acc tcc cac tac acc aac ggg gcc cct ctg gcg gtc gag ccc acc cta<br>Thr Ser His Tyr Thr Asn Gly Ala Pro Leu Ala Val Glu Pro Thr Leu<br>     875                    880                    885 | 3233 |
| acc att aag cta gag caa gag cgg ggc tcg cac tgc tgagggccga<br>Thr Ile Lys Leu Glu Gln Glu Arg Gly Ser His Cys<br>890                         895                    900 | 3279 |
| agcaggaaca gcgccccccc aaaaaaaacc caagaaagac tgcaaacacg ttgcctcgat | 3339 |
| tttgcacttt ttttctcctc gcctagtctc tgtgtgaacc ctcagacatc tctctccagg | 3399 |
| gtccccaacc ctgagcgctc tcatgtaccc cacaccattc tctgtggttc ttggttccgg | 3459 |
| tttctctttg ctctgatatt gtttgttttt aatcattatt ttttttcctt ttcttctttc | 3519 |
| cttttaatct tctctctttt attcctttct ccctccccg ccccgccttt ttctaatgat | 3579 |
| tttaaaccaa ctctaatgct gcatctggaa tcccagaaga gacccgcccc taagcacttc | 3639 |
| acaacccaag gctctgttgg ttttgttcca gagacaggcc ctgttgtttt ctcccttgc | 3699 |
| cttatcccat ccctcctctc ctgggcaggc tgccaggtgt cttgagggga gcctggtcct | 3759 |
| gtatgtatgt acacagtaca ctcccatgtg aagaggtgtg tgtgtgtgtg tgtgtgtgtg | 3819 |
| tgtattttcg agggagagac tgattcactg tggaagggg ggagtgtggg tgtgtgtaga | 3879 |
| gagggcccc ttccctctta tgttgcttct tctggggtac ttttcaagaa aataatatac | 3939 |
| tgtacacatt tgttttactt ggagaagaga ttggagcttt tttgttgcct tatctagctc | 3999 |
| tggctgggtt tctgttggct gtcattgtca tctccaggta cctagacaaa tagagaccat | 4059 |
| tgggaatgca atgtggcttc acccatcctt atccccatcc caagccaccc aagactatgg | 4119 |
| ttcctccagt gcactcagac atgacccctt ttgttatgtt cctggtgtc tttgaagtca | 4179 |
| caagataaca gccattgggt gcatggagtc atttctactt ccagccctga agcaaatgtg | 4239 |
| tctcatgttg cctataaaa aaaaccggaa ttcctgtagt tgaagagtaa gattttgtac | 4299 |
| ggtacatttt taatgacagc ttggatattg gaatactcaa cttttgttgt agccaatgag | 4359 |

-continued

```
agggatatgc cactaatggt atctaaatca tacagtacgt actttaggat ggggacaaaa    4419
atcacaacga tttatttatt tatttactta gtgtatgtga gtgcactgtt ggtgtcttca    4479
gacacaccag aagatgactt cagatccgat tacatatggg ttgtgagcca ccatgtggtt    4539
gctgggattt gaactctgga cctctggaag agcagtcagt gcttgtaact ctgagccatc    4599
tttctagccc ccccccccc cccgctatct tttagaaatg taatttgcca tactttgagc     4659
aatgttcttg atgtcattag gatatttcac agataacttc acttaagata attagagcaa    4719
aaaaaaaaaa aaaaaaaaaa aaaaaaaaaa aaaaaaaaaa aaaaa                    4765
```

<210> SEQ ID NO 22
<211> LENGTH: 901
<212> TYPE: PRT
<213> ORGANISM: mouse

<400> SEQUENCE: 22

```
Met Asp Met Phe Pro Leu Thr Trp Val Phe Leu Ala Leu Tyr Phe Ser
  1               5                  10                  15

Gly His Glu Val Arg Ser Gln Gln Asp Pro Pro Cys Gly Gly Arg Pro
             20                  25                  30

Asn Ser Lys Asp Ala Gly Tyr Ile Thr Ser Pro Gly Tyr Pro Gln Asp
         35                  40                  45

Tyr Pro Ser His Gln Asn Cys Glu Trp Ile Val Tyr Ala Pro Glu Pro
     50                  55                  60

Asn Gln Lys Ile Val Leu Asn Phe Asn Pro His Phe Glu Ile Glu Lys
 65                  70                  75                  80

His Asp Cys Lys Tyr Asp Phe Ile Glu Ile Arg Asp Gly Asp Ser Glu
                 85                  90                  95

Ser Ala Asp Leu Leu Gly Lys His Cys Gly Asn Ile Ala Pro Pro Thr
            100                 105                 110

Ile Ile Ser Ser Gly Ser Val Leu Tyr Ile Lys Phe Thr Ser Asp Tyr
        115                 120                 125

Ala Arg Gln Gly Ala Gly Phe Ser Leu Arg Tyr Glu Ile Phe Lys Thr
    130                 135                 140

Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                165                 170                 175

Phe Thr Ile Leu Ala Lys Pro Arg Met Glu Ile Ile Leu Gln Phe Leu
            180                 185                 190

Thr Phe Asp Leu Glu His Asp Pro Leu Gln Val Gly Glu Gly Asp Cys
        195                 200                 205

Lys Tyr Asp Trp Leu Asp Ile Trp Asp Gly Ile Pro His Val Gly Pro
    210                 215                 220

Leu Ile Gly Lys Tyr Cys Gly Thr Lys Thr Pro Ser Lys Leu Arg Ser
225                 230                 235                 240

Ser Thr Gly Ile Leu Ser Leu Thr Phe His Thr Asp Met Ala Val Ala
                245                 250                 255

Lys Asp Gly Phe Ser Ala Arg Tyr Tyr Leu Ile His Gln Glu Pro Pro
            260                 265                 270

Glu Asn Phe Gln Cys Asn Val Pro Leu Gly Met Glu Ser Gly Arg Ile
        275                 280                 285

Ala Asn Glu Gln Ile Ser Ala Ser Ser Thr Phe Ser Asp Gly Arg Trp
    290                 295                 300
```

-continued

```
Thr Pro Gln Gln Ser Arg Leu His Gly Asp Asp Asn Gly Trp Thr Pro
305                 310                 315                 320

Asn Leu Asp Ser Asn Lys Glu Tyr Leu Gln Val Asp Leu Arg Phe Leu
            325                 330                 335

Thr Met Leu Thr Ala Ile Ala Thr Gln Gly Ala Ile Ser Arg Glu Thr
            340                 345                 350

Gln Lys Gly Tyr Tyr Val Lys Ser Tyr Lys Leu Glu Val Ser Thr Asn
            355                 360                 365

Gly Glu Asp Trp Met Val Tyr Arg His Gly Lys Asn His Lys Ile Phe
    370                 375                 380

Gln Ala Asn Asn Asp Ala Thr Glu Val Val Leu Asn Lys Leu His Met
385                 390                 395                 400

Pro Leu Leu Thr Arg Phe Ile Arg Ile Arg Pro Gln Thr Trp His Leu
                405                 410                 415

Gly Ile Ala Leu Arg Leu Glu Leu Phe Gly Cys Arg Val Thr Asp Ala
            420                 425                 430

Pro Cys Ser Asn Met Leu Gly Met Leu Ser Gly Leu Ile Ala Asp Thr
            435                 440                 445

Gln Ile Ser Ala Ser Ser Thr Arg Glu Tyr Leu Trp Ser Pro Ser Ala
    450                 455                 460

Ala Arg Leu Val Ser Ser Arg Ser Gly Trp Phe Pro Arg Asn Pro Gln
465                 470                 475                 480

Ala Gln Pro Gly Glu Glu Trp Leu Gln Val Asp Leu Gly Thr Pro Lys
            485                 490                 495

Thr Val Lys Gly Val Ile Ile Gln Gly Ala Arg Gly Gly Asp Ser Ile
            500                 505                 510

Thr Ala Val Glu Ala Arg Ala Phe Val Arg Lys Phe Lys Val Ser Tyr
    515                 520                 525

Ser Leu Asn Gly Lys Asp Trp Glu Tyr Ile Gln Asp Pro Arg Thr Gln
530                 535                 540

Gln Thr Lys Leu Phe Glu Gly Asn Met His Tyr Asp Thr Pro Asp Ile
545                 550                 555                 560

Arg Arg Phe Asp Pro Val Pro Ala Gln Tyr Val Arg Val Tyr Pro Glu
                565                 570                 575

Arg Trp Ser Pro Ala Gly Ile Gly Met Arg Leu Glu Val Leu Gly Cys
            580                 585                 590

Asp Trp Thr Asp Ser Lys Pro Thr Val Glu Thr Leu Gly Pro Thr Val
    595                 600                 605

Lys Ser Glu Glu Thr Thr Thr Pro Tyr Pro Met Asp Glu Asp Ala Thr
610                 615                 620

Glu Cys Gly Glu Asn Cys Ser Phe Glu Asp Asp Lys Asp Leu Gln Leu
625                 630                 635                 640

Pro Ser Gly Phe Asn Cys Asn Phe Asp Phe Pro Glu Glu Thr Cys Gly
                645                 650                 655

Trp Val Tyr Asp His Ala Lys Trp Leu Arg Ser Thr Trp Ile Ser Ser
            660                 665                 670

Ala Asn Pro Asn Asp Arg Thr Phe Pro Asp Lys Asn Phe Leu Lys
    675                 680                 685

Leu Gln Ser Asp Gly Arg Arg Glu Gly Gln Tyr Gly Arg Leu Ile Ser
            690                 695                 700

Pro Pro Val His Leu Pro Arg Ser Pro Val Cys Met Glu Phe Gln Tyr
705                 710                 715                 720
```

```
Gln Ala Met Gly Gly His Gly Val Ala Leu Gln Val Val Arg Glu Ala
            725                 730                 735

Ser Gln Glu Ser Lys Leu Leu Trp Val Ile Arg Glu Asp Gln Gly Ser
            740                 745                 750

Glu Trp Lys His Gly Arg Ile Ile Leu Pro Ser Tyr Asp Met Glu Tyr
            755                 760                 765

Gln Ile Val Phe Glu Gly Val Ile Gly Lys Gly Arg Ser Gly Glu Ile
            770                 775                 780

Ser Ile Asp Asp Ile Arg Ile Ser Thr Asp Val Pro Leu Glu Asn Cys
785                 790                 795                 800

Met Glu Pro Ile Ser Ala Phe Ala Gly Gly Thr Leu Pro Pro Gly Thr
            805                 810                 815

Glu Pro Thr Val Asp Thr Val Pro Val Gln Pro Ile Pro Ala Tyr Trp
            820                 825                 830

Tyr Tyr Val Met Ala Ala Gly Gly Ala Val Leu Val Leu Ala Ser Val
            835                 840                 845

Val Leu Ala Leu Val Leu His Tyr His Arg Phe Arg Tyr Ala Ala Lys
            850                 855                 860

Lys Thr Asp His Ser Ile Thr Tyr Lys Thr Ser His Tyr Thr Asn Gly
865                 870                 875                 880

Ala Pro Leu Ala Val Glu Pro Thr Leu Thr Ile Lys Leu Glu Gln Glu
            885                 890                 895

Arg Gly Ser His Cys
            900

<210> SEQ ID NO 23
<211> LENGTH: 4780
<212> TYPE: DNA
<213> ORGANISM: mouse
<220> FEATURE:
<221> NAME/KEY: CDS
<222> LOCATION: (567)..(3284)

<400> SEQUENCE: 23
aaactggagc tccaccgcgg tgcggccgc ccgggcaggt ctagaattca gcggccgctg      60
aattctatcc agcggtcggt gcctctgccc gcgtgtgtgt cccgggtgcc ggggGacctg    120
tgtcagttag cgcttctgag atcacacagc tgccTAgggg ccgtgtgatg cccagggcaa    180
ttcttggctt tgattttat tattattact attattttgc gttcagcttt cgggaaaccc    240
tcgtgatgtt gtaggataaa ggaaatgaca ctttgaggaa ctgagagaa catacacgcg    300 tttgggtttg aagaggaaac cggtctccgc ttccttagct tgctccctct ttgctgattt    360
caagagctat ctcctatgag gtggagatat ccagcaaga ataaaggtga agacagactg    420
actgccagga cccaggagga aaacgttgat cgttagagac ctttgcagaa gacaccacca    480
ggaggaaaat tagagaggaa aaacacaaag acataattat aggagatccc acaaacctag    540
cccgggagag agcctctctg tcaaaa atg gat atg ttt cct ctt acc tgg gtt    593
                              Met Asp Met Phe Pro Leu Thr Trp Val
                                1               5 ttc tta gct ctg tac ttt tca gga cac gaa gtg aga agc cag caa gat    641
Phe Leu Ala Leu Tyr Phe Ser Gly His Glu Val Arg Ser Gln Gln Asp
 10              15                  20                  25 cca ccc tgc gga ggt cgg ccg aat tcc aaa gat gct ggc tac atc act    689
Pro Pro Cys Gly Gly Arg Pro Asn Ser Lys Asp Ala Gly Tyr Ile Thr
             30                  35                  40 tcc cca ggc tac ccc cag gac tat ccc tcc cac cag aac tgt gag tgg    737
Ser Pro Gly Tyr Pro Gln Asp Tyr Pro Ser His Gln Asn Cys Glu Trp
```

```
att gtc tac gcc ccc gaa ccc aac cag aag att gtt ctc aac ttc aac      785
Ile Val Tyr Ala Pro Glu Pro Asn Gln Lys Ile Val Leu Asn Phe Asn
            60                  65                  70 cct cac ttt gaa atc gag aaa cac gac tgc aag tat gac ttc att gag      833
Pro His Phe Glu Ile Glu Lys His Asp Cys Lys Tyr Asp Phe Ile Glu
     75                  80                  85 att cgg gat ggg gac agt gag tca gct gac ctc ctg ggc aag cac tgt      881
Ile Arg Asp Gly Asp Ser Glu Ser Ala Asp Leu Leu Gly Lys His Cys
 90                  95                 100                 105 ggg aac atc gcc ccg ccc acc atc atc tcc tca ggc tcc gtg tta tac      929
Gly Asn Ile Ala Pro Pro Thr Ile Ile Ser Ser Gly Ser Val Leu Tyr
                110                 115                 120 atc aag ttc acc tca gac tac gcc cgg cag ggg gca ggt ttc tct cta      977
Ile Lys Phe Thr Ser Asp Tyr Ala Arg Gln Gly Ala Gly Phe Ser Leu
            125                 130                 135 cgc tat gag atc ttc aaa aca ggc tct gaa gat tgt tcc aag aac ttt     1025
Arg Tyr Glu Ile Phe Lys Thr Gly Ser Glu Asp Cys Ser Lys Asn Phe
        140                 145                 150 aca agc ccc aat ggg acc att gaa tct cca ggg ttt cca gag aag tat     1073
Thr Ser Pro Asn Gly Thr Ile Glu Ser Pro Gly Phe Pro Glu Lys Tyr
    155                 160                 165 cca cac aat ctg gac tgt acc ttc acc atc ctg gcc aaa ccc agg atg     1121
Pro His Asn Leu Asp Cys Thr Phe Thr Ile Leu Ala Lys Pro Arg Met
170                 175                 180                 185 gag atc atc cta cag ttc ctg acc ttt gac ctg gag cat gac cct cta     1169
Glu Ile Ile Leu Gln Phe Leu Thr Phe Asp Leu Glu His Asp Pro Leu
                190                 195                 200 caa gtg ggg gaa gga gac tgt aaa tat gac tgg ctg gac atc tgg gat     1217
Gln Val Gly Glu Gly Asp Cys Lys Tyr Asp Trp Leu Asp Ile Trp Asp
            205                 210                 215 ggc att cca cat gtt gga cct ctg att ggc aag tac tgt ggg acg aaa     1265
Gly Ile Pro His Val Gly Pro Leu Ile Gly Lys Tyr Cys Gly Thr Lys
        220                 225                 230 aca ccc tcc aaa ctc cgc tcg tcc acg ggg atc ctc tcc ttg acc ttt     1313
Thr Pro Ser Lys Leu Arg Ser Ser Thr Gly Ile Leu Ser Leu Thr Phe
    235                 240                 245 cac acg gac atg gca gtg gcc aag gat ggc ttc tcc gca cgt tac tat     1361
His Thr Asp Met Ala Val Ala Lys Asp Gly Phe Ser Ala Arg Tyr Tyr
250                 255                 260                 265 ttg atc cac cag gag cca cct gag aat ttt cag tgc aat gtc cct ttg     1409
Leu Ile His Gln Glu Pro Pro Glu Asn Phe Gln Cys Asn Val Pro Leu
                270                 275                 280 gga atg gag tct ggc cgg att gct aat gaa cag atc agt gcc tcc tcc     1457
Gly Met Glu Ser Gly Arg Ile Ala Asn Glu Gln Ile Ser Ala Ser Ser
            285                 290                 295 acc ttc tct gat ggg agg tgg act cct caa cag agc cgg ctc cat ggt     1505
Thr Phe Ser Asp Gly Arg Trp Thr Pro Gln Gln Ser Arg Leu His Gly
        300                 305                 310 gat gac aat ggc tgg aca ccc aat ttg gat tcc aac aag gag tat ctc     1553
Asp Asp Asn Gly Trp Thr Pro Asn Leu Asp Ser Asn Lys Glu Tyr Leu
    315                 320                 325 cag gtg gac ctg cgc ttc cta acc atg ctc aca gcc att gca aca cag     1601
Gln Val Asp Leu Arg Phe Leu Thr Met Leu Thr Ala Ile Ala Thr Gln
330                 335                 340                 345 gga gcc att tcc agg gaa acc cag aaa ggc tac tac gtc aaa tcg tac     1649
Gly Ala Ile Ser Arg Glu Thr Gln Lys Gly Tyr Tyr Val Lys Ser Tyr
                350                 355                 360 aag ctg gaa gtc agc aca aat ggt gaa gat tgg atg gtc tac cgg cat     1697
```

-continued

```
Lys Leu Glu Val Ser Thr Asn Gly Glu Asp Trp Met Val Tyr Arg His
        365                 370                 375 ggc aaa aac cac aag ata ttc caa gcg aac aat gat gcg acc gag gtg      1745
Gly Lys Asn His Lys Ile Phe Gln Ala Asn Asn Asp Ala Thr Glu Val
        380                 385                 390 gtg cta aac aag ctc cac atg cca ctg ctg act cgg ttc atc agg atc      1793
Val Leu Asn Lys Leu His Met Pro Leu Leu Thr Arg Phe Ile Arg Ile
        395                 400                 405 cgc ccg cag acg tgg cat ttg ggc att gcc ctt cgc ctg gag ctc ttt      1841
Arg Pro Gln Thr Trp His Leu Gly Ile Ala Leu Arg Leu Glu Leu Phe
410                 415                 420                 425 ggc tgc cgg gtc aca gat gca ccc tgc tcc aac atg ctg ggg atg ctc      1889
Gly Cys Arg Val Thr Asp Ala Pro Cys Ser Asn Met Leu Gly Met Leu
                430                 435                 440 tcg ggc ctc att gct gat acc cag atc tct gcc tcc tcc acc cga gag      1937
Ser Gly Leu Ile Ala Asp Thr Gln Ile Ser Ala Ser Ser Thr Arg Glu
                445                 450                 455 tac ctc tgg agc ccc agt gct gcc cgc ctg gtt agt agc cgc tct ggc      1985
Tyr Leu Trp Ser Pro Ser Ala Ala Arg Leu Val Ser Ser Arg Ser Gly
        460                 465                 470 tgg ttt cct cgg aac cct caa gcc cag cca ggt gaa gaa tgg ctt cag      2033
Trp Phe Pro Arg Asn Pro Gln Ala Gln Pro Gly Glu Glu Trp Leu Gln
        475                 480                 485 gta gac ctg ggg aca ccc aag aca gtg aaa ggg gtc atc atc cag gga      2081
Val Asp Leu Gly Thr Pro Lys Thr Val Lys Gly Val Ile Ile Gln Gly
490                 495                 500                 505 gcc cga gga gga gac agc atc act gcc gtg gaa gcc agg gcg ttt gta      2129
Ala Arg Gly Gly Asp Ser Ile Thr Ala Val Glu Ala Arg Ala Phe Val
                510                 515                 520 cgc aag ttc aaa gtc tcc tac agc cta aat ggc aag gac tgg gaa tat      2177
Arg Lys Phe Lys Val Ser Tyr Ser Leu Asn Gly Lys Asp Trp Glu Tyr
        525                 530                 535 atc cag gac ccc agg act cag cag aca aag ctg ttt gaa ggg aac atg      2225
Ile Gln Asp Pro Arg Thr Gln Gln Thr Lys Leu Phe Glu Gly Asn Met
        540                 545                 550 cac tat gac acc cct gac atc cga agg ttc gat cct gtt cca gcg cag      2273
His Tyr Asp Thr Pro Asp Ile Arg Arg Phe Asp Pro Val Pro Ala Gln
        555                 560                 565 tat gtg cgg gtg tac cca gag agg tgg tcg cca gca ggc atc ggg atg      2321
Tyr Val Arg Val Tyr Pro Glu Arg Trp Ser Pro Ala Gly Ile Gly Met
570                 575                 580                 585 agg ctg gag gtg ctg ggc tgt gac tgg aca gac tca aag ccc aca gtg      2369
Arg Leu Glu Val Leu Gly Cys Asp Trp Thr Asp Ser Lys Pro Thr Val
                590                 595                 600 gag acg ctg gga ccc acc gtg aag agt gaa gag act acc acc cca tat      2417
Glu Thr Leu Gly Pro Thr Val Lys Ser Glu Glu Thr Thr Thr Pro Tyr
        605                 610                 615 ccc atg gat gag gat gcc acc gag tgt ggg gaa aac tgc agc ttt gag      2465
Pro Met Asp Glu Asp Ala Thr Glu Cys Gly Glu Asn Cys Ser Phe Glu
        620                 625                 630 gat gac aaa gat ttg caa ctt cct tca gga ttc aac tgc aac ttt gat      2513
Asp Asp Lys Asp Leu Gln Leu Pro Ser Gly Phe Asn Cys Asn Phe Asp
        635                 640                 645 ttt ccg gaa gag acc tgt ggt tgg gtg tac gac cat gcc aag tgg ctc      2561
Phe Pro Glu Glu Thr Cys Gly Trp Val Tyr Asp His Ala Lys Trp Leu
650                 655                 660                 665 cgg agc acg tgg atc agc agc gct aac ccc aat gac aga aca ttt cca      2609
Arg Ser Thr Trp Ile Ser Ser Ala Asn Pro Asn Asp Arg Thr Phe Pro
                670                 675                 680
```

```
gat gac aag aac ttc ttg aaa ctg cag agt gat ggc cga cga gag ggc    2657
Asp Asp Lys Asn Phe Leu Lys Leu Gln Ser Asp Gly Arg Arg Glu Gly
            685                 690                 695 cag tac ggg cgg ctc atc agc cca ccg gtg cac ctg ccc cga agc cct    2705
Gln Tyr Gly Arg Leu Ile Ser Pro Pro Val His Leu Pro Arg Ser Pro
        700                 705                 710 gtg tgc atg gag ttc cag tac caa gcc atg ggc ggc cac ggg gtg gca    2753
Val Cys Met Glu Phe Gln Tyr Gln Ala Met Gly Gly His Gly Val Ala
    715                 720                 725 ctg cag gtg gtt cgg gaa gcc agc cag gaa agc aaa ctc ctt tgg gtc    2801
Leu Gln Val Val Arg Glu Ala Ser Gln Glu Ser Lys Leu Leu Trp Val
730                 735                 740                 745 atc cgt gag gac cag ggc agc gag tgg aag cac ggg cgc att atc ctg    2849
Ile Arg Glu Asp Gln Gly Ser Glu Trp Lys His Gly Arg Ile Ile Leu
                750                 755                 760 ccc agc tat gac atg gag tat cag atc gtg ttc gag gga gtg ata ggg    2897
Pro Ser Tyr Asp Met Glu Tyr Gln Ile Val Phe Glu Gly Val Ile Gly
            765                 770                 775 aag gga cga tcg gga gag att tcc atc gat gac att cgg ata agc act    2945
Lys Gly Arg Ser Gly Glu Ile Ser Ile Asp Asp Ile Arg Ile Ser Thr
        780                 785                 790 gat gtc cca ctg gag aac tgc atg gaa ccc ata tca gct ttt gca ggt    2993
Asp Val Pro Leu Glu Asn Cys Met Glu Pro Ile Ser Ala Phe Ala Gly
    795                 800                 805 gag gat ttt aaa ggg ggc acc ctc ccg cca ggg acc gag ccc aca gtg    3041
Glu Asp Phe Lys Gly Gly Thr Leu Pro Pro Gly Thr Glu Pro Thr Val
810                 815                 820                 825 gac acg gtg ccc gtg cag ccc atc cca gcc tac tgg tat tac gtt atg    3089
Asp Thr Val Pro Val Gln Pro Ile Pro Ala Tyr Trp Tyr Tyr Val Met
                830                 835                 840 gcg gcc ggg ggc gcc gtg ctg gtg ctg gcc tcc gtc gtc ctg gcc ctg    3137
Ala Ala Gly Gly Ala Val Leu Val Leu Ala Ser Val Val Leu Ala Leu
            845                 850                 855 gtg ctc cac tac cac cgg ttc cgc tat gcg gcc aag aag acc gat cac    3185
Val Leu His Tyr His Arg Phe Arg Tyr Ala Ala Lys Lys Thr Asp His
        860                 865                 870 tcc atc acc tac aaa acc tcc cac tac acc aac ggg gcc cct ctg gcg    3233
Ser Ile Thr Tyr Lys Thr Ser His Tyr Thr Asn Gly Ala Pro Leu Ala
    875                 880                 885 gtc gag ccc acc cta acc att aag cta gag caa gag cgg ggc tcg cac    3281
Val Glu Pro Thr Leu Thr Ile Lys Leu Glu Gln Glu Arg Gly Ser His
890                 895                 900                 905 tgc tgagggccga agcaggaaca gcgccccccc aaaaaaaacc caagaaagac         3334
Cys tgcaaacacg ttgcctcgat tttgcacttt ttttctcctc gcctagtctc tgtgtgaacc  3394
ctcagacatc tctctccagg gtccccaacc ctgagcgctc tcatgtaccc cacaccattc  3454
tctgtggttc ttggttccgg tttctctttg ctctgatatt gtttgttttt aatcattatt  3514
ttttttcctt tcttcttttc cttttaatct tctctctttt attcctttct cccctccccg  3574
ccccgccttt ttctaatgat tttaaaccaa ctctaatgct gcatctggaa tcccagaaga  3634
gacccgcccc taagcacttc acaacccaag gctctgttgg ttttgttcca gagacaggcc  3694
ctgttgtttt ctccccttgc cttatcccat ccctcctctc ctgggcaggc tgccaggtgt  3754
cttgagggga gcctggtcct gtatgtatgt acacagtaca ctcccatgtg aagaggtgtg  3814
tgtgtgtgtg tgtgtgtgtg tgtatttccg agggagagac tgattcactg tggaagggg   3874 ggagtgtggg tgtgtgtaga gaggggcccc ttccctctta tgttgcttct tctggggtac  3934
```

```
ttttcaagaa aataatatac tgtacacatt ttgtttactt ggagaagaga ttggagcttt    3994
tttgttgcct tatctagctc tggctgggtt tctgttggct gtcattgtca tctccaggta    4054
cctagacaaa tagagaccat tgggaatgca atgtggcttc acccatcctt atccccatcc    4114
caagccaccc aagactatgg ttcctccagt gcactcagac atgacccctt tgttatgtt     4174 tcctggtgtc tttgaagtca caagataaca gccattgggt gcatggagtc atttctactt    4234
ccagccctga agcaaatgtg tctcatgttg ccttataaaa aaaaccggaa ttcctgtagt    4294
tgaagagtaa gattttgtac ggtacatttt taatgacagc ttggatattg gaatactcaa    4354
cttttgttgt agccaatgag agggatatgc cactaatggt atctaaatca tacagtacgt    4414
actttaggat ggggacaaaa atcacaacga tttatttatt tatttactta gtgtatgtga    4474
gtgcactgtt ggtgtcttca gacacaccag aagatgactt cagatccgat tacatatggg    4534
ttgtgagcca ccatgtggtt gctgggattt gaactctgga cctctggaag agcagtcagt    4594
gcttgtaact ctgagccatc tttctagccc ccccccccc cccgctatct tttagaaatg     4654
taatttgcca tactttgagc aatgttcttg atgtcattag gatatttcac agataacttc    4714
acttaagata attagagcaa aaaaaaaaaa aaaaaaaaaa aaaaaaaaaa aaaaaaaaaa    4774
aaaaaa                                                                4780
```

<210> SEQ ID NO 24
<211> LENGTH: 906
<212> TYPE: PRT
<213> ORGANISM: mouse

<400> SEQUENCE: 24

```
Met Asp Met Phe Pro Leu Thr Trp Val Phe Leu Ala Leu Tyr Phe Ser
 1               5                  10                  15

Gly His Glu Val Arg Ser Gln Gln Asp Pro Cys Gly Gly Arg Pro
            20                  25                  30

Asn Ser Lys Asp Ala Gly Tyr Ile Thr Ser Pro Gly Tyr Pro Gln Asp
        35                  40                  45

Tyr Pro Ser His Gln Asn Cys Glu Trp Ile Val Tyr Ala Pro Glu Pro
    50                  55                  60

Asn Gln Lys Ile Val Leu Asn Phe Asn Pro His Phe Glu Ile Glu Lys
65                  70                  75                  80

His Asp Cys Lys Tyr Asp Phe Ile Glu Ile Arg Asp Gly Asp Ser Glu
                85                  90                  95

Ser Ala Asp Leu Leu Gly Lys His Cys Gly Asn Ile Ala Pro Pro Thr
            100                 105                 110

Ile Ile Ser Ser Gly Ser Val Leu Tyr Ile Lys Phe Thr Ser Asp Tyr
        115                 120                 125

Ala Arg Gln Gly Ala Gly Phe Ser Leu Arg Tyr Glu Ile Phe Lys Thr
    130                 135                 140

Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                165                 170                 175

Phe Thr Ile Leu Ala Lys Pro Arg Met Glu Ile Ile Leu Gln Phe Leu
            180                 185                 190

Thr Phe Asp Leu Glu His Asp Pro Leu Gln Val Gly Glu Gly Asp Cys
        195                 200                 205

Lys Tyr Asp Trp Leu Asp Ile Trp Asp Gly Ile Pro His Val Gly Pro
    210                 215                 220
```

-continued

```
Leu Ile Gly Lys Tyr Cys Gly Thr Lys Thr Pro Ser Lys Leu Arg Ser
225                 230                 235                 240

Ser Thr Gly Ile Leu Ser Leu Thr Phe His Thr Asp Met Ala Val Ala
            245                 250                 255

Lys Asp Gly Phe Ser Ala Arg Tyr Tyr Leu Ile His Gln Glu Pro Pro
        260                 265                 270

Glu Asn Phe Gln Cys Asn Val Pro Leu Gly Met Glu Ser Gly Arg Ile
    275                 280                 285

Ala Asn Glu Gln Ile Ser Ala Ser Ser Thr Phe Ser Asp Gly Arg Trp
290                 295                 300

Thr Pro Gln Gln Ser Arg Leu His Gly Asp Asp Asn Gly Trp Thr Pro
305                 310                 315                 320

Asn Leu Asp Ser Asn Lys Glu Tyr Leu Gln Val Asp Leu Arg Phe Leu
            325                 330                 335

Thr Met Leu Thr Ala Ile Ala Thr Gln Gly Ala Ile Ser Arg Glu Thr
            340                 345                 350

Gln Lys Gly Tyr Tyr Val Lys Ser Tyr Lys Leu Glu Val Ser Thr Asn
        355                 360                 365

Gly Glu Asp Trp Met Val Tyr Arg His Gly Lys Asn His Lys Ile Phe
    370                 375                 380

Gln Ala Asn Asn Asp Ala Thr Glu Val Val Leu Asn Lys Leu His Met
385                 390                 395                 400

Pro Leu Leu Thr Arg Phe Ile Arg Ile Arg Pro Gln Thr Trp His Leu
            405                 410                 415

Gly Ile Ala Leu Arg Leu Glu Leu Phe Gly Cys Arg Val Thr Asp Ala
            420                 425                 430

Pro Cys Ser Asn Met Leu Gly Met Leu Ser Gly Leu Ile Ala Asp Thr
        435                 440                 445

Gln Ile Ser Ala Ser Ser Thr Arg Glu Tyr Leu Trp Ser Pro Ser Ala
    450                 455                 460

Ala Arg Leu Val Ser Ser Arg Ser Gly Trp Phe Pro Arg Asn Pro Gln
465                 470                 475                 480

Ala Gln Pro Gly Glu Glu Trp Leu Gln Val Asp Leu Gly Thr Pro Lys
            485                 490                 495

Thr Val Lys Gly Val Ile Ile Gln Gly Ala Arg Gly Gly Asp Ser Ile
        500                 505                 510

Thr Ala Val Glu Ala Arg Ala Phe Val Arg Lys Phe Lys Val Ser Tyr
    515                 520                 525

Ser Leu Asn Gly Lys Asp Trp Glu Tyr Ile Gln Asp Pro Arg Thr Gln
530                 535                 540

Gln Thr Lys Leu Phe Glu Gly Asn Met His Tyr Asp Thr Pro Asp Ile
545                 550                 555                 560

Arg Arg Phe Asp Pro Val Pro Ala Gln Tyr Val Arg Val Tyr Pro Glu
            565                 570                 575

Arg Trp Ser Pro Ala Gly Ile Gly Met Arg Leu Glu Val Leu Gly Cys
            580                 585                 590

Asp Trp Thr Asp Ser Lys Pro Thr Val Glu Thr Leu Gly Pro Thr Val
        595                 600                 605

Lys Ser Glu Glu Thr Thr Thr Pro Tyr Pro Met Asp Glu Asp Ala Thr
    610                 615                 620

Glu Cys Gly Glu Asn Cys Ser Phe Glu Asp Asp Lys Asp Leu Gln Leu
625                 630                 635                 640
```

```
Pro Ser Gly Phe Asn Cys Asn Phe Asp Phe Pro Glu Glu Thr Cys Gly
                645                 650                 655

Trp Val Tyr Asp His Ala Lys Trp Leu Arg Ser Thr Trp Ile Ser Ser
        660                 665                 670

Ala Asn Pro Asn Asp Arg Thr Phe Pro Asp Lys Asn Phe Leu Lys
    675                 680                 685

Leu Gln Ser Asp Gly Arg Arg Glu Gly Gln Tyr Gly Arg Leu Ile Ser
690                 695                 700

Pro Pro Val His Leu Pro Arg Ser Pro Val Cys Met Glu Phe Gln Tyr
705                 710                 715                 720

Gln Ala Met Gly Gly His Gly Val Ala Leu Gln Val Val Arg Glu Ala
                725                 730                 735

Ser Gln Glu Ser Lys Leu Leu Trp Val Ile Arg Glu Asp Gln Gly Ser
            740                 745                 750

Glu Trp Lys His Gly Arg Ile Ile Leu Pro Ser Tyr Asp Met Glu Tyr
        755                 760                 765

Gln Ile Val Phe Glu Gly Val Ile Gly Lys Gly Arg Ser Gly Glu Ile
    770                 775                 780

Ser Ile Asp Asp Ile Arg Ile Ser Thr Asp Val Pro Leu Glu Asn Cys
785                 790                 795                 800

Met Glu Pro Ile Ser Ala Phe Ala Gly Glu Asp Phe Lys Gly Gly Thr
                805                 810                 815

Leu Pro Pro Gly Thr Glu Pro Thr Val Asp Thr Val Pro Val Gln Pro
            820                 825                 830

Ile Pro Ala Tyr Trp Tyr Tyr Val Met Ala Ala Gly Gly Ala Val Leu
        835                 840                 845

Val Leu Ala Ser Val Val Leu Ala Leu Val Leu His Tyr His Arg Phe
850                 855                 860

Arg Tyr Ala Ala Lys Lys Thr Asp His Ser Ile Thr Tyr Lys Thr Ser
865                 870                 875                 880

His Tyr Thr Asn Gly Ala Pro Leu Ala Val Glu Pro Thr Leu Thr Ile
                885                 890                 895

Lys Leu Glu Gln Glu Arg Gly Ser His Cys
            900                 905

<210> SEQ ID NO 25
<211> LENGTH: 195
<212> TYPE: DNA
<213> ORGANISM: human
<220> FEATURE:
<221> NAME/KEY: CDS
<222> LOCATION: (1)..(195)

<400> SEQUENCE: 25 ttc gag gga gtg ata ggg aaa gga cgt tcc gga gag att gcc att gat    48
Phe Glu Gly Val Ile Gly Lys Gly Arg Ser Gly Glu Ile Ala Ile Asp
 1               5                  10                  15 gac att cgg ata agc act gat gtc cca ctg gag aac tgc atg gaa ccc    96
Asp Ile Arg Ile Ser Thr Asp Val Pro Leu Glu Asn Cys Met Glu Pro
             20                  25                  30 atc tcg gct ttt gca ggg ggc acc ctc ctg cca ggg acc gag ccc aca   144
Ile Ser Ala Phe Ala Gly Gly Thr Leu Leu Pro Gly Thr Glu Pro Thr
         35                  40                  45 gtg gac acg gtg ccc atg cag ccc atc cca gcc tac tgg tat tac gta   192
Val Asp Thr Val Pro Met Gln Pro Ile Pro Ala Tyr Trp Tyr Tyr Val
     50                  55                  60 atg                                                               195
```

```
Met
 65

<210> SEQ ID NO 26
<211> LENGTH: 65
<212> TYPE: PRT
<213> ORGANISM: human

<400> SEQUENCE: 26

Phe Glu Gly Val Ile Gly Lys Gly Arg Ser Gly Glu Ile Ala Ile Asp
 1               5                  10                  15

Asp Ile Arg Ile Ser Thr Asp Val Pro Leu Glu Asn Cys Met Glu Pro
            20                  25                  30

Ile Ser Ala Phe Ala Gly Gly Thr Leu Leu Pro Gly Thr Glu Pro Thr
        35                  40                  45

Val Asp Thr Val Pro Met Gln Pro Ile Pro Ala Tyr Trp Tyr Tyr Val
    50                  55                  60

Met
 65
```

SEMAPHORIN RECEPTORS

CROSS-REFERENCE TO RELATED APPLICATIONS

This application is a divisional application of U.S. application Ser. No. 08/936,135, filed Sep. 24, 1997, now U.S. Pat. No. 6,054,293, which is a continuation of U.S. application Ser. No. 08/889,458, filed Jul. 8, 1997, now abandoned, the entirety of which are all incorporated herein by reference.

The research carried out in the subject application was supported in part by grants from the National Institutes of Health. The government may have rights in any patent issuing on this application.

FIELD OF THE INVENTION

The field of this invention is proteins involved in nerve cell guidance.

BACKGROUND

During nervous system development, axons migrate along prescribed pathways in the embryo to reach their appropriate synaptic targets (reviewed in Tessier-Lavigne and Goodman, 1996). One mechanism that contributes to accurate path-finding is chemorepulsion, the guidance of axons away from non-target regions by diffusible chemorepellent factors secreted by non-target cells. Experiments in which axons are confronted with non-target tissues in tissue culture and are repelled by these tissues at a distance have demonstrated the existence of diffusible chemorepellent activities for numerous axonal classes (Pini, 1993; Fitzgerald et al., 1993; Colamarino and Tessier-Lavigne, 1995; Tamada et al., 1995; Guthrie and Pini, 1995; Shirasaki et al., 1996) as well as for migrating neuronal cells (Hu and Rutishauser, 1996). At the molecular level, two families of guidance cues, the netrin and semaphorin families, have been shown to comprise members that can function as chemorepellents. In Caenorhaditis elegans, the netrin UNC-6 is thought to repel axons that migrate away from the netrin source since these axons are misrouted at a certain frequency in unc-6 mutants; this presumed repulsion appears to be mediated by the candidate receptors UNC-5 and UNC-40, which are members of the immunoglobulin superfamily (Hedgecock et al., 1990; Leung-Hagesteijn et al, 1992; Hamelin et al., 1993; Wadsworth et al., 1996; Chan et al., 1996). Similarly, in vertebrates netrin-1 can repel subsets of motor axons that migrate away from a source of netrin-1 (Colamarino and Tessier-Lavigne, 1994; Varela-Echavarria et al., 1997), a process which might involve vertebrate homologues of UNC-5 and UNC-40, which have been shown to be netrin-binding proteins (Leonardo et al., 1997; Ackermann: et al., 1997; Keino-Masu et al., 1996).

The semaphorins are a large family of structurally diverse secreted and transmembrane proteins characterized by the presence of a conserved ~500 amino acid semaphorin domain at their amino termini (reviewed in Kolodkin, 1996). The family was first described and implicated in axon guidance through antibody perturbation studies in insects (Kolodkin et al., 1992; Kolodkin et al., 1993). The connection of this family to chemorepulsion was made with the purification of chicken collapsin-1 as a factor that can cause collapse of sensory growth cones when added acutely in cell culture (Luo et al., 1993). Collapsin-1 and its mammalian homologues (Semaphorin III, also known as Semaphorin D) are secreted semaphorins that possess in addition to the semaphorin domain an immunoglobulin domain and a highly basic carboxy-terminal domain (Luo et al., 1993; Kolodkin et al., 1993; Messersmith et al., 1995; Püschel et al., 1995). When presented chronically from a point source, collapsin-1/SemaIII/D (hereafter referred to as SemaIII) can repel sensory and sympathetic axons and has been implicated in patterning sensory axon projections into the ventral spinal cord (Messersmith et al., 1995; Püschel et al., 1995, 1996; Behar et al., 1996; Shepherd et al., 1997). Sema E, which is structurally-related to SemaIII, has also been reported to repel sympathetic axons in culture (cited in Varela-Echavarria and Guthrie, 1997). In Drosophila, the secreted semaphorin SemaII has been implicated as an inhibitor of axon terminal branch formation (Matthes et al., 1995). However, the mechanisms through which semaphorins produce their repellent or inhibitory actions have not been determined.

To elucidate the mechanisms through which semaphorin proteins produce their repulsive actions on axons, we have sought to identify binding proteins for semphorins on the surfaces of sensory axons. Here we identify two classes of semaphorin receptors, SR1 and SR2, expressed by axons whose function is required for the collapse-inducing and repulsive actions of semaphorins.

SUMMARY OF THE INVENTION

The invention provides methods and compositions relating to isolated semaphorin receptor class 1 and 2 (SR1 and SR2. collectively SR) polypeptides, related nucleic acids, polypeptide domains thereof having SR-specific structure and activity, and modulators of SR function, particularly semaphorin-binding activity. SR polypeptides can regulate cell, especially nerve cell, function and morphology. The polypeptides may be produced recombinantly from transformed host cells from the subject SR polypeptide encoding nucleic acids or purified from mammalian cells. The invention provides isolated SR hybridization probes and primers capable of specifically hybridizing with the disclosed SR genes, SR-specific binding agents such as specific antibodies, and methods of making and using the subject compositions in diagnosis (e.g. genetic hybridization screens for SR transcripts), therapy (e.g. SR inhibitors to promote nerve cell growth) and in the biopharmaceutical industry (e.g. as immunogens, reagents for isolating other Srs, reagents for screening chemical libraries for lead pharmacological agents, etc.).

BRIEF DESCRIPTION OF THE FIGURES

FIGS. 1A1, 1A2 and 1B. Structure of rat and human SR1.
(A) Alignment of the amino acid sequences of mouse, rat and human SR1s (SEQ ID NO:6, 4 and 2 respectively).
(B) Diagram displaying the modular structure of SR1s conserved among different species, and the five SR1 domains (a1, a2, b1, b2, c). S: signal peptide; C1r/s, complement C1r/s homology domain (CUB domain); FV/VIII, regions of homology to coagulation factors V and VIII, the DDR tyrosine kinase, and MFGPs; MAM, MAM domain; TM, transmembrane domain.

FIGS. 3A–3B. Alignment of the amino acid sequences of neuropilin-1 (SR1) and neuropilin-2 (SR2). Alignment of the mouse neuropilin-1 (m-npn-1, SEQ ID NO:6), mouse neuropilin-2 (m-npn-2, SEQ ID NO:10) and human neuropilin-2 (h-npn-2, SEQ ID NO:18) sequences was performed using the Clustal V program. Different domains of the molecules, named according to Kawakami et al. (1996) (see, FIG. 2A), are indicated. The a0 isoform of neuropilin-2 (see FIG. 2) was used to create the alignment.

(A) Diagram illustrating the domain structures of mouse neuropilin-1 (Kawakami, et al., 1996) and the full length mouse neuropilin-2(a0) and neuropilin-2(b0) isoforms. s: signal peptide; a1 and a2 domains are CUB domains (Busby and Ingham, 1990; Bork and Beckmann, 1993); b1 and b2 domains show homology to the C1 and C2 domains of coagulation factors V and VIII and of milk fat globular membrane protein; c domain contains a MAM domain, which is found in the metalloendopeptidase meprin and receptor tyrosine phosphatases μ, λ, and κ; TM: transmembrane domain; Cy: cytoplasmic domain. The numbers with arrows indicate percent amino acid identity in the indicated domains. The dashed line and arrow indicate the site in neuropilin-2 where the neuropilin-2a and -2b isoforms diverge; this is also the site of the 5-, 17- and 22- amino acid insertions (see also FIG. 2B).

(B) Isoforms of neuropilin-2(a) with 0, 5, 17 and 22 amino acid insertions after amino acid 809 (isoforms 2(a0), 2(a5), 2(a17) and 2(a22), SEQ ID NO:10, 12, 14 and 16, respectively), and of neuropilin-2(b) without and with the 5 amino acid insertion (isoforms 2(b0) and 2(b5), SEQ ID NO:22 and 24 respectively). Shown are the sequences of the insertions, flanked by 3 amino acids N terminal to the insertion (AFA) and 4 amino acids C terminal to the insertions (DEYE in neuropilin-2a, GGTL in neuropilin-2b).

(C) Sequence of neuropilin-2(b0) SEQ ID NO:22 and partial sequence of human neuropilin-2(b0) SEQ ID NO:26 from EST (AA25804) in the region where the sequence of neuropilin-2(b0) diverges from that of neuropilin-2(a0). Three amino acids N terminal to the site of divergence (AFA) are shown.

Figure 5A:
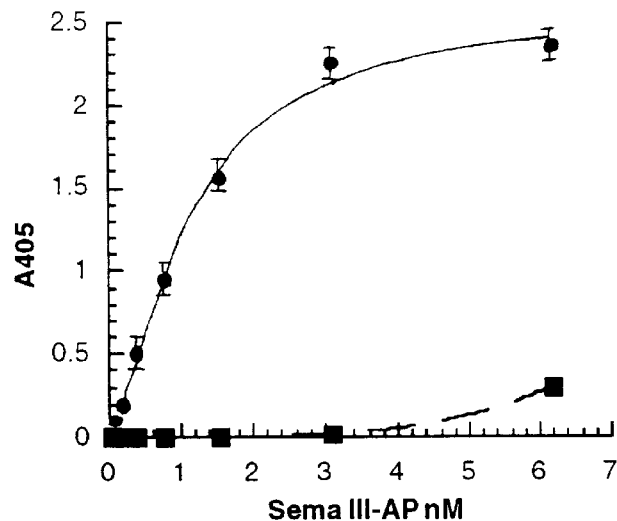
Figure 5B:
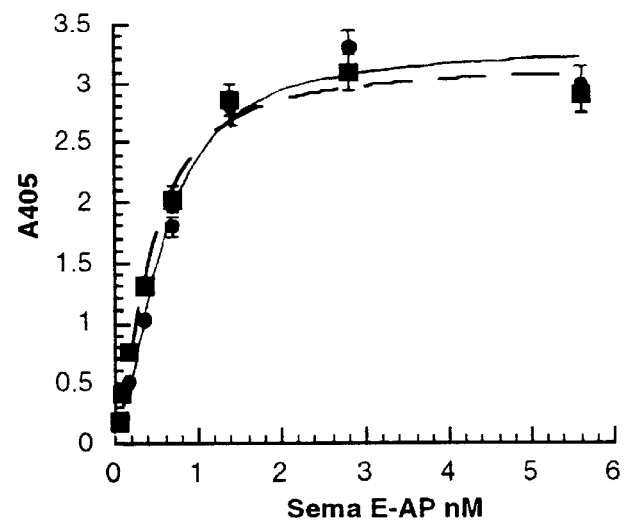
Figure 5C:
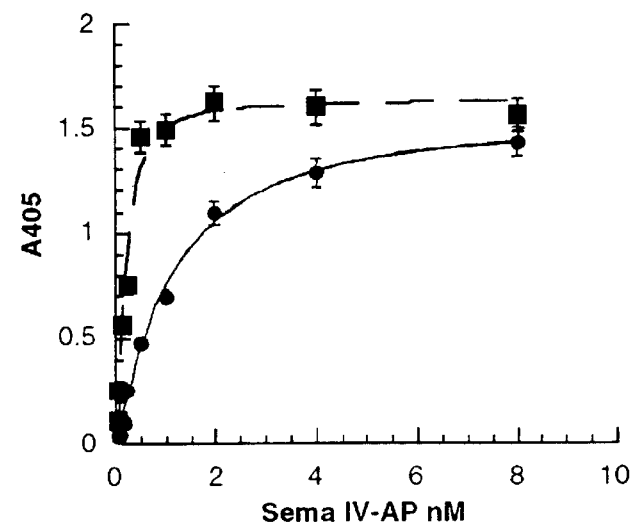

FIGS. 5A–5C. Equilibrium binding of semaphorin-AP fusion proteins to neuropilin-expressing cells. Transfected or control COS cells were incubated with concentrated media containing the indicated concentrations of semaphorin-AP fusion proteins. AP activity derived from bound fusion proteins was measured calorimetrically at 405 nm; specific binding was obtained after subtraction of background from control cells. Specific binding curves to cells expressing neuropilin-1 (closed circles) or neuropilin-1 (closed squares) are shown for Sema III-AP (A), Sema E-AP (B), and Sema IV-AP (C). Dissociation constants for interaction with neuropilin-2-expressing cells were 0.29 for Sema E-AP and 0.09 nM for Sema IV-AP.

DETAILED DESCRIPTION OF THE INVENTION

Figure 3A:
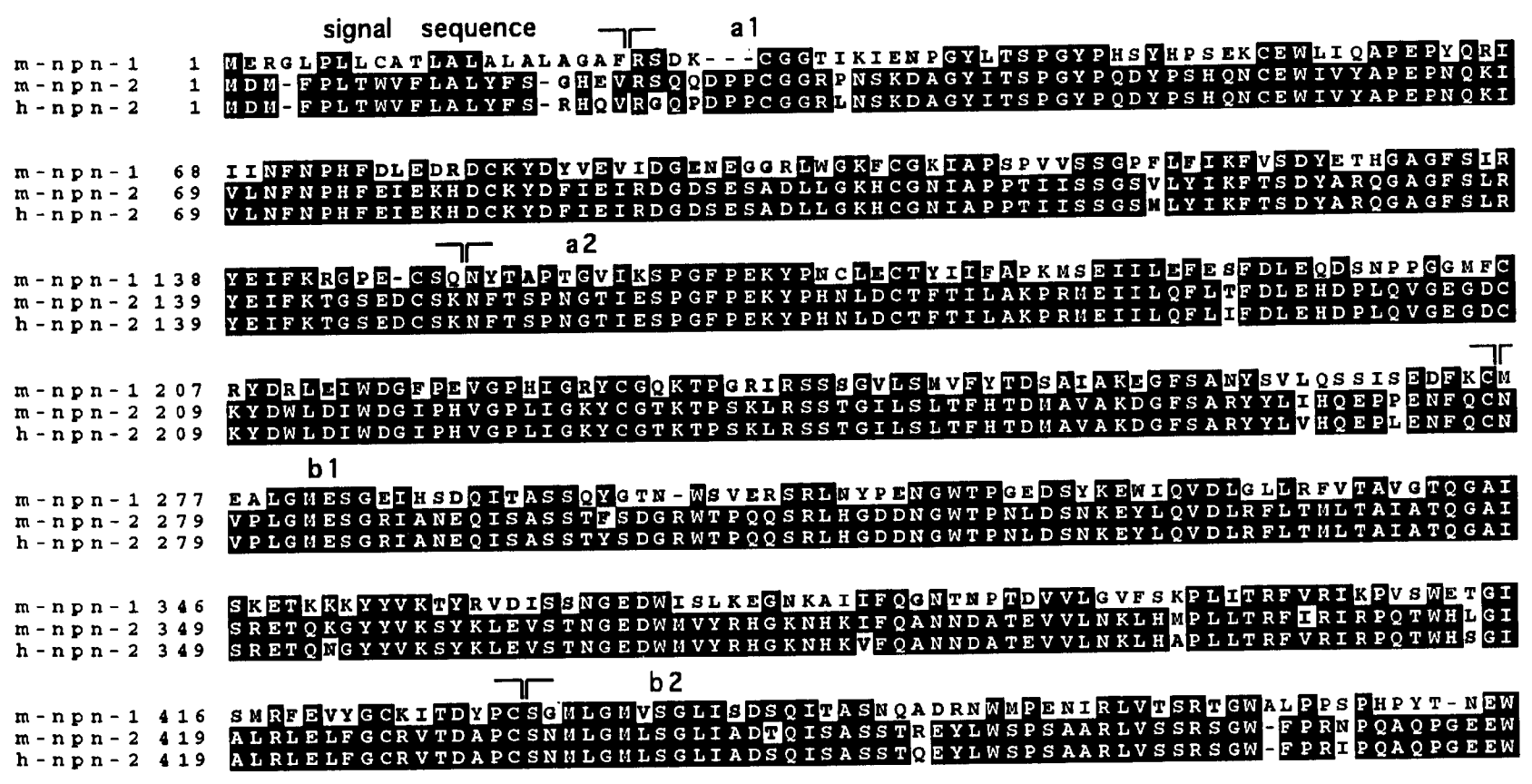
Figure 3B:
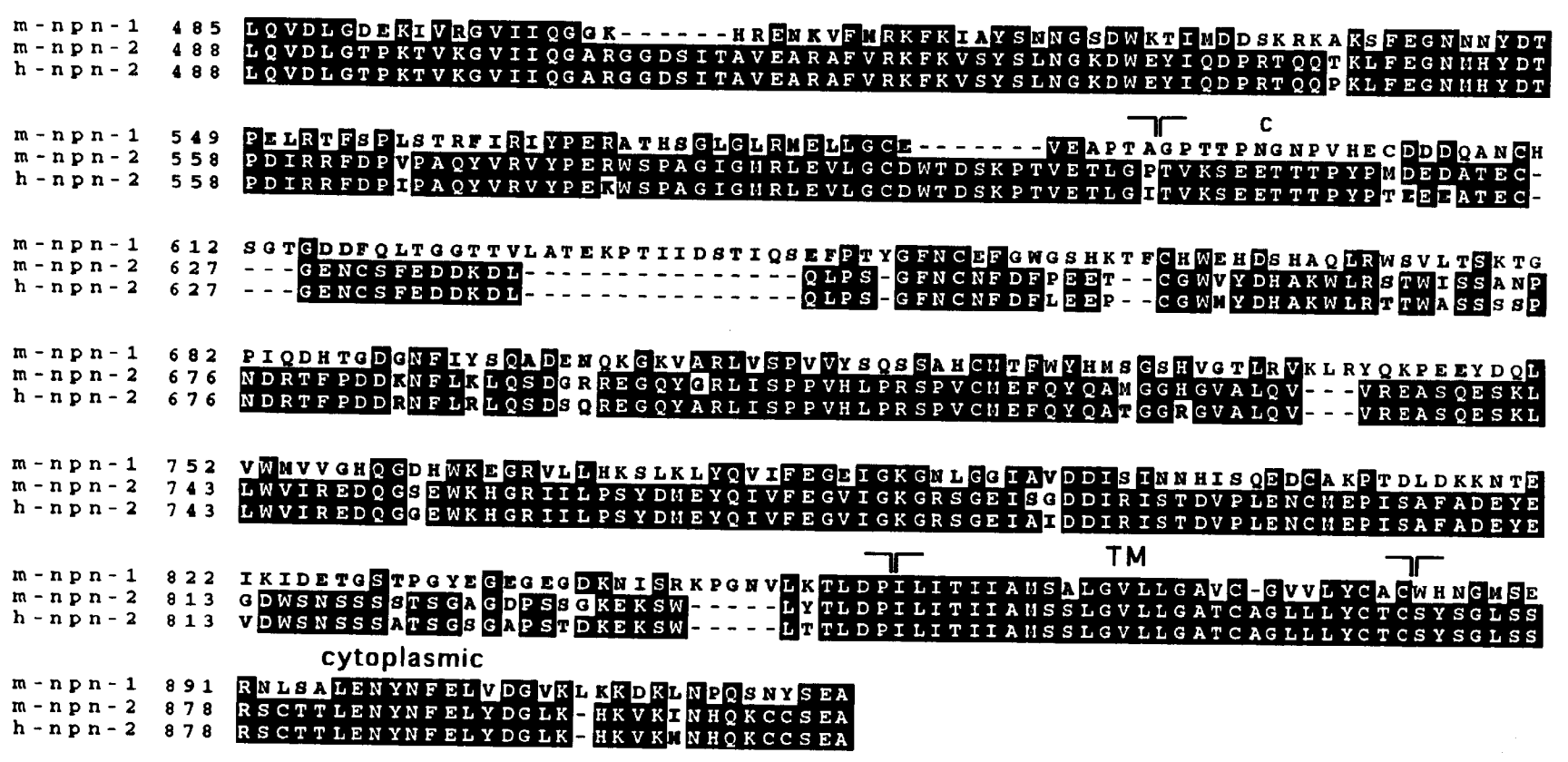

The nucleotide sequences of exemplary natural cDNAs encoding human, rat and mouse SR1 polypeptides are shown as SEQ ID NOS:1, 3 and 5, respectively, and the full conceptual translates are shown as SEQ ID NOS:2, 4 and 6. Natural SR-2 cDNAs are found in (a) and (b) forms deriving from two distinct genes, with transcripts of each found in four alternatively spliced forms designated 0, 5, 17 and 22, depending on the size of an insert (below). For example, the nucleotide sequences of exemplary natural cDNAs encoding mouse SR2(a)0, 5, 17 and 22 polypeptides are shown as SEQ ID NOS:9, 11, 13 and 15, respectively, and the full conceptual translates are shown as SEQ ID NOS:10, 12, 14 and 16. Other sequences recited in the Sequence Listing include the nucleotide sequences of exemplary natural cDNAs encoding mouse SR2(b)0 and 5 polypeptides (SEQ ID NOS:21 and 23) and their full conceptual translates (SEQ ID NOS:22 and 24); rat SR2(a)0 polypeptide (SEQ ID NO:7) and its full conceptual translate (SEQ ID NO:8); human SR2(a)0 and 17 polypeptides (SEQ ID NOS:17 and 19) and their full conceptual translates (SEQ ID NOS:18 and 20); and human SR2(b)0 polypeptide (SEQ ID NO:25) and its full conceptual translate (SEQ ID NO:26). The SR polypeptides of the invention include incomplete translates of SEQ ID NOS:1, 3, 7, 9, 11, 13, 15, 17, 19, 21, 23 and 25 and deletion mutants of SEQ ID NOS:2, 4, 8, 10, 12, 14, 16, 18, 20, 22, 24 and 26, which translates and deletion mutants have SR-specific amino acid sequence, binding specificity or function. Preferred translates/deletion mutants comprise at least a 6, preferably at least an 8, more preferably at least a 10, most preferably at least a 12 residue domain of the translates not found in mouse, drosophila or chick neuropilin-1. Other preferred mutants comprise a domain comprising at least one SR2 and/or human specific residue. Such domains are readily discernable from alignments of the disclosed SR1 and SR2 polypeptides, e.g. FIGS. 1 and 3. For example, human SR1 specific residues include FV11, V15, P18, A19, N24, E26, D29, S35, D62, M68, F90, N96, H98, F99, R100, T153, S155, S170, V177, P196, D219, I242, V269, S298, A303, R323, K360, I361, V363, T372, I373, P379, V380, L381, V-393, A394, P399, A40, T411, S449, G453, S469, A476. S479, I481, I487, E491, I498, G518, M528, T553, P555, A556, G572, A587, L599, D601, V634, N667, V669, K672, S674, N717, R737, A755, 1756, S805, A813, P820, G835, E838, E855, T916, Q917 and T919.

The subject domains provide SR domain specific activity or function, such as SR-specific cell, especially neuron modulating or modulating inhibitory activity, semaphorin-binding or binding inhibitory activity. SR-specific activity or function may be determined by convenient in vitro, cell-based, or in vivo assays: e.g. in vitro binding assays, cell culture assays, in animals (e.g. gene therapy, transgenics, etc.), etc. Binding, assays encompass any assay where the molecular interaction of an SR polypeptide with a binding target is evaluated. The binding target may be a natural intracellular binding target such as a semaphorin, a SR regulating protein or other regulator that directly modulates SR activity or its localization; or non-natural binding target such a specific immune protein such as an antibody, or an SR specific agent such as those identified in screening assays such as described below. SR-binding specificity may assayed by binding equilibrium constants (usually at least about $10^7$ $M^{-1}$, preferably at least about $10^8$ $M^{-1}$, more preferably at least about $10^9$ $M^{-1}$), by the ability of the subject polypeptide to function as negative mutants in SR-expressing cells, to elicit SR specific antibody in a heterologous host (e.g a rodent or rabbit), etc. In any event, the SR binding specificity of the subject SR polypeptides necessarily distinguishes mouse, chick and drosophila neuropilin-1.

Figures 4A, 4B, 4C:
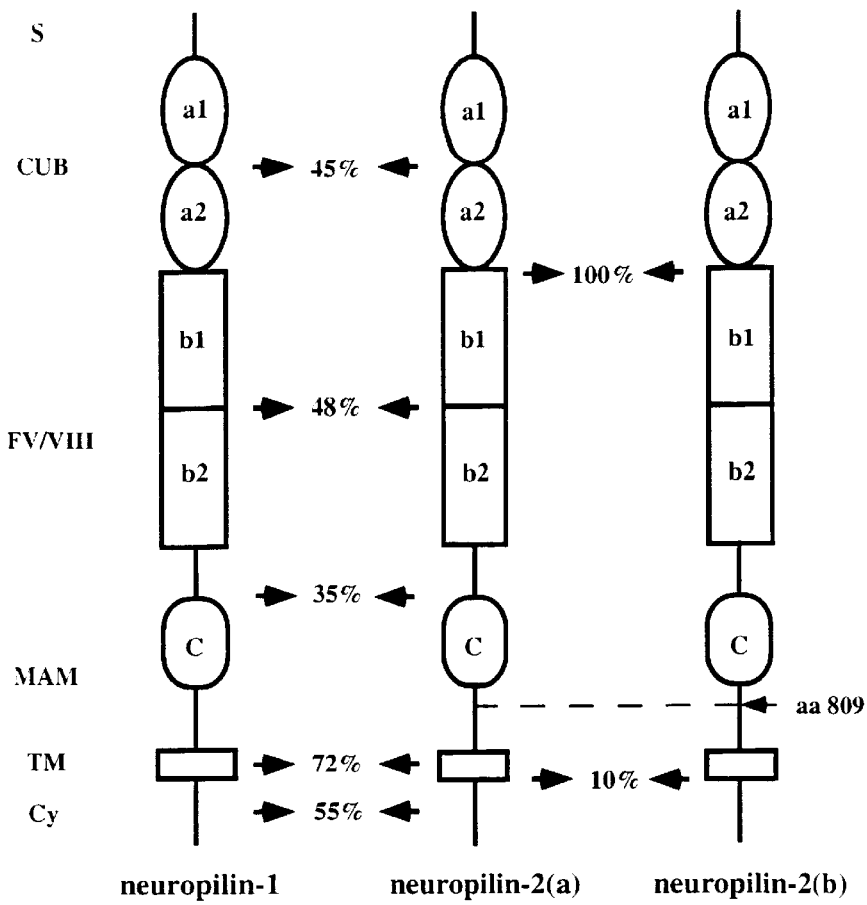
FIGS. 4A–4C. Domain structure and isoforms of neuropilin-2.

For example, the a1, a2, b1. b2, c, TM and Cy domains (FIG. 4A) and the polypeptides comprising the inserts shown in FIGS. 4B and 4C are all shown to exhibit SR specific binding. Similarly, high throughput screens (e.g. see below) using SR-specific binding agents such as SemaIII and anti-SR antibodies are used to readily demonstrate, SR-specific binding agents in a wide variety of deletion mutants of the disclosed SR polypeptides. For example, human SR1 peptides with assay demonstrable SR-specific activity include: SEQ ID NO:2, residues 24–34; SEQ ID NO:2, residues 57–68; SEQ ID NO:2, residues 85–111; SEQ ID NO:2, residues 147–155; SEQ ID NO:2, residues 166–178; SEQ ID NO:2, residues 288–299 SEQ ID NO:2, residues 354–366; SEQ ID NO:2. residues 368–690; SEQ ID NO:2, residues 397–415; SEQ ID NO:2. residues 595–615; SEQ ID NO:2, residues 671–689; SEQ ID NO:2, residues 911–919. Human SR2 peptides with assay demonstrable SR-specific activity include: SEQ ID NO:20, residues 14–35; SEQ ID NO:20, residues 261–278; SEQ ID NO:20, residues 285–301; SEQ ID NO:20, residues 471–485; SEQ ID NO:20. residues 616–628; SEQ ID NO:20, residues 651–685; SEQ ID NO:20, residues 682–696; SEQ ID NO:20. residues 719–745; SEQ ID NO:20, residues 802–825; SEQ ID NO:20, residues 815–830; SEQ ID NO:20, residues 827–839; and SEQ ID NO:20, residues 898–929.

The claimed SR polypeptides are isolated or pure: an "isolated" polypeptide is unaccompanied by at least some of the material with which it is associated in its natural state, preferably constituting at least about 0.5%, and more preferably at least about 5% by weight of the total polypeptide in a given sample and a pure polypeptide constitutes at least about 90%, and preferably at least about 99% by weight of the total polypeptide in a given sample. A polypeptide, as used herein, is an polymer of amino acids, generally at least 6 residues, preferably at least about 10 residues, more preferably at least about 25 residues, most preferably at least about 50 residues in length. The SR polypeptides and polypeptide domains may be synthesized, produced by recombinant technology, or purified from mammalian, preferably human cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, N.Y.) or that are otherwise known in the art.

The invention provides binding agents specific to the claimed SR polypeptides. including natural intracellular binding targets, etc., methods of identifying and making such agents, and their use in diagnosis, therapy and pharmaceutical development. For example, specific binding agents are useful in a variety of diagnostic and therapeutic applications, especially where disease or disease prognosis is associated with improper or undesirable axon outgrowth or orientation. Novel SR-specific binding agents include SR-specific receptors, such as somatically recombined polypeptide receptors like specific antibodies or T-cell antigen receptors (see, e.g Harlow and Lane (1988) Antibodies, A Laboratory Manual, Cold Spring Harbor Laboratory), semaphorins and other natural intracellular binding agents identified with assays such as one-, two- and three-hybrid screens, non-natural intracellular binding agents identified in screens of chemical libraries such as described below, etc. Agents of particular interest modulate SR function, e.g. semaphorin-mediated cell modulation. For example, a wide variety of inhibitors of SR activity may be used to cell function involving SR, especially SR-semaphorin interations. Exemplary SR activity inhibitors include SR-derived peptide inhibitors, esp. dominant negative deletion mutants, etc., see Experimental, below.

Accordingly, the invention provides methods for modulating cell function comprising the step of modulating SR activity, e.g. by contacting the cell with an SR inhibitor. The cell may reside in culture or in situ, i.e. within the natural host. Preferred inhibitors are orally active in mammalian hosts. For diagnostic uses, the inhibitors or other SR binding agents are frequently labeled, such as with fluorescent, radioactive, chemiluminescent, or other easily detectable molecules, either conjugated directly to the binding agent or conjugated to a probe specific for the binding agent.

The amino acid sequences of the disclosed SR polypeptides are used to back-translate SR polypeptide-encoding nucleic acids optimized for selected expression systems (Holler et al. (1993) Gene 136, 323–328; Martin et al. (1995) Gene 154, 150–166) or used to generate degenerate oligonucleotide primers and probes for use in the isolation of natural SR-encoding nucleic acid sequences ("GCG" software, Genetics Computer Group, Inc, Madison Wis.). SR-encoding nucleic acids used in SR-expression vectors and incorporated into recombinant host cells, e.g. for expression and screening, transgenic animals, e.g. for functional studies such as the efficacy of candidate drugs for disease associated with SR-modulated cell function, etc.

The invention also provides nucleic acid hybridization probes and replication/amplification primers having a SR cDNA specific sequence comprising SEQ ID NO:1, 3, 7, 9, 11, 13, 15, 17, 19, 21, 23, or 25, and sufficient to effect specific hybridization thereto (i.e. specifically hybridize with SEQ ID NO:1, 3, 7, 9, 11, 13, 15, 17, 19, 21, 23, or 25, respectively, in the presence of mouse, drosophila and chick neuropilin cDNA. Such primers or probes are at least 12, preferably at least 24, more preferably at least 36 and most preferably at least 96 bases in length. Demonstrating specific hybridization generally requires stringent conditions, for example, hybridizing in a buffer comprising 30% formamide in 5×SSPE (0.18 M NaCl, 0.01 M NaPO$_4$, pH7.7, 0.001 M EDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C. with 0.2×SSPE buffer at 42° C. SR nucleic acids can also be distinguished using alignment algorithms, such as BLASTX (Altschul et al. (1990) Basic Local Alignment Search Tool, J Mol Biol 215, 403–410).

The subject nucleic acids are of synthetic/non-natural sequences and/or are isolated. i.e. unaccompanied by at least some of the material with which it is associated in its natural state, preferably constituting at least about 0.5%, preferably at least about 5% by weight of total nucleic acid present in a given fraction, and usually recombinant, meanin, they comprise a non-natural sequence or a natural sequence joined to nucleouide(s) other than that which it is joined to on a natural chromosome. The subject recombinant nucleic acids comprising the nucleotide sequence of SEQ ID NO:1, 3, 7, 9, 11, 13, 15, 17, 19, 21, 23, or 25, or fragments thereof, contain such sequence or fragment at a terminus, immediately flanked by (i.e. contiguous with) a sequence other than that which it is joined to on a natural chromosome, or flanked by a native flanking region fewer than 10 kb, preferably fewer than 2 kb, which is at a terminus or is immediately flanked by a sequence other than that which it is joined to on a natural chromosome. While the nucleic acids are usually RNA or DNA, it is often advantageous to use nucleic acids comprising other bases or nucleotide analogs to provide modified stability, etc. The subject nucleic acids find a wide variety of applications including use as translatable transcripts, hybridization probes, PCR primers, diagnostic nucleic acids, etc.; use in detecting the presence of SR genes and gene transcripts and in detecting or amplifying nucleic acids encoding additional SR homologs and structural analogs. In diagnosis. SR hybridization probes find use in identifying wild-type and mutant SR alleles in clinical and laboratory samples. Mutant alleles are used to generate allele-specific oligonucleotide (ASO) probes for high-throughput clinical diagnoses. In therapy, therapeutic SR nucleic acids are used to modulate cellular expression or intracellular concentration or availability of active SR.

The invention provides efficient methods of identifying agents, compounds or lead compounds for agents active at the level of a SR modulatable cellular function. Generally, these screening methods involve assaying for compounds which modulate SR interaction with a natural SR binding target such as a semaphorin. A wide variety of assays for binding agents are provided including labeled in vitro protein-protein binding assays, immunoassays, cell based assays, etc. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development.

In vitro binding assays employ a mixture of components including an SR polypeptide, which may be part of a fusion product with another peptide or polypeptide, e.g. a tag for detection or anchoring, etc. The assay mixtures comprise a natural intracellular SR binding target. In a particular embodiment, the binding target is a semaphorin polypeptide. While native full-length binding targets may be used, it is frequently preferred to use portions (e.g. peptides) thereof so long as the portion provides binding affinity and avidity to the subject SR polypeptide conveniently measurable in the assay. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like salts, buffers, neutral proteins, e.g. albumin, detergents, protease inhibitors, nuclease inhibitors, antimicrobial agents, etc. may be used.

The resultant mixture is incubated under conditions whereby, but for the presence of the candidate pharmacological agent, the SR polypeptide specifically binds the cellular binding target, portion or analog with a reference binding affinity. The mixture components can be added in any order that provides for the requisite bindings and incubations may be performed at any temperature which facilitates optimal binding. Incubation periods are likewise selected for optimal binding but also minimized to facilitate rapid, high-throughput screening.

After incubation, the agent-biased binding between the SR polypeptide and one or more binding targets is detected by any convenient way. Where at least one of the SR or binding target polypeptide comprises a label, the label may provide for direct detection as radioactivity, luminescence, optical or electron density, etc. or indirect detection such as an epitope tag, etc. A variety of methods may be used to detect the label depending on the nature of the label and other assay components, e.g. through optical or electron density, radiative emissions, nonradiative energy transfers, etc. or indirectly detected with antibody conjugates, etc.

A difference in the binding affinity of the SR polypeptide to the target in the absence of the agent as compared with the binding affinity in the presence of the agent indicates that the agent modulates the binding of the SR polypeptide to the SR binding target. For example, in the cell-based assay also described below, a difference in SR-dependent modulation of axon outgrowth or orientation in the presence and absence of an agent indicates the agent modulates SR function. A difference, as used herein, is statistically significant and preferably represents at least a 50%, more preferably at least a 90% difference.

The following experimental section and examples are offered by way of illustration and not by way of limitation.

EXPERIMENTAL

Expression Cloning of a cDNA Encoding a SemaIII-binding Protein

To facilitate isolation of SemaIII-binding proteins through expression cloning, we fused the coding region of SemaIII to that of alkaline phosphatase (AP), a readily detectable histochemical reporter, and expressed the resulting chimeric protein in human embryonic kidney 293 cells. This protein could be detected by Western blotting in conditioned medium from these cells as a major band of ~180 kDa, consistent with the combined sizes of SemaIII and AP; a few smaller products, apparently degradation products, were also detected in this medium. When this medium was applied to dissociated sensory neurons from dorsal root ganglia (DRG), AP-reactivity could be detected on the axons and cell bodies of neurons from E14 DRG but not E18 DRG. AP alone, also expressed in 293 cells, did not bind cells at either age. The binding of Sema-AP to E14 but not E18 DRG cells is not unexpected since at E14 DRG axons are beginning to project into the spinal cord and can be repelled by a factor, likely Sema III, secreted by the ventral spinal cord (Fitzgerald et al., 1993; Messersmith et al., 1995; Shepherd et al., 1997), whereas by E18 they are no longer repelled by ventral spinal cord tissue (Fitzgerald et al., 1993), perhaps reflecting a downregulation of their responsiveness to SemaIII.

To identify SemaIII-binding proteins on E14 rat DRG neurons, a cDNA expression library was constructed in a COS cell expression vector using cDNA derived from E14 DRG tissue (see Experimental Procedures). Pools of ~1000–2000 cDNA clones from the library were transfected into COS cells and screened for the presence of cells that bound SemaIII-AP. A positive pool was identified after screening 70 pools. After three rounds of screening subpools from this pool, a single cDNA encoding a SemaIII-AP binding activity was identified. COS-7 cells transfected with this cDNA specifically bound SemaIII-AP but not AP or a netrin-Fc fusion protein (Keino-Masu et al., 1996).

Figure 1A1:
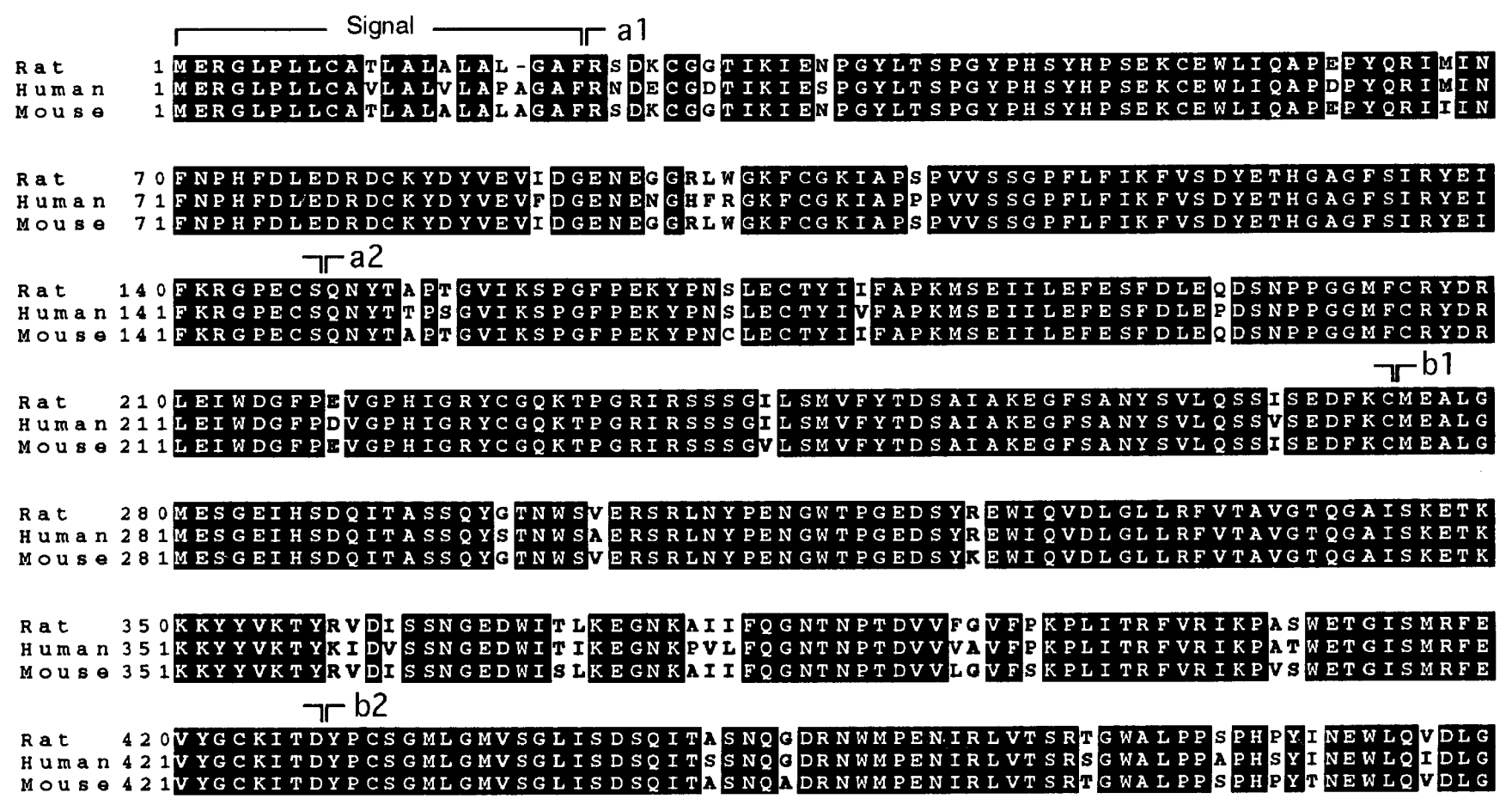
Figure 1B:
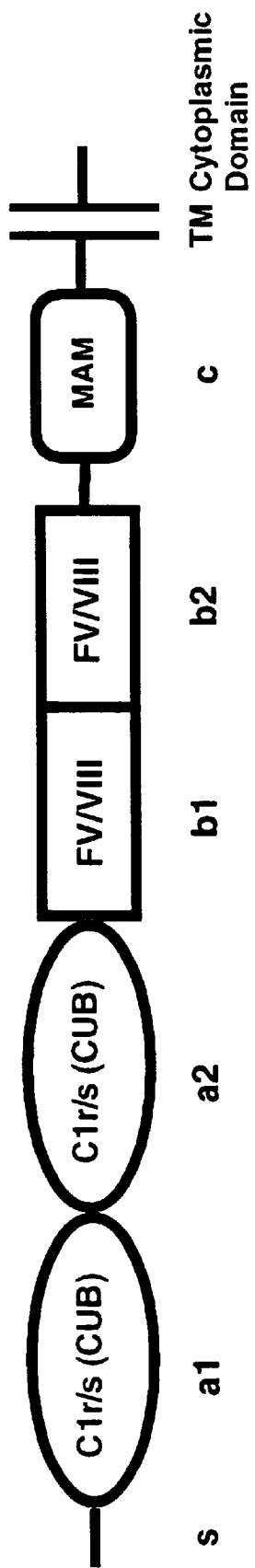

Nucleotide sequencing of the entire 5 kB cDNA insert revealed a single long open reading frame predicted to encode a protein (rat semaphorin receptor 1, rSR1) of 921 amino acids with sequence similarity with mouse, chicken and Xenopus neuropilin (Takagi et al., 1991, 1995; Kawakami et al., 1996). We further isolated a cDNA encoding a human homolog of our semphorin binding protein (hSR1) from a fetal human brain library (see Experimental Procedures), and FIG. 1A shows an alignment of the full conceptual translated amino acid sequences of our rat and human proteins with mouse neuropilin. The rat and human proteins share a high degree of sequence homology with the mouse protein (97% and 93% identity at the amino acid level, respectively), and are predicted to have the domain structure previously described for neuropilins from other species, including a short but highly conserved cytoplasmic domain (FIG. 1B).

We next performed coimmunoprecipitation experiments to test whether the binding of SemaIII-AP to COS-7 cells expressing rSR1 reflected a direct interaction between SemaIII and rSR1 or required cellular factors made by the COS-7 cells. For this purpose we constructed a soluble version of the ectodomain of rSR1 fused to AP. A myc-tagged SemaIII protein could be precipitated by beads conjugated with this SR-AP fusion, but not with beads conjugated with a control fusion protein, c-kit-AP (Flanagan and Leder, 1990), indicating a direct interaction between the SR1 ectodomain and SemaIII.

SR1 Binds Both the Semaphorin and the C-terminal Domains of SemaIII

SemaIII consists of a signature semaphorin domain, a single immunoglobulin (Ig) domain, and a carboxy terminal (C) domain that is rich in basic residues (Luo et al., 1993; Kolodkin et al., 1993; Messersmith et al., 1995; Püschel et al., 1995). The conservation of semaphorin domains among different semaphorin family members (reviewed in Tessi-Lavigne and Goodman, 1996; Kolokin, 1996) suggests the potential importance of this domain for function. The functions of the other two domains are unknown, although the basic nature of the C domain has suggested a role for this domain in mediating interactions with cell surfaces or the extracellular matrix (Luo et al., 1993). To determine which domain of SemaIII mediates the interaction between SemaIII and SR1, constructs encoding various fusions of AP to different portions of SemaIII were expressed in COS cells. Media conditioned by these cells were applied to COS-7 cells expressing SR1 to test for binding of AP fusion proteins; in positive control experiments, binding was observed with medium containing full length SemaIII-AP but not AP alone. Binding was also observed with an AP fusion protein comprising the semaphorn and Ig domains (AP-SI) and a fusion protein comprising just the semaphorin domain (AP-S), but not with a fusion protein comprising a truncated semaphorin domain, suggesting that the integrity of the semaphorin domain is required for binding. Surprisingly, binding was also observed with AP fusion proteins comprising only the C domain (AP-C) and a fusion protein comprising the Ig and C domains. These results provide evidence that both the semaphorin and the C domains of SemaIII can bind SR1. The binding of the C domain does not appear to reflect a non-specific interaction arising from the basic nature of the C domain since we found that the C terminal domain of netrin-1 (Serafini et al., 1994), which is also highly basic but does not share any sequence homology with the SemaIII C domain, did not bind SR1.

Figure 2A:
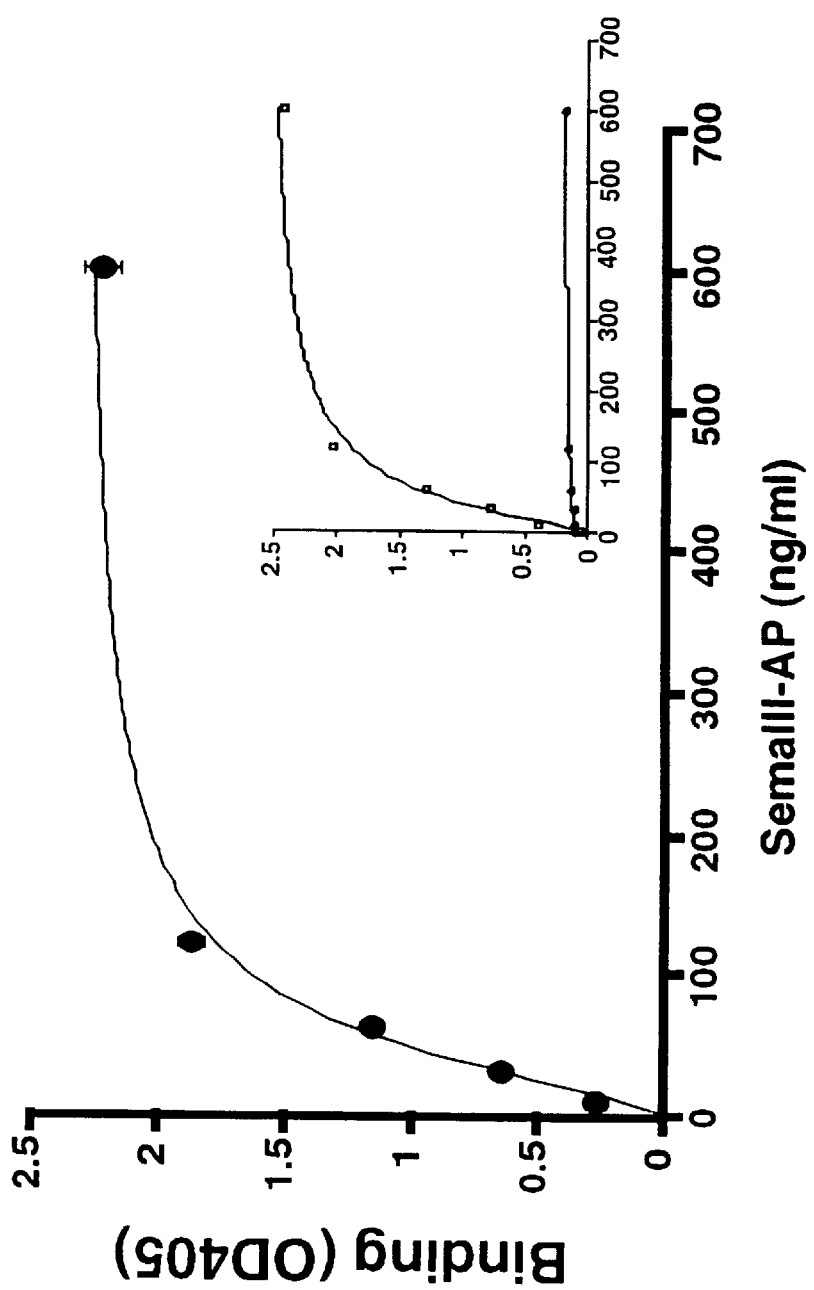
FIGS. 2A–2C Equilibrium Binding of Fusion Proteins of AP and different portions of SemaIII to SR1-Expressing cells.
Figure 2B:
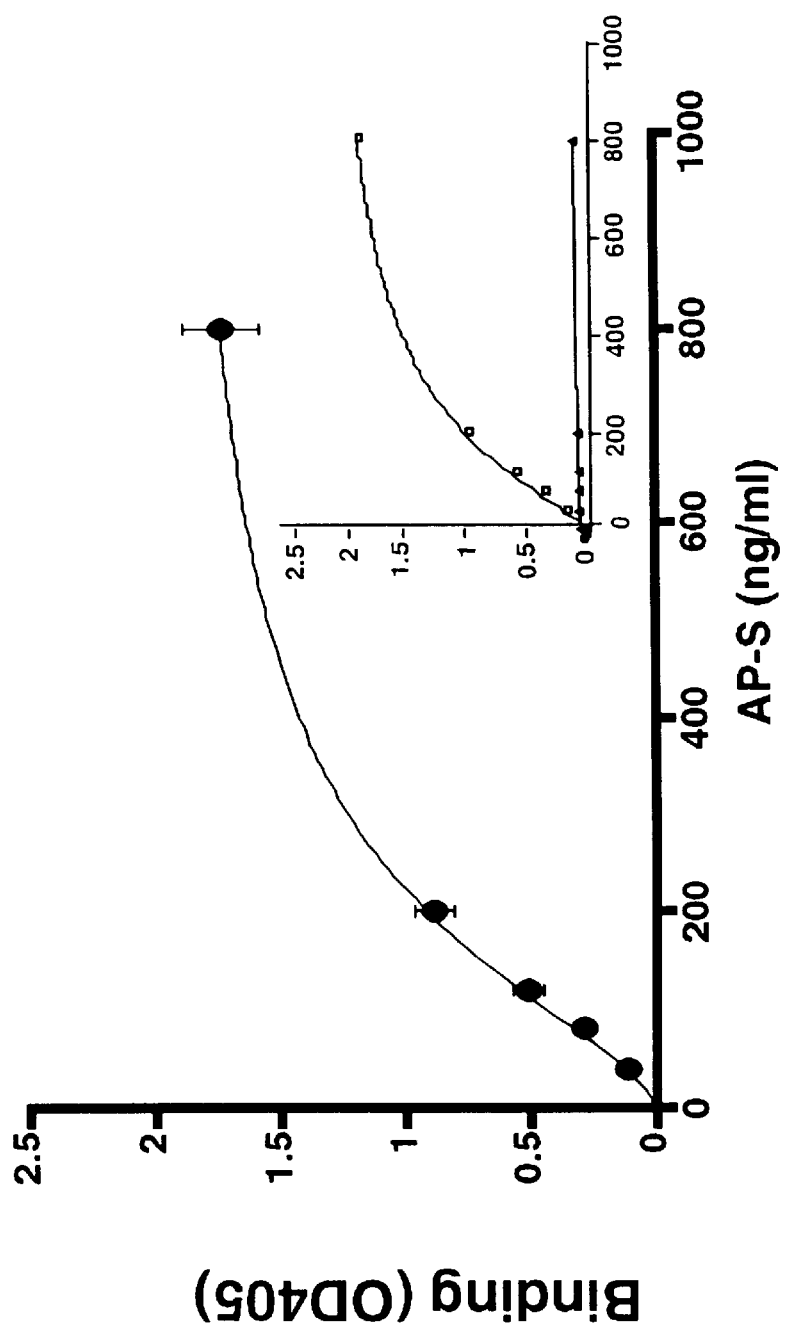
Figure 2C:
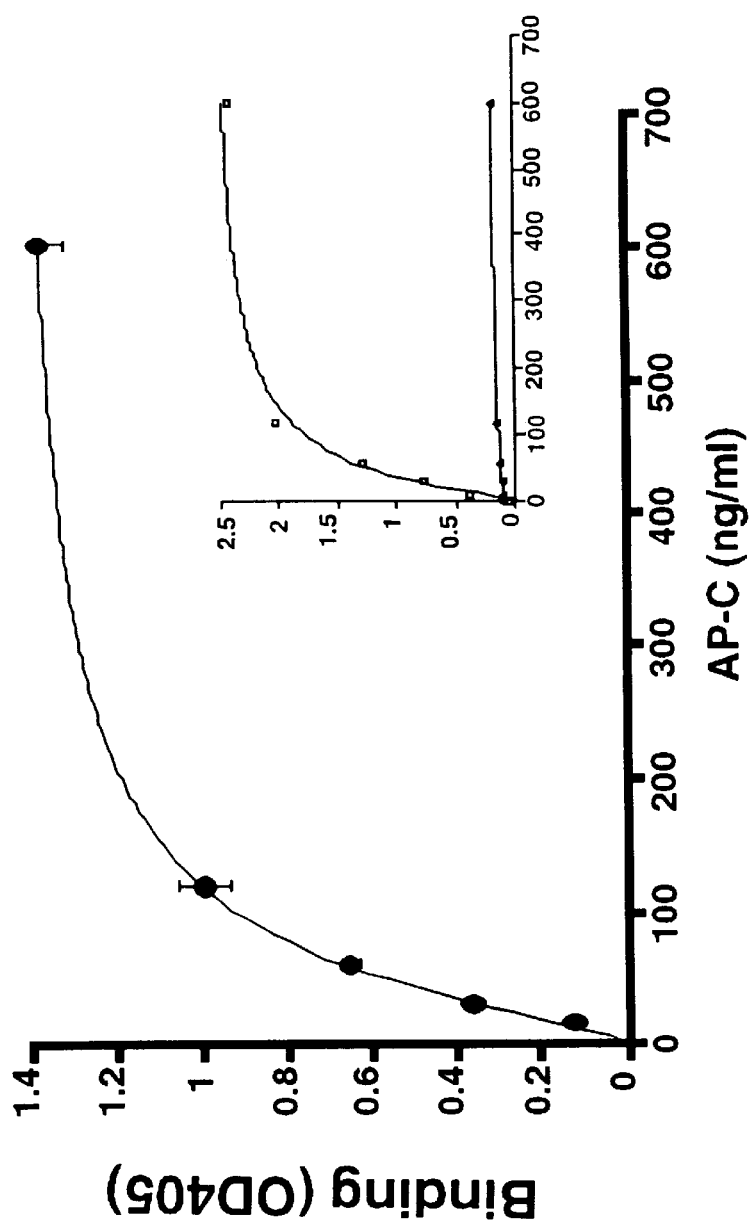

We next measured the binding affinity of the full-length and two of the truncated fusion ligands (AP-S and AP-C) to cells expressing SR1 in equilibrium binding experiments. based on the relative amounts of AP activity in the supernatant and bound to cells (FIG. 2). One limitation of these experiments is that we used partially purified conditioned media (see Experimental Procedures) which in the case of SemaIII-AP and AP-C contain both the full length fusion proteins as well as truncated forms that are presumed to. arise by proteolysis. For each of these fusions, the estimated dissociation constant would be accurate only if all the degradation products that possess AP activity bind with the same affinity as the intact fusion protein; this is unlikely to be the case since the media contain protein species that appear to correspond to AP or fragments of AP, which do not bind SR1. This limitation does not apply to AP-S since in this case only the full length species is found in the supernatant; the estimated dissociation constant should therefore accurately reflect the affinity of AP-S for the SR1-expressing cells. With these caveats, we found that the specific binding curves of SemaIII-AP, AP-S and AP-C to cells expressing SR1 showed saturation and could be fitted with the Hill equation (FIGS. 2A–C). Predicted values for the dissociation constants (Kd) for SemaIII-AP, AP-S and AP-C binding to SR1-expressing cells were 0.325 nM, 1.45 nM, and 0.84 nM; respectively. For comparison, in the collapse assay, a half maximal collapse response is observed with conditioned medium containing 0.44 nM SemaIII-AP. This value is comparable to the estimated Kd for the interaction of SemaIII-AP with SR1. These results support the role of an interaction of SemaIII with SR1 on DRG axons in causally mediating collapse.

For these experiments, control 293-EBNA cells or 293-EBNA cells stably expressing rat SR1 were treated for 90 min with concentrated conditioned media containing the indicated concentrations of SemaIII-AP (A), AP-S (B), or AP-C (C). After washing six times in HBHA buffer, the cells were lysed and endogenous AP activity was heat-inactivated. AP activity derived from the bound recombinant AP fusion proteins was measured calorimetrically (optical density at 405 nm). Specific binding was determined by subtraction of values obtained from binding to SR1-expressing cells and to control cells; values obtained in this way were fitted to the Hill equation. Insets in FIG. 2 show raw data (circles, total binding to SR1-expressing cells; triangles, total binding to control cells). Kd values for the interactions of SemaIII-AP, AP-S and AP-C with SR1 were 55.3±6.5 ng/ml, 218.6±11.0 ng/ml, and 67.2±3.0 ng/ml, respectively (1 nM corresponds to 170 ng/ml, 150 ng/ml, and 80 ng/ml for SemaIII-AP, AP-S and AP-C, respectively). Bars indicated s.e.m. for triplicates. Hill coefficients for SemaIII-AP, AP-S and AP-C were 1.51±0.24, 1.70±0.10, and 1.44±0.07, respectively.

SR1 Function is Required for the Repulsive Action of SemaIII

We next raised antibodies to a portion of the SR1 ectodomain for use in tests of the functional role of SR1 in mediating responses to SemaIII (see Experimental Procedures). To verify the potential usefulness of the antiserum, we first examined whether it could detect SR1 protein on axons. The spatial and temporal pattern of expression of SR1 detected with this antiserum in transverse sections of rat embryos at spinal levels corresponded to the sites of SR1 gene expression detected by in situ hybridization, and matched the pattern previously observed in mouse and chick embryos (Kawakami et al., 1995; Takagi et al., 1995). At E14, when afferent fibers of DRG neurons start to penetrate the dorsal spinal cord (Windle and Baxter, 1936; Smith, 1983; Altman and Bayer, 1994; Snider et al., 1992; Zhang et al., 1994), SR1 transcripts were found in the DRG as well as in the ventral and dorsal spinal cord, and corresponding immunoreactivity for SR1 protein was detected on sensory and motor axons, as well as in the dorsal spinal cord. SR1 immunoreactivity could also be detected with this antiserum on the axons and growth cones of E14 rat DRG neurons in culture, as previously shown for neuropilin with chick DRG axons (Takagi et al., 1995). At E18, much lower levels of SR1 transcripts were detected in DRG and the ventral horn (see also Kawakami et al., 1995; Takagi et al., 1995 for similar results with neuropilin in mice and chickens). The timing of expression in DRG is consistent with the pattern of SemaIII-AP binding to E14 and E18

DRG cells in culture and with what might be expected of a SemaIII receptor (see Fitzgerald et al., 1993; Messersmith et al., 1995; and discussions therein)

Protein A-purified anti-SR1 antiserum was used to test the involvement of SR1 in mediating the function of SemaIII. Inclusion of the antiserum in the culture medium inhibited the repulsive effect of SemaIII-AP and SemaIII on E14 rat DRG axons in collagen gel cultures in a dose-dependent manner, whereas preimmune IgG, also purified on protein A, did not inhibit the repulsion. To verify that this neutralizing effect was due to antibodies directed against SR1 in the antiserum. aliquots of the antiserum were subjected to immunodepletion by incubation with beads conjugated with the portion of the SR1 ectodomain used to make the antiserum (depleted antiserum) or with control beads (mock-depleted antiserum). The mock-depleted antiserum still detected the SR1 ectodomain-AP fusion protein by Western blotting and was still capable of blocking the inhibitory effect of SemaIII-AP. In contrast, the depleted antiserum did not detect the SR1 ectodomain-AP fusion protein by Western blotting and did not block the inhibitory activity of SemaIII-AP, consistent with the hypothesis that the starting antiserum blocks SemaIII-AP activity by interfering with SR1 function. To rule out the possibility that the antiserum to SR1 affected a general mechanism required for axonal repulsion, the same protein A-purified antiserum was tested for its effect on netrin-mediated repulsion of trochlear motor axons (Colamarino and Tessier-Lavigne, 1995), a group of axons that can also be repelled by SemaIII (Serafini et al., 1996; Varela-Echavaria et al., 1997). The anti-SR1 antiserum stained these axons but did not block the repulsive effect of netrin-1 on these axons, consistent with a specific involvement of SR1 in SemaIII-mediated repulsion.

SR1 Function is Also Required for the Collapse-inducing Effect of SemaIII

In addition to steering DRG axons away when presented chronically from a point source, SemaIII can also induce collapse of DRG growth cones when added acutely and uniformly to growth cones in culture (Luo et al., 1993). We therefore examined whether the anti-SR1 antiserum could affect the activity of SemaIII in the collapse assay. The anti-SR1 antiserum inhibited collapse of E14 rat DRG growth cones elicited by SemaIII-AP or SemaIII-myc; the blocking effect showed a dose-dependence that was similar to that observed for the block of repulsion (Table 1). As expected, the mock-depleted antiserum also blocked the collapse, whereas the depleted antiserum did not. To test the specificity of this blockade, we took advantage of the fact that lysophosphatidic acid (LPA) can also cause collapse of DRG growth cones (Jalink et al., 1994). Neither the preimmune serum nor the anti-SR1 antiserum inhibited the collapse of DRG growth cones induced by LPA, consistent with the hypothesis that the antiserum blocks SemaIII-induced collapse by specifically inhibiting SR1 function.

Cloning of a cDNA encoding SR2

To identify additional members of the SR family, we designed PCR primers which would selectively amplify rat cDNA molecules containing both the CUB the MAM motifs of SR1. A single cDNA (SEQ ID NO:7) encoding an 936 amino acid SR1 homolog, designated SR2 (SEQ ID NO:8) was identified. With these data, we were able to identify and composite ESTs in public databases to generate a cDNA sequence encoding hSR2. cDNA's comprising this clone are also isolated from a fetal human brain library (see Experimental Procedures). SR-specific function, including semaphorin binding and neuron axon outgrowth and/or orientation modulating activity are demonstrated as described herein for SR1 polypeptides.

SR1 is a SemaIII Receptor

Neuropilin is a transmembrane protein initially identified by Fujisawa and colleagues as an epitope recognized by a monoclonal antibody (A5) that labels specific subsets of axons in the developing Xenopus nervous system (Takagi et al., 1987; Fujisawa et al., 1989; Takagi et al., 1991). Neuropilin comprises in its extracellular domain two so-called CUB motifs, which are found in the noncatalytic regions of the complement components C1r and C1s and several metalloproteinases (for review see Bork and Beckmann, 1993). These domains are followed in neuropilin by two domains with significant similarity to many proteins, including the C1 and C2 domains of coagulation factors V and VIII (Toole et al., 1984; Jenny et al., 1987), the milk fat globule membrane proteins (MFGPs) (Stubbs et al., 1990), and the discoidin domain receptor (DDR) (Johnson et al., 1993; Sanchez et al., 1994). More proximal to the transmembrane region is a MAM domain, a type of motif implicated in protein-protein interactions (Beckmann and Bork, 1993). The cytoplasmic domain of neuropilin is short (40 amino acids) and does not possess obvious motifs, but is highly conserved among Xenopus, mouse and chick (Takagi et al., 1995; Kawakami et al., 1996). In the developing nervous, systems of these three species, neuropilin is expressed in dynamic fashion by a variety of different classes of axons (including motor and sensory axons) as they project to their targets (e.g., Takagi et al., 1987, 1991, 1995; Kawakami et al., 1996). Neuropilin can promote neurite outgrowth in vitro (Hirata et al., 1993) and forced expression of neuropilin under control of the β-actin promoter in transgenic mice results in axonal defasciculation (Kitsukawa et al., 1995). The forced ectopic expression of neuropilin also leads to abnormalities in development of the heart and limbs, two of the non-neural regions where neuropilin is expressed, which has suggested a role for neuropilin in organogenesis outside the nervous system (Kitsukawa et al., 1995).

We have identified SR1 and SR2 semaphorin receptors with sequence similarity to the neuropilin proteins. The spatiotemporal expression pattern of SR1 is consistent with SR1's role as a SemaIII receptor. In the region of the developing spinal cord, SR1 is most prominently expressed by sensory neurons in the DRG, particularly on their axons in the spinal nerves, the dorsal roots, and the dorsal funiculus and SR1 can also be detected on the growth cones of axons derived from dissociated DRG neurons in culture The period during which SR1 and neuropilin is expressed by DRG neurons (between E9 and E15.5 in the mouse, decreasing sharply thereafter (Kawakami et al., 1995)) corresponds to the timing of projection of SemaIII-responsive DRG axon projections into the spinal cord. During this period, Sema III is expressed at a high level in the ventral spinal cord and has been implicated as a diffusible chemorepellent that prevents inappropriate targeting of NGF-responsive axons that normally terminate in the dorsal spinal cord (Messersmith et al., 1995, Püschel et al., 1995, 1996; Shepherd et al., 1997). Our in situ hybridization studies suggest that SR1 may be expressed in only some populations of rat DRG cells at E14—possibly the NGF-responsive neurons, which are SemaIII responsive. In addition to developing DRG axons, several other classes of developing axons are repelled by or collapse in response to SemaIII, including sympathetic axons (Püschel et al., 1996), spinal motor axons (Shepherd et al., 1996; Varela-Echavarria et al., 1997), and many cranial motor axons such as trochlear, trigeminal motor, glossopharyngeal and vagal axons (Serafini et al., 1996; Varela-Echavarria et al., 1997). All of these axons express SR1.

SR1 also plays a role in mediating actions of SemaIII outside the nervous system SR1, the neuropilins and SemaIII are expressed in a variety of non-neural tissues, including the developing cardiovascular system and limbs (Takagi et al., 1987, 1991, 1995; Kitsukawa et al., 1995; Püschel et al., 1995; Behar et al., 1996). Ectopic expression of m-neuropilin under control of the β-actin promoter in transgenic mice, in addition to causing sprouting and defasciculation of axons, leads to a variety of morphological abnormalities in non-neural tissues including the presence of excess capillaries and blood vessels, dilation of blood vessels, malformed hearts, and extra digits (Kitsukawa et al., 1995; see also, the defects in axonal, heart and skeletal development seen in SemaIII knock-out mice, Behar et al., 1996).

Our experiments have provided evidence that both the C domain and the semaphorin domain of SemaIII can independently bind SR1. The ability of both poles of the full length SemaIII molecule to bind SR1 could provide an explanation for the data suggesting that full length SemaIII has a higher affinity for SR1 than do either of the individual domains alone, since sequential binding of the two domains of each SemaIII molecule to neighboring SR1 molecules in the cell membrane would result in a higher apparent affinity. This observation indicates that signaling in response to SemaIII might be triggered by dimerization of SR1 molecules brought together by single SemaIII molecules; which is also supported by the observation that AP-S and AP-C, the fusions of AP to the semaphorin domain or the C domain, failed to induce repulsion or to cause collapse of DRG axons in vitro.

SR1 contains at its amino terminus two CUB domains, motifs implicated in protein-protein interactions whose structure is predicted to be an antiparallel β-barrel similar to those in two adhesive domains, immunoglobulin-like domains and fibronectin type III repeats (Bork et al., 1993; Bork and Beckmann, 1993). CUB domains in complement C1r/s appear to mediate calcium-dependent tetrameric complex formation between C1r/s dimers, as well as their association with C1q to form the mature C1 complex (Busby and Ingham, 1988, 1990), whereas a CUB domain in the metalloproteinase Tolloid (a relative of BMP-1) is suggested from genetic evidence to mediate an interaction with the BMP family member decapentaplegic (Childs and O'Connor, 1994; Finelli et al., 1995). In the central portion of the SR1 molecule, the b1 and b2 domains show homology to protein binding domains of coagulation factors V and VIII (Toole et al., 1984; Jenny et al., 1987), MFGF (Larocca et al., 1991) and two receptor protein-tyrosine kinases, DDR (Johnson et al., 1993) and Ptk-3 (Sanchez et al., 1994). Finally, SR1 also possesses a MAM domain, a ~170 amino acid module found in diverse transmembrane proteins (Beckmann and Bork, 1993), which has been suggested to mediate homophilic interactions (Zondag et al., 1995). We found that a truncated form of SR1 which lacks the amino terminal-most 264 amino acids retains the ability to bind SemaIII-AP, indicating that at least one of the semaphorin and C domains of SemaIII may interact with domains b1 or b2 or the MAM domain of SR1. SemaIII may also modulate. the interactions of SR1 with other SR1 binding partner. In the repulsion assay the most obvious effect of Sema III is the steering away of DRG axons from a local source of SemaIII, rather than a change in fasciculation patterns (Messersmith et al, 1995). Furthermore, individual growth cones can be induced to collapse in vitro in response to SemaIII (Luo et al., 1993) in a SR1-dependent fashion, indicating a distinct signaling pathway involving SR1 that can be triggered by SemaIII.

The semaphorin family comprises over 20 proteins, secreted and transmembrane, which have been divided into five subfamilies based on sequence and structural similarity (reviewed by Tessier-Lavigne and Goodman, 1996; Kolodkin, 1996). We have found that the secreted semaphorins SemaA, SemaE and SemaIV, which belong to the same subfamily as SemaIII, can all bind SR1, suggesting promiscuity in interactions between SR1 and members of this subfamily of the semaphorin family. The bewildering diversity of semaphorin proteins may mask an underlying simplicity in interactions of these proteins and their receptors, much as the diversity of Eph receptors and ephrin ligands masks simpler binding relations, in which GPI-anchored ligands of the ephrin-A subclass interact primarily and promiscuously with EphA class receptors, and ligands of the ephrin-B subclass interact primarily and promiscuously with EphB class receptors (Gale et al.; 1996; Eph Nomenclature Committee, 1997).

Experimental Procedures: Construction and Expression of AP fusion Proteins

To produce a Sema III-AP fusion protein, the cDNA encoding full-length Sema III was amplified by PCR and subcloned into APTag-1 (Flanagan and Leder, 1990). From the resulting plasmid, the fragment encoding both Sema III and AP was then transferred to the expression vector pCEP4 (Invitrogen), and used to transfect 293-EBNA cells (Invitrogen). A cell line stably expressing Sema-AP was established after selection with geneticin and hygromycin. Cells were grown to confluence and then cultured in Optimen medium (BRL) for 3 days. The conditioned medium was collected and partially purified using a Centriprep-100 device (Amicon). A construct encoding the ectodomain of SR1 (amino acids 1 to 857) fused to AP was similarly made in pCEP4 and used to derived a stable cell line. Conditioned medium from this line was prepared in the same way.

For other AP fusion proteins, sequences encoding the Sema domain and Ig domain (amino acids 25 to 654), the Sema domain alone (amino acids 25 to 585), a truncated Sema domain (amino acids 25 to 526), the Ig domain and C-domain together (amino acids 586 to 755), or the C-domain alone (amino acids 655 to 755) were amplified, by PCR, fused to the sequence encoding AP, and subcloned into cloning sites after the Ig_κ-chain signal sequence of the expression vector pSecTag B (Invitrogen). These resulting constructs were transiently transfected into Cos-1 or Cos-7 cells with Lipofectamine (GIBCO BRL). Conditioned media were collected as described above.

Expression Library Construction and Screening 80 mg of DRG tissue was dissected from two litters of E14 rat embryos (with kind help of K. Wang) and frozen on dry ice. mRNA was isolated from these rat DRGs using a QuickPrep mRNA purification kit (Phamicia), and used to generate cDNA using a Stratagene cDNA synthesis kit according to manufacturer's instructions, except that the cDNA was size-fractionated using a DNA Size Fractionation Column (GIBCO BRL). Fractions containing cDNA larger than 500 bp were collected and ligated to the EcoRI-XhoI sites of the COS cell expression vector pMT21 (Genetics Institute). Ligated DNA was ethanol precipitated, resuspended in water at 10 ng/µl, electroporated into SURE 2 supercompetent cells (Stratagene) (1 µl DNA to 40 µl bacteria), and the resulting transfomants were divided into pools of ~1000 to 2000 colonies.

To screen the library, DNA was extracted from the bacteria in each pool using the SNAP miniprep kit (Invitrogen) and transiently transfected into COS-1 cells in six wells plates with lipofectamine (GIBCO BRL). After 48 hr, the cells were washed once with Hank's balanced salt solution (HBHA, Cheng and Flanagen, 1994), and then incubated in HBHA containing 50–100 ng/ml SemaIII-AP fusion protein for 75 min at room temperature. Plates were washed in HBHA six times, fixed with acetone-formaldehyde, then washed twice in HBS as described by Cheng and Flanagen (1994). Plates were kept in a 65° C. incubator for 2 hr to inactivate the endogenous alkaline phosphatase activity in COS cells. The cells in the plates were stained for 2–6 hr in AP buffer containing the AP substrate BCIP and NBT (GIBCO BRL) as described previously by Cheng and Flanagan (1994). Staining of the cells was monitored using a dissecting microscope.

After identification of a positive pool, 10 ng of DNA from the pool was transfected into DH5α_competent cells and the transfomants were subdivided into subpools of 200–300 colonies. These subpools were rescreened as described above, and a positive subpool subdivided further through two more rounds until a single positive plasmid (p28) was isolated. The insert DNA in the p28 plasmid was sequenced from both strands using a Licor (L4000) automated sequencer as well as by $^{33}P$ cycle sequencing.

Human cDNA Library Screening

A search of the human expressed sequence tag (EST) databases with the sequence of rat SR1 (p28) revealed many short sequences with homology to its middle portion. An EST clone (Genbank accession number R61632) was obtained from Genome System Inc. and used as a probe to screen a human fetal brain cDNA library (Stratagene) at high stingency, leading to the isolation of four overlapping cDNAs covering the full-length coding region of human SR1.

In situ Hybridization

Cryosat sections (10 µm) were made from the brachial region of E14 rat embryos prefixed with 4% paraformaldehyde (PFA). In situ hybridization of these sections was performed as described by Schaeren-Wiemers and Gerfin-Moser (1993) and Kennedy et al (1994). A 1285 bp fragment including 490 bp of 5'-untranslated region and 795 bp of 5' SR1 coding region was released by Pst I digestion of the p28 plasmid and subcloned into pBluescript (Stratagene). Antisense and sense RNA probes were transcribed in the presence of digoxygenin-UTP (Boehringer Mannheim) using T7 and T3 polymerases as recommended by the manufacturer.

Cell Surface Binding and Kinetic Analysis

To examine the binding of SemaIII-AP to dissociated DRG cells, DRGs dissected from E14 or E18 rat embryos were digested with 0.25% of trypsin for 10 min at 37° C. and further dissociated by trituration with a fire-polished pipette. After removing the undissociated tissue clumps by precipitation, dissociated cells were collected by spinning at 430×g for 5 min, then cultured in eight-well chamber slides at 37° C. in 5% $CO_2$ for 20 hr in F12/N3 medium (Tessier-Lavigne et al., 1988) containing 0.5% fetal calf serum (FCS) and 25 ng/ml 2.5S NGF ((Bioproducts for Science Inc.). To examine binding activity, cells were incubated with HBHA buffer containing the indicated recombinant protein for 90 min, followed by washing, fixing, heating, and staining as described above 293-EBNA cells stably expressing the full-length rat SR1 protein were established by transfection of a pCEP4-SR1 plasmid and selection with geneticin and hygromycin. The equilibrium-binding experiments were performed essentially as described (Flanagan and Leder, 1990; Cheng and Flanagan, 1994) using control 293-EBNA cells or SR1-expressing 293-EBNA cells cultured on six-well plates precoated with poly-D-lysine.

Generation of Antibodies to SemaIII and SR1

For Western blotting studies on SemaIII, purified AP-S, a fusion of AP to the Sema domain of SemaIII, was used to raise a rabbit anti-serum. For function-blocking studies on SR1, a 1775 bp DNA fragment encoding amino acids 265 to 857 of SR1 was PCR amplified and subcloned into a bacterial expression vector pQE-9 (Qiagen) for the generation in $E.\ Coli$ of a fusion protein comprising six histidine residues at its amino terminus. The His-tagged SR1 was expressed in XL1-Blue cells and purified according to manufacturer's instructions, and used to raise a rabbit anti-SR1 antiserum. Immunoglobulins in the anti-SR1 or preimmune sera were purified on protein A-Agarose (GIBCO BRL) columns. After application of the sera to the columns, the columns were washed first with 15 bed-volumns of 100 mM Tris (pH 8.0) and then with another 20 bed-volumns of 10 mM Tris (pH 8.0), then eluted with 5 bed volumns of 50 mM glycine (pH 3.0). The eluates from the columns were immediately neutralized by addition of ⅒ volume of 1 M Tris (pH 8.0), followed by concentration on a Centricon-10 device (Amicon). To deplete anti-SR1 antibodies from the antiserum, an equal volume of nickle-agarose beads was incubated with (or, for control, without) purified His-SR1 protein (1 mg/ml) at 4° C. for 4 hr. After washing three times with F12 medium, the beads were incubated at 4° C. for 3 hr with an equal volume of anti-SR1 serum. The supernatants were collected and then subjected to protein A-agarose affinity purification as described above.

Immunoprecipitation and Western Analysis

To detect AP or AP fusion proteins by Western blotting, aliquots of the concentrated conditioned media were resolved by SDS-PAGE (8% gel). After transfer to nitrocellulose (Amersham), the proteins were probed with rabbit anti-AP antibody (DAKO). The blot was developed with BCIP and NBT as the substrate.

To detect an interaction between SR1 and SemaIII, 100 µl protein A-agarose beads (GIBCO BRL) were first incubated with 5 µg of anti-AP monoclonal antibody (Medix Biotech) in IP buffer (20 mM Hepes, pH 7.0, 100 mM NaCl, 1 mM EDTA, 1 mM DTT, and 0.02% NP-40) at 4° C. for 2 hr. After washing three times with 1 ml of IP buffer, half of the beads (50 µl) were incubated with 2 µg of Kit-AP (Flanagan and Leder, 1990) or SR1-AP protein (containing the entire SR1 ectodomain) at 4° C. for another 2 hr. Beads conjugated with recombinant proteins were then washed three times with IP buffer, and resuspended into 40 µl IP buffer containing 2 µg of myc-tagged Sema III protein. After the mixtures were incubated at 4° C. for 3 hr, the beads were washed six times with 1 ml IP buffer. The bound proteins were released by boiling the beads in 50 µl SDS-containing sample buffer and analyzed by SDS-PAGE (8% gel) and Western blotting with a monoclonal antibody (9E10) against a C-terminal Myc-epitope tag.

Immunohistochemistry

For immunostaining to detect the expression of SR1 in E14 rat spinal cord, cryostat sections (10 μm) from unfixed frozen embryos were collected and fixed with acetone for 5 min. The staining was performed with preimmune serum (1:500), or anti-SR1 serum (1:500) as the primary antibody and biotinylated goat anti-rabbit Ig (5 ng/ml, Biorad) as the secondary antibody. Diaminobenzidine (Sigma) was used as a chromogen, with signal enhancement by a Vectastain Elite ABC kit (Vector). For staining of cultured cells, E14 rat DRG were cultured as above for 20 hr, incubated with the anti-SR1 antiserum or preimmune serum (1/500 dilution) for 1 hr at room temperature, washed 3 times, fixed with methanol, and the bound antibody was visualized using a Cy3-conjugated secondary antibody (Jackson Immunological Laboratories).

Collapse Assay

The collapse assay was performed essentially as described by Raper and Kapfhammer (1990) and Luo et al. (1993), with minor modifications. In brief, DRG explants were dissected from E14 rat embryos, and cultured at 37° C. in 5% $CO_2$ for 16–20 hr on six-well plates precoated with poly-D-lysine (Sigma) and laminin (Becton Dickinson Labware) in F12/N3 medium containing 0.5% FCS and 25 ng/ml 2.5 S NGF. Small volumes of concentrated conditioned medium containing AP, SemaIII-AP, or SemaIII-myc were gently added into the culture medium, and the cultures were kept at 37° C. for 1 hr. The explants were fixed with 4% PFA in PBS containing 10% sucrose for 15 min, then incubated with PHTX (PBS/1% heat-inactivated goat serum/1% Triton X-100) for 15 min. The explants were then stained with 2 μg/ml Rhodamine-Phalloidin (Molecular Probes) for 30 min, washed, and mounted with Fluoromount G (Fisher). As a control, aliquots of L-a-lysophosphatidic acid (LPA, Sigma) were added into the cultures at a final concentration of 1 μM (Jalink et al., 1994) and the cultures were incubated at 37° C. for 3 min prior to fixation and staining. To examine the effect of preimmune or anti-SR1 antisera, aliquots of each antiserum were added into the explant cultures, which were kept at 37° C. for 30 min prior to the addition of SemaIII protein or LPA.

Repulsion Assay

The repulsion assay was essentially as previously described (Messersmith et al., 1995). In brief, E14 rat DRG explants were dissected and embedded in collagen gels with control 293 EBNA cells or 293 EBNA cells expressing SemaIII-AP. The indicated amount of antibodies were included into the culture medium (F12/N3 medium containing 0.5% FCS and 25 ng/ml 2.5 S NGF). After incubation at 37° C. for 40 hr, the explants were fixed with 4% PFA in PBS for 2 hr, and followed by immunostaining with a neurofilament-specific antibody (NF-M, 1:1500; Lee et al., 1987) and a horseradish peroxidase-conjugated secondary antibody (Boehringer-Mannheim; 1:250) as described (Kennedy et al., 1994; Messersmith et al., 1995). The quantification of neurite outgrowth was performed as described (Messersmith et al., 1995).

Identification of Neuropilin-2

The extracellular domain of neuropilin-1 is comprised of several predicted structural domains: two CUB motifs (domains a1 and a2), two domains of homology to coagulation factors V and VIII (domains b1 and b2) and a MAM domain (domain c) (Takagi et al., 1991; Kawakami et al., 1996) (FIGS. 1 and 2a). To determine whether neuropilin-1 is a member of a family of related molecules, we searched for relatives by reverse transcription-PCR (RT-PCR) using three sets of degenerate forward primers (5.1, 5.2 and 5.3) and three sets of degenerate reverse primers (3.1, 3.2, and 3.3). The primers were designed based on the sequences conserved among domain a2 and other CUB domain proteins (primer set 5.1), domains b1 and/or b2 and coagulation factors V and VIII (primer sets 5.2, 5.3 and 3.1), domain c and other MAM domain proteins (primer set 3.2), or a sequence in the cytoplasmic domain that is highly conserved among neuropilin homologues from different species (primer set 3.3) (see Experimental Procedures). Sequences were amplified from whole E11 mouse embryo mRNA and adult mouse brain mRNA using all pairwise combinations of 5' and 3' primer sets (except 5.3 and 3.1). In all cases, products of the size expected for neuropilin-1 were amplified and subcloned. More than a dozen cDNAs for each pair of primer sets were sequenced, and in all cases mouse neuropilin-1 sequences were recovered. In addition, several of the cDNAs obtained by RT-PCR using primer sets 5.2 (b1 domain) and 3.3 (cytoplasmic domain) encoded overlapping sequences that were related but not identical to a portion of the neuropilin-1 sequence. These sequences were extended in both the 5' and 3' directions using a combination of cDNA library screening and RACE (rapid amplification of cDNA ends) (see Experimental Procedures).

From these experiments, the full length sequence of a new neuropilin-1-related molecule was assembled (FIG. 3), which has been named neuropilin-2. By screening the expressed sequence tag (EST) data bases, we were also able to assemble the sequences of several human ESTs to predict the sequence of human neuropilin-2, which shares high homology (90% identity) with that of mouse neuropilin-2. The overall structure predicted for neuropilin-2 is identical to that of neuropilin-1, with all the same functional domains (FIG. 4A). At the amino acid level, the sequence of neuropilin-2 is 44% identical to that of neuropilin-1, in both mouse and human. The homology is distributed over the entire length of the proteins, with highest homology in the transmembrane domain.

In the course of these experiments (see Experimental Procedures), we also discovered evidence for the existence of alternative forms of neuropilin-2 which may arise by alternative splicing. First, an alternate form with a divergent carboxy terminus was identified, which we have named neuropilin-2(b0) (we will use the names neuropilin-2 and neuropilin-2(a0) interchangeably to refer to the original isoform). The sequence of neuropilin-2(b0) diverges from that of neuropilin-2(a0) at amino acid 809, between the MAM domain and the transmembrane domain of neuropilin-2(a0) (FIG. 4C). Neuropilin-2(b0) is predicted from hydrophobicity analysis to have a transmembrane domain, followed by a cytoplasmic domain of similar length to that in neuropilin-2(a0), but these two domains are highly divergent from those of neuropilin-2(a0), sharing only 10% identity. An expressed sequence tag (EST) encoding human sequences (346 bp fragment) corresponding to a portion of this diverged sequence was also found in the dbEST database (AA25840) (FIG. 4C). To test the prediction that neuropilin-2(b0) is a transmembrane protein, we tagged this protein at its carboxyl terminus with a myc-epitope, expressed the tagged construct by transient transfection into COS 7 cells, and examined expression of the tagged protein using monoclonal antibody 9E10 directed against the epitope tag (Evan et al., 1985). Detection of the myc-tag at the carboxyl terminus of neuropilin-2(b0) by immunostaining required detergent permeabilization of the transfected cells, indicating that neuropilin-2 is indeed a transmembrane protein.

In addition, we found other isoforms of neuropilin-2(a0), including isoforms with insertions of 5, 17, or 22 (5+17) amino acids at amino acid 809 in neuropilin-2(a0), i.e. at the site of divergence of the a and b isoforms of neuropilin-2 (FIG. 4B). The 22 amino acid insertion is the sum of the 5 and the 17 amino acid insertions (FIG. 4B). We term these isoforms neuropilin-2(a5), neuropilin-2(a17) and neuropilin-2(a22). The isoform reported by Kolodkin et al. (1997) appears to be the rat neuropilin-2(a17) isoform. Similarly, we have found an isoform of neuropilin-2(b0) with the very same 5 amino acid insertion at amino acid 809, and which we name neuropilin-2(b5) (FIG. 4B). The pattern of combinations of the 5 and 17 amino acid inserts that we have observed in different neuropilin-2 isoforms indicates that these different isoforms arise from splicing in of separate exons encoding the 5 and 17 amino acid stretches.

To determine whether the a and b isoforms of neuropilin-2 show different temporal patterns of expression, we performed RT-PCR using a 5' primer designed to a sequence shared between all neuropilin-2 isoforms, and two 3' primers unique to the sequences in the cytoplasmic domains of neuropilin-2(a) and of neuropilin-2(b) (see Experimental Procedures). Using E11 whole mouse embryo mRNA as a template we found that at E11only an amplification product corresponding to neuropilin-2(a) could be detected. However, using adult mouse brain mRNA as a template, we detected amplification products corresponding to both neuropilin-2(a) and neuropilin-2(b). Taken together, these results indicate that different isoforms of neuropilin-2 might arise by alternative splicing and that this splicing are regulated in a time-dependent or a cell type-dependent fashion.

Neuropilin-2 is expressed by specific classes of developing neurons. To determine whether neuropilin-2, like neuropilin, is a candidate for a receptor involved in axonal growth or guidance, we examined by in situ hybridization whether neuropilin-2 mRNA is expressed by embyronic neurons during the period of axonal extension. Given the large number of isoforms of neuropilin-2 that appear to exist, we decided in this first survey to use a probe corresponding to sequences that extend from domain b2 through the cytoplasmic domain of neuropilin-2(a0) (see Experimental Procedures). Most of this probe corresponds to sequences that are shared between all isoforms.

Spinal cord. We first examined the pattern of expression of neuropilin-2 in the region of the developing mouse spinal cord during the period of initial extension of axons of motor and sensory neurons (from E9.5), at the level of the forelimbs. This pattern was highly dynamic. Neuropilin-2 mRNA was detected in the ventral spinal cord of E9.5 embryos, including the region of developing motorneurons. Expression was also strong in the floor plate and in tissue adjacent to the neural tube, including the somites and prospective dorsal root ganglia (DRGs) but not the notochord. Between E10.5 and E13.5 we compared the expression of neuropilin-2 to that of neuropilin-1, which has already been described (Kawakami et al., 1996). By E10.5, the level of neuropilin-2 expression had increased in the spinal cord. The whole ventral half of the spinal cord including the floor plate was heavily labeled, but expression was also strong in cells localized in the lateral margin of the dorsal aspect of the spinal cord, which may include commissural neuron cell bodies. Neuropilin-1 expression was also detected in the ventral spinal cord but only in motorneurons, and was very weak or absent from the floor and roof plates. Neuropilin-2 and neuropilin-1 mRNAs were also coexpressed in prospective DRGS, although neuropilin-2 expression was in addition high in non-neural tissues surrounding the spinal cord. A similar pattern of neuropilin-2 expression was observed at E11.5. At E13.5, nieuropilin-2 expression had decreased and was now restricted to the ventral portion of the spinal cord. Both neutropilins were still expressed in motorneurons, but neuropilin-2-expressing cells were found througout in the entire ventral spinal cord whereas the expression pattern of neuropilin-1 was more restricted. In addition, neuropilin-1 was now strongly expressed in the dorsal spinal cord and in the DRGs, whereas neuropilin-2 expression in the DRGs was very weak, and only just above background level. Weak expression of neuropilin-1 was also detected in the floor plate at this stage, but contrary to neuropilin-2, it was absent form the roof plate. Expression of neuropilin-2 at E15.5 was unchanged in the spinal cord, though no expression was detectable in DRGs at this stage.

Sympathetic ganglia. As early as E11.5, neuropilin-2 was detected in the ganglia of the sympathetic chain. This expression was more intense by E13.5, and had slightly decreased by E15.5). At this stage neuropilin-2 mRNA could also be detected in neurons of the superior cervical ganglion. Expression was also observed in the region of the enteric nervous system.

Olfactory system. High level neuropilin-2 expression was detected in all components of the olfactory system. Intense staining was observed at E13.5 and E15.5 in the vomeronasal organ, as well as in the accessory olfactory bulb, its target territory in the forebrain. Neuropilin-1 is not expressed in the accessory olfactory system (Kawakami et al., 1996).

By E15.5, the olfactory epithelium strongly expressed neuropilin-2, but this expression was not homogenous, being higher rostrally. A high level of neuropilin-2 mRNA was observed in the anterior olfactory nucleus and in the telencephalic regions interconnected to the olfactory bulb, such as the amygdala, the piriforn cortex and the entorhinal cortex.

Neocortex. Neuropilin-2 expression in the cortex was first detected around E13.5, and was restricted to the intermediate zone of the ventral and lateral regions of the cortex. The mesenchymal cells covering the cortex also showed high level expression of neuropilin-2. By E15.5 the staining was still confined to the intermediate zone, and was stronger in its lower portion. At birth, neuropilin-2 expression was no longer detected in the cortex, with the exception of the cingulate cortex.

Hippocampal formation. The pattern of expression of neuropilin-2 was particularly interesting in the components of the hippocampal formation. Neuropilin-2 could be detected as early as E13.5 in the hippocampus, and by E15.5 expression was evident in both the dentate gyrus and in cells of CA3 and CA1 fields. The hybridization signal was uninterrupted and formed a continuum with neuropilin-2 expressing cells in the intermediate zone of the neocortex. By P0, expression of neuropilin-2 was still very high in granule cells of the dentate gyrus, the hilus, and in the pyramidal cell layer, intermediate zone, and in the interneurons of the CA3-CA1 fields. Expression was also observed in the subiculum but not the presubiculum or the parasubiculum. At this stage, neuropilin-2 expression was also very intense in most of the brain regions that project to the hippocampus. The neurons of the entorhinal cortex which project massively through the so-called perforant pathway to the dentate gyrus, the hippocampus and the subiculum, expressed neuropilin-2. Cells in the septal region (medial septum, diagonal band of Broca), another major source of afferent fibers to the hippocampal formation, also strongly expressed neuropilin-2 at E15.5 and at birth.

Visual system. At E11.5, neuropilin-2 was very highly expressed in the mesenchyme surrounding the eye-cup and the optic nerve, but was absent from the retina. At E15.5, low expression of neuropilin-2 mRNA was detected in the ganglion cell layer, and diffuse expression was observed in the superior colliculus, one of the targets of retinal axons. By P0, neuropilin-2 was very highly expressed in the most superficial layers of the superior colliculus, and at a lower level in the other layers. Expression stopped abruptly at the boundary between superior and inferior colliculus. Expression was not observed in the lateral geniculate nucleus of the thalamus at birth.

Thalamus. Neuropilin-2 was also expressed at birth in several thalamic nuclei such as the medial habenula.

Cerebellum. Neuropilin-2 expression was detected as early as E13.5 in the cerebellar primordium, and increased in level by E15.5. At P0, neuropilin-2 was expressed in subsets of deep nuclei neurons as well as in stripes of Purkinje cells. Neuropilin-1, in contrast, is not expressed in the cerebellum (Kawakami et al., 1996).

Hindbrain nuclei. Neuropilin-2 was detected at E15.5 and at birth (P0), in several branchiomotor nuclei, such as the trigeminal, facial and hypoglossal motor nuclei, but not in the dorsal motor nucleus of the vagus. We have not determined when expression in these nuclei starts. Lower levels of expression were observed in the regions of the inferior olive and vestibular nuclei. Expression was not detected in the pons, a region known to express neuropilin-1 at high level (Kawakami et al., 1996).

Expression of neuropilin-2 in non-neural tissues. In addition to its expression in the CNS, neuropilin-2 was also detected in many non-neural tissues. At E10.5 it was expressed in the limb bud in restricted areas in the regions of the dorsal and ventral muscle masses. Later on, expression was also observed in the developing bones, in particular in the vertebrae, ribs and digits. Expression of neuropilin-2 was also observed in several muscles such as the back muscles and the tongue, and the strongest expression was observed in the region of the smooth muscles of the gut. Expression was also observed in the intestinal epithelium, as well as in cells in the kidney, the submandibular) gland, the lung, the whisker follicles of the snout, and in the inner ear. In contrast to neuropilin-1 (Kawakami et al., 1996), neuropilin-2 expression was not detected in the heart or in capillaries, but was found in the dorsal aorta.

Different binding patterns of neuropilin-1 and neuropilin-2 to different semaphorin family members. To test whether neuropilin-2, like neuropilin-1, is also a receptor for Sema III, we transiently expressed neuropilin-1, neuropilin-2(a0), -2(a5), -2(a22) and -2(b5) in COS-7 cells, for use in binding experiments. We were able to detect expression of neuropilin-1 and the different isoforms of neuropilin-2 in COS cells by immunostaining using either a polyclonal antibody against neuropilin-1 (He and Tessier-Lavigne, 1997) or monoclonal antibody 9E10 against the myc-tag at the carboxy terminus of all the neuropilin-2 isoforms. Western blot analysis showed that neuropilin-2 isoforms expressed in COS cells had the expected size of ~120 kDa. To test for interactions with Sema III, we used a chimeric molecule in which Sema III was fused at its carboxy terminus to the histochemical reporter alkaline phosphatase (Sema III-AP: He and Tessier-Lavigne, 1997). Partially purified conditioned medium containing Sema III-AP was incubated with COS cells expressing neuropilins, and bound protein was detected by alkaline phosphatase hiistochemistry. As expected, Sema III-AP bound cells expressing neuropilin-1 (He and Tessier-Lavigne, 1997), and the alkaline phosphatase protein (AP) itself did not bind mock-transfected cells. cells expressing neuropilin-1, or any of the neuropilin-2 isoforms. Surprisingly, none of the isoforms of neuropilin-2 tested showed any detectable binding of Sema III-AP. We considered the possibility that neuropilin-2 binds the C terminal domain of Sema III and that the absence of binding was an artifact resulting from fusion of AP to the carboxy terminal portion of Sema III, masking the binding site. To address this possibility, we made use of a chimeric molecule in which AP is fused to the amino terminus of C domain of Sema III (AP-C: He and Tessier-Lavigne, 1997). The AP-C protein bound cells expressing neuropilin-1 but not cells expressing any of the neuropilin-2 isoforms. Thus. the absence of binding of full length Sema III-AP to cells expressing the different neuropilin-2 isoforms reflects a bona fide absence of binding of Sema III to neuropilin-2.

Since Sema III itself does not appear to bind neuropilin-2, we wondered whether neuropilin-2 might be a receptor for other members of the semaphorin family. Sema III is a member of a subfamily of structurally-related molecules within the semaphorin family that includes the members Sema E/Collapsin-3 (Luo et al., 1995; Püschel et al., 1995), Sema IV/Sema 3F (Sekido et al., 1996; Roche et al., 1996; Xiang et al., 1996), Sema A/Sema V (Sekido et al., 1996), and Sema H. Like Sema III, all of these proteins are secreted proteins possessing a semaphorin domain, an immunoglubulin domain and a basic carboxy terminal domain (Püshel et al., 1995; Luo et al., 1995). We therefore examined whether two of these molecules, Sema E and Sema IV, are ligands for neuropilin-1 and/or neuropilin-2. In addition, we tested another secreted semaphorin, Drosophila Sema II (Kolodkin et al., 1993), which is more distantly related in sequence, as well as a more divergent semaphorin, the transmembrane Sema VIa (Zhou, et al 1997). As for Sema III, we tested the ability of COS cells expressing neuropilin-1 or neuropilin-2 to bind chimeric molecules in which alkaline phosphatase was fused to Sema E, Sema IV, Drosophila D-Sema II or the ectodomain of Sema VIa (see Experimental Procedures). These AP fusion proteins were presented to the cells in the form of partially purified conditioned media from cells expressing each of the proteins; media were matched for AP activity. We found that both neuropilin and different isoforms of neuropilin-2 expressing cells bound Sema E-AP and Sema IV-AP. In contrast, neither neuropilin-1 nor any of the neuropilin-2 isoforms expressed in COS cells showed detectable binding to the AP fusions with D-Sema II or the Sema VIa ectodomain. In control experiments, we found that Sema E-AP and Sema IV-AP did not bind mock-transfected COS cells or COS cells expressing the netrin-1 receptor DCC.

We estimated the binding affinity of the AP fusions of Sema III, Sema E and Sema IV to cells expressing neuropilin-1 or neuropilin-2 in equilibrium binding experiments. For these experiments, we used the a5 isoform of neuropilin-2. Specific binding curves of these molecules showed saturation and could be fitted with the Hill equation (FIGS. 5A–5C). The estimated dissociation constants (Kd) for Sema E binding to neuropilin-1 and neuropilin-2 were 5 nM and 18 nM, respectively. Those for Sema IV binding to neuropilin-1 and neuropilin-2 were 30 nM and 5 nM, respectively. No detectable binding of Sema III to neuropilin-2 expressing cells was detected, while the estimated Kd for Sema III binding to neuropilin-1 was 0.325 nM (see also He and Tessier-Lavigne, 1997). Similar Kd values were obtained using the b5 isoform of neuropilin-2 and the degree of binding of different semaphorins to cells all isoforms tested appeared similar.

Dynamic expression of neuropilin-2 complementary to that of neuropilin-1. The specific pattern of expression of neuropilin-2 indicates the involvement of members of the Sema III subfamily other than Sema III itself in the guidance of a variety of different axonal classes, in particular in the spinal cord, olfactory system, and hippocampus.

In the spinal cord, commissural axons are guided along a dorso-ventral trajectory at least partly in response to the diffusible chemoattractant netrin-1 (Serafini et al., 1996). neuropilin-2 transcripts are detected in the region of commissural neuron cell bodies, indicating that commissural neurons express neuropilin-2. Since Sema E is expressed in the ventral spinal cord (Püschel et al., 1995), this semaphorin might contribute to the guidance of commissural axons. Our in situ hybridization studies also indicate that different motomeuron populations express different complements of neuropilins, and therefore might respond differentially to different secreted semaphorins expressed in the periphery (Püschel et al., 1995; Wright et al., 1995; Giger et al., 1996). Thus, different semaphorins can contribute to patterning the projections of motor axons to distinct peripheral targets (Tsushida et al., 1994). The olfactory system is another site of significant neuropilin-2 expression, suggesting a role for secreted semaphorins distinct from Sema III in guidance in this system. Axons from the olfactory bulb are known to be repelled by an unidentified septum-derived chemorepellent (Pini, 1993). neuropilin-2 transcripts are expressed in the region of the cell bodies of origin of these axons in the bulb, indicating that a secreted semaphorin can function as a septal-derived chemorepellent. Another interesting finding is that neuropilin-2 expression in the olfactory epithelium (presumably by primary olfactory neurons) is not uniform, indicating that secreted semaphorins can play a role in differential guidance of different complements of primary olfactory axons, contributing to the creation of an olfactory map.

Neuropilins are also expressed in the sites of origin of afferent projections to the hippocampus. Afferents to the hippocampus are known to be topographically organized, with septal, hippocampal, and entorhinal axons projecting to distinct dendritic locations on granule and pyramidal neurons (Paxinos 1995). neuropilin-1 and-2 are expressed by, the septal and hippocampal neurons, whereas only neuropilin-2 is expressed by entorhinal neurons. Sema E and Sema IV are highly expressed in the hippocampus (Püschel et al., 1995; Sekido et al., 1996), and these semaphorins can therefore contribute to the patterning of hippocampal afferent projections as well.

Finally, the observation that neuropilin-2 is expressed in many non-neuronal tissues also indicates the involvement of semaphorins other than Sema III in organogenesis outside the nervous system. A role for secreted semaphorins in tumor suppression is indicated by the fact that neuropilin-2 is expressed in the lung, since Sema IV and Sema A/V map to a region of chromosome 3p that is frequently deleted in small cell lung cancer, and which is thought to contain a tumor suppressor gene for lung cancer (Roche et al., 1996; Sekido et al., 1996; Xiang et al., 1996).

Experimental Procedures: Isolation of neuropilin-2 and its splice variants

Six sets of fully degenerate oligonucleotides were used to perform RT-PCR using pfu polymerase (Stratagene) on mRNA isolated from E11 whole mouse embryo and adult mouse brain. Primers were designed to conserved amino acid sequences in the a2 domain of neuropilin, the b1 domain, the b2 domain, the MAM domain and the cytoplasmic domain. For each of the reactions, DNA bands of the size expected for neuropilin-1 were excised, and the gel purified DNA was subjected to secondary PCR amplification using the same primers but with an EcoR I site at the 5' terminus of forward primers and an Xba I site in the reverse primers. The PCR products were cloned into pBluescript KS(−) and sequenced. From one of these reactions, a novel sequence corresponding to neuropilin-2 was isolated (see Results). A 1.2 kb fragment of neuropilin-2 was used as a probe to screen an adult mouse brain gt11 lambda phage library (Clontech). Partial cDNA fragments isolated in this way corresponded to two presumptive differential splicing isoforms, the a and b forms, with or without the 5, 17 and 22 amino acid insertions (FIG. 4). In order to obtain a full length cDNA, 5' RACE was performed on cDNA isolated from E11 mouse whole embryo and adult mouse brain. The 5'-RACE products were cloned into pBluescript KS(−) with 5' Not I and 3' Xho I sites, and sequenced. cDNAs containing the entire coding regions of the a and b isoforms of neuropilin-2 were assembled, with and without various combinations of the 5, 17 and 22 amino acid insertions (see Results).

In situ hybridization. A 1200 nucleotide fragment of neuropilin-2 was used to generate digoxygenin (DIG)-labeled and $^{35}$S-labeled antisense and sense RNA probes. In situ hybridization was performed on vibratome sections of P0 mouse brain with the DIG-labeled probe, and using the radioactive probe on cryosections taken at various stages between E9.5 and P0. The in situ hybridization procedures using digoxygenin-labeled probes were as described previously (Chédotal et al., 1996), and procedure using radioactive probes was as described by Messersmith et al. (1995).

Plasmid construction. The coding regions of neuropilin-2 of alternative splicing forms, deleted of their signal sequences, were subcloned into the expression vector pSecTag-A (Invitrogen) in the Hind III (5'-end) and Xba I (3'-end) sites and transiently transfected into COS 7 cells using Lipofectamine (GIBCO BRL). Expression of neuropilin-2 isoforms was detected by immunocytochemistry and Western analysis using monoclonal antibody 9E10 (to the myc tag at the C terminus of the neuropilin-2 isoforms).

The semaphorin III-AP fusion protein was described previously (He and Tessier-Lavigne, 1997). The mouse Sema E clone was obtained by PCR from P0 mouse brain cDNAs, using the PCR primers. The amplified band was subcloned into the expression vector, APtag-4 vector which a sequence coding for secreted alkaline phosphatase. The human Sema IV clone was subcloned in pSecTag-A (Invitrogen), which also contains the secreted alkaline phosphatase.

Semaphorin-AP fusion protein binding assay. The semaphorin-AP fusion protein binding experiments was as described by Cheng and Flanagan (1994), with the exception that in order to reduce background binding, 2 $\mu$g/ml of heparin was included in the binding mixture. Briefly, neuropilin-1 and neuropilin-2 expression constructs were transiently expressed in COS 7 cells as described above.

After 48 hours of transfection, expressing cells were rinsed with HBHA buffer (Hank's balanced salt solution with 20 mM HEPES pH 7.0. 0.05% sodium azide) (Cheng and Flanagan, 1994). Concentrated supernatant containing semaphorin-AP fusion proteins in the presence of 20 mM HEPES and 0.05% of sodium azide was incubated with expressing COS cells at room temperature for 75 minutes, followed by heat inactivation of endogenous alkaline phosphatase, washing, and color development as described by Cheng and Flanagan (1994).

Protocol for High Throughput SR-SemaIII Binding Assay

A. Reagents:
  Neutralite Avidin: 20 μg/ml in PBS.
  Blocking buffer: 5% BSA, 0.5% Tween 20 in PBS; 1 hour at room temperature.
  Assay Buffer: 100 mM KCl, 20 mM HEPES pH 7.6, 1 mM $MgCl_2$, 1% glycerol. 0.5% NP-40, 50 mM β-mercaptoethanol, 1 mg/ml BSA, cocktail of protease inhibitors.
  $^{33}$P SR polypeptide 10xstock: $10^{-8}$–$10^{-6}$ M "cold" SR polypeptide specific SR domain supplemented with 200,000–250,000 cpm of labeled SR (Beckman counter). Place in the 4° C. microfridge during screening.
  Protease inhibitor cocktail (1000X): 10 mg Trypsin Inhibitor (BMB #109894), 10 mg Aprotinin (BMB # 236624), 25 mg Benzamidine (Sigma #B-6506), 25 mg Leupeptin (BMB #1017128), 10 mg APMSF (BMB #917575), and 2mM $NaVO_3$ (Sigma #S-6508) in 10 ml of PBS.
  SemaIII: $10^{-7}$–$10^{-5}$ M biotinylated SemaIII in PBS.

B. Preparation of assay plates:
  Coat with 120 μl of stock N-Avidin per well overnight at 4° C.
  Wash 2 times with 200 μl PBS.
  Block with 150 μl of blocking buffer.
  Wash 2 times with 200 μl PBS.

C. Assay:
  Add 40 μl assay buffer/well.
  Add 10 μl compound or extract.
  Add 10 μl $^{33}$P-SR (20–25,000 cpm/0.1–10 pmoles/well= $10^{-9}$–$10^{-7}$ M final conc).
  Shake at 25° C. for 15 minutes.
  Incubate additional 45 minutes at 25° C.
  Add 40 μM biotinylated SemaIII (0.1–10 pmoles/40 ul in assay buffer)
  Incubate 1 hour at room temperature.
  Stop the reaction by washing 4 times with 200 μM PBS.
  Add 150 μM scintillation cocktail.
  Count in Topcount.

D. Controls for all assays (located on each plate):
  a. Non-specific binding
  b. Soluble (non-biotinylated SemaIII) at 80% inhibition.

References

Ackerman, S. L., et al. (1997). Nature 386, 838–42.
Adams, R. H., et al. (1996). Mech. Dev. 57, 33–45.
Altman, J. and Bayer, S. A. (1984). Adv Anat Embryol Cell Biol 85, 1–164.
Arlaud, G. L., Colomb, M. G. and Gagnon, G. (1987). Immunology Today 8, 106–111.
Beckmann, G. and Bork, P. (1993). Trends Biochem Sci 18, 40–1.
Bebar, O., et al., (1996). Nature 383, 525–8.
Bork, P. and Beckmann, G. (1993). J Mol Biol 231, 539–45.
Busby, T. F. and Ingham, K. C. (1988). Biochemistry 27, 6127–35.
Busby, T. F. and Ingham, K. C. (1990). Biochemistry 29, 4613–8.
Chan, S. S., et al. (1996). Cell 87, 187–95.
Chedotal, A., et al. (1996). J. Neurosci. 16, 3296–3310.
Cheng, H. J. and Flanagan, J. G. (1994). Cell 79, 157–68.
Childs, S. R. and O'Connor, M. B. (1994). Dev Biol 162, 209–20.
Colamarino, S. A. and Tessier-Lavigne, M. (1995). Cell 81, 621–9.
Culotti, J. G., et al. (1996). Curr. Opin. Neurobiol. 6, 81–88.
Evan, G. I., et al. (1985) Mol. Cell. Biol. 5, 3610–3616.
Finelli, A. L., Bossie, C. A., Xie, T. and Padgett, R. W. (1994). Development 120, 861–70.
Fitzgerald, M., Kwiat, G. C., Middleton, J. and Pini, A. (1993). Development 117, 1377–84.
Flanagan, J. G. and Leder, P. (1990). Cell 63, 185–94.
Fujisawa, H., Ohtsuki, T., Takagi, S. and Tsuji, T. (1989). Dev Biol 135, 231–40.
Fujisawa, H., Takagi, S. and Hirata. T. (1995). Dev Neurosci 17, 343–9.
Furuyania, T., et al. (1996). J. Biol. Chem. 271, 33376–33381.
Gale, N. W., et al. (1996). Neuron 17, 9–19.
Giger, R. J., et al. (1996). J. Comp. Neurol. 375, 378–392.
Goshima, Y., et al. (1995). Nature 376, 509–14.
Guthrie, S. and Pini, A. (1995). Neuron 14, 1117–30.
Hamelin, M., et al. (1993). Nature 364, 327–30.
He, Z.-H., et al. (1997). Cell in press.
Hedoecock, E. M., Culotti, J. G. and Hall, D. H. (1990). Neuron 4, 61–85.
Hirata, T., Takazi, S. and Fujisawa, H. (1993). Neurosci Res 17, 159–69.
Hu, H. and Rutishauser, U. (1996). Neuron 16, 933–40.
Igarashi, M., et al., (1993). Science 259, 77–9.
Inagaki, S., et al. (1995). FEBS Lett. 370, 269–272.
Jalink, K., et al. (1994). J Cell Biol 126, 801–10.
Jenny, R. J., et al. (1987). Proc Natl Acad Sci USA 84, 4846–50.
Johnson, J. D., et al. (1993). Proc Natl Acad Sci USA 90, 10891.
Kawakami, A., Kitsukawa, T., Takagi, S. and Fujisawa, H. (1996). J Neurobiol 29, 1–17.
Keino-Masu, K., et al. (1996). Cell 87, 175–85.
Kennedy, T. E., et al. (1994). Cell 78, 425–35.
Kindt, R. M. and Lander, A. D. (1995). Neuron 15, 79–88.
Kitsukawa, T., et al. (1995). Development 121, 4309–18.
Kolodkin, A. L. (1996). Trends in Cell Biology 6, 15–22.
Kolodkin, A. L., Matthes, D. J. and Goodman, C. S. (1993). Cell 75, 1389–99.
Kolodkin, A. L., et al. (1992). Neuron 9, 831–45.
Kolodziej, P. A., et al. (1996). Cell 87,197–204
Larocca, D., et al. (1991). Cancer Res 51, 4994–8.
Leonardo, E. D., et al. (1997). Nature 386, 833–8.
Leung-Hagesteijn, C., et al. (1992).. Cell 71, 289–99.
Li, W., Herman, R. K. and Shaw, J. E. (1992). Genetics 132, 675–89.
Luo, Y., Raible, D. and Raper, J. A. (1993). Cell 75, 217–27.
Matthes. D. J., Sink, H., Kolodkin, A. L. and Goodman, C. S. (1995). Cell 81. 631–9.
Messersmith, E. K., et al. (1995). Neuron 14, 949–59.
Pini, A. (1993). Science 261, 95–8.

Püschel, A. W., Adams, R. H. and Betz, H. (1995). Neuron 14, 941–8.
Püschel, A. W., Adams, R. H. and Betz, H. (1996). Mol Cell Neurosci 7, 419–31.
Sanchez, M. P., et al. (1994). Proc Natl Acad Sci U S A 91, 1819–23.
Schaeren-Wiemers, N. and Gerfin-Moser, A. (1993). Histochemistry 100, 431–40.
Sekido, Y., et al. (1996). Proc. Natl. Acad. Sci. USA 93, 4120–4125.
Serafini, T., et al. (1994).-6. Cell 78, 409–24.
Serafini, T., et al. (1996). Cell 87, 1001–1014.
Shepherd, I., Luo, Y., Raper, J. A. and Chang, S. (1996). Dev Biol 1 73, 185–99.
Shepherd, I. T., et al. (1997). Development 124, 1377–85.
Shirasaki, R., et al. (1996). Neuron 17, 1079–1088.
Smith, C. L. (1983). J Comp Neurol 220, 29–43.
Snider, W. D., et al. (1992). J Neurosci 12, 3494–508.
Stubbs, J. D., et al. (1990). Proc. Natl. Acad. Sci. USA 87, 8417–8421.
Takagi, S., et al. (1991). Neuron 7, 295–307.
Takagi, S., et al. (1995). Dev Biol 170, 207–22.
Takagi, S., et al. (1987). Dev Biol 122, 90–100.
Tamada, A., Shirasaki, R. and Murakami, F. (1995). Neuron 14, 1083–93.
Tessier-Lavigne, M. and Goodman, C. S. (1996). Science 274, 1123–33.
Tessier-Lavigne, M., et al. (1988). Nature 336, 775–8.
Toole, J. J., et al. (1984). Nature 312, 342–7.
Varela-Echavarria, A. and Guthrie, S. (1997). Genes Dev 11, 545–57.
Varela-Echavarria, A., et al.. (1997). Neuron 18, 193–207.
Wadsworth, W. G., Bhatt, H. and Hedgecock, E. M. (1996). Neuron 16, 35–46.
Windle, W. F., and Baxter, R. E. (1936). J. Comp. Neuro. 63, 189–209.
Wringht, D. E., et al. (1995). J Comp Neurol 361, 321–33.
Xiang, R. H., et al. (1996). Genomics 32, 39–48.
Zhang, L., et al. (1994). J Neurosci 14, 5187–201.
Zhou, L., et al. (1997). Mol. Cell. Neurosci. 9,26–41.
Zondag, G. C., et al. (1995). J Biol Chem 270, 14247–50.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An antibody which specifically binds a semaphorin receptor (SR) polypeptide consisting of an amino acid sequence selected from SEQ ID NO: 2 and 4, said antibody cross-reactive with neither mouse, chick nor drosophila neuropilin-1.

2. An antibody according to claim 1, wherein the polypeptide consists of the amino acid sequence of SEQ ID NO: 2.

3. An antibody according to claim 1, wherein the polypeptide consists of the amino acid sequence of SEQ ID NO: 4.

4. A method for detecting an SR polypeptide in a sample comprising the steps of:
   (a) contacting a sample with an antibody according to claim 1, and
   (b) detecting specific binding of the antibody the SR polypeptide as an indication of the presence of the SR polypeptide in the sample.

5. A method for detecting an SR polypeptide in a sample comprising the steps of:
   (a) contacting a sample with an antibody according to claim 2, and
   (b) detecting specific binding of the antibody the SR polypeptide as an indication of the presence of the SR polypeptide in the sample.

6. A method for detecting an SR polypeptide in a sample comprising the steps of:
   (a) contacting a sample with an antibody according to claim 3, and
   (b) detecting specific-binding of the antibody the SR polypeptide as an indication of the presence of the SR polypeptide in the sample.

* * * * *